US011542517B2

(12) United States Patent
Cui et al.

(10) Patent No.: US 11,542,517 B2
(45) Date of Patent: Jan. 3, 2023

(54) MATERIALS AND METHODS FOR CONTROLLING BUNDLE SHEATH CELL FATE AND FUNCTION IN PLANTS

(71) Applicant: FLORIDA STATE UNIVERSITY RESEARCH FOUNDATION, INC., Tallahassee, FL (US)

(72) Inventors: Hongchang Cui, Tallahassee, FL (US); Danyu Kong, Blacksburg, VA (US); Yueling Hao, Tallahassee, FL (US)

(73) Assignee: Florida State University Research Foundation, Inc., Tallahassee, FL (US)

(*) Notice: Subject to any disclaimer, the term of this patent is extended or adjusted under 35 U.S.C. 154(b) by 74 days.

(21) Appl. No.: 17/007,043

(22) Filed: Aug. 31, 2020

(65) Prior Publication Data

US 2020/0407740 A1 Dec. 31, 2020

Related U.S. Application Data

(62) Division of application No. 14/898,046, filed as application No. PCT/US2014/041975 on Jun. 11, 2014, now Pat. No. 10,865,420.

(60) Provisional application No. 61/833,771, filed on Jun. 11, 2013.

(51) Int. Cl.
*C12N 15/82* (2006.01)

(52) U.S. Cl.
CPC ..... *C12N 15/8225* (2013.01); *C12N 15/8261* (2013.01); *C12N 15/8269* (2013.01)

(58) Field of Classification Search
None
See application file for complete search history.

(56) References Cited

U.S. PATENT DOCUMENTS 4,962,028 A 10/1990 Bedbrook et al.
5,034,322 A 7/1991 Rogers et al.
5,106,739 A 4/1992 Comai et al.
5,589,610 A 12/1996 De Beuckeleer et al.
5,625,136 A 4/1997 Koziel et al.
5,639,948 A 6/1997 Michiels et al.
5,661,017 A 8/1997 Dunahay et al.
6,388,173 B2 5/2002 Benfey et al.
6,441,270 B1 8/2002 Benfey et al.
6,455,760 B1 9/2002 Zhao et al.
6,462,185 B1 10/2002 Takakura et al.
6,610,840 B2 8/2003 Sonnewald et al.
6,610,913 B1 8/2003 Arai et al.
6,696,623 B1 2/2004 Doerner et al.
6,809,234 B1 10/2004 Benfey et al.
6,927,320 B1* 8/2005 Benfey ............. C12N 15/8227 800/300
7,663,025 B2 2/2010 Heard et al.
10,865,420 B2* 12/2020 Cui .................... C12N 15/8225
2003/0084486 A1 5/2003 Bruce et al.
2003/0088073 A1 5/2003 Benfey et al.
2003/0177536 A1 9/2003 Grundler
2004/0019934 A1 1/2004 Ekramoddoullah et al.
2004/0067506 A1 4/2004 Scheres et al.
2004/0078841 A1 4/2004 Atkinson et al.
2004/0123349 A1 6/2004 Xie et al.
2013/0096032 A1* 4/2013 Bush .................... C12Q 1/6895 506/16

FOREIGN PATENT DOCUMENTS

EP 1528104 5/2005

OTHER PUBLICATIONS

Bolle, C., "The role of GRAS proteins in plant signal transduction and development," *Planta*, 2004, vol. 218, pp. 683-692.
Bosabalidis, A.M., et al., "Ontogeny of the vascular bundles and contiguous tissues in the maize leaf blade,". *Am. J. Bot*., 1994, vol. 81, No. 6, pp. 745-752.
Brown, N.J. et al., "Independent and parallel recruitment of preexisting mechanisms underlying $C_4$ photosynthesis," *Science*, 2011, vol. 331, pp. 1436-1439.
Brutnell, T.P., et al., "Bundle Sheath Defective2, a novel protein required for post-translational regulation of the rbcL gene of maize," *Plant Cell*, 1999, vol. 11, pp. 849-864 (1999).
Cermak, T., et al., "Efficient design and assembly of custom TALEN and other TAL effector-based constructs for DNA targeting," *Nucleic Acids Res*., 2011, vol. 39, No. 12, e82.
Clancy, M., et al. "Splicing of the maize Sh1 first intron is essential for enhancement of gene expression, and a T-rich motif increases expression without affecting splicing," *Plant Physiol*., 2002, vol. 130, No. 2, pp. 918-929.

(Continued)

*Primary Examiner* — Cynthia E Collins
(74) *Attorney, Agent, or Firm* — Saliwanchik, Lloyd & Eisenschenk

(57) ABSTRACT

The subject invention concerns materials and methods for increasing and/or improving photosynthetic efficiency in plants, and in particular, C3 plants. In particular, the subject invention provides for means to increase the number of bundle sheath (BS) cells in plants, to improve the efficiency of photosynthesis in BS cells, and to increase channels between BS and mesophyll (M) cells. In one embodiment, a method of the invention concerns altering the expression level or pattern of one or more of SHR, SCR, and/or SCL23 in a plant. The subject invention also pertains to genetically modified plants, and in particular, C3 plants, that exhibit increased expression of one or more of SHR, SCR, and/or SCL23. Transformed and transgenic plants are contemplated within the scope of the invention. The subject invention also concerns methods for increasing expression of photosynthetically important genes in a plant, wherein one or more genes of interest are operably linked with a plant SHR, SCR or SCL23 promoter sequence and expressed in a plant.

12 Claims, 10 Drawing Sheets
(9 of 10 Drawing Sheet(s) Filed in Color)
Specification includes a Sequence Listing.

(56) References Cited

OTHER PUBLICATIONS

Clough, S. et al., "Floral dip: a simplified method for *Agrobacterium*-mediated transformation of *Arabidopsis thaliana," Plant J.*, 1998, vol. 16, No. 6, pp. 735-743.
Cruz-Ramirez, A., et al., "A bistable circuit involving Scarecrow-Retinoblastoma integrates cues to inform asymmetric stem cell division," *Cell*, 2012, vol. 150, pp. 1-14.
Cui, H. et al., An evolutionarily conserved mechanism delimiting SHR movement defines a single layer of endodermis in plants, *Science*, 2007, vol. 316, pp. 421-425.
Cui, H. et al., Genome-Wide Direct Target Analysis Reveals a Role for Short-Root in Root Vascular Patterning through Cytokinin Homeostasis, *Plant Physiol.*, 2011, vol. 157, pp. 1221-1231.
Cui, H. et al., "Interplay between Scarecrow, GA and Like Heterochromatin Protein 1 in ground tissue patterning in the *Arabidopsis* root," *Plant J.*, 2009, vol. 58, pp. 1016-1027.
Cui, H., et al., "Scarecrow has a Short-Root-independent role in modulating the sugar response," *Plant Physiol.*, 2012, vol. 158, pp. 1769-1778.
Dhondt, S. et al., "Short-Root and Scarecrow regulate leaf growth in *Arabidopsis* by stimulating S-phase progression of the cell cycle," *Plant Physiol.*, 2010, vol. 154, pp. 1183-1195.
Di Laurenzio, L. et al., The Scarecrow gene regulates an asymmetric cell division that is essential for generating the radial organization of the *Arabidopsis* root, *Cell*, 1996, vol. 86, pp. 423-433.
Fukaki, H., et al., "Genetic evidence that the endodermis is essential for shoot gravitropism in *Arabidopsis thaliana," Plant J.*, 1998, vol. 14, No. 4, pp. 425-430.
Furtado, A. et al., "Tools for Use in the Genetic Engineering of Barley," *Proceedings of the 10th Australian Barley Technical Symposium*, 2002, Canberra, ACT, Australia.
Gardiner, J., et al., "Simultaneous activation of SHR and ATHB8 expression defines switch to preprocambial cell state in *Arabidopsis* leaf development," *Dev. Dyn.*, 2010, vol. 240, pp. 261-270.
Gendrel, A.V., et al., "Profiling histone modification patterns in plants using genomic tiling microarray," *Nat. Methods*, 2005, vol. 2, No. 3, pp. 213-218.
Good, X. et al., "Reduced ethylene synthesis by transgenic tomatoes expressing S-adenosylmethionine hydrolase," *Plant Molec. Biol.*, 1994, vol. 26, pp. 781-790.
Hall, L. et al., "GOLDEN 2: a novel transcriptional regulator of cellular differentiation in the maize leaf," *Plant Cell*, 1998, vol. 10, pp. 925-936.
Haritatos, E. et al., "Minor vein structure and sugar transport in *Arabidopsis thaliana," Planta*, 2000, vol. 2111, pp. 105-111.
Helariutta, Y. et al., "The Short-Root gene controls radial patterning of the *Arabidopsis* root through radial signaling," *Cell*, 2000, vol. 101, pp. 555-567.
Hibberd, J.M. et al., "Using $C_4$ photosynthesis to increase the yield of rice—rationale and feasibility," *Curr. Opin. Plant Biol.*, 2008, vol. 11, pp. 228-231.
Hirner, A. et al., "*Arabidopsis* LHT1 is a high-affinity transporter for cellular amino acid uptake in both root epidermis and leaf mesophyll," *Plant Cell*, 2006, vol. 18, pp. 1931-1946.
Hwang, Y.S. et al., "Analysis of the Rice Endosperm-Specific Globulin Promoter in Transformed Rice Cells," *Plant Cell Rep.*, 2002, vol. 20, pp. 842-847.
Jankovsky, J.P. et al., "Specification of bundle sheath cell fates during maize leaf development: roles of lineage and positional information evaluated through analysis of the tangled1 mutant," *Development*, 2001, vol. 128, pp. 2747-2753.
Kajala, K. et al., "Strategies for engineering a two-celled $C_4$ photosynthetic pathway into rice," *J. Exp. Bot.*, 2011, vol. 62, No. 9, pp. 3001-3010.
Kamiya, N., et al., "The Scarecrow gene's role in asymmetric cell divisions in rice plants," *Plant J.*, 2003, vol. 36, pp. 45-54.
Kangasjärvi, S. et al., "Cell-specific mechanisms and systemic signalling as emerging themes in light acclimation of C3 plants," *Plant Cell Environ.*, 2009, vol. 32, pp. 1230-1240.
Karlin, S. et al., "Methods for Assessing the Statistical Significance of Molecular Sequence Features by Using General Scoring Schemes," *Proc. Natl. Acad. Sci. USA*, 1990, vol. 87, pp. 2264-2268.
Karlin, S. et al., "Applications and Statistics for Multiple High-Scoring Segments in Molecular Sequences," *Proc. Natl. Acad. Sci. USA*, 1993, vol. 90, pp. 5873-5877.
Kausch, A.P. et al., "Mesophyll-specific, light and metabolic regulation of the $C_4$ PPCZm1 promoter in transgenic maize," *Plant Molecular Biology*, 2001, vol. 45, pp. 1-15.
Kinsman, E.A. et al., "Bundle sheath cells and cell-specific plastid development in *Arabidopsis* leaves," *Development*, 1998, vol. 125, pp. 1815-1822.
Laajanen, K. et al., "Cloning of Pinus sylvestris Scarecrow gene and its expression pattern in the pine root system, mycorrhiza and NPA-treated short roots," *New Phytol.*, 2007, vol. 175, pp. 230-243.
Langdale, J.A., "$C_4$ cycles: past, present, and future research on $C_4$ photosynthesis," *Plant Cell*, 2011, vol. 23, pp. 3879-3892.
Langdale, J.A. et al., "Cell-specific accumulation of maize phospho enolpyruvate carboxylase is correlated with demethylation at a specific site >3 kb upstream of the gene," *Mol. Gen. Genet.*, 1991, vol. 225, pp. 49-55.
Langdale, J.A. et al., "Cell position and light influence C4 versus C3 patterns of photosynthetic gene expression in maize," *EMBO J.*, 1988, vol. 7, No. 12, pp. 3643-3651.
Lee, M.H. et al., "Large-scale analysis of the GRAS gene family in *Arabidopsis thaliana," Plant Mol. Biol.*, 2008, Vo. 67, pp. 659-670.
Leegood, R.C., "Roles of the bundle sheath cells in leaves of $C_3$ plants," *J. Exp. Bot.*, 2007, doi: 10/1093/jxb/erm335, pp. 1-11.
Levesque, M.P. et al., "Whole-genome analysis of the Short-Root developmental pathway in *Arabidopsis," PLoS Biol.*, 2006, vol. 4, No. 5, e143.
Lim, J. et al., "Molecular analysis of the Scarecrow gene in maize reveals a common basis for radial patterning in diverse meristems," *Plant Cell*, 2000, vol. 12, pp. 1307-1318.
Nakajima, K. et al., "Intercellular movement of the putative transcription factor SHR in root patterning," *Nature*, 2001, vol. 413, pp. 307-311.
Nelson, T., "The grass leaf developmental gradient as a platform for a systems understanding of the anatomical specialization of $C_4$ leaves," *J. Exp. Bot.*, 2011, doi: 10/1093/jxb/err072, pp. 1-10.
Nomura, M. et al., "The promoter of rbcS in a C3 plant (rice) directs organ-specific, light-dependent expression in a C4 plant (maize), but does not confer bundle sheath cell-specific expression," *Plant Mol Biol.*, 2000, vol. 44, pp. 99-106.
Petricka, J.J. et al., "Vein patterning screens and the defectively organized tributaries mutants in *Arabidopsis thaliana," Plant J.*, 2008, vol. 56, pp. 251-263.
Pysh, L.D. et al., "The GRAS gene family in *Arabidopsis*: sequence characterization and basic expression analysis of the Scarecrow-Like genes," *Plant J.*, 1999, vol. 18, No. 1, pp. 111-119.
Rossini, L. et al., "The maize golden2 gene defines a novel class of transcriptional regulators in plants," *Plant Cell*, 2001, vol. 13, pp. 1231-1244.
Sage, R.F. et al., "Exploiting the engine of $C_4$ photosynthesis," *J. Exp. Bot.*, 2011, vol. 62, No. 9, pp. 2989-3000.
Sakamoto et al., "Structure and Characterization of a Gene for Light-Harvesting Chl a/b Binding Protein from Rice," *Plant Cell Physiology*, 1991, vol. 32, pp. 385-393.
Sassa, N. et al., "The molecular characterization and in situ expression pattern of pea Scarecrow gene," *Plant Cell Physiol.*, 2001, vol. 42, No. 4, pp. 385-394.
Schäffner, A.R. et al., "Maize rbcS Promoter Activity Depends on Sequence Elements Not Found in Dicot rbcS Promoters," *Plant Cell*, 1991, vol. 3, pp. 997-1012.
Slewinski, T.L. et al., "Scarecrow plays a role in establishing Kranz anatomy in maize leaves," Oxford University Press, 2012, pp. 1-25.
Solé, A. et al., "Characterization and expression of a *Pinus radiata* putative ortholog to the *Arabidopsis* Short-Root gene," *Tree Physiol.*, 2008, vol. 28, pp. 1629-1639.
Spreitzer, R.J. et al., "RUBISCO: structure, regulatory interactions, and possibilities for a better enzyme," *Ann. Rev. Plant Biol.*, 2002, vol. 53, pp. 449-475.

(56) References Cited

OTHER PUBLICATIONS

Stockhaus, J. et al., "The Promoter of the Gene Encoding the $C_4$ Form of Phosphoenolpyruvate Carboxylase Directs Mesophyll-Specific Expression in Transgenic $C_4$ *Flaveria* spp," *Plant Cell*, 1997, vol. 9, pp. 479-489.
Sun, X. et al., "A functionally required unfoldome from the plant kingdom: intrinsically disordered N-terminal domains of GRAS proteins are involved in molecular recognition during plant development," *Plant Mol. Biol.*, 2011, vol. 77, pp. 205-223.
Takahashi, H. et al., "The roles of three functional sulphate transporters involved in uptake and translocation of sulphate in *Arabidopsis thaliana,*" *Plant J.*, 2000, vol. 23, No. 2, pp. 171-182.
Taniguchi, Y. et al., "Overproduction of $C_4$ photosynthetic enzymes in transgenic rice plants: an approach to introduce the $C_4$-like photosynthetic pathway into rice," *J. Exp. Bot.*, 2008, vol. 59, No. 7, pp. 1799-1809.
Von Caemmerer, S. et al., "The Development of $C_4$ Rice: Current Progress and Future Challenges," *Science*, 2012, vol. 336, pp. 1671-1672.
Wang, L. et al., "Regulatory mechanisms underlying $C_4$ photosynthesis," *New Phytol.*, 2011, vol. 190, pp. 1-12.
Weigel, D.J. Glazebrook, *Arabidopsis*: A Laboratory Manual, CSHL Press, New York, 2002, pp. 241-248.
Welch, D. et al., "*Arabidopsis* Jackdaw and Magpie zinc finger proteins delimit asymmetric cell division and stabilize tissue boundaries by restricting Short-Root action," *Genes Dev.*, 2007, vol. 21, pp. 2196-2204.
Wu, C.Y. et al., "Promoters of Rice Seed Storage Protein Genes Direct Endosperm-Specific Gene Expression in Transgenic Rice," *Plant and Cell Physiology*, 1998, vol. 39, No. 8, pp. 885-889.
Wysocka-Diller, J.W. et al., "Molecular analysis of Scarecrow function reveals a radial patterning mechanism common to root and shoot," *Development*, 2000, vol. 127, pp. 595-603.
Xu, D. et al., "Systemic induction of a potato pin2 promoter by wounding, methyl jasmonate, and abscisic acid in transgenic rice plants," *Plant Molecular Biology*, 1993, vol. 22, pp. 573-588.
GenBank Accession No. AAB06318.1, "Scarecrow [*Arabidopsis thaliana*]," Nov. 18, 2014, p. 1.
GenBank Accession No. U62798.1, "*Arabidopsis thaliana* Scarecrow (Scarecrow1) gene, complete cds," Nov. 18, 2014, pp. 1-2.
GenBank Accession No. EF104556.1, "*Arabidopsis suecica* clone scr_24 genomic sequence," Nov. 18, 2014, pp. 1-2.
GenBank Accession No. AF233752, "*Arabidopsis thaliana* short-root protein (shr) gene, complete cds", Jun. 11, 2000, pp. 1-2.
Franken, P. et al. "The duplicated chalcone synthase genes C2 and Whp (white pollen) of *Zea mays* are independently regulated; evidence for translational control of Whp expression by the anthocyanin intensifying gene in" *The EMBO Journal*, 1991, vol. 10, No. 9, pp. 2605-2612.
Kim, Y. et al. "A 20 nucleotide upstream element is essential for the nopaline synthase (nos) promoter activity" *Plant Molecular Biol.*, 1994, vol. 24, pp. 105-117.
Ha, S.B. et al. "Cis-acting regulatory elements controlling temporal and organ-specific activity of nopaline synthase promoter" *Nucleic Acids Res.*, 1989, vol. 17, No. 1, pp. 215-223.
Whisstock, J.C. et al. "Prediction of protein function from protein sequence and structure" *Q. Rev. Biophys.*, 2003, vol. 36, No. 3, pp. 307-340.
Zhou et al. "The plant cyclin-dependent kinase inhibitor ICK1 has distinct functional domains for in vivo kinase inhibition, protein instability and nuclear localization" *Plant J.*, 2003, vol. 35, No. 4, pp. 476-489.
Hill, M.A. et al. "Functional analysis of conserved histidines in ADP-glucose pyrophosphorylase from *Escherichia coli" Biochem. Biophys. Res. Commun.*, 1998, vol. 244, No. 2, pp. 573-577.

* cited by examiner

FIG. 1A
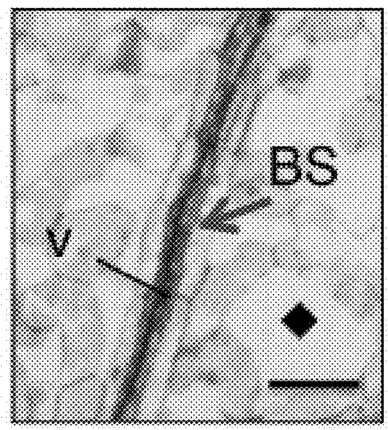
FIG. 1C
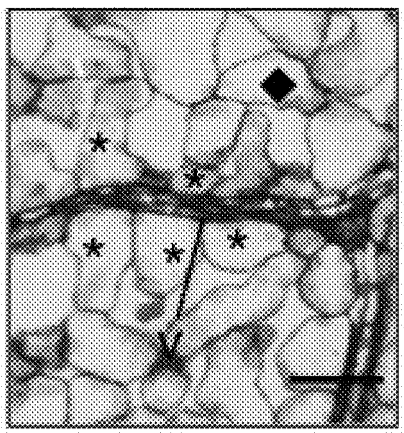
FIG. 1E
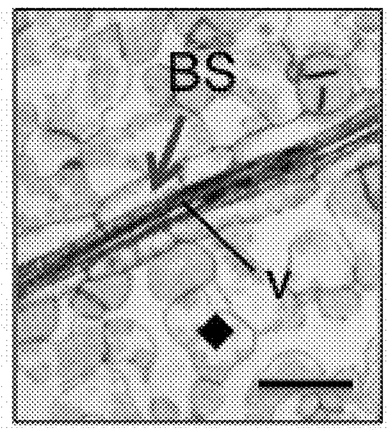
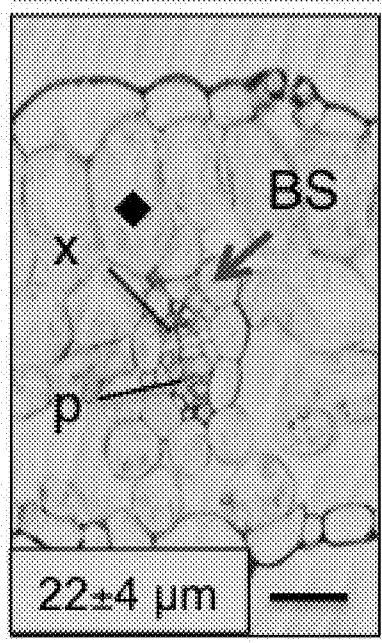
FIG. 1A-1
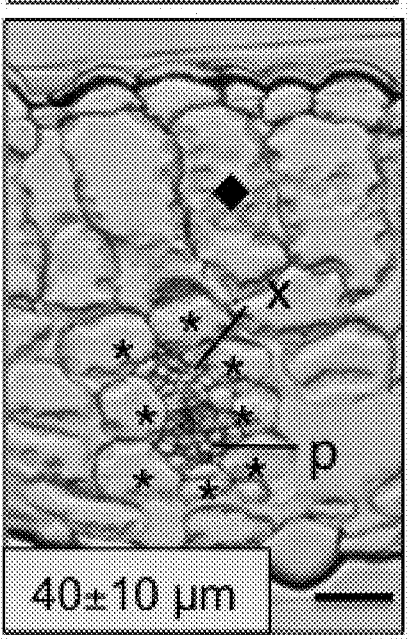
FIG. 1C-1
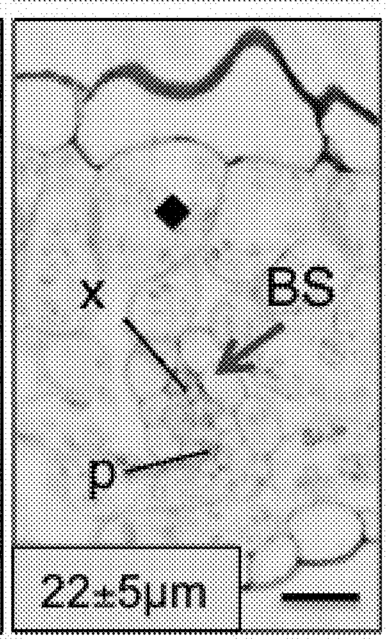
FIG. 1E-1

FIG. 1B
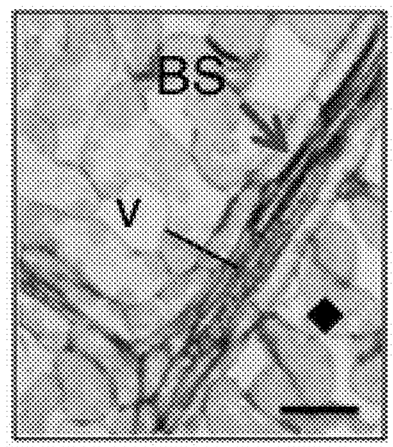
FIG. 1D
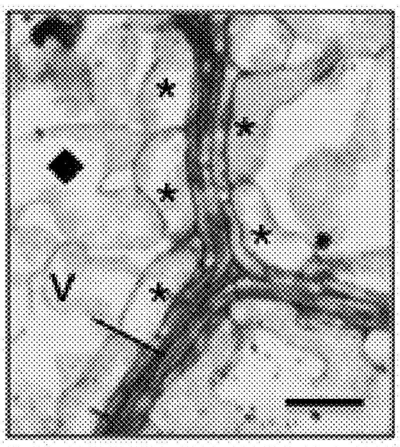
FIG. 1F
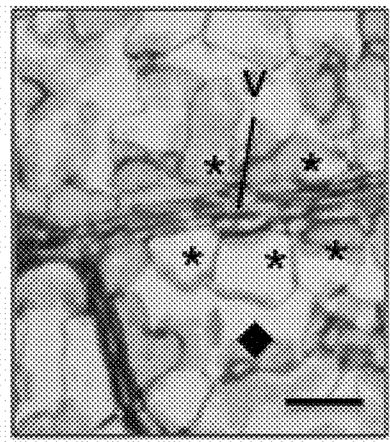
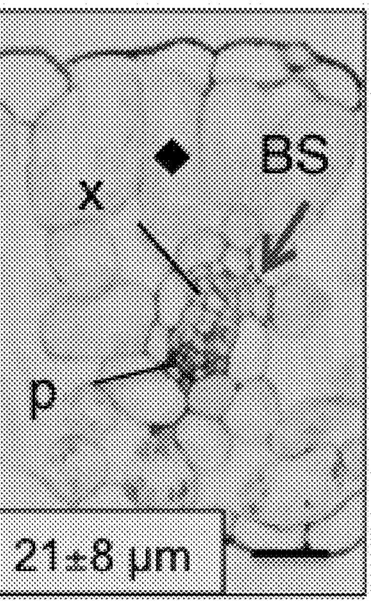
FIG. 1B-1
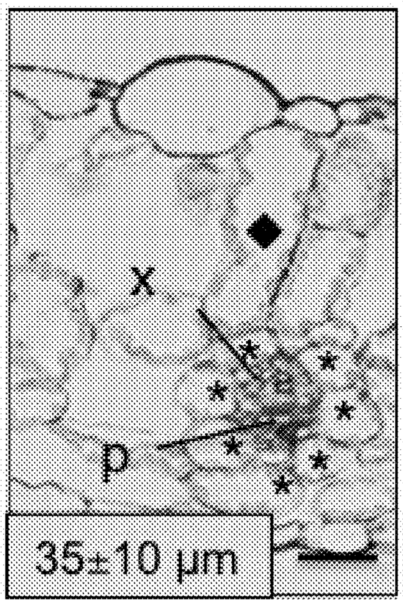
FIG. 1D-1
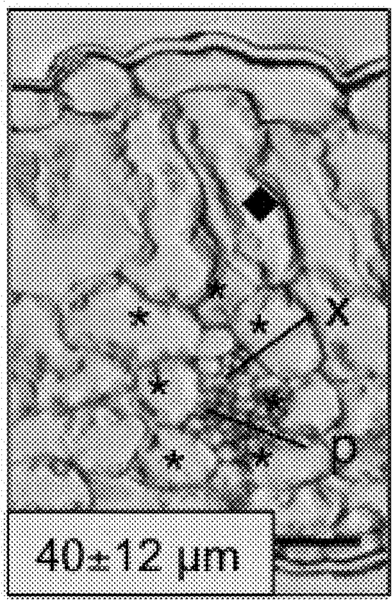
FIG. 1F-1

FIG. 2A
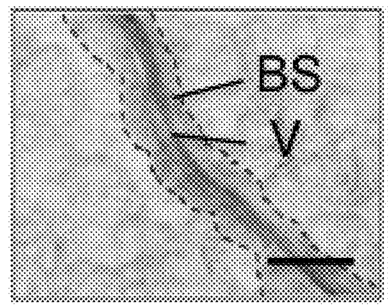
FIG. 2B
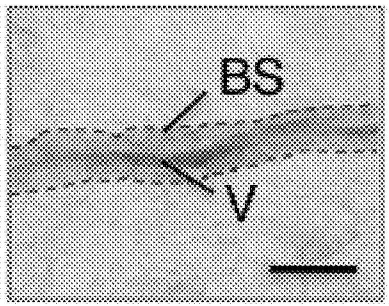
FIG. 2C
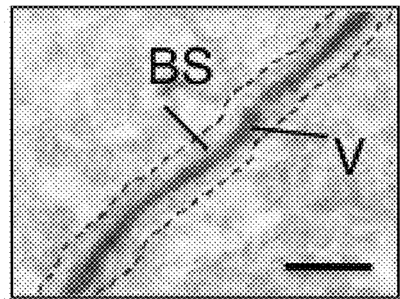
FIG. 2D
FIG. 2E
FIG. 2F
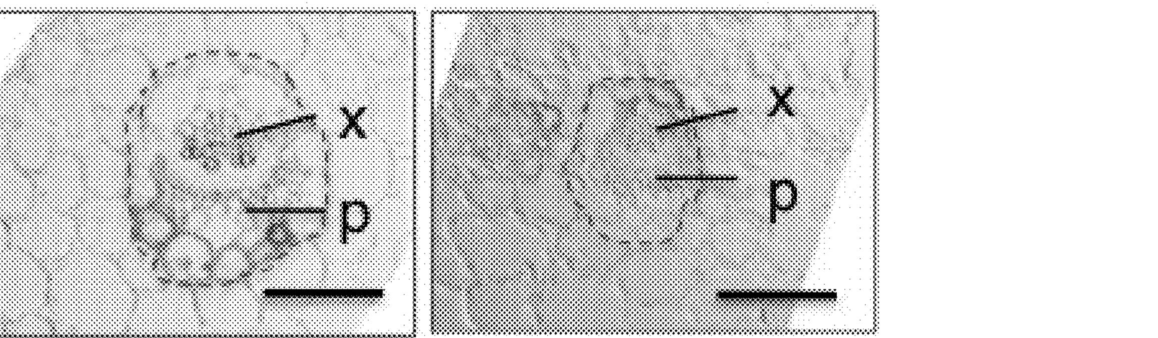
FIG. 2G
FIG. 2H FIG. 5A
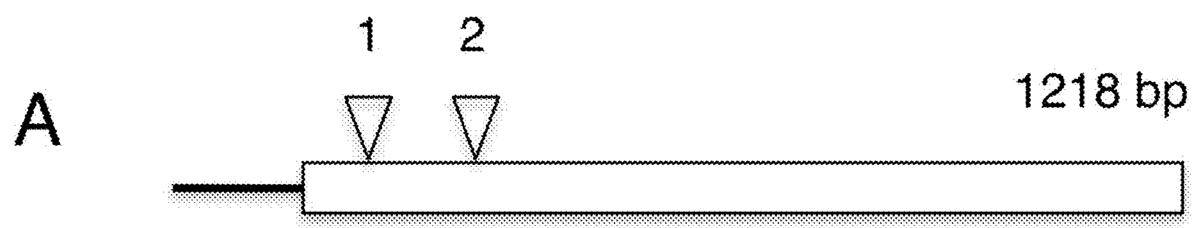
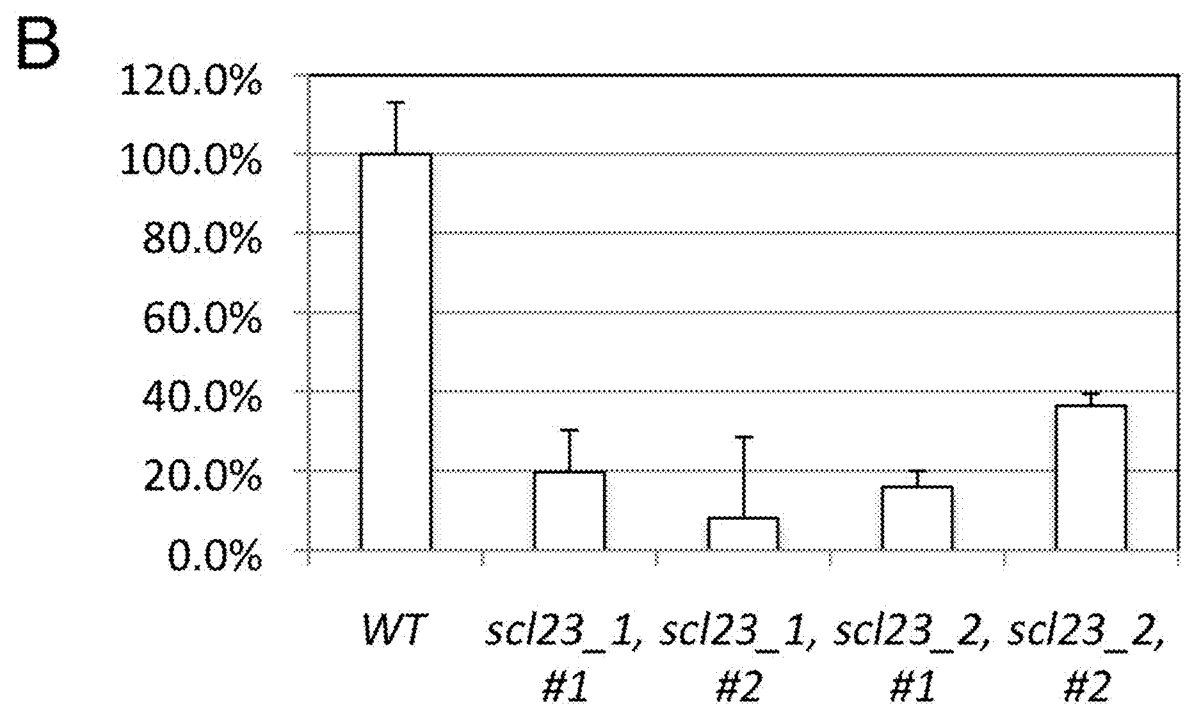
FIG. 5B FIG. 6A
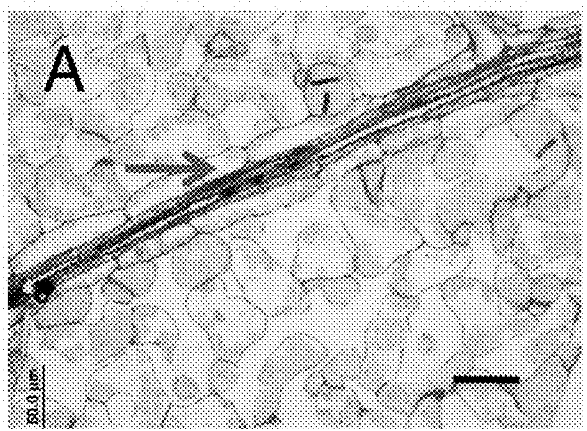
FIG. 6C
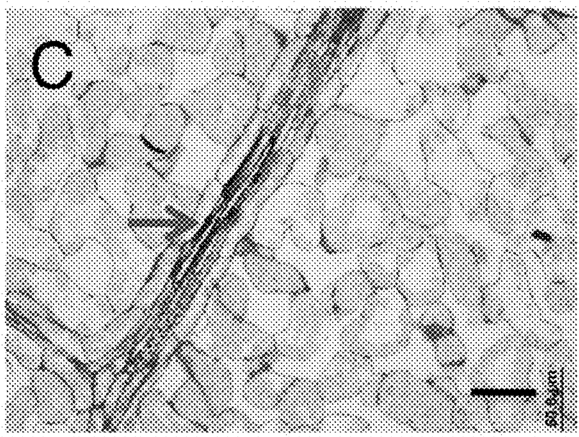
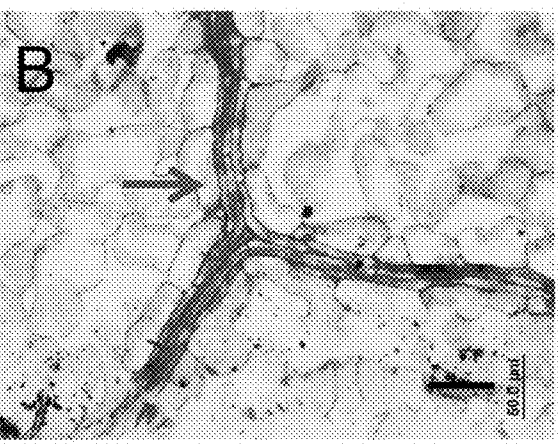
FIG. 6B
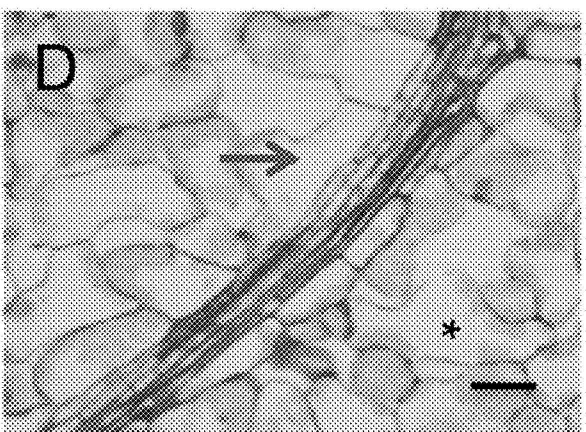
FIG. 6D

MATERIALS AND METHODS FOR CONTROLLING BUNDLE SHEATH CELL FATE AND FUNCTION IN PLANTS

CROSS-REFERENCE TO RELATED APPLICATIONS

The present application is a divisional of U.S. application Ser. No. 14/898,046, filed Dec. 11, 2015, which is the National Stage of International Application Number PCT/US2014/041975, filed Jun. 11, 2014, which claims the benefit of U.S. Provisional Application No. 61/833,771, filed Jun. 11, 2013, each of which is hereby incorporated by reference herein in its entirety, including any figures, tables, nucleic acid sequences, amino acid sequences, or drawings.

SEQUENCE LISTING

The Sequence Listing for this application is labeled "2QK2480.TXT" which was created on Sep. 17, 2020 and is 187 KB. The entire contents of the sequence listing is incorporated herein by reference in its entirety.

BACKGROUND OF THE INVENTION

With a rapidly growing world population and dwindling natural resources, we are facing an enormous challenge of increasing crop yields while simultaneously improving the efficiency of resource utilization. In C3 plants, a 3-carbon molecule is the first product of carbon fixation, whereas in C4 plants, a 4-carbon molecule is the first product. Because C4 plants are much more efficient than C3 plants in photosynthesis as well as water and nitrogen usage, particularly in hot climates (Langdale (2011)), tremendous efforts are being taken to introduce C4 photosynthesis into economically important C3 crops (Sage and Zhu (2011)), such as rice (Hibberd et al. (2008)). It is estimated that yields can be increased by 50% if rice is transformed into a C4 plant (Hibberd et al. (2008)).

Evidence indicates that C4 plants have evolved multiple times from C3 plants (Brown et al. (2011)), but all C4 plants share some common features that make them perform better. A critical innovation is the deployment of phosphoenolpyruvate (PEP) carboxylase as the enzyme for the initial fixation of $CO_2$ in C4 plants. Unlike RUBISCO, the enzyme used for the initial fixation of $CO_2$ in C3 plants, PEP carboxylase does not have an oxygenase activity and therefore can maintain a high rate of photosynthesis even under conditions of low $CO_2$ (stomates partially closed) and high temperature (RUBISCO's oxygenase activity is stimulated at high temperatures (Spreitzer et al. (2002)). Another critical feature of C4 plants is the separation of the two phases of photosynthesis, namely $CO_2$ fixation and carbohydrate biosynthesis, into the mesophyll and bundle sheath cells, respectively. To sustain a high rate of photosynthesis, C4 plants also have numerous plasmodesmata and various types of nutrient transporters distributed along the cell wall between the mesophyll and bundle sheath cells (Haritatos et al. (2000); Takahashi et al. (2000)), which ensure efficient transport of the primary products from the $CO_2$ fixation process. In the bundle sheath cells, $CO_2$ is released from the primary photosynthetic product and is then utilized in a standard C3-type photosynthesis involving RUBISCO. RUBISCO is expressed only in the bundle sheath cells, whereas PEP carboxylase is mesophyll cell specific. Due to the spatial separation of the photosynthetic processes along with the active transport system, $CO_2$ is effectively concentrated in the bundle sheath cells, which in turn leads to the repression of the oxygenase activity of RUBISCO. Last but not least, each bundle sheath cell layer is associated with a central cylinder of vascular tissue, which provides water and inorganic nutrients, and is surrounded by a single layer of mesophyll cells, a feature characteristic of C4 plants called the Kranz anatomy (Wang et al. (2011)).

Attempts to increase yield by expressing PEP carboxylase in both mesophyll and bundle sheath cells in rice have failed (Taniguchi et al. (2008)), suggesting that the mesophyll and bundle sheath cells must be engineered separately (Kajala et al. (2011)).

Despite the pivotal role of bundle sheath cells in C4 photosynthesis, the mechanisms that determine their cell identity and patterning are still unknown. Extensive mutant screening efforts in the past decades have identified several maize and *Arabidopsis* mutants defective in chloroplast development in the bundle sheath cells (Nelson (2011); Brutnell et al. (1999); Hall et al. (1998); Kinsman and Pyke (1998); Petricka et al. (2008); Rossini et al. (2001)), but none of these mutants affects bundle sheath cell identity.

Bundle sheath cells are a leaf cell type that forms a single cell layer between the mesophyll cells and the central vascular tissue. In C3 plants, both the mesophyll cells and BS cells are photosynthetic, but the BS cells are small with fewer chloroplasts. In contrast, the BS cells are the major sites of photosynthesis in most C4 plants, whereas the mesophyll cells are involved in $CO_2$ fixation only. Accordingly, the BS cells are much larger in size. The spatial separation of the two phases of photosynthesis into mesophyll and BS cells is one of the features that make C4 plants significantly more efficient photosynthetically. Another feature that improves the photosynthetic efficiency in C4 plants is the Kranz anatomy, characterized by an approximately 1:1 ratio between mesophyll and BS cells. The close association between the two cell types facilitates metabolite transport, which is critical for the C4 mechanism. In C3 plants, this ratio is greater than 2:1.

Many important crops, such as rice (*Oryza sativa*) and wheat (*Triticum aestivum*), are C3 plants. To meet the needs for food of a rapidly growing population, tremendous efforts are being undertaken to introduce the C4 mechanism into C3 crops (Langdale, 2011). For example, millions of dollars have been invested at the C4 rice consortium to convert this important crop into a C4 plant (von Caemmerer et al., 2012). Although the input is huge and the risk is high, the potential reward is enormous. It is estimated that a 10% increase in the photosynthetic efficiency would increase the yield by 50% (Langdale, 2011). However, to achieve C4 photosynthesis in C3 plants requires engineering of the BS and mesophyll cells at many levels, including an increase in the density of BS cells and modification of the physiology in the BS and mesophyll cells. This in turn demands a good understanding of the mechanisms that control BS and mesophyll cell fate. However, at present, the molecular basis of BS cell-fate specification is still unclear (Nelson, 2011).

There is evidence that the development of BS cells is determined by a signal from the vascular tissue (Langdale et al., 1988; Langdale et al., 1991; Jankovsky et al., 2001), but nothing is known about the nature of this positional information. Although several factors with a role in chloroplast development in BS cells have been reported, none of these appears to control BS cell fate. In maize (*Zea mays*), for example, mutations in the genes encoding GOLDEN2 and related transcription factors (Hall et al., 1998; Rossini et al., 2001), as well as BSD2 (BUNDLE SHEATH DEFECTIVE 2), a DnaJ-like protein (Brutnell et al., 1999), disrupt chloroplast development in the BS cells but do not affect BS cell fate. Mutants defective in chloroplast development in BS cells (Kinsman and Pyke, 1998) and vein patterning (Petricka et al., 2008) have also been isolated in Arabidopsis, but these mutants have a normal layer of BS cells.

SCARECROW (SCR, AT3G54220) and SHORT-ROOT (SHR, AT4G37650) are key regulators of radial patterning in the Arabidopsis root (Di Laurenzio et al., 1996; Helariutta et al., 2000). In the scr and shr mutants, the cortex/endodermis initial fails to divide longitudinally, resulting in loss of one cell layer (Di Laurenzio et al., 1996). Unlike SCR, which is expressed specifically in the endodermis and cortex/endodermis initial cells (Di Laurenzio et al., 1996), SHR is expressed exclusively in the central vascular tissue (Helariutta et al., 2000). However, the SHR protein moves into the adjacent cell layer (Nakajima et al., 2001), where it activates transcription of SCR (Levesque et al., 2006). SCR in turn restricts SHR movement by physical interaction and nuclear sequestration, thus defining a single layer of endodermis (Cui et al., 2007).

SHR and SCR are also expressed in the shoot (Wysocka-Diller et al., 2000; Dhondt et al., 2010; Gardiner et al., 2010). In addition to the shoot apical meristem and young leaf primordia, SCR is also expressed in BS cells (Wysocka-Diller et al., 2000). Although BS cells and the endodermis are produced from different groups of stem cells (the shoot apical meristem and the root apical meristem, respectively), and at different stages of plant development (during and after embryogenesis, respectively) (Kangasjarvi et al., 2009), they are considered as analogous cell types (Bosabalidis et al., 1984).

BRIEF SUMMARY OF THE INVENTION

The subject invention concerns materials and methods for increasing and/or improving photosynthetic efficiency in plants. In particular, the subject invention provides for means to increase the number of bundle sheath (BS) cells in plants, to improve the efficiency of photosynthesis in BS cells, to improve carbohydrate biosynthesis, and to increase channels between BS and mesophyll (M) cells. In one embodiment, a method of the invention concerns increasing expression of one or more of SHR (Short-Root), SCR (Scarecrow), and/or SCL23 (Scarecrow-like 23) polypeptides in a plant. In one embodiment, one or more of SHR, SCR, and/or SCL23 are expressed in mesophyll cells wherein a cell-type specific promoter is operably linked with a polynucleotide encoding the SHR, SCR, and/or SCL23 polypeptide. Any method that can be used to increase expression is contemplated within the scope of the present invention. In one embodiment, a polynucleotide encoding for one or more of a SHR, SCR, and/or SCL23 polypeptide is incorporated into a plant. For example, a plant can be transformed with a polynucleotide encoding one or more of a SHR, SCR, and/or SCL23 and subsequently screened for increased expression of SHR, SCR, and/or SCL23. In one embodiment, the plant is a C3 plant. In one embodiment, the polynucleotide can be provided in an expression construct that provides for expression of the polynucleotide in a plant. In one embodiment, the expression construct provides for cell-type specific expression in the plant. In a further embodiment, the expression construct provides for leaf-specific expression of the polynucleotide. In a more specific embodiment, the expression construct provides for mesophyll-specific expression. In a preferred embodiment, the polynucleotide is stably incorporated into the plant genome.

The subject invention also pertains to modified plants that exhibit increased expression of one or more of SHR, SCR, and/or SCL23 polypeptides, as well as plants that comprise an SHR, SCR, or SCL23 promoter sequence operably linked with a gene of interest. In one embodiment, the plant is a C3 plant. In a specific embodiment, the plant is a rice, soybean, tobacco, wheat, barley, tomato, cotton, or potato plant. Transformed and transgenic plants are contemplated within the scope of the invention. In one embodiment, the plant expresses higher levels of one or more of SHR, SCR, and/or SCL23 relative to a corresponding wild type plant.

The subject invention also concerns methods for increasing expression of photosynthetically important genes in a plant. In one embodiment, one or more genes of interest are operably linked with an SHR, SCR or SCL23 promoter sequence and expressed in a plant. In one embodiment, the genes are expressed in BS cells in order to modify the morphology, anatomy, and/or physiology of BS cells.

Herein we show that three GRAS (Gibberallic-acid insensitive (GAI), Repressor of GAI (RGA), and Scarecrow (SCR)) family transcriptional factors, namely SHORT-ROOT (SHR), SCARECROW (SCR) and SCARECROW-like 23, constitute a developmental pathway that regulates bundle sheath cell fate, positioning and function in the leaves of C3 plants.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIGS. 1A, 1A-1, 1B, 1B-1, 1C, 1C-1, 1D, 1D-1, 1E, 1E-1, 1F, 1F-1. Semi-thin sectioning and toluidine blue staining, showing leaf anatomy. (1A, 1A-1) Ws, (1B, 1B-1) Col-0, (1C, 1C-1) shr-2, (1D, 1D-1) scr-1, (1E, 1E-1) scl23-2, (1F, 1F-1) scr-1 scl23-2. FIGS. 1A, 1B, 1C, 1D, 1E, and 1F show paradermal sectioning, whereas FIGS. 1A-1, 1B-1, 1C-1, 1D-1, 1E-1, and 1F-1 show cross-sectioning. The numbers at the bottom left-hand corners are the cross-sectional area of the BS cells ($\mu m^2$, mean±standard deviation), as measured using ImageJ (imagej.nih.gov/ij). Arrows indicate the position of BS cells; diamonds indicate the location of mesophyll cells; asterisks indicate cells in the mutant cell layer. BS, bundle sheath cells; v, vascular tissue; x, xylem; p, phloem. Scale bars=50 μm.

FIGS. 2A-2H. GUS staining showing the cell type-specific expression pattern of SHR, SCR and SCL23. (FIGS. 2A, 2D, 2G) SCRpro:GUS, (FIGS. 2B, 2E, 2H) SCL23pro:GUS, (FIGS. 2C, 2F) SHRpro:GUS; FIGS. 2A-2C are longitudinal views of small veins; FIGS. 2D-2F are cross-sectional views after semi-thin sectioning; FIGS. 2G and 2H are cross-sections of major veins. The dashed lines indicate the boundary between the BS cells and mesophyll cells; BS, bundle sheath cells; V, vascular bundle; x, xylem; p, phloem. Scale bars=50 μm.

(FIGS. 3A and 3B) SCRpro:GUS and SCL23pro:GUS expression in wild-type (WT) or shr leaves. (FIG. 3C) ChIP-PCR assay showing binding of SHR to the SCR promoter in leaves. (FIG. 3D) ChIP-PCR assay showing SHR and SCR binding to the SCL23 promoter in leaves. In FIGS. 3C and 3D, the numbers on the x axis represent the distance from the first codon (kb); the y axis shows the fold enrichment. (FIG. 3E) SCL23pro:GUS expression in WT, scr-1, scl23-2 and scr-1 scl23-2 leaves.

(FIGS. 4A and 4B) Starch level in wild-type (Ws and Col-0 ecotypes), scr-1 and shr-2 mutants at the end of the day (FIG. 4A) or morning (FIG. 4B). (FIG. 4C) Starch level in scr-1, scl23-2 and scr-1 scl23-2 mutants at the end of the day (PM) or morning (AM). (FIG. 4D) Free sugar concentration (mg $g^{-1}$ fresh weight) in leaves of 1-month-old plants. (FIG. 4E) Size of plants grown in soil at 4 weeks after germination.

FIGS. 5A and 5B. Characterization of T-DNA insertional mutants for SCL23. (FIG. 5A) Diagram showing the position of the T-DNA insert in scl23-1 (Salk_054051) and scl23-2 (GT_5_16303). (FIG. 5B) Quantitative RT-PCR assay of SCL23 transcript in leaves of one-month-old plants, using primers SCL23_FW, TCATTGGATGCAGCACCGGTTA (SEQ ID NO:50), and SCL23_RV, TCCGTGCGCCACAATGTTTCTT (SEQ ID NO:51). For each line, two plants were analyzed. The error bars represent standard deviations from triplicate experiments.

FIGS. 6A-6D. Thin sectioning showing leaf anatomy. (FIG. 6A) Col. (FIG. 6B) scr-1. (FIG. 6C) scl23-1. (FIG. 6D) scr-1 scl23-1. Arrows mark the position of bundle sheath cells. Bars=50 μm.

(FIG. 7A) Root apical meristem. (FIG. 7B) Maturation zone. Bars=50 μm.

BRIEF DESCRIPTION OF THE SEQUENCES

Figure 3A:
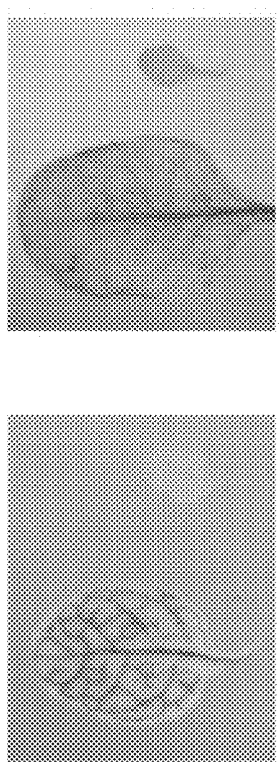
FIGS. 3A-3E. SCL23 is regulated by SHR and SCR in leaves.

SEQ ID NO:1 is an amino acid sequence of an *Arabidopsis* SCR protein [AAB06318.1].

SEQ ID NO:2 is a nucleotide sequence comprising a coding sequence of an *Arabidopsis* SCR protein [U62798.1].

SEQ ID NO:3 is an amino acid sequence of a rice SCR protein [BAD22576].

SEQ ID NO:4 is a nucleotide sequence comprising a coding sequence of a rice SCR protein [AB180961.1].

SEQ ID NO:5 is an amino acid sequence of a maize SCR protein [AAG13663].

SEQ ID NO:6 is a nucleotide sequence comprising a coding sequence of a maize SCR protein [AF263457.1].

SEQ ID NO:7 is an amino acid sequence of an *Arabidopsis* SHR protein [AEE86820].

SEQ ID NO:8 is a nucleotide sequence comprising a coding sequence of an *Arabidopsis* SHR protein [AF233752.1].

SEQ ID NO:9 is an amino acid sequence of a rice SHR protein [Q8H2X8.2].

SEQ ID NO:10 is a nucleotide sequence comprising a coding sequence of a rice SHR protein [NM_001066668].

SEQ ID NO:11 is an amino acid sequence of an apple SHR protein [ADL36816]. SEQ ID NO:12 is a nucleotide sequence comprising a coding sequence of an apple SHR protein [HM122677].

SEQ ID NO:13 is an amino acid sequence of a rice SCL23 protein [Os07g38030.1].

SEQ ID NO:14 is a nucleotide sequence comprising a coding sequence of a rice SCL23 protein [Os07g38030.1].

SEQ ID NO:15 is an amino acid sequence of a rice SCR protein [Os11g03110.1].

SEQ ID NO:16 is a nucleotide sequence comprising a coding sequence of a rice SCR protein [Os11g03110.1].

SEQ ID NO:17 is an amino acid sequence of a rice SCR protein [Os12g02870.1].

SEQ ID NO:18 is a nucleotide sequence comprising a coding sequence of a rice SCR protein [Os12g02870.1].

SEQ ID NO:19 is an amino acid sequence of a rice SHR protein [Os07g39820.1].

SEQ ID NO:20 is a nucleotide sequence comprising a coding sequence of a rice SHR protein [Os07g39820.1].

SEQ ID NO:21 is an amino acid sequence of a rice SHR protein [Os03g31880.1].

SEQ ID NO:22 is a nucleotide sequence comprising a coding sequence of a rice SHR protein [Os03g31880.1].

SEQ ID NO:23 is an amino acid sequence of a maize SCR protein [GRMZM2G131516].

SEQ ID NO:24 is a nucleotide sequence comprising a coding sequence of a maize SCR protein [GRMZM2G131516].

SEQ ID NO:25 is an amino acid sequence of a maize SCR protein [GRMZM2G015080].

SEQ ID NO:26 is a nucleotide sequence comprising a coding sequence of a maize SCR protein [GRMZM2G015080].

SEQ ID NO:27 is an amino acid sequence of a maize SHR protein [GRMZM2G172657].

SEQ ID NO:28 is a nucleotide sequence comprising a coding sequence of a maize SHR protein [GRMZM2G172657].

SEQ ID NO:29 is an amino acid sequence of a maize SHR protein [GRMZM2G019060].

SEQ ID NO:30 is a nucleotide sequence comprising a coding sequence of a maize SHR protein [GRMZM2G019060].

SEQ ID NO:31 is an amino acid sequence of a maize SHR protein [GRMZM2G132794].

SEQ ID NO:32 is a nucleotide sequence comprising a coding sequence of a maize SHR protein [GRMZM2G132794].

SEQ ID NO:33 is an amino acid sequence of a maize SCL23 protein [GRMZM2G106548].

SEQ ID NO:34 is a nucleotide sequence comprising a coding sequence of a maize SCL23 protein [GRMZM2G106548].

SEQ ID NO:35 is an amino acid sequence of a Brachypodium SCR protein [Bradi4g44090.1].

SEQ ID NO:36 is a nucleotide sequence comprising a coding sequence of a Brachypodium SCR protein [Bradi4g44090.1].

SEQ ID NO:37 is an amino acid sequence of a Brachypodium SHR protein [Bradi1g23060.1].

SEQ ID NO:38 is a nucleotide sequence comprising a coding sequence of a Brachypodium SHR protein [Bradi1g23060.1].

SEQ ID NO:39 is an amino acid sequence of a Brachypodium SCL23 protein [Bradi4g44090].

SEQ ID NO:40 is a nucleotide sequence comprising a coding sequence of a Brachypodium SCL23 protein [Bradi4g44090].

SEQ ID NO:41 is an amino acid sequence of an *Arabidopsis* SCR protein [AT3G54220].

SEQ ID NO:42 is a nucleotide sequence comprising a coding sequence of an *Arabidopsis* SCR protein [AT3G54220].

SEQ ID NO:43 is an amino acid sequence of an *Arabidopsis* SHR protein [AT4G37650].

SEQ ID NO:44 is a nucleotide sequence comprising a coding sequence of an *Arabidopsis* SHR protein [AT4G37650].

SEQ ID NO:45 is an amino acid sequence of an *Arabidopsis* SCL23 protein [AT5G41920].

SEQ ID NO:46 is a nucleotide sequence comprising a coding sequence of an *Arabidopsis* SCL23 protein [AT5G41920].

SEQ ID NO:47 is an *Arabidopsis* SCR promoter sequence.

SEQ ID NO:48 is an *Arabidopsis* SCL23 promoter sequence.

SEQ ID NO:49 is an *Arabidopsis* SHR promoter sequence.

SEQ ID NOs:50-77 are oligonucleotide primers.

DETAILED DESCRIPTION OF THE INVENTION

The subject invention concerns materials and methods for increasing and/or improving photosynthetic efficiency in plants. In particular, the subject invention provides for means to increase the number of bundle sheath (BS) cells in plants, to improve the efficiency of photosynthesis in BS cells, to improve carbohydrate biosynthesis, and to increase channels between BS and mesophyll (M) cells. The methods of the invention can also be used to increase the number of BS cells relative to mesophyll cells in a plant, for example, increasing the ratio of BS cells to M cells close to about 1:1. In one embodiment, a method of the invention concerns ectopically expressing or increasing expression of one or more of SHR, SCR, and/or SCL23 polypeptides in a plant (non-limiting examples of each are shown in SEQ ID NOs:1, 3, 5, 7, 9, 11, 13, 15, 17, 19, 21, 23, 25, 27, 29, 31, 33, 35, 37, 39, 41, 43, and 45, or an amino acid sequence that has at least 60%, or at least 70%, or at least 80%, or at least 90%, or at least 95% sequence identity with the SEQ ID NO.). Any method that can be used to increase expression or altered expression pattern is contemplated within the scope of the present invention. In one embodiment, one or more polynucleotide encoding for one or more of a SHR, SCR, and/or SCL23 polypeptide is incorporated into a plant. For example, a plant can be transformed with a polynucleotide encoding one or more of a SHR, SCR, and/or SCL23 and subsequently screened for increased expression or ectopic expression or altered expression pattern of SHR, SCR, and/or SCL23. In one embodiment, the polynucleotide comprises the protein coding sequence of a SHR, SCR, and/or SCL23 gene. In one embodiment, the plant is a C3 plant. Examples of contemplated C3 plants include, but are not limited to, rice, barley, thale cress (*Arabidopsis*), wheat, rye, oat, fescue, sunflower, tomato, cucumber, potato, peanut, cotton, sugar beet, tobacco, soybeans, spinach, and most trees. In a specific embodiment, the plant is a rice, soybean, tobacco, wheat, barley, tomato, cotton, or potato plant. In one embodiment, the polynucleotide is heterologous to the plant. In one embodiment, the polynucleotide can be provided in an expression construct that provides for expression of the polynucleotide in a plant. In one embodiment, the expression construct provides for cell-type specific expression in the plant. In a further embodiment, the expression construct provides for leaf-specific expression of the polynucleotide. In a more specific embodiment, the expression construct provides for mesophyll-specific expression, or BS cell-specific expression, or vascular bundle-specific expression. In one embodiment, an expression construct comprises a lysine histidine transporter (LHT1) promoter, a PEPC promoter, or ribulose-1,5-biphoshate carboxylase small subunit (rbcS) promoter, or a functional fragment or variant of any of these that is able to promote expression. In a preferred embodiment, the polynucleotide is stably incorporated into the plant genome. Examples of polynucleotides encoding an SHR, SCR, or SCL23 polypeptide contemplated within the scope of the invention include, but are not limited to, those in SEQ ID NO:2, 4, 6, 8, 10, 12, 14, 16, 18, 20, 22, 24, 26, 28, 30, 32, 34, 36, 38, 40, 42, 44, and 46, or the polypeptide coding region thereof, or a nucleotide sequence that has at least 60%, or at least 70%, or at least 80%, or at least 90%, or at least 95% sequence identity with the SEQ ID NO. In one embodiment, the SHR, SCR, or SCL23 and/or the expression construct is heterologous to the plant. In one embodiment, the polynucleotide and/or expression construct can comprise cDNA. In one embodiment, a plant ectopically expressing or having increased expression of one or more of SHR, SCR, and/or SCL23 using the subject method exhibits a cell pattern similar to Kranz anatomy.

The subject invention also pertains to modified plants that exhibit increased expression or ectopic expression or altered expression pattern of one or more of SHR, SCR, and/or SCL23. The subject invention also concerns plants that comprise an SHR, SCR, or SCL23 promoter sequence operably linked with a gene of interest. In one embodiment, one or more polynucleotide coding for one or more of a SHR, SCR, and/or SCL23 polypeptide is incorporated into a plant. In one embodiment, the polynucleotide is heterologous to the plant. In one embodiment, the polynucleotide can be provided in an expression construct that provides for expression of the polynucleotide in a plant. In one embodiment, the expression construct provides for cell-type specific expression in the plant. In a further embodiment, the expression construct provides for leaf-specific expression of the polynucleotide. In a more specific embodiment, the expression construct provides for mesophyll-specific expression, or BS cell-specific expression, or vascular bundle-specific expression. In one embodiment, an expression construct comprises a lysine histidine transporter (LHT1) promoter, a PEPC promoter, or ribulose-1,5-biphoshate carboxylase small subunit (rbcS) promoter, or a functional fragment or variant of any of these that is able to promote expression. In a preferred embodiment, the polynucleotide is stably incorporated into the plant genome. In one embodiment, the plant is a C3 plant. In a specific embodiment, the plant is a rice plant. Transformed and transgenic plants are contemplated within the scope of the invention. In one embodiment, the plant expresses higher levels of one or more of SHR, SCR, and/or SCL23 relative to a corresponding wild type plant. C3 plants are contemplated within the scope of the invention. Examples of contemplated C3 plants include, but are not limited to, rice, barley, thale cress (*Arabidopsis*), wheat, rye, oat, fescue, sunflower, tomato, cucumber, potato, peanut, cotton, sugar beet, tobacco, soybeans, spinach, and most trees. In one embodiment, the SHR, SCR, and/or SCL23, or the promoter sequence thereof, is heterologous to the plant. In one embodiment, the polynucleotide and/or expression construct can comprise cDNA. In one embodiment, the modified plant exhibits a cell pattern similar to Kranz anatomy.

The subject invention also concerns plant SHR, SCR, and SCL23 promoters and methods for increasing expression of genes or polypeptides of interest, such as photosynthetically important genes or polypeptides, in a plant. In one embodiment, one or more polynucleotides or genes of interest are operably linked with a promoter sequence of a plant SHR, SCR or SCL23 gene, or a functional homolog or fragment or variant of the promoter sequence that is able to promote expression of the operably linked polynucleotide or gene of interest, and the operably linked polynucleotide or gene of interest and the promoter are incorporated into and expressed in a plant, plant tissue, or plant cell. The polynucleotide comprising the polynucleotide or gene of interest and promoter can be incorporated in the plant using any suitable method in the art. The plant, plant tissue, or plant cell can be screened for expression of the polynucleotide or gene of interest. In one embodiment, the promoter and polynucleotide or gene of interest is provided in an expression construct of the invention. In one embodiment, the promoter, polynucleotide, and/or gene of interest is heterologous to the plant. The polynucleotide and/or gene of interest can comprise cDNA. In one embodiment, any plant gene whose product is associated with photosynthesis is contemplated for use in the present invention, such as phosphoenolpyruvate carboxylase (PEPC), or pyruvate phosphate dikinase (PPDK). In one embodiment, the photosynthesis-associated genes are expressed in BS cells in order to modify the morphology, anatomy, and/or physiology of BS cells. The SHR, SCR, and SCL23 promoter sequences can be from any plant. SHR, SCR, and SCL23 promoters can be readily identified in other plants using information provided herein and techniques known in the art. In one embodiment, the promoter is from a C3 plant, such as rice, barley, thale cress (*Arabidopsis*), wheat, rye, oat, fescue, sunflower, tomato, cucumber, potato, peanut, cotton, sugar beet, tobacco, soybeans, spinach, and most trees. In a specific embodiment, a promoter of the invention comprises the nucleotide sequence of SEQ ID NO:47, SEQ ID NO:48, or SEQ ID NO:49, or a functional fragment or variant thereof that is able to promote expression of the operably linked gene of interest in a plant cell, or a nucleotide sequence that has at least 60%, or at least 70%, or at least 80%, or at least 90%, or at least 95% sequence identity with the SEQ ID NO. In one embodiment, a method of the invention comprises transforming a plant, plant tissue, or plant cell with one or more genes of interest operably linked with one or more promoter sequence of a plant SHR, SCR, or SCL23 gene, or a functional fragment or variant thereof that is able to promote expression of the operably linked gene of interest in a plant cell, and generating from the plant, plant tissue, or plant cell a transgenic plant expressing the one or more genes of interest. In one embodiment, the plant is a C3 plant, such as rice, barley, thale cress (*Arabidopsis*), wheat, rye, oat, fescue, sunflower, tomato, cucumber, potato, peanut, cotton, sugar beet, tobacco, soybeans, spinach, and most trees. In a specific embodiment, the plant is a rice, soybean, tobacco, wheat, barley, tomato, cotton, or potato plant. Agronomic genes and polypeptides of interest include, but are not limited to, those involved in carbohydrate (starch, sucrose, etc.) synthesis, resistance to disease and pathogens (fungus, nematode, virus, bacteria, insects, etc.), herbicide resistance, increased yield, oil production, and resistance to stress conditions.

Sequences of numerous plant SHR, SCR, and SCL23 proteins (and nucleic acid encoding the same) are known in the art and are all contemplated within the scope of the present invention. Examples of SCR include those having Genbank accession numbers AAB06318.1 and U62798.1 (*Arabidopsis*) (SEQ ID NOs:1 and 2); BAD22576 and AB180961.1 (rice) (SEQ ID NOs:3 and 4); and AAG13663 and AF263457.1 (maize) (SEQ ID NOs:5 and 6); *Arabidopsis* Information Resource locus AT3G54220 (SEQ ID NOs: 41 and 42). Examples of SHR include Genbank accession numbers AEE86820 and AF233752.1 (*Arabidopsis*) (SEQ ID NOs:7 and 8); and Q8H2X8.2 and NM_001066668 (rice) (SEQ ID NOs:9 and 10); maizesequence.org gene ID GRM2M2G172657, GRMZM2G019060, and GRMZM2G132794 (SEQ ID NOs:27-32, respectively); PlantGDB.org ID Si29296m and Si034653m (*Setaria viridis*); Arabidopsis Information Resource locus AT4G37650 (SEQ ID NOs: 43 and 44). Examples of SCL23 include those having Genbank accession numbers ADL36816 and HM122677 (apple) (SEQ ID NOs:11 and 12); maizesequence.org gene ID GRMZM2G106548 (SEQ ID NOs:33 and 34); PlantGDB.org ID Si032551m (*Setaria viridis*); Arabidopsis Information Resource locus AT5G41920 (SEQ ID NOs:45 and 46). Additional sequences of rice SHR, SCR, and SCL23 polynucleotides and the polypeptides encoded are shown in SEQ ID NOs: 13-22.

In one embodiment, a method of the invention comprises producing a transgenic plant with increased expression and/or ectopic expression of one or more of SHR, SCR, and/or SCL23 polypeptides relative to a wild type variety of the plant, wherein the method comprises transforming a plant, plant tissue, or plant cell with a polynucleotide (e.g., in an expression construct) encoding one or more of a plant SHR, SCR, and/or SCL23 polypeptide, or a biologically active fragment or variant thereof; and generating from the plant, plant tissue, or plant cell a transgenic plant that exhibits one or more of the following: increased number of BS cells, improved photosynthetic efficiency of BS cells, and/or increased number of channels and improved nutrient exchange between BS and M cells. In one embodiment, the transgenic plant exhibits a cell pattern similar to Kranz anatomy. The polynucleotide can be incorporated in the plant, plant tissue, or plant cell using any suitable method in the art. In one embodiment, the plant is a C3 plant, such as rice, barley, thale cress (*Arabidopsis*), wheat, rye, oat, fescue, sunflower, tomato, cucumber, potato, peanut, cotton, sugar beet, tobacco, soybeans, spinach, and most trees. In a specific embodiment, the plant is a rice, soybean, tobacco, wheat, barley, tomato, cotton, or potato plant. Transformed and transgenic plants are contemplated within the scope of the invention. In one embodiment, the plant expresses one or more of SHR, SCR, and/or SCL23 at higher levels or in other cell types relative to a corresponding wild type plant or a non-transformed or non-transgenic plant. In one embodiment, the polynucleotide encodes a polypeptide comprising the amino acid sequence shown in SEQ ID NO:1, 3, 5, 7, 9, 11, 13, 15, 17, 19, 21, 23, 25, 27, 29, 31, 33, 35, 37, 39, 41, 43, or 45, or a biologically active fragment or variant thereof. In a specific embodiment, the polynucleotide encodes a rice, barley, thale cress (*Arabidopsis*), wheat, rye, oat, fescue, sunflower, tomato, cucumber, potato, peanut, cotton, sugar beet, tobacco, soybeans, or spinach SHR, SCR, or SCL23 polypeptide. Examples of polynucleotides contemplated within the scope of the invention include, but are not limited to, those in SEQ ID NO:2, 4, 6, 8, 10, 12, 14, 16, 18, 20, 22, 24, 26, 28, 30, 32, 34, 36, 38, 40, 42, 44, and 46, or the polypeptide coding region thereof.

The subject invention also concerns plants, plant tissue, and plant cells of the invention that comprise or express a polynucleotide of the invention or a SHR, SCR, and/or SCL23 protein encoded by a polynucleotide of the invention, or a biologically active fragment or variant thereof. Plant tissue includes, but is not limited to, seed, scion, leaf, and rootstock. Plants within the scope of the present invention include monocotyledonous plants, such as, for example, rice, wheat, barley, oats, rye, sorghum, maize, sugarcane, pineapple, onion, bananas, coconut, lilies, turf grasses, and millet. Plants within the scope of the present invention also include dicotyledonous plants, such as, for example, tomato, cucumber, squash, peas, alfalfa, melon, chickpea, chicory, clover, kale, lentil, soybean, beans, tobacco, potato, sweet potato, yams, cassava, radish, broccoli, spinach, cabbage, rape, apple trees, citrus (including oranges, mandarins, grapefruit, lemons, limes and the like), grape, cotton, sunflower, strawberry, lettuce, and hop. Herb plants containing a polynucleotide of the invention are also contemplated within the scope of the invention. Herb plants include parsley, sage, rosemary, thyme, and the like. In one embodiment, the plant is a C3 plant, such as rice, barley, thale cress (*Arabidopsis*), wheat, rye, oat, fescue, sunflower, tomato, cucumber, potato, peanut, cotton, sugar beet, tobacco, soybeans, spinach, and most trees. In a specific embodiment, the plant is a rice, soybean, tobacco, wheat, barley, tomato, cotton, or potato plant. In one embodiment, a plant, plant tissue, or plant cell is a transgenic plant, plant tissue, or plant cell. Specifically contemplated within the scope of the invention are plant seeds produced by a transgenic plant of the invention. In another embodiment, a plant, plant tissue, or plant cell is one that has been obtained through a breeding program.

Polynucleotides encoding a SHR, SCR, and/or SCL23 polypeptide and/or a polynucleotide comprising a SHR, SCR, and/or SCL23 gene promoter sequence of the present invention can be provided in an expression construct. Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include, for example, promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation. In one embodiment, an expression construct comprises a polynucleotide encoding an amino acid sequence of any of SEQ ID NO:1, 3, 5, 7, 9, 11, 13, 15, 17, 19, 21, 23, 25, 27, 29, 31, 33, 35, 37, 39, 41, 43, or 45, or a biologically active fragment or variant thereof. Polynucleotides that can be used in an expression construct include, but are not limited to, any of SEQ ID NOs: 2, 4, 6, 8, 10, 12, 14, 16, 18, 20, 22, 24, 26, 28, 30, 32, 34, 36, 38, 40, 42, 44, or 46, or the protein coding region thereof, and/or any of SEQ ID NOs:47, 48, or 49, or a functional fragment or variant thereof that is able to promote expression of the operably linked gene of interest.

An expression construct of the invention can comprise a promoter sequence (including, for example, an SHR, SCR, or SCL23 promoter of the invention) operably linked to one or more polynucleotide sequences, for example a sequence encoding a polypeptide of the invention, or to one or more genes or polynucleotides of interest. The expression construct can be a chimeric or recombinant expression construct. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, prolifera promoter, Ap3 promoter, heat shock promoters, T-DNA 1'- or 2'-promoter of *A. tumefaciens*, polygalacturonase promoter, chalcone synthase A (CHS-A) promoter from petunia, tobacco PR-la promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. Nos. 5,034,322 and 4,962,028) can also be used. Leaf-specific promoters include, for example, light harvest chlorophyll a/b binding protein (CAB) promoter of rice (Sakamoto et al. (1991)). The LHT1 promoter (Hirner et al. (2006)), or a functional fragment or variant thereof, which is mesophyll specific, can also be used. Other mesophyll-specific promoters that are contemplated for use within the scope of the invention include, but are not limited to, the phosphoenolpyruvate carboxylase (PEPC) (Stockhaus et al. (1997); Kausch et al. (2001)), or a functional fragment or variant thereof, and rbcS promoter (Schäffner and Sheen (1991); Nomura et al. (2000)), or a functional fragment or variant thereof. U.S. Pat. No. 6,610,840 also describes mesophyll-specific promoters. Other tissue-specific promoters include, for example, fruit-specific promoters, such as the E8 promoter of tomato (accession number: AF515784; Good et al. (1994)) can be used. Fruit-specific promoters such as flower organ-specific promoters can be used with an expression construct of the present invention for expressing a polynucleotide of the invention in the flower organ of a plant. Examples of flower organ-specific promoters include any of the promoter sequences described in U.S. Pat. Nos. 6,462,185; 5,639,948; and 5,589,610. Seed-specific promoters such as the promoter from a β-phaseolin gene (for example, of kidney bean) or a glycinin gene (for example, of soybean), and others, can also be used. Endosperm-specific promoters include, but are not limited to, MEG1 (EPO application No. EP1528104) and those described by Wu et al. (1998), Furtado et al. (2002), and Hwang et al. (2002). Root-specific promoters, such as any of the promoter sequences described in U.S. Pat. Nos. 6,455,760 or 6,696,623, or in published U.S. patent application Nos. 20040078841; 20040067506; 20040019934; 20030177536; 20030084486; or 20040123349, can be used with an expression construct of the invention. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention. Expression constructs of the invention can also comprise one or more plant SHR, SCR, and/or SCL23 promoter sequences. The SHR, SCR, and SCL23 promoter sequences can be from any plant. SHR, SCR, and SCL23 promoters can be readily identified in other plants using information provided herein and techniques known in the art. In one embodiment, the promoter is from a C3 plant. In a specific embodiment, a promoter of the invention comprises the nucleotide sequence of SEQ ID NO:47, SEQ ID NO:48, and SEQ ID NO:49, or a functional fragment or variant thereof that is able to promote expression of the operably linked gene of interest in a plant cell.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal. The expression constructs of the invention can also include a polynucleotide sequence that directs transposition of other genes, i.e., a transposon.

Polynucleotides of the present invention can be composed of either RNA or DNA. Preferably, the polynucleotides are composed of DNA. In one embodiment, the DNA is complementary DNA (cDNA) prepared from or based on a messenger RNA (mRNA) template sequence. The subject invention encompasses those polynucleotides that are complementary in sequence to the polynucleotides disclosed herein. Polynucleotides and polypeptides of the invention can be provided in purified or isolated form.

Because of the degeneracy of the genetic code, a variety of different polynucleotide sequences can encode polypeptides of the present invention. A table showing all possible triplet codons (and where U also stands for T) and the amino acid encoded by each codon is described in Lewin (1985). In addition, it is well within the skill of a person trained in the art to create alternative polynucleotide sequences encoding the same, or essentially the same, polypeptides of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention. Allelic variants of the nucleotide sequences encoding a wild type polypeptide of the invention are also encompassed within the scope of the invention.

Substitution of amino acids other than those specifically exemplified or naturally present in a wild type polypeptide of the invention are also contemplated within the scope of the present invention. For example, non-natural amino acids can be substituted for the amino acids of a polypeptide, so long as the polypeptide having the substituted amino acids retains substantially the same biological or functional activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a wild type polypeptide of the present invention are also encompassed within the scope of the invention.

Amino acids can be generally categorized in the following classes: non-polar, uncharged polar, basic, and acidic. Conservative substitutions whereby a polypeptide of the present invention having an amino acid of one class is replaced with another amino acid of the same class fall within the scope of the subject invention so long as the polypeptide having the substitution still retains substantially the same biological or functional activity (e.g., enzymatic) as the polypeptide that does not have the substitution. Polynucleotides encoding a polypeptide having one or more amino acid substitutions in the sequence are contemplated within the scope of the present invention. Table 1 below provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that retain biological activity (e.g., promoter activity) or that encode functional polypeptides of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a polypeptide of the present invention can be generated as described herein and tested for the presence of biological function using standard techniques known in the art. Thus, an ordinarily skilled artisan can readily prepare and test fragments and variants of a polypeptide of the invention and determine whether the fragment or variant retains functional or biological activity relative to full-length or a non-variant polypeptide.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and)(BLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and)(BLAST) can be used. See NCBI/NIH website.

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

Techniques for transforming plant cells with a polynucleotide or gene are known in the art and include, for example, *Agrobacterium* infection, transient uptake and gene expression in plant seedlings, biolistic methods, electroporation, calcium phosphate or calcium chloride treatment, lipofection, DEAE-dextran mediated transfection, PEG-mediated transformation, etc. U.S. Pat. No. 5,661,017 teaches methods and materials for transforming an algal cell with a heterologous polynucleotide. Transformed cells can be selected, redifferentiated, and grown into plants that contain and express a polynucleotide of the invention using standard methods known in the art. The seeds and other plant tissue and progeny of any transformed or transgenic plant cells or plants of the invention are also included within the scope of the present invention. In one embodiment, the cell is transformed with a polynucleotide sequence comprising a sequence encoding the amino acid sequence shown in SEQ ID NO:1, 3, 5, 7, 9, 11, 13, 15, 17, 19, 21, 23, 25, 27, 29, 31, 33, 35, 37, 39, 41, 43, or 45, or a biologically active fragment or variant thereof. In one embodiment, the polynucleotide comprises a nucleotide sequence of any of SEQ ID NOs:2, 4, 6, 8, 10, 12, 14, 16, 18, 20, 22, 24, 26, 28, 30, 32, 34, 36, 38, 40, 42, 44, or 46, or the protein coding region thereof, and/or any of SEQ ID NOs:47, 48, or 49, or a functional fragment or variant thereof that is able to promote expression of the operably linked gene of interest.

Transgenic plants of the invention can be self-pollinated, or they can be pollinated with pollen from a non-transgenic plant, such as an inbred plant line. Pollen from transgenic plants of the invention can be used to pollinate a non-transgenic plant, such as an inbred plant line.

The subject invention also concerns cells transformed with a polynucleotide of the present invention, such as a polynucleotide comprising a plant SHR, SCR, or SCL23 gene promoter sequence, or a polynucleotide encoding a polypeptide of the invention. In one embodiment, the cell is transformed with a polynucleotide sequence comprising a sequence encoding the amino acid sequence shown in SEQ ID NO:1, 3, 5, 7, 9, 11, 13, 15, 17, 19, 21, 23, 25, 27, 29, 31, 33, 35, 37, 39, 41, 43, or 45, or a biologically active fragment or variant thereof. In one embodiment, the polynucleotide comprises a nucleotide sequence of any of SEQ ID NOs:2, 4, 6, 8, 10, 12, 14, 16, 18, 20, 22, 24, 26, 28, 30, 32, 34, 36, 38, 40, 42, 44, or 46, or the protein coding region thereof, and/or any of SEQ ID NOs:47, 48, or 49, or a functional fragment or variant thereof that is able to promote expression of the operably linked gene of interest in a cell. In one embodiment, the polynucleotide sequence of the invention is provided in an expression construct of the invention. The transformed cell can be a prokaryotic cell, for example, a bacterial cell such as *E. coli* or *B. subtilis*, or the transformed cell can be a eukaryotic cell, for example, a plant cell, including protoplasts, or an animal cell. Plant cells include, but are not limited to, dicotyledonous, monocotyledonous, and conifer cells. In one embodiment, the cell is an embryonic cell. In one embodiment, the plant cell is a cell of a C3 plant. In another embodiment, the plant cell is a cell of a C4 plant. In a specific embodiment, the plant cell is a rice, barley, thale cress (*Arabidopsis*), wheat, rye, oat, fescue, sunflower, tomato, cucumber, potato, peanut, cotton, sugar beet, tobacco, soybeans, or spinach plant cell. Animal cells include human cells, mammalian cells, avian cells, and insect cells. Mammalian cells include, but are not limited to, COS, 3T3, and CHO cells. Transgenic cells comprising a polynucleotide of the present invention are also contemplated within the scope of the invention.

Single letter amino acid abbreviations are defined in Table 2.

TABLE 2

| Letter Symbol | Amino Acid |
|---|---|
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |

TABLE 2-continued

| Letter Symbol | Amino Acid |
|---|---|
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

Materials and Methods

Plant Materials

The plants used in this study were in the WS or Col-0 backgrounds, and were grown at 22° C. and 50% humidity with 16 h daily illumination in a controlled-environment growth room. The scl23-2 mutant (GT_5_16303), which is in the Ler background, was introduced into the Ws background by genetic crossing. All transgenic plants were generated in the Col-0 ecotype by the flower-dip method (Clough and Bent, 1998).

Molecular Cloning

All the constructs described here were cloned using the multi-site Gateway system (Invitrogen). The SCR promoter (2 kb) and the SCL23 promoter (1.3 kb) were first PCR-amplified from genomic DNA using Phusion DNA polymerase (NEB). Both promoters were then cloned into pDONR-P4-P1R (Invitrogen), yielding the entry clones pENTR-SCRpro and pENTR-SCL23pro. The SCL23 cDNA was amplified by RT-PCR and cloned into pDONR221 (Invitrogen), resulting in the entry clone pENTR-SCL23. The entry clone for SHRpro has been described previously (Nakajima et al., 2001). To clone the SCRpro:GUS, SCL23pro:GUS and SHRpro:GUS constructs, the entry clones for the SCR, SCL23 and SHR promoters were cloned into binary vector dpGreenBarT (Levesque et al., 2006), together with the entry clones for the GUS gene and the Nos terminator. To clone the SCL23pro:SCL23-GFP construct, the entry clones for the promoter and cDNA of SCL23 as well as the GFP gene were cloned into binary vector dpGreen-BarT. The primers used for the cloning were B4_pSCR_F (5'-ggggacaactttgtatagaaaagttgCCAAACAGATATTTGCATTTGGGC-3') (SEQ ID NO:52) and B1_pSCR_R (5'-ggggactgctttttgtacaaacttgGAGATTGAAGGGTTGTTGGTCG-3') (SEQ ID NO:53) for the SCR promoter, attB4_pSCL23_FW (5'-ggggacaactttgtatagaaaagttgATTTCACCAATTCCGGC-3') (SEQ ID NO:54) and attB1_pSCL23_RV (5'-ggggactgctttttgtacaaacttgTCGATACGGCGTTTAGCGGAG-3') (SEQ ID NO:55) for the SCL23 promoter, and attB1_SCL23_FW (5'-ggggacaagtttgtacaaaaaagcaggctCCATGACTACAAAACGCA-3') (SEQ ID NO:56) and attB2_SCL23_RV (5'-ggggaccactttgtacaagaaagctgggtACGGCTGAGATTTCCAGGC-3') (SEQ ID NO:57) for the SCL23 cDNA. The uppercase letters in the primers are gene-specific sequences, whereas the lowercase letters are adaptor sequences used for the gateway cloning method.

Genotyping

Genotyping of the T-DNA insertional mutant for SCL23 was performed by PCR using RedTaq DNA polymerase (Sigma). For scl23-1_(Salk_054051), primers SCL23_LP1 (5'-TAATAATGCAAAGCCTCCACG-3') (SEQ ID NO:58) and SCL23_RP1 (5'-TTTTCAAGAAACTGATCCATCC-3') (SEQ ID NO:59) were used to amplify the wild-type gene, and primers SCL23_RP1 and LBb1 (5'-GCGTGGACCGCTTGCTGCAACT-3') (SEQ ID NO:60) were used for the T-DNA insert. For scl23-2 (GT_5_16303), primers SCL23_LP2 (5'-GGTGGAGATGGTTCTGAATCTC-3') (SEQ ID NO:61) and SCL23_RP2 (5'-CAGTTGAAGCGAGTAGATCGG-3') (SEQ ID NO:62) were used for amplification of the wild-type gene, and primers SCL23_RP2 and Ds3-1 (5'-ACCCGACCGGATCGTATCGGT-3') (SEQ ID NO:63) were used for the T-DNA insert.

ChIP-PCR and ChIP-Chip Assay

ChIP was performed as previously described (Cui et al., 2011), using a GFP antibody (Ab290, Abcam), except that 0.5 g of leaves of 3-week-old plants was used for each experiment. A transgenic line with a functional SHR-GFP fusion protein expressed under the control of the SHR promoter in the shr-2 background (SHRpro: SHR-GFP/shr-2) (Nakajima et al., 2001) was used for ChIP with SHR, whereas transgenic line SCRpro:GFPSCR/scr-4 (Cui and Benfey, 2009) was used for SCR. To identify direct targets of SCL23, we generated transgenic plants expressing a SCL23-GFP fusion protein in the scl23 mutant background.

```
The primers used for the ChIP assay were
SCR_F2
                                        (SEQ ID NO: 64)
(5'-CTCTACGTCTTGTCCAATTCC-3'),

SCR_R2
                                        (SEQ ID NO: 65)
(5'-CAAAGTGTGGTACGATGTGCT-3'),

SCR_F1
                                        (SEQ ID NO: 66)
(5'-AGAAACGAAATGGATCGGCAAACG-3'),

SCR_R1
                                        (SEQ ID NO: 67)
(5'-ATTTGGAAGGATGTGGGTTGGAGA-3'),

SCR_FW
                                        (SEQ ID NO: 68)
(5'-ACTTCTTCCGGTAGTAGCAGCA-3'),
and

SCR_RV
                                        (SEQ ID NO: 69)
(5'-AGAGACGGTGGTTGTTGTGGT-3')
for the SCR promoter,

SCL23_F2
                                        (SEQ ID NO: 70)
(5'-TCCGGCGATTGTGTTCTGTGT-3'),

SCL23_R2
                                        (SEQ ID NO: 71)
(5'-CTTCTTCTTCGTCGGTGGTCCT-3'),

SCL23_F1
                                        (SEQ ID NO: 72)
(5'-CTGGTTAAGTATCAATCCATGA-3'),

SCL23_R1
                                        (SEQ ID NO: 73)
(5'-ACCAACGAAACCAAGTGAACA-3'),

SCL23_FW
                                        (SEQ ID NO: 74)
(5'-TGCTGCCGCAATCAAACTCCT-3'),
and
```

-continued

```
SCL23_RV
                                  (SEQ ID NO: 75)
(5'-AGCTGATCACGCGCGTTTGTA-3')
for the SCL23 promoter,
and

18S-5
                                  (SEQ ID NO: 76)
(5'-TACCGTCCTAGTCTCAACCA-3')
and

18S-3
                                  (SEQ ID NO: 77)
(5'-AACATCTAAGGGCATCACAG-3')
for 18S (used as an internal control).
```

To identify genome-wide targets by the ChIP-chip technique, the DNA from the ChIP experiments as well as mock ChIP experiments (ChIP with extract from the wildtype) was first amplified using a GENOMEPLEX complete WGA kit (WGA2, Sigma) and then re-amplified using a GENOMEPLEX WGA re-amplification kit (WGA3, Sigma). DNA (1 μg) from re-amplification of each pair of mock and ChIP samples was labeled with Cy3 and Cy5 nucleotides using a NimbleGen dual-color DNA labeling kit (06370250001, NimbleGen), and, after mixing, both samples were hybridized to a custom *Arabidopsis* whole-genome microarray containing 720 K probes. This microarray has been validated previously (Gendrel et al., 2005). For each protein, two biological replicates were performed, and promoters with at least two probes that had a Cy5/Cy3 ratio>2 in all biological replicates were identified as target genes. For data analysis, we used the method described previously (Cui et al., 2011). Briefly, probes with greater than twofold enrichment and P<0.001 were identified from each replicate, and target genes were defined as those whose promoters have at least one probe meeting these criteria in at least two of the three replicates.

Other Methods

Starch staining and sugar measurement were performed as previously described (Cui et al., 2012). GUS staining and thin sectioning were performed according to the standard procedure (Weigel and Glazebrook, 2002). Leaves from 2-4-week-old plants grown in soil were incubated for 4 h in GUS staining buffer (50 mM sodium phosphate buffer, pH 7.2, containing 0.2% Triton X-100, 2 mM potassium ferrocyanide, 2 mM potassium ferricyanide and 2 mM X-Gluc). For microscopy, the leaves were fixed in FAA (50% ethanol, 10% Glacial acetic acid and 5% formaldehyde), and cleared using chloral hydrate solution for microscopy. For sectioning, the leaves were first fixed for 12 h with 4% glutaraldehyde, embedded in TECHNOVIT 7100 resin (Heraeus Kulzer), sectioned using a microtome (Bausch & Lomb Optical Co.), and stained with 1% toluidine blue solution for 1 min followed by de-staining for 2 min under running water.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—SHR, SCR and SCL23 are Essential for BS Cell-Fate Specification

To determine whether SCR and SHR play a role in BS cellfate specification, we examined the leaf anatomy in scr-1 and shr-2 mutants by thin sectioning. In the wild-type (Ws and Col-0), BS cells may be easily recognized by their rectangular cell shape, ordered organization and intermediate cell size relative to the vascular cells and mesophyll cells, which are large and irregularly shaped (Bosabalidis et al., 1984) (FIGS. 1A and 1B). As expected, the BS cell layer appeared to be missing in the shr mutant (FIG. 1C). Surprisingly, we found that the scr mutant has a normal cell pattern (FIG. 1D). However, the cells surrounding the vascular tissue became slightly enlarged, suggesting that SCR may play a role in BS cell-fate specification but that additional factors are involved (FIG. 1D).

Among the GRAS family of transcriptional regulators (Bolle, 2004), to which both SHR and SCR belong (Pysh et al., 1999), SCL23 is the closest paralog to SCR (Bolle, 2004), and therefore may also play a role in BS cell-fate specification. To test this hypothesis, we obtained two T-DNA insertion lines from the *Arabidopsis* Biological Resource Center (SALK_054051 and GT_5_16303), both of which harbor a T-DNA insertion in the 5' end of the coding region, and thus are likely to be null mutants. Quantitative RT-PCR analysis showed that levels of the SCL23 transcript were dramatically reduced in both lines (FIG. 5). However, neither mutant showed any obvious defects in BS cells (FIG. 1E and FIG. 6). We therefore generated a double mutant for SCR and SCL23. Interestingly, the cells surrounding the vascular tissue in the scr scl23 double mutant were large and irregular in shape, similarly to what was observed in the shr mutant (FIG. 1F and FIG. 6).

To determine whether the BS cell layer is lost in the shr and scr scl23 mutants, we examined the cell pattern by cross-sectioning. Interestingly, in both mutants, there was still a cell layer tightly associated with the vascular tissue (FIGS. 1C-1 and 1F-1). However, compared to the BS cells in the wild-type (FIG. 1A-1, 1B-1), the BS cells in the mutants were larger and some also became less regular in shape. This result suggests that, although the BS cell layer is not lost, the cells have become more mesophyll-like. A similar but less significant expansion of the BS cells was observed in scr leaves (FIG. 1D-1). As expected, the BS cell layer in the scl23 mutant was apparently normal (FIG. 1E-1). Together, these results suggest that all three proteins are required to maintain BS cell fate, and that, although SCR and SCL23 act redundantly, SCR appears to play a more important role.

Example 2—SCR and SCL23 are Expressed Specifically in BS Cells

The observation that SCR and SCL23 function redundantly in BS cell-fate specification suggests that SCL23, like SCR, may also be expressed in this cell type. To investigate this possibility, we created transgenic plants that express the GUS reporter gene under the control of the promoters of SCR and SCL23 (SCRpro:GUS and SCL23pro:GUS, respectively), and examined the GUS expression pattern. This histological analysis confirmed that both SCR and SCL23 were expressed specifically in BS cells (FIGS. 2A, 2B, 2D, and 2E). However, the similar expression pattern of SCR and SCL23 was observed only in small veins during early stages of leaf development. In major veins or later developmental stages, SCR expression became restricted to BS cells on the lower side of the leaf blade (FIG. 2G), where the phloem is located. In contrast, SCL23 was preferentially expressed in BS cells associated with the xylem on the upper side of the leaf (FIG. 2H). Hence, although SCR and SCL23 act redundantly in BS cell-fate specification, they function differently at later stage of leaf development.

Example 3—SCR and SCL23 Act Downstream of SHR

Previous studies have shown that, in leaves, SHR is expressed exclusively in the vascular tissue (Gardiner et al., 2010). However, it has also been reported that SHR is expressed in other leaf cell types as well, including BS cells (Dhondt et al., 2010). Due to this discrepancy, we also examined the GUS staining pattern in transgenic plants expressing the SHRpro:GUS construct (Helariutta et al., 2000). Our results clearly show that SHR is expressed only in the vascular tissue (FIG. 2C). Furthermore, by cross-sectioning, we found that SHR expression was xylem-specific (FIG. 2F).

The distinct expression domains of SHR, SCR and SCL23 suggest that SHR must act non-cell-autonomously, similarly to its mode of action in the root (Nakajima et al., 2001). This is indeed the case, because a recent study showed that the SHR promoter confers gene expression only in the vascular tissue, but an SHR-GFP protein expressed under the control of this promoter is present in BS cells (Gardiner et al., 2010). In other words, the SHR protein must have moved from the vascular tissue into the adjacent cells to control BS cell-fate specification.

Figure 3B:
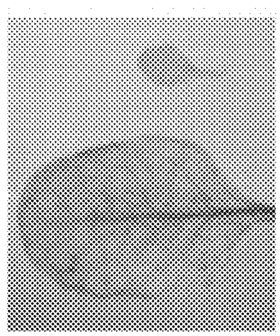

The cell type-specific expression patterns of SHR, SCR and SCL23, as well as their respective mutant phenotypes, suggest that both SCR and SCL23 are under the control of SHR. To determine whether this is the case, we introduced the SCRpro:GUS and SCL23pro:GUS constructs into the shr background by genetic crossing. As shown in FIGS. 3A and 3B, GUS activity from either construct was no longer detectable in the shr mutant, lending support to the possibility that SCR and SCL23 are regulated by SHR.

Figure 3C:
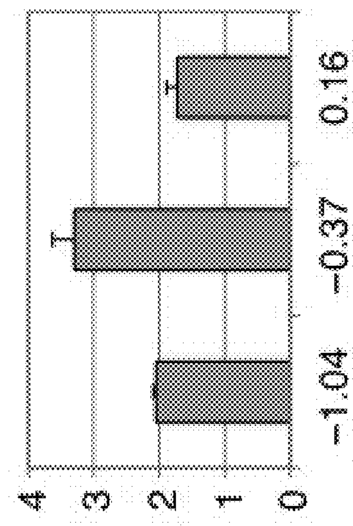
Figure 3D:
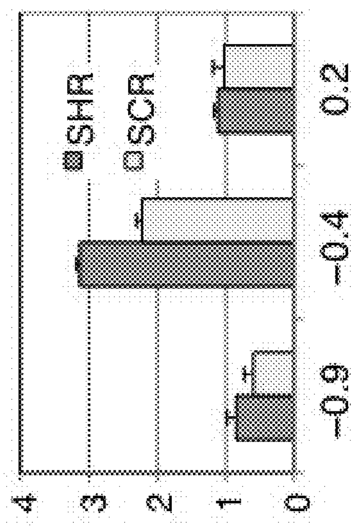
Figure 3E:
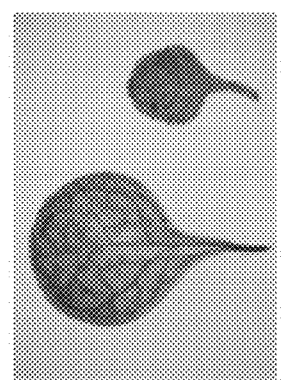
Figure 3E:
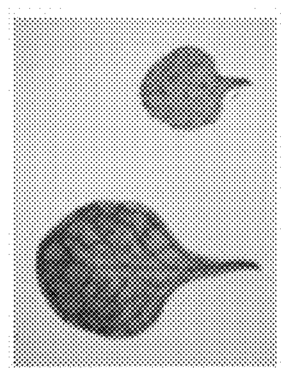
Figure 3E:
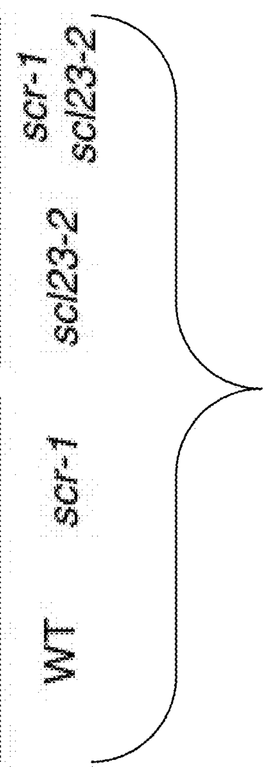

To determine whether SHR regulates SCR and SCL23 expression directly, we performed ChIP assays using a functional SHR-GFP fusion protein expressed in the shr mutant background (Cui et al., 2007). As SHR and SCR control a common set of genes in the root, we predicted that SCL23 is also a direct target of SCR. We therefore also performed a ChIP-PCR assay using a GFP-SCR fusion protein expressed in the scr mutant background (Cui et al., 2012). This experiment showed that SHR and SCR bind to the promoters of SCR and SCL23 (FIGS. 3C and 3D). Intriguingly, although no GUS staining was detectable in most scr mutant leaves, the SCRpro:GUS and SCL23pro:GUS reporters were still expressed in approximately 20% of the leaves (FIG. 3E). This result suggests that, similarly to the situation in the root, factors other than SHR are involved in regulation of SCR and SCL23 expression in the leaves.

Example 4—Genome-Wide Identification of SHR, SCR and SCL23 Direct Targets

Figure 8:
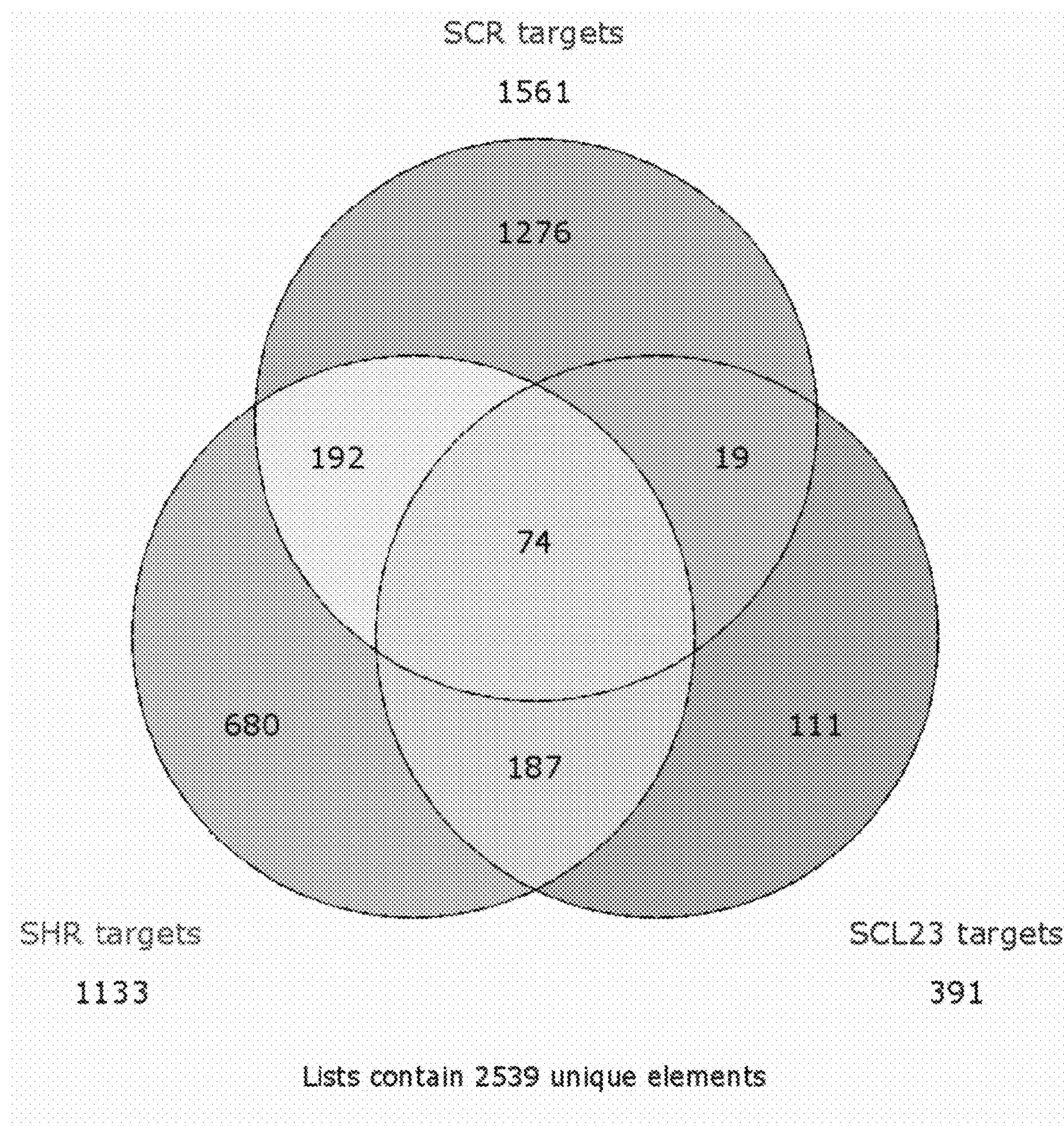
FIG. 8. Venn diagram showing the common and distinct targets of SHR, SCR and SCL23 as identified by the ChIP-chip technique.

To understand how SCR and SCL23 control BS cell fate, and whether they function differently in leaves, we identified their direct targets at the genome scale by the ChIP-chip technique. Using the same criteria for both proteins (twofold enrichment and P<0.001, see also Materials and Methods), we identified 1566 and 391 genes as direct targets of SCR and SCL23, respectively (Tables 4 and 5, and FIG. 8), of which 93 are common targets. The small number of common targets and larger number of SCR direct targets lend support to the possibility that SCR and SCL23 function differently but SCR plays a major role in BS cells. To determine the extent of functional overlap between SHR, SCR and SCL23, we also performed a ChIP-chip assay with SHR in leaves, and identified 1133 direct targets (Table 6). Consistent with our recent finding that SCR has both SHR-dependent and-independent functions (Cui et al., 2012), the SHR and SCR direct targets are only partially overlapping (266 genes, i.e., 23 and 17% of all SHR and SCR targets, respectively). Surprisingly, we found that SHR shared a larger number of targets with SCL23 than with SCR (261 and 93 genes, respectively). Only 74 genes were regulated by SHR, SCR and SCL23. Because SCR and SCL23 diverged in their expression patterns during late stages of leaf development, it is likely that SCR and SHR determine the expression of SCL23 in phloem-associated BS cells, whereas additional factors are involved in specification of SCL23 expression in xylem-associated BS cells.

Example 5—the Expression Pattern and Function of SCR and SCL23 Diverge at Later Stages of Leaf Development In most C3 plants, a major role for the BS cells is metabolite transport between mesophyll cells and the vascular tissue (Leegood, 2008). Because of their preferential association with phloem and xylem, which are involved in uploading of sugar and unloading of minerals, respectively, SCR and SCL23 may regulate different aspects of metabolite and nutrient transport in BS cells. To test this hypothesis, we focused our analysis on genes involved in metabolite and mineral transport. This analysis showed indeed that, relative to SCL23, SCR had a much larger number of direct targets that encode transporter proteins (Table 3). Particularly interesting is that a number of genes involved in sugar transport are among the list of SCR direct targets, but none appear to be a target of SCL23 (Table 3). Intriguingly, there is little overlap between the transporter genes identified as SHR and SCR direct targets, but most SCR targets that are sugar transporter genes appear also to be SHR direct targets.

Figure 4A:
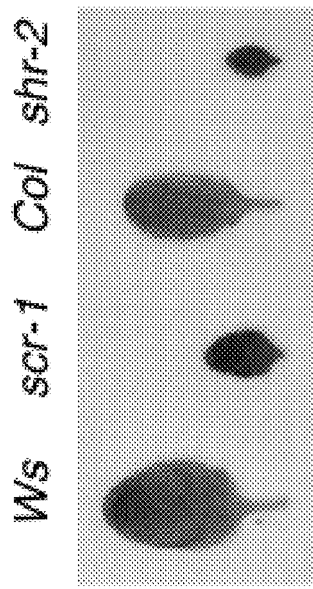
FIGS. 4A-4E. SHR, SCR and SCL23 play a role in sugar homeostasis.
Figure 4B:
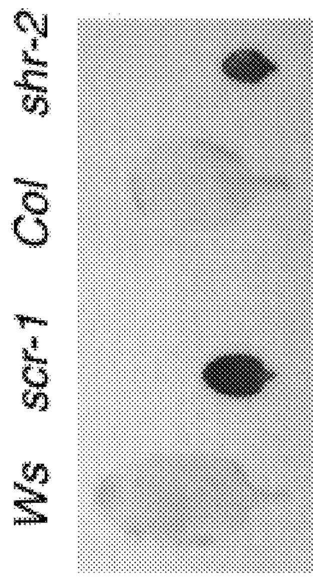
Figure 4C:
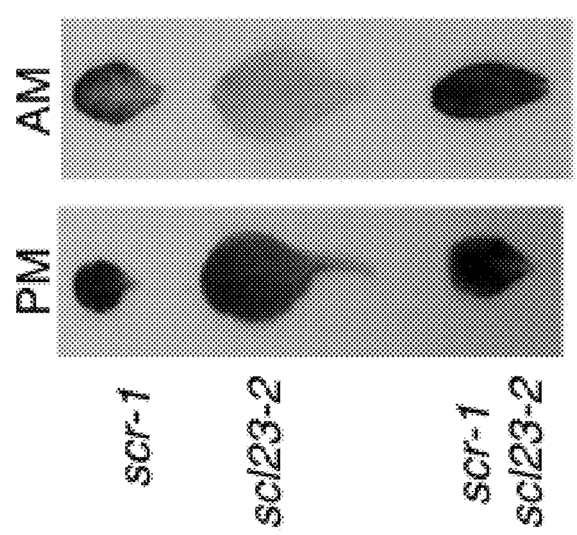
Figure 4D:
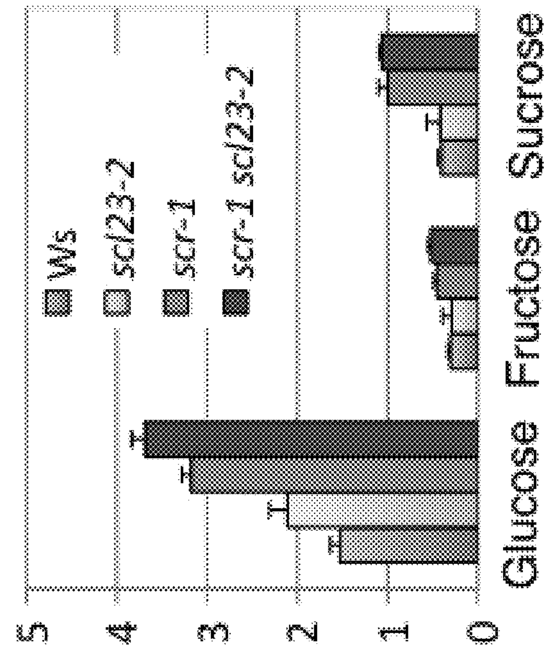
Figure 4E:
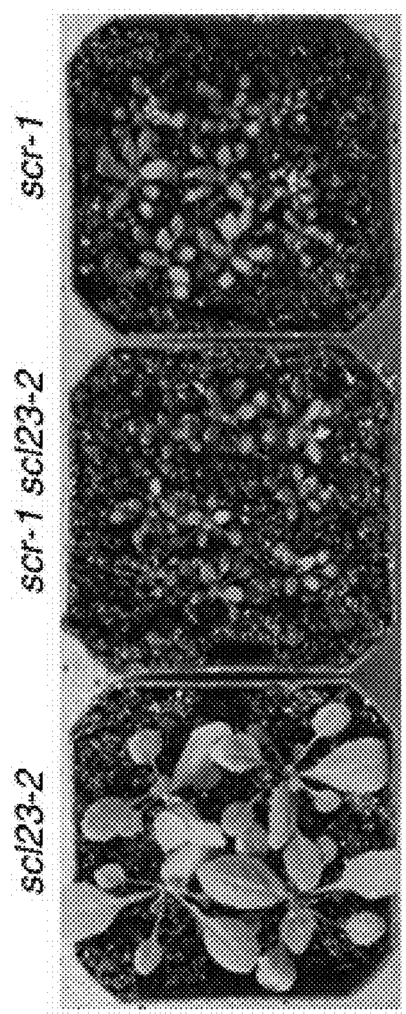

Our ChIP-chip data provide an explanation for our recent finding that SCR plays an important role in sugar homeostasis (Cui et al., 2012). To assess the role of SCL23 in BS cells, we next measured sugar content in the scl23 single mutant and the scr scl23 double mutant. Both free sugars and starch were accumulated to a slightly higher level in the scr scl23 mutant than in the scr mutant, but the scl23 single mutation did not seem to affect sugar homeostasis (FIGS. 4C and 4D). Consistent with these results, the scr scl23 mutant also had a slightly smaller stature (FIG. 4E). These results are consistent with the notion that SCR and SCL23 are both required for normal plant growth and development, but they function differently in BS cells.

Example 6

Taken together, the results shown here demonstrate that SHR, SCR and SCL23 constitute a developmental pathway controlling BS cell fate in the leaves of *Arabidopsis thaliana*. Although a role for SHR and SCR in bundle sheath cell-fate specification had been predicted (Nelson, 2011), they appear to regulate cell patterning differently in the root and shoot. In the root, mutation in either gene causes loss of a cell layer, whereas in shr and scr mutant leaves, the cell pattern is normal. However, we do not consider that the cells surrounding the vascular tissue in the shr and scr mutants are the same cell type as in the wild-type for the following reasons. First, these cells were expanded in size, and some were even irregular in shape, suggesting that they have become more mesophyll cell-like. Second, these cells do not express the SCRpro:GUS and SCL23pro:GUS constructs, which may be considered as BS cell type specific markers. Third, because SHR and SCR control a number of genes directly many additional genes should be affected in the mutant cell layer in the shr and scr mutants. Inevitably, this will result in a change in physiology in these cells, even though they are still associated with the vascular tissue.

The finding that SCL23 is required for BS cell-fate specification and function is unexpected, because SCL23 does not have an N-terminal domain, which has been shown to be critical for the function of other GRAS family transcriptional regulators (Sun et al., 2011). The GRAS family transcriptional regulators typically have a variable N-terminal domain and a conserved C-terminal GRAS domain (Pysh et al., 1999). In SCR, the GRAS domain is required for physical interaction with SHR (Cui et al., 2007), and the N-terminal domain is also a protein-protein interaction domain, through which a number of proteins interact with SCR (Cui and Benfey, 2009; Cruz-Ramirez et al., 2012). The N-terminal domain of SCR also confers nuclear localization, and nuclear localization of SCR is important for its function in root radial patterning (Cui and Benfey, 2009). Truncated SCR protein without the N-terminal domain is still localized in the nucleus, probably by forming a multiprotein complex (Welch et al., 2007), but the ability of SCR to block SHR movement is compromised, as an additional ground tissue cell layer is formed in plants expressing the truncated protein in the scr background (Cui and Benfey, 2009). As no additional layers of BS cells are produced in the scr mutant, SCL23 must be sufficient to block SHR movement. Nevertheless, SCL23 does not appear to have the same spectrum of functions as SCR, because SCR controls much a larger set of genes and the scr mutation causes much more serious defects in the morphology and function of the BS cells. In addition, SCL23 does not appear to play an important role in other organs, as the scr mutation alone causes loss of the endodermis in the root or starch sheath cells in the inflorescence stem (Di Laurenzio et al., 1996; Fukaki et al., 1998).

Figure 7A:
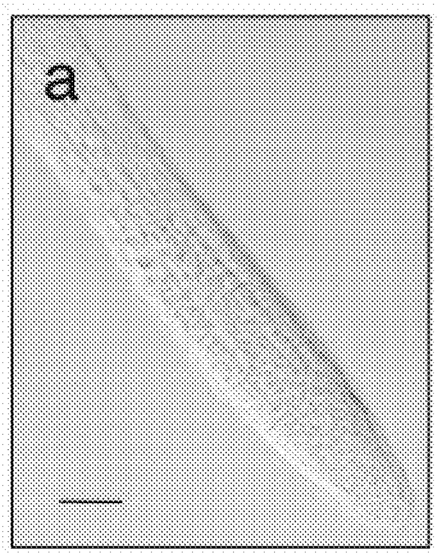
FIGS. 7A and 7B. SCL23pro:GUS expression pattern in primary roots of one-week-old seedlings.
Figure 7B:
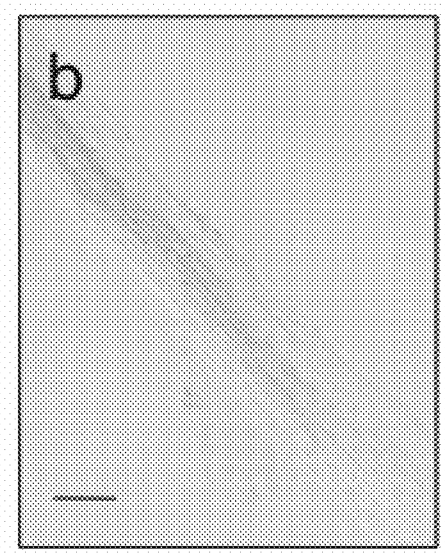

Another unexpected finding is that, despite their redundant roles in BS cell-fate specification, SCL23 and SCR function distinctly in later stages of leaf development. This is suggested by the observation that SCR is preferentially expressed in phloem-associated BS cells but SCL23 is more strongly expressed in xylem-associated BS cells. Consistent with this complementary expression pattern, we found that SCR directly controls genes involved in sugar and amino acid transport, whereas SCL23 direct target genes are involved in the transport of inorganic compounds. Compared to the scl23 mutant, the scr mutant also shows a much more severe defect in sugar homeostasis. Although the scl23 mutation alone does not result in obvious plant growth defects, the scr scl23 double mutant has smaller leaves, which indicates that SCL23 is important for normal plant growth and development. Interestingly, we found that SCL23 is also expressed in the root, albeit with a different expression pattern to that of SCR (FIGS. 7A and 7B).

Although the expression pattern of SHR in leaves has been described previously (Dhondt et al., 2010; Gardiner et al., 2010), how SHR regulates BS cell fate has been unclear due to inconsistency in the results from previous studies. According to Gardiner et al. (2010), SHR is specifically expressed in the vascular tissue. In contrast, Dhondt et al. (2010) showed that SHR is expressed in both the vascular tissue and BS cells. This discrepancy may be due to the use of different reporter genes. Gardiner et al. used GFP, which may not be able to reveal SHR expression in mesophyll cells because of its relative low sensitivity, whereas Dhondt et al. used the GUS gene, which may cause non-specific staining after an extended period of staining when GUS activity is strong and the stringency of the staining conditions is low. The SHR promoter is strong, so the broader expression domain of SHR revealed by GUS staining may be an artifact. To resolve this issue, we re-examined the SHR expression pattern in the same transgenic plants containing the SHRpro:GUS construct as used by Dhondt et al. but under more stringent conditions (2 mM potassium ferrocyanide and 2 mM potassium ferricyanide in this study versus 2 mM potassium ferricyanide in the study by Dhondt et al.) and a shorter incubation time (4 h in this study versus 12-24 h in the previous study). Strikingly, we observed strong GUS activity in the vascular tissue but no activity in the BS cells. Moreover, by cross-sectioning, we showed that the SHRpro:GUS reporter gene is expressed specifically in the xylem. These results, together with the studies by Gardiner et al. (2010) suggest that, in the leaves, SHR is expressed in the vascular tissue but the protein moves into the adjacent cell layer, where it controls SCR and SCL23 expression and BS cell fate. The non-cell-autonomous action of SHR suggests that it is an important component of the positional information that is derived from the vascular tissue and determines the position of the BS cell layer. Homologs of SHR and SCR have been identified in many plants (Lim et al., 2000; Sassa et al., 2001; Kamiya et al., 2003; Cui et al., 2007; Laajanen et al., 2007; Sole et al., 2008; Cermak et al., 2011). This suggests that the mechanism for BS cell-fate specification revealed in this study is likely to be evolutionarily conserved. In support of this possibility, an abnormal number of BS cell layers were produced in the maize scr mutant (Slewinski et al., 2012).

TABLE 3

Direct targets of SHR, SCR and SCL23 involved in nutrient transport, as identified by ChIP-chip.

| Arabidopsis Genome Initiative (AGI) identification number | SHR target | SCR target | SCL23 target | Gene function |
|---|---|---|---|---|
| AT2G28070 | Yes | Yes | Yes | ABC-2 type transporter family protein |
| AT1G59870 | Yes | | Yes | ABC-type transporter family protein |
| AT2G27240 | Yes | | Yes | Aluminium activated malate transporter |
| AT2G30070 | Yes | | Yes | K transporter |

TABLE 3-continued

Direct targets of SHR, SCR and SCL23 involved in nutrient transport, as identified by ChIP-chip.

| Arabidopsis Genome Initiative (AGI) identification number | SHR target | SCR target | SCL23 target | Gene function |
|---|---|---|---|---|
| AT4G16370 | Yes | Yes | | Oligopeptide transporter |
| AT1G11260 | Yes | Yes | | Sugar transporter 1 |
| AT1G71880 | Yes | Yes | | Sucrose transporter 1 |
| AT5G26340 | | Yes | | STP13, glucose transporter |
| AT1G50310 | | Yes | | Sugar transporter 9 |
| AT2G02810 | | Yes | | UDP-galactose transporter 1 |
| AT4G32390 | | Yes | | Nucleotide-sugar transporter |
| AT5G55950 | | Yes | | Nucleotide/sugar transporter |
| AT4G27970 | | Yes | | Malic acid transport family protein |
| AT5G64560 | | Yes | | Mg transporter |
| AT3G58970 | | Yes | | Mg transporter 6 |
| AT2G46800 | | Yes | | Zn transporter |
| AT3G46900 | | Yes | | Copper transporter |
| AT5G52860 | | Yes | | ABC-2 type transporter family protein |
| AT1G12940 | | Yes | | Nitrate transporter |
| AT3G45060 | | Yes | | High affinity nitrate transporter 2.6 |
| AT5G43360 | | Yes | | Phosphate transporter |
| AT1G23090 | | Yes | | Sulfite transporter |
| AT2G41190 | | Yes | | Transmembrane amino acid transporter |
| AT5G01180 | | Yes | | Peptide transporter 5 |
| AT5G07630 | | Yes | | Lipid transporters |
| AT3G21090 | | Yes | | ABC-2 type transporter family protein |
| AT3G55110 | | Yes | | ABC-2 type transporter family protein |
| AT4G27420 | | Yes | | ABC-2 type transporter family protein |
| AT3G18830 | Yes | | | Polyol/monosaccharide transporter 5 |
| AT1G12110 | Yes | | | Nitrate transporter 1.1 |
| AT1G69850 | Yes | | | Nitrate transporter 1: 2 |
| AT1G69870 | Yes | | | Nitrate transporter 1.7 |
| AT4G21680 | Yes | | | Nitrate transporter 1.8 |
| AT5G14570 | Yes | | | High affinity nitrate transporter 2.7 |
| AT1G80310 | Yes | | | Sulfate transmembrane transporters |
| AT1G60160 | Yes | | | Potassium transporter family protein |
| AT5G43810 | Yes | | | Stabilizer of iron transporter SufD |
| AT2G38120 | Yes | | | Transmembrane amino acid transporter |
| AT2G36590 | Yes | | | Proline transporter 3 |
| AT5G04770 | Yes | | | Cationic amino acid transporter 6 |
| AT4G27730 | Yes | | | Oligopeptide transporter 1 |
| AT1G80300 | Yes | | | Nucleotide transporter 1 |
| AT5G45370 | Yes | | | Nodulin MtN21/EamA-like transporter |
| AT1G70610 | Yes | | | Transporter activity |

TABLE 4

SCL23 direct targets identified by ChIP-chip

| Arabidopsis Genome Initiative (AGI) identification number | Short_description |
|---|---|
| AT2G40008 | other RNA |
| AT1G78090 | trehalose-6-phosphate phosphatase |
| AT2G22520 | unknown protein |
| AT4G29780 | unknown protein |
| AT2G25480 | TPX2 (targeting protein for Xklp2) protein family |
| AT3G19030 | unknown protein |
| AT2G23140 | RING/U-box superfamily protein with ARM repeat domain |
| AT5G64370 | beta-ureidopropionase |
| AT3G19020 | Leucine-rich repeat (LRR) family protein |
| AT5G42110 | unknown protein |
| AT1G61890 | MATE efflux family protein |
| AT2G22510 | hydroxyproline-rich glycoprotein family protein |
| AT1G32920 | unknown protein, LOCATED IN: endomembrane system |
| AT1G32928 | unknown protein |
| AT2G30040 | mitogen-activated protein kinase kinase kinase 14 |
| AT1G09070 | soybean gene regulated by cold-2 |

TABLE 4-continued

SCL23 direct targets identified by ChIP-chip

| Arabidopsis Genome Initiative (AGI) identification number | Short_description |
|---|---|
| AT3G62280 | GDSL-like Lipase/Acylhydrolase superfamily protein |
| AT5G67350 | unknown protein |
| AT2G23142 | Plant self-incompatibility protein S1 family |
| AT2G29490 | glutathione S-transferase TAU 1 |
| AT1G76620 | Protein of unknown function, DUF547 |
| AT5G59770 | Protein-tyrosine phosphatase-like, PTPLA |
| AT5G59880 | actin depolymerizing factor 3 |
| AT2G30070 | potassium transporter 1 |
| AT4G13395 | ROTUNDIFOLIA like 12 |
| AT3G30320 | unknown protein |
| AT3G24670 | Pectin lyase-like superfamily protein |
| AT5G11750 | Ribosomal protein L19 family protein |
| AT4G01250 | WRKY family transcription factor |
| AT1G79130 | SAUR-like auxin-responsive protein family |
| AT5G57020 | myristoyl-CoA: protein N-myristoyltransferase |
| AT1G76660 | unknown protein, LOCATED IN: plasma membrane |
| AT1G22190 | Integrase-type DNA-binding superfamily protein |
| AT4G27654 | unknown protein |
| AT1G18740 | Protein of unknown function (DUF793) |
| AT5G51490 | Plant invertase/pectin methylesterase inhibitor superfamily |
| AT4G36920 | Integrase-type DNA-binding superfamily protein |
| AT1G58037 | Cysteine/Histidine-rich C1 domain family protein |
| AT5G59780 | myb domain protein 59 |
| AT3G56010 | unknown protein |
| AT4G39800 | myo-inositol-1-phosphate synthase 1 |
| AT4G27270 | Quinone reductase family protein |
| AT5G64360 | Chaperone DnaJ-domain superfamily protein |
| AT4G15610 | Uncharacterised protein family (UPF0497) |
| AT2G30380 | Plant protein of unknown function (DUF641) |
| AT5G53420 | CCT motif family protein |
| AT4G20362 | other RNA |
| AT2G35960 | NDR1/HIN1-like 12 |
| AT1G27730 | salt tolerance zinc finger |
| AT3G07360 | plant U-box 9 |
| AT4G25490 | C-repeat/DRE binding factor 1 |
| AT1G20823 | RING/U-box superfamily protein |
| AT5G11530 | embryonic flower 1 (EMF1) |
| AT3G04732 | unknown protein |
| AT1G29920 | chlorophyll A/B-binding protein 2 |
| AT2G41140 | CDPK-related kinase 1 |
| AT1G60130 | Mannose-binding lectin superfamily protein |
| AT5G44090 | Calcium-binding EF-hand family protein |
| AT2G46530 | auxin response factor 11 |
| AT5G25220 | KNOTTED1-like homeobox gene 3 |
| AT1G64385 | unknown protein, LOCATED IN: endomembrane |
| AT5G47940 | unknown protein |
| AT4G01720 | WRKY family transcription factor |
| AT4G37610 | BTB and TAZ domain protein 5 |
| AT4G27280 | Calcium-binding EF-hand family protein |
| AT1G07135 | glycine-rich protein |
| AT5G06320 | NDR1/HIN1-like 3 |
| AT4G25470 | C-repeat/DRE binding factor 2 |
| AT1G35560 | TCP family transcription factor |
| AT4G27657 | unknown protein |
| AT2G22460 | Protein of unknown function, DUF617 |
| AT2G28070 | ABC-2 type transporter family protein |
| AT5G11060 | KNOTTED1-like homeobox gene 4 |
| AT1G20330 | sterol methyltransferase 2 |
| AT5G63170 | GDSL-like Lipase/Acylhydrolase superfamily protein |
| AT5G65340 | Protein of unknown function, DUF617 |
| AT1G25550 | myb-like transcription factor family protein |
| AT5G23280 | TCP family transcription factor |
| AT1G15750 | Transducin family protein/WD-40 repeat family protein |
| AT1G17420 | lipoxygenase 3 |
| AT4G32020 | unknown protein |
| AT1G19180 | jasmonate-zim-domain protein 1 |
| AT4G28230 | unknown protein |
| AT4G28240 | Wound-responsive family protein |
| AT4G17453 | This gene encodes a small protein and has either evidence of transcription or purifying selection |
| AT3G53450 | Putative lysine decarboxylase family protein |
| AT5G08139 | RING/U-box superfamily protein |

TABLE 4-continued

SCL23 direct targets identified by ChIP-chip

| Arabidopsis Genome Initiative (AGI) identification number | Short_description |
|---|---|
| AT4G19700 | SBP (S-ribonuclease binding protein) family protein |
| AT5G11740 | arabinogalactan protein 15 |
| AT4G15800 | ralf-like 33 |
| AT1G68450 | VQ motif-containing protein |
| AT1G35750 | pumilio 10 |
| AT4G26690 | PLC-like phosphodiesterase family protein |
| AT1G27290 | unknown protein |
| AT3G12320 | unknown protein |
| AT4G11280 | 1-aminocyclopropane-1-carboxylic acid (acc) synthase 6 |
| AT5G01850 | Protein kinase superfamily protein |
| AT5G34830 | unknown protein |
| AT1G01490 | Heavy metal transport/detoxification superfamily protein |
| AT2G23340 | DREB and EAR motif protein 3 |
| AT3G23810 | S-adenosyl-1-homocysteine (SAH) hydrolase 2 |
| AT3G56000 | cellulose synthase like A14 |
| AT1G78030 | unknown protein |
| AT1G01470 | Late embryogenesis abundant protein |
| AT5G59613 | unknown protein |
| AT5G67290 | FAD-dependent oxidoreductase family protein |
| AT3G44610 | Protein kinase superfamily protein |
| AT3G15210 | ethylene responsive element binding factor 4 |
| AT4G37260 | myb domain protein 73 |
| AT5G63580 | flavonol synthase 2 |
| AT5G21940 | unknown protein |
| AT5G67440 | Phototropic-responsive NPH3 family protein |
| AT3G16830 | TOPLESS-related 2 |
| AT4G05320 | polyubiquitin 10 |
| AT4G32030 | unknown protein |
| AT3G17860 | jasmonate-zim-domain protein 3 |
| AT4G24120 | YELLOW STRIPE like 1 |
| AT1G70550 | Protein of Unknown Function (DUF239) |
| AT1G02350 | protoporphyrinogen oxidase-related |
| AT1G09390 | GDSL-like Lipase/Acylhydrolase superfamily protein |
| AT5G65700 | Leucine-rich receptor-like protein kinase family protein |
| AT3G28340 | galacturonosyltransferase-like 10 |
| AT4G01960 | unknown protein |
| AT1G05710 | basic helix-loop-helix (bHLH) DNA-binding superfamily protein |
| AT2G23148 | Plant self-incompatibility protein S1 family |
| AT3G22380 | time for coffee |
| AT1G73550 | Bifunctional inhibitor/lipid-transfer protein/seed storage 2S albumin superfamily protein |
| AT3G50770 | calmodulin-like 41 |
| AT5G20190 | Tetratricopeptide repeat (TPR)-like superfamily protein |
| AT5G13730 | sigma factor 4 |
| AT2G27240 | Aluminium activated malate transporter family protein |
| AT2G45970 | cytochrome P450, family 86, subfamily A, polypeptide 8 |
| AT1G55230 | Family of unknown function (DUF716) |
| AT4G13340 | Leucine-rich repeat (LRR) family protein |
| AT4G17500 | ethylene responsive element binding factor 1 |
| AT3G11700 | FASCICLIN-like arabinogalactan protein 18 precursor |
| AT1G03730 | unknown protein; BEST Arabidopsis thaliana protein match is: unknown protein (TAIR: AT4G03600.1); Has 50 Blast hits to 50 prot . . . |
| AT5G13740 | zinc induced facilitator 1 |
| AT1G20340 | Cupredoxin superfamily protein |
| AT5G61990 | Pentatricopeptide repeat (PPR) superfamily protein |
| AT4G20830 | FAD-binding Berberine family protein |
| AT5G45470 | Protein of unknown function (DUF594) |
| AT5G65207 | unknown protein |
| AT3G14450 | CTC-interacting domain 9 |
| AT3G63006 | pre-tRNA |
| AT1G02065 | squamosa promoter binding protein-like 8 |
| AT1G19050 | response regulator 7 |
| AT1G70370 | polygalacturonase 2 |
| AT5G65210 | bZIP transcription factor family protein |
| AT1G64380 | Integrase-type DNA-binding superfamily protein |
| AT3G52490 | Double Clp-N motif-containing P-loop nucleoside triphosphate hydrolases superfamily protein |
| AT3G17120 | unknown protein |
| AT5G08790 | NAC (No Apical Meristem) domain transcriptional regulator superfamily protein |
| AT4G22980 | Pyridoxal phosphate (PLP)-dependent transferases superfamily protein |
| AT3G44730 | kinesin-like protein 1 |
| AT3G16570 | rapid alkalinization factor 23 |
| AT4G13830 | DNAJ-like 20 |

TABLE 4-continued

SCL23 direct targets identified by ChIP-chip

| Arabidopsis Genome Initiative (AGI) identification number | Short_description |
|---|---|
| AT2G41340 | RNA polymerase II fifth largest subunit, D |
| AT1G07580 | pre-tRNA |
| AT3G16860 | COBRA-like protein 8 precursor |
| AT3G52840 | beta-galactosidase 2 |
| AT1G22180 | Sec14p-like phosphatidylinositol transfer family protein |
| AT3G06070 | unknown protein |
| AT1G02340 | basic helix-loop-helix (bHLH) DNA-binding superfamily protein |
| AT4G27510 | unknown protein |
| AT3G13310 | Chaperone DnaJ-domain superfamily protein |
| AT3G50660 | Cytochrome P450 superfamily protein |
| AT4G01540 | NAC with transmembrane motif1 |
| AT5G15410 | Cyclic nucleotide-regulated ion channel family protein |
| AT3G15200 | Tetratricopeptide repeat (TPR)-like superfamily protein |
| AT1G73600 | S-adenosyl-L-methionine-dependent methyltransferases superfamily protein |
| AT1G73602 | conserved peptide upstream open reading frame 32 |
| AT1G04130 | Tetratricopeptide repeat (TPR)-like superfamily protein |
| AT5G46730 | glycine-rich protein |
| AT5G43030 | Cysteine/Histidine-rich C1 domain family protein |
| AT1G13240 | pre-tRNA |
| AT5G64690 | neurofilament triplet H protein-related |
| AT1G01550 | Protein of unknown function (DUF793) |
| AT3G02150 | plastid transcription factor 1 |
| AT3G04730 | indoleacetic acid-induced protein 16 |
| AT5G67450 | zinc-finger protein 1 |
| AT1G21810 | Plant protein of unknown function (DUF869) |
| AT1G73560 | Bifunctional inhibitor/lipid-transfer protein/seed storage 2S albumin superfamily protein |
| AT2G27320 | Protein of Unknown Function (DUF239) |
| AT2G46380 | Protein of unknown function (DUF3133) |
| AT3G19380 | plant U-box 25 |
| AT3G20340 | Expression of the gene is downregulated in the presence of paraquat, an inducer of photoxidative stress. |
| AT5G35750 | histidine kinase 2 |
| AT3G26511 | unknown protein |
| AT1G18300 | nudix hydrolase homolog 4 |
| AT3G63050 | unknown protein |
| AT5G64310 | arabinogalactan protein 1 |
| AT2G23700 | Protein of unknown function, DUF547 |
| AT5G45120 | Eukaryotic aspartyl protease family protein |
| AT1G23710 | Protein of unknown function (DUF1645) |
| AT1G13260 | related to ABI3/VP1 1 |
| AT1G07000 | exocyst subunit exo70 family protein B2 |
| AT4G38520 | Protein phosphatase 2C family protein |
| AT5G17300 | Homeodomain-like superfamily protein |
| AT3G22104 | Phototropic-responsive NPH3 family protein |
| AT5G67240 | small RNA degrading nuclease 3 |
| AT1G76190 | SAUR-like auxin-responsive protein family |
| AT3G13080 | multidrug resistance-associated protein 3 |
| AT5G60890 | myb domain protein 34 |
| AT5G13100 | unknown protein |
| AT3G11410 | protein phosphatase 2CA |
| AT3G11660 | NDR1/HIN1-like 1 |
| AT1G24150 | formin homologue 4 |
| AT1G14740 | Protein of unknown function (DUF1423) |
| AT2G41200 | unknown protein |
| AT2G41430 | dehydration-induced protein (ERD 15) |
| AT1G12610 | Integrase-type DNA-binding superfamily protein |
| AT3G48530 | SNF1-related protein kinase regulatory subunit gamma 1 |
| AT4G32410 | cellulose synthase 1 |
| AT3G05800 | AtBS1(activation-tagged BRI1 suppressor 1)-interacting factor 1 |
| AT1G25560 | AP2/B3 transcription factor family protein |
| AT1G80450 | VQ motif-containing protein |
| AT1G13360 | unknown protein |
| AT5G15420 | unknown protein |
| AT4G34410 | redox responsive transcription factor 1 |
| AT4G08950 | Phosphate-responsive 1 family protein |
| AT4G36040 | Chaperone DnaJ-domain superfamily protein |
| AT1G79120 | Ubiquitin carboxyl-terminal hydrolase family protein |
| AT5G57690 | diacylglycerol kinase 4 |
| AT1G32640 | Basic helix-loop-helix (bHLH) DNA-binding family protein |
| AT4G27310 | B-box type zinc finger family protein |
| AT2G41910 | Protein kinase superfamily protein |

TABLE 4-continued

SCL23 direct targets identified by ChIP-chip

| Arabidopsis Genome Initiative (AGI) identification number | Short_description |
| --- | --- |
| AT5G62060 | F-box and associated interaction domains-containing protein |
| AT5G62065 | Bifunctional inhibitor/lipid-transfer protein/seed storage 2S albumin superfamily protein |
| AT5G21960 | Integrase-type DNA-binding superfamily protein |
| AT1G64470 | Ubiquitin-like superfamily protein |
| AT1G15820 | light harvesting complex photosystem II subunit 6 |
| AT3G10720 | Plant invertase/pectin methylesterase inhibitor superfamily |
| AT3G15630 | unknown protein |
| AT5G06865 | other RNA |
| AT4G33920 | Protein phosphatase 2C family protein |
| AT1G78080 | related to AP2 4 |
| AT3G24050 | GATA transcription factor 1 |
| AT1G01720 | NAC (No Apical Meristem) domain transcriptional regulator superfamily protein |
| AT5G11090 | serine-rich protein-related |
| AT3G23920 | beta-amylase 1 |
| AT1G30360 | Early-responsive to dehydration stress protein (ERD4) |
| AT3G07790 | DGCR14-related |
| AT2G47090 | zinc ion binding; nucleic acid binding |
| AT1G20440 | cold-regulated 47 |
| AT3G11420 | Protein of unknown function (DUF604) |
| AT3G59090 | tobamovirus multiplication 1 |
| AT1G72520 | PLAT/LH2 domain-containing lipoxygenase family protein |
| AT3G19580 | zinc-finger protein 2 |
| AT3G22968 | conserved peptide upstream open reading frame 59 |
| AT3G22970 | Protein of unknown function (DUF506) |
| AT5G62050 | homolog of yeast oxidase assembly 1 (OXA1) |
| AT5G61670 | unknown protein |
| AT3G15810 | Protein of unknown function (DUF567) |
| AT4G39840 | unknown protein |
| AT1G53850 | 20S proteasome alpha subunit E1 |
| AT3G46660 | UDP-glucosyl transferase 76E12 |
| AT2G29980 | fatty acid desaturase 3 |
| AT5G06390 | FASCICLIN-like arabinogalactan protein 17 precursor |
| AT5G20230 | blue-copper-binding protein |
| AT5G47260 | ATP binding; GTP binding; nucleotide binding; nucleoside-triphospliatases |
| AT5G67330 | natural resistance associated macrophage protein 4 |
| AT4G22780 | ACT domain repeat 7 |
| AT3G10930 | unknown protein |
| AT2G20585 | nuclear fusion defective 6 |
| AT4G27652 | unknown protein |
| AT1G02660 | alpha/beta-Hydrolases superfamily protein |
| AT1G51710 | ubiquitin-specific protease 6 |
| AT2G01670 | nudix hydrolase homolog 17 |
| AT1G04000 | unknown protein; BEST Arabidopsis thaliana protein match is: unknown protein (TAIR: AT5G44060.1); Has 62 Blast hits to 62 prot . . . |
| AT1G05370 | Sec14p-like phosphatidylinositol transfer family protein |
| AT1G19210 | Integrase-type DNA-binding superfamily protein |
| AT1G20450 | Dehydrin family protein |
| AT1G20510 | OPC-8: 0 CoA ligase 1 |
| AT1G25400 | unknown protein |
| AT1G27100 | Actin cross-linking protein |
| AT1G31130 | unknown protein |
| AT1G32930 | Galactosyltransferase family protein |
| AT1G45150 | unknown protein |
| AT1G49100 | Leucine-rich repeat protein kinase family protein |
| AT1G50300 | TBP-associated factor 15 |
| AT1G50430 | Ergosterol biosynthesis ERG4/ERG24 family |
| AT1G55680 | Transducin/WD40 repeat-like superfamily protein |
| AT1G59870 | ABC-2 and Plant PDR ABC-type transporter family protein |
| AT1G60110 | Mannose-binding lectin superfamily protein |
| AT1G60200 | splicing factor PWI domain-containing protein/RNA recognition motif (RRM)-containing protein |
| AT1G66730 | DNA LIGASE 6 |
| AT1G68850 | Peroxidase superfamily protein |
| AT1G70300 | K+ uptake permease 6 |
| AT1G70710 | glycosyl hydrolase 9B1 |
| AT1G72180 | Leucine-rich receptor-like protein kinase family protein |
| AT1G72460 | Leucine-rich repeat protein kinase family protein |
| AT1G73480 | alpha/beta-Hydrolases superfamily protein |
| AT1G73490 | RNA-binding (RRM/RBD/RNP motifs) family protein |
| AT1G74950 | TIFY domain/Divergent CCT motif family protein |
| AT1G76050 | Pseudouridine synthase family protein |
| AT1G76610 | Protein of unknown function, DUF617 |

TABLE 4-continued

| SCL23 direct targets identified by ChIP-chip | |
|---|---|
| Arabidopsis Genome Initiative (AGI) identification number | Short_description |
| AT1G77460 | Armadillo/beta-catenin-like repeat; C2 calcium/lipid-binding domain (CaLB) protein |
| AT1G80500 | SNARE-like superfamily protein |
| AT2G05940 | Protein kinase superfamily protein |
| AT2G06050 | oxophytodienoate-reductase 3 |
| AT2G06520 | photosystem II subunit X |
| AT2G23830 | PapD-like superfamily protein |
| AT2G24810 | Pathogenesis-related thaumatin superfamily protein |
| AT2G25270 | unknown protein; LOCATED IN: plasma membrane |
| AT2G25470 | receptor like protein 21 |
| AT2G27100 | C2H2 zinc-finger protein SERRATE (SE) |
| AT2G28350 | auxin response factor 10 |
| AT2G30580 | DREB2A-interacting protein 2 |
| AT2G32170 | S-adenosyl-L-methionine-dependent methyltransferases superfamily protein |
| AT2G34460 | NAD(P)-binding Rossmann-fold superfamily protein |
| AT2G34470 | urease accessory protein G |
| AT2G36070 | translocase inner membrane subunit 44-2 |
| AT2G40010 | Ribosomal protein L10 family protein |
| AT2G41040 | S-adenosyl-L-methionine-dependent methyltransferases superfamily protein |
| AT2G41945 | unknown protein |
| AT2G42790 | citrate synthase 3 |
| AT2G43040 | tetratricopeptide repeat (TPR)-containing protein |
| AT2G43360 | Radical SAM superfamily protein |
| AT2G45500 | AAA-type ATPase family protein |
| AT2G45620 | Nucleotidyltransferase family protein |
| AT2G45700 | sterile alpha motif (SAM) domain-containing protein |
| AT2G46520 | cellular apoptosis susceptibility protein, putative/importin-alpha re-exporter, putative |
| AT3G03990 | alpha/beta-Hydrolases superfamily protein |
| AT3G05200 | RING/U-box superfamily protein |
| AT3G07350 | Protein of unknown function (DUF506) |
| AT3G07390 | auxin-responsive family protein |
| AT3G11170 | fatty acid desaturase 7 |
| AT3G14440 | nine-cis-epoxycarotenoid dioxygenase 3 |
| AT3G20310 | ethylene response factor 7 |
| AT3G20600 | Late embryogenesis abundant (LEA) hydroxyproline-rich glycoprotein family |
| AT3G23820 | UDP-D-glucuronate 4-epimerase 6 |
| AT3G24518 | other RNA |
| AT3G24520 | heat shock transcription factor C1 |
| AT3G46658 | other RNA |
| AT3G47990 | SUGAR-INSENSITIVE 3 |
| AT3G50370 | unknown protein |
| AT3G54230 | suppressor of abi3-5 |
| AT3G55460 | SC35-like splicing factor 30 |
| AT3G56408 | other RNA |
| AT3G56410 | Protein of unknown function (DUF3133) |
| AT3G56750 | unknown protein |
| AT3G56920 | DHHC-type zinc finger family protein |
| AT3G57060 | binding |
| AT3G57470 | Insulinase (Peptidase family M16) family protein |
| AT3G58120 | Basic-leucine zipper (bZIP) transcription factor family protein |
| AT3G60440 | Phosphoglycerate mutase family protein |
| AT3G61480 | Quinoprotein amine dehydrogenase, beta chain-like; RIC1-like guanyl-nucleotide exchange factor |
| AT3G63460 | transducin family protein/WD-40 repeat family protein |
| AT3G62660 | galacturonosyltransferase-like 7 |
| AT4G00360 | cytochrome P450, family 86, subfamily A, polypeptide 2 |
| AT4G02330 | Plant invertase/pectin methylesterase inhibitor superfamily |
| AT4G05050 | ubiquitin 11 |
| AT4G05070 | Wound-responsive family protein |
| AT4G21740 | unknown protein |
| AT4G24240 | WRKY DNA-binding protein 7 |
| AT4G27410 | NAC (No Apical Meristem) domain transcriptional regulator superfamily protein |
| AT4G27520 | early nodulin-like protein 2 |
| AT4G30440 | UDP-D-glucuronate 4-epimerase 1 |
| AT4G31500 | cytochrome P450, family 83, subfamily B, polypeptide 1 |
| AT4G32060 | calcium-binding EF hand family protein |
| AT4G36648 | other RNA |
| AT4G36500 | unknown protein |
| AT4G36988 | conserved peptide upstream open reading frame 49 |
| AT4G36990 | heat shock factor 4 |
| AT5G06310 | Nucleic acid-binding, OB-fold-like protein |
| AT5G06860 | polygalacturonase inhibiting protein 1 |
| AT5G09760 | Plant invertase/pectin methylesterase inhibitor superfamily |

TABLE 4-continued

| SCL23 direct targets identified by ChIP-chip | |
|---|---|
| Arabidopsis Genome Initiative (AGI) identification number | Short_description |
| AT5G11000 | Plant protein of unknown function (DUF868) |
| AT5G20110 | Dynein light drain type 1 family protein |
| AT5G22630 | arogenate dehydratase 5 |
| AT5G24590 | TCV-interacting protein |
| AT5G24930 | CONSTANS-like 4 |
| AT5G27420 | carbon/nitrogen insensitive 1 |
| AT5G42120 | Concanavalin A-like lectin protein kinase family protein |
| AT5G42690 | Protein of unknown function, DUF547 |
| AT5G45110 | NPR1-like protein 3 |
| AT5G49410 | unknown protein |
| AT5G51500 | Plant invertase/pectin methylesterase inhibitor superfamily |
| AT5G57015 | casein kinase I-like 12 |
| AT5G57700 | BNR/Asp-box repeat family protein |
| AT5G57770 | Plant protein of unknown function (DUF828) with plant pleckstrin homology-like region |
| AT5G58690 | phosphatidylinositol-speciwc phospholipase C5 |
| AT5G60690 | Homeobox-leucine zipper family protein/lipid-binding START domain-containing protein |
| AT5G61000 | Replication factor-A protein 1-related |
| AT5G62600 | ARM repeat superfamily protein |
| AT5G63180 | Pectin lyase-like superfamily protein |
| AT5G63470 | nuclear factor Y, subunit C4 |
| AT5G67360 | Subtilase family protein |
| AT5G67460 | O-Glycosyl hydrolases family 17 protein |
| AT1G01300 | Eukaryotic aspartyl protease family protein |

TABLE 5

| SCR direct targets identified by ChIP-chip | |
|---|---|
| Arabidopsis Genome Initiative (AGI) identification number | Description |
| AT2G29220 | Concanavalin A-like lectin protein kinase family protein |
| AT5G26340 | STP13 |
| AT1G13260 | EDF4, RAV1, AP2/B3 domain transcription factor which is upregulated in response to low temperature |
| AT3G32260 | Nucleic acid-binding proteins superfamily; |
| AT1G27290 | unknown protein; |
| AT1G47570 | RING/U-box superfamily protein |
| AT5G24660 | RESPONSE TO LOW SULFUR 2 (LSU2) |
| AT3G02170 | LONGIFOLIA2 (LNG2). Regulates leaf morphology by promoting cell expansion in the leaf-length direction |
| AT4G08700 | ATPUP13. Likely involved in purine transport |
| AT5G24655 | RESPONSE TO LOW SULFUR 4 (LSU4) |
| AT4G16780 | ATHB-2; light & auxin response & development. Encodes a homeodomain-leucine zipper protein that is rapidly and strongly induced by changes in the ratio of red to far-red light. It is also involved in cell expansion and cell proliferation and in the response to auxin |
| AT3G42950 | Pectin lyase-like superfamily protein |
| AT2G07280 | unknown protein |
| AT5G43820 | Pentatricopeptide repeat (PPR) superfamily protein |
| AT1G70550 | expressed protein, similar to putative putative carboxyl-terminal peptidase |
| AT3G07360 | AtPUB9, ARABIDOPSIS THALIANA PLANT U-BOX 9 |
| AT1G03840 | MGP |
| AT3G42060 | myosin heavy chain-related |
| AT4G36920 | AP2, FL1, FLO1 |
| AT2G15420 | myosin heavy chain-related |
| AT1G69530 | expansin, ATEXP1. |
| AT2G21340 | MATE efflux family protein |
| AT1G19850 | MP, IAA24, ARF5 |
| AT2G45190 | YABBY1/abnormal floral organs protein (AFO)/filamentous flower protein (FIL) |
| AT3G45000 | ESCRT III complex, vesicle-mediated transport; SNF7 family protein. |
| AT2G23320 | WRKY15, H2O2 responsive |
| AT3G06070 | unknown protein |
| AT1G31910 | GHMP kinase family protein |
| AT2G21330 | FBA1, fructose-bisphosphate aldolase 1 |
| AT4G27430 | COP1-interacting protein 7 |

TABLE 5-continued

SCR direct targets identified by ChIP-chip

| Arabidopsis Genome Initiative (AGI) identification number | Description |
|---|---|
| AT1G71880 | SUC1, sucrose-proton symporter |
| AT3G19380 | plant U-box 25 |
| AT3G23810 | SAHH2, S-adenosyl-1-homocysteine (SAH) hydrolase 2 |
| AT5G53420 | CCT motif family protein |
| AT1G47820 | unknown protein |
| AT4G16447 | unknown protein |
| AT1G23100 | GroES-like family protein |
| AT2G19980 | CAP (Cysteine-rich secretory proteins, Antigen 5, and Pathogenesis-related 1 protein) superfamily protein) |
| AT3G66656 | AGL91 |
| AT5G24670 | EMB2820, CAP (Cysteine-rich secretory proteins, Antigen 5 |
| AT3G54240 | alpha/beta-Hydrolases superfamily protein |
| AT1G47810 | F-box and associated interaction domains-containing protein |
| AT1G45976 | S-ribonuclease binding protein 1 (SBP1) |
| AT1G09970 | RLK7, Leucine-rich receptor-like protein kinase family protein |
| AT4G39800 | myo-inositol-1-phosphate synthase 1 |
| AT4G34760 | SAUR-like auxin-responsive protein family |
| AT2G36410 | Family of unknown function (DUF662) |
| AT3G06080 | TBL10, TRICHOME BIREFRINGENCE-LIKE 10 (2nd cell wall synthesis) |
| AT5G38030 | MATE efflux family protein, similar to ripening regulated protein DDTFR18 (Lycopersicon esculentum) GI: 12231296; |
| AT3G23820 | GAE6, UDP-D-glucuronate 4-epimerase |
| AT5G40930 | TRANSLOCASE OF OUTER MEMBRANE 20-4 (component of the TOM complex involved in transport of nuclear-encoded mitochondrial proteins) |
| AT5G25220 | KNAT3, KNOTTED1-like homeobox gene 3 |
| AT5G62430 | CDF1, CYCLING DOF FACTOR 1 |
| AT1G30950 | UFO (weak allele specifically affects petal -transformation into carpel or stamen) |
| AT5G24830 | Tetratricopeptide repeat (TPR)-like superfamily protein |
| AT4G33080 | AGC (cAMP-dependent, cGMP-dependent and protein kinase C) kinase family protein |
| AT1G33590 | Leucine-rich repeat (LRR) family protein |
| AT3G11590 | unknown protein; |
| AT4G01690 | PPOX1, HEMG1, protoporphyrinogen oxidase |
| AT2G46530 | ARF11 |
| AT1G07090 | LSH6, LIGHT SENSITIVE HYPOCOTYLS 6 (LSH6) |
| AT3G03770 | Leucine-rich repeat protein kinase family protein |
| AT1G23010 | LPR1, LOW PHOSPHATE ROOT1. Encodes a protein with multicopper oxidase activity |
| AT3G19390 | Granulin repeat cysteine protease family protein; |
| AT4G28703 | RmlC-like cupins superfamily protein |
| AT3G61460 | BRH1, BRASSINOSTEROID-RESPONSIVE RING-H2; zinc finger (C3HC4-type RING finger) family protein (BRH1) |
| AT5G67350 | unknown protein |
| AT1G47660 | unknown protein |
| AT5G42790 | proteasome alpha subunit F1 |
| AT4G25480 | encodes a member of the DREB subfamily A-1 of ERF/AP2 transcription factor family (CBF3). |
| AT5G08330 | TCP family transcription factor |
| AT1G72310 | RING/U-box superfamily protein |
| AT5G67450 | ZINC-FINGER PROTEIN 1, Zinc finger (C2H2 type) protein 1 (AZF1), |
| AT4G01960 | unknown protein; |
| AT1G01650 | SIGNAL PEPTIDE PEPTIDASE-LIKE 4 |
| AT3G57860 | OSD1, OMISSION OF SECOND DIVISION (2nd in meiosis); UVI4-LIKE |
| AT5G25190 | encodes a member of the ERF (ethylene response factor) subfamily B-6 of ERF/AP2 transcription factor family |
| AT5G03140 | Concanavalin A-like lectin protein kinase family protein |
| AT1G76890 | GT-2 factor (GT2), trihelix DNA-binding protein |
| AT5G55230 | MICROTUBULE-ASSOCIATED PROTEINS 65-1; microtubule associated protein (MAP65/ASE1) family protein, low similarity to protein regulating cytokinesis 1 (PRC1) (*Homo sapiens*) |
| AT3G23040 | unknown protein |
| AT1G29195 | expressed protein |
| AT4G36860 | LIM domain-containing protein |
| AT2G44500 | O-fucosyltransferase family protein |
| AT5G51490 | Plant invertase/pectin methylesterase inhibitor superfamily |
| AT1G04240 | IAA3, SHY2, regulates multiple auxin responses in roots. |
| AT1G25390 | Protein kinase superfamily protein |
| AT2G33710 | encodes a member of the ERF (ethylene response factor) subfamily B-4 of ERF/AP2 transcription factor family. |
| AT1G53180 | unknown protein; |
| AT1G05710 | bHLH family protein |
| AT2G38120 | AUX1 |
| AT3G27020 | YELLOW STRIPE like 6 |
| AT4G35490 | MRPL11, mitochondrial ribosomal protein L11 |
| AT1G19040 | NAC (No Apical Meristem) domain transcriptional regulator superfamily protein |

TABLE 5-continued

SCR direct targets identified by ChIP-chip

| Arabidopsis Genome Initiative (AGI) identification number | Description |
|---|---|
| AT4G14770 | AtTCX2, TESMIN/TSO1-like CXC 2 |
| AT1G47870 | ATE2F2, Member of the E2F transcription factors |
| AT3G02140 | TMAC2, ABI FIVE BINDING PROTEIN 4 |
| AT1G30825 | ACTIN-RELATED PROTEIN C2A, ARPC2A, DIS2DISTORTED TRICHOMES 2 (mutant display enlarge trichomes) |
| AT1G72630 | ELF4-like 2 |
| AT3G23220 | ERF (ethylene response factor) subfamily B-3 of ERF/AP2 transcription factor family. |
| AT3G53450 | Putative lysine decarboxylase family protein |
| AT2G04550 | IBR5, indole-3-butyric acid response 5 |
| AT2G21140 | proline-rich protein 2 |
| AT1G33860 | unknown protein |
| AT5G59270 | Concanavalin A-like lectin protein kinase family protein |
| AT1G68450 | PIGMENT DEFECTIVE 337; VQ motif-containing protein, contains PF05678: VQ motif |
| AT5G67240 | small RNA degrading nuclease 3 |
| AT5G44250 | Protein of unknown function DUF829, transmembrane 53 |
| AT1G28360 | ERF domain protein 12 |
| AT3G27170 | chloride channel B |
| AT2G35960 | NDR1/HIN1-like 12 |
| AT3G25905 | CLE27, CLAVATA3/ESR-RELATED 27 |
| AT1G26920 | |
| AT1G19410 | FBD/Leucine Rich Repeat domains containing protein |
| AT1G29060 | Target SNARE coiled-coil domain protein |
| AT4G16770 | 2-oxoglutarate (2OG) and Fe(II)-dependent oxygenase superfamily protein |
| AT4G40050 | Protein of unknown function (DUF3550/UPF0682) |
| AT1G31290 | ARGONAUTE 3 |
| AT5G28770 | bZIP transcription factor family protein |
| AT3G06500 | Plant neutral invertase family protein |
| AT1G20620 | catalase 3 |
| AT1G12330 | |
| AT1G78240 | S-adenosyl-L-methionine-dependent methyltransferases superfamily protein |
| AT4G37840 | hexokinase-like 3 |
| AT4G35780 | ACT-like protein tyrosine kinase family protein |
| AT3G12130 | KH domain-containing protein/zinc finger (CCCH type) family protein |
| AT1G15670 | Galactose oxidase/kelch repeat superfamily protein |
| AT1G31350 | KAR-UP F-box 1 |
| AT1G02270 | Calcium-binding endonuclease/exonuclease/phosphatase family |
| AT3G28930 | AIG2-like (avirulence induced gene) family protein |
| AT1G13300 | myb-like transcription factor family protein |
| AT4G30140 | GDSL-like Lipase/Acylhydrolase superfamily protein |
| AT4G17670 | Protein of unknown function (DUF581) |
| AT3G24550 | proline extensin-like receptor kinase 1 |
| AT4G01680 | myb domain protein 55 |
| AT2G40750 | WRKY DNA-binding protein 54 |
| AT4G28290 | |
| AT2G01150 | RING-H2 finger protein 2B |
| AT5G17300 | Homeodomain-like superfamily protein |
| AT4G01250 | WRKY family transcription factor |
| AT3G05110 | Domain of unknown function (DUF3444) |
| AT2G46800 | zinc transporter of Arabidopsis thaliana |
| AT2G44350 | Citrate synthase family protein |
| AT5G16190 | cellulose synthase like A11 |
| AT5G53550 | YELLOW STRIPE like 3 |
| AT2G01830 | CHASE domain containing histidine kinase protein |
| AT1G68480 | C2H2 and C2HC zinc fingers superfamily protein |
| AT5G14800 | pyrroline-5- carboxylate (P5C) reductase |
| AT1G19180 | jasmonate-zim-domain protein 1 |
| AT1G50490 | ubiquitin-conjugating enzyme 20 |
| AT3G18280 | Bifunctional inhibitor/lipid-transfer protein/seed storage 2S albumin superfamily protein |
| AT3G44730 | kinesin-like protein 1 |
| AT1G23000 | Heavy metal transport/detoxification superfamily protein |
| AT2G15790 | peptidyl-prolyl cis-trans isomerase/cyclophilin-40 (CYP40)/rotamase |
| AT1G22520 | Domain of unknown function (DUF543) |
| AT2G01850 | endoxyloglucan transferase A3 |
| AT1G53170 | ethylene response factor 8 |
| AT3G50690 | Leucine-rich repeat (LRR) family protein |
| AT4G31800 | WRKY DNA-binding protein 18 |
| AT5G17840 | DnaJ/Hsp40 cysteine-rich domain superfamily protein |
| AT4G16444 | |
| AT1G52180 | Aquaporin-like superfamily protein |
| AT4G05090 | Inositol monophosphatase family protein |
| AT4G22120 | ERD (early-responsive to dehydration stress) family protein |

TABLE 5-continued

SCR direct targets identified by ChIP-chip

| Arabidopsis Genome Initiative (AGI) identification number | Description |
|---|---|
| AT3G63020 | Protein of unknown function (DUF3049) |
| AT3G15200 | Tetratricopeptide repeat (TPR)-like superfamily protein |
| AT4G21430 | Zinc finger, RING-type; Transcription factor jumonji/aspartyl beta-hydroxylase |
| AT1G14920 | GRAS family transcription factor family protein |
| AT5G17760 | P-loop containing nucleoside triphosphate hydrolases superfamily protein |
| AT5G57360 | Galactose oxidase/kelch repeat superfamily protein |
| AT1G21010 | |
| AT5G67340 | ARM repeat superfamily protein |
| AT1G24625 | zinc finger protein 7 |
| AT2G41310 | response regulator 3 |
| AT2G36970 | UDP-Glycosyltransferase superfamily protein |
| AT5G13820 | telomeric DNA binding protein 1 |
| AT5G53120 | spermidine synthase 3 |
| AT3G18060 | transducin family protein/WD-40 repeat family protein |
| AT2G03240 | EXS (ERD1/XPR1/SYG1) family protein |
| AT5G14080 | Tetratricopeptide repeat (TPR)-like superfamily protein |
| AT3G63040 | expressed protein |
| AT5G67360 | Subtilase family protein |
| AT2G28570 | unknown protein; |
| AT5G35450 | Disease resistance protein (CC-NBS-LRR class) family |
| AT1G48330 | |
| AT4G19710 | aspartate kinase-homoserine dehydrogenase ii |
| AT5G03210 | unknown protein; |
| AT3G05320 | O-fucosyltransferase family protein |
| AT5G53590 | SAUR-like auxin-responsive protein family |
| AT1G59790 | Cullin family protein |
| AT5G22950 | SNF7 family protein |
| AT1G17380 | jasmonate-zim-domain protein 5 |
| AT3G16800 | Protein phosphatase 2C family protein |
| AT5G26680 | 5'-3' exonuclease family protein |
| AT4G27970 | SLAC1 homologue 2, C4-dicarboxylate transporter/malic acid transport family protein |
| AT3G10870 | methyl esterase 17 |
| AT5G51580 | unknown protein; |
| AT1G69430 | unknown protein; |
| AT2G05710 | ACO3, aconitase 3 |
| AT3G23920 | beta-amylase 1 |
| AT5G41080 | PLC-like phosphodiesterases superfamily protein |
| AT4G32620 | Enhancer of polycomb-like transcription factor protein |
| AT5G24930 | CONSTANS-like 4 |
| AT1G43730 | RNA-directed DNA polymerase (reverse transcriptase)-related family protein |
| AT5G22570 | WRKY DNA-binding protein 38 |
| AT2G17620 | Cyclin B2; 1 |
| AT4G30720 | FAD/NAD(P)-binding oxidoreductase family protein |
| AT2G39180 | CRINKLY4 related 2 |
| AT1G80450 | VQ motif-containing protein |
| AT3G03990 | alpha/beta-Hydrolases superfamily protein |
| AT1G76100 | plastocyanin 1 |
| AT5G42150 | Glutathione S-transferase family protein |
| AT5G01830 | ARM repeat superfamily protein |
| AT4G38550 | Arabidopsis phospholipase-like protein (PEARLI 4) family |
| AT5G50450 | HCP-like superfamily protein with MYND-type zinc finger |
| AT5G62040 | PEBP (phosphatidylethanolamine-binding protein) family protein |
| AT1G05860 | |
| AT5G44700 | Leucine-rich repeat transmembrane protein kinase |
| AT5G04030 | |
| AT3G02580 | sterol 1 |
| AT3G46500 | 2-oxoglutarate (2OG) and Fe(II)-dependent oxygenase superfamily protein |
| AT1G21590 | Protein kinase protein with adenine nucleotide alpha hydrolases-like domain |
| AT1G36070 | Transducin/WD40 repeat-like superfamily protein |
| AT1G48260 | CBL-interacting protein kinase 17 |
| AT4G35090 | catalase 2 |
| AT5G38790 | |
| AT1G50300 | TBP-associated factor 15 |
| AT3G55110 | ABC-2 type transporter family protein |
| AT5G51590 | AT hook motif DNA-binding family protein |
| AT4G39950 | cytochrome P450, family 79, subfamily B, polypeptide 2 |
| AT1G47780 | alpha/beta-Hydrolases superfamily protein |
| AT5G14920 | Gibberellin-regulated family protein |
| AT3G50780 | |
| AT5G16520 | |

TABLE 5-continued

SCR direct targets identified by ChIP-chip

| Arabidopsis Genome Initiative (AGI) identification number | Description |
|---|---|
| AT4G26540 | Leucine-rich repeat receptor-like protein kinase family protein |
| AT5G61660 | glycine-rich protein |
| AT1G30610 | pentatricopeptide (PPR) repeat-containing protein |
| AT1G30610 | pentatricopeptide (PPR) repeat-containing protein |
| AT2G19810 | CCCH-type zinc finger family protein |
| AT1G75540 | salt tolerance homolog2 |
| AT5G22390 | Protein of unknown function (DUF3049) |
| AT3G05840 | Protein kinase superfamily protein |
| AT2G22430 | homeobox protein 6 |
| AT2G30550 | alpha/beta-Hydrolases superfamily protein |
| AT4G27420 | ABC-2 type transporter family protein |
| AT2G39190 | Protein kinase superfamily protein |
| AT3G13110 | serine acetyltransferase 2; 2 |
| AT3G24770 | CLAVATA3/ESR-RELATED 41 |
| AT5G03320 | Protein kinase superfamily protein |
| AT4G11440 | Mitochondrial substrate carrier family protein |
| AT3G21220 | MAP kinase kinase 5 |
| AT5G24500 | |
| AT1G35614 | |
| AT3G50660 | Cytochrome P450 superfamily protein |
| AT1G70300 | K+ uptake permease 6 |
| AT5G44080 | Basic-leucine zipper (bZIP) transcription factor family protein |
| AT5G66960 | Prolyl oligopeptidase family protein |
| AT2G01890 | purple acid phosphatase 8 |
| AT1G35500 | |
| AT3G17860 | jasmonate-zim-domain protein 3 |
| AT1G50280 | Phototropic-responsive NPH3 family protein |
| AT5G55950 | Nucleotide/sugar transporter family protein |
| AT3G23050 | indole-3-acetic acid 7 |
| AT2G46420 | Plant protein 1589 of unknown function |
| AT2G01910 | Microtubule associated protein (MAP65/ASE1) family protein |
| AT1G19360 | Nucleotide-diphospho-sugar transferase family protein |
| AT5G25460 | Protein of unknown function, DUF642 |
| AT1G23020 | ferric reduction oxidase 3 |
| AT4G15920 | Nodulin MtN3 family protein |
| AT3G19680 | Protein of unknown function (DUF1005) |
| AT3G16500 | phytochrome-associated protein 1 |
| AT5G22860 | Serine carboxypeptidase S28 family protein |
| AT3G10530 | Transducin/WD40 repeat-like superfamily protein |
| AT1G52200 | PLAC8 family protein |
| AT1G69170 | Squamosa promoter-binding protein-like (SBP domain) transcription factor family protein |
| AT3G53670 | |
| AT1G65420 | Protein of unknown function (DUF565) |
| AT3G54570 | Plant calmodulin-binding protein-related |
| AT5G04560 | HhH-GPD base excision DNA repair family protein |
| AT2G26040 | PYR1-like 2 |
| AT1G71400 | receptor like protein 12 |
| AT4G20790 | Leucine-rich repeat protein kinase family protein |
| AT1G28230 | purine permease 1 |
| AT4G04750 | Major facilitator superfamily protein |
| AT3G13750 | beta galactosidase 1 |
| AT3G25805 | |
| AT4G25835 | P-loop containing nucleoside triphosphate hydrolases superfamily protein |
| AT1G69080 | Adenine nucleotide alpha hydrolases-like superfamily protein |
| AT3G56070 | rotamase cyclophilin 2 |
| AT2G15640 | F-box family protein |
| AT5G15160 | BANQUO 2 |
| AT2G44940 | Integrase-ripe DNA-binding superfamily protein |
| AT4G20240 | cytochrome P450, family 71, subfamily A, polypeptide 27 |
| AT2G18050 | histone H1-3 |
| AT2G23340 | DREB and EAR motif protein 3 |
| AT5G49570 | peptide-N-glycanase 1 |
| AT1G21340 | Dof-type zinc finger DNA-binding family protein |
| AT2G17110 | Protein of unknown function (DUF630 and DUF632) |
| AT2G13840 | Polymerase/histidinol phosphatase-like |
| AT4G25470 | C-repeat/DRE binding factor 2 |
| AT5G36260 | Eukaryotic aspartyl protease family protein |
| AT1G20900 | Predicted AT-hook DNA-binding family protein |
| AT1G70420 | Protein of unknown function (DUF1645) |
| AT4G27440 | protochlorophyllide oxidoreductase B |
| AT5G07590 | Transducin/WD40 repeat-like superfamily protein |

TABLE 5-continued

SCR direct targets identified by ChIP-chip

| Arabidopsis Genome Initiative (AGI) identification number | Description |
|---|---|
| AT1G07280 | Tetratricopeptide repeat (TPR)-like superfamily protein |
| AT3G47390 | cytidine/deoxycytidylate deaminase family protein |
| AT1G55370 | NDH-dependent cyclic electron flow 5 |
| AT1G61667 | Protein of unknown function, DUF538 |
| AT3G43700 | BTB-POZ and MATH domain 6 |
| AT1G59980 | ARG1-like 2 |
| AT3G46900 | copper transporter 2 |
| AT5G61420 | myb domain protein 28 |
| AT5G45830 | delay of germination 1 |
| AT3G54190 | Transducin/WD40 repeat-like superfamily protein |
| AT4G36910 | Cystathionine beta-synthase (CBS) family protein |
| AT4G39780 | Integrase-type DNA-binding superfamily protein |
| AT5G52860 | ABC-2 type transporter family protein |
| AT2G14910 | unknown protein |
| AT3G23750 | Leucine-rich repeat protein kinase family protein |
| AT4G39410 | WRKY DNA-binding protein 13 |
| AT3G52890 | KCBP-interacting protein kinase |
| AT1G69580 | Homeodomain-like superfamily protein |
| AT5G57070 | hydroxyproline-rich glycoprotein family protein |
| AT1G33770 | Protein kinase superfamily protein |
| AT2G23470 | Protein of unknown function, DUF647 |
| AT5G05440 | Polyketide cyclase/dehydrase and lipid transport superfamily protein |
| AT3G16860 | COBRA-like protein 8 precursor |
| AT2G10020 | unknown protein |
| AT5G45280 | Pectinacetylesterase family protein |
| AT1G71970 | unknown protein |
| AT5G18270 | Arabidopsis NAC domain containing protein 87 |
| AT1G78090 | trehalose-6-phosphate phosphatase |
| AT5G07440 | glutamate dehydrogenase 2 |
| AT2G22860 | phytosulfokine 2 precursor |
| AT3G45260 | C2H2-like zinc finger protein |
| AT3G56050 | Protein kinase family protein |
| AT2G01670 | nudix hydrolase homolog 17 |
| AT1G46696 | Protein of unknown function, DUF601 |
| AT3G06130 | Heavy metal transport/detoxification superfamily protein |
| AT5G08139 | RING/U-box superfamily protein |
| AT1G22640 | myb domain protein 3 |
| AT1G07570 | Protein kinase superfamily protein |
| AT5G44170 | S-adenosyl-L-methionine-dependent methyltransferases superfamily protein |
| AT1G70710 | glycosyl hydrolase 9B1 |
| AT5G47240 | nudix hydrolase homolog 8 |
| AT4G23690 | Disease resistance-responsive (dirigent-like protein) family protein |
| AT4G26210 | Mitochondrial ATP synthase subunit G protein |
| AT1G44350 | IAA-leucine resistant (ILR)-like gene 6 |
| AT4G38940 | Galactose oxidase/kelch repeat superfamily protein |
| AT3G12920 | SBP (S-ribonuclease binding protein) family protein |
| AT3G61590 | Galactose oxidase/kelch repeat superfamily protein |
| AT3G61590 | Galactose oxidase/kelch repeat superfamily protein |
| AT5G44190 | GOLDEN2-like 2 |
| AT1G69560 | myb domain protein 105 |
| AT2G40110 | Yippee family putative zinc-binding protein |
| AT4G08960 | phosphotyrosyl phosphatase activator (PTPA) family protein |
| AT2G24330 | Protein of unknown function (DUF2296) |
| AT3G11410 | protein phosphatase 2CA |
| AT1G52320 | unknown protein |
| AT1G25560 | AP2/B3 transcription factor family protein |
| AT1G01360 | regulatory component of ABA receptor 1 |
| AT5G10780 | unknown protein |
| AT5G59820 | C2H2-type zinc finger family protein |
| AT2G40470 | LOB domain-containing protein 15 |
| AT1G30110 | nudix hydrolase homolog 25 |
| AT3G08660 | Phototropic-responsive NPH3 family protein |
| AT4G11380 | Adaptin family protein |
| AT5G47940 | unknown protein |
| AT1G21080 | DNAJ heat shock N-terminal domain-containing protein |
| AT2G32980 | unknown protein |
| AT3G55980 | salt-inducible zinc finger 1 |
| AT1G02620 | Ras-related small GTP-binding family protein |
| AT3G57550 | guanylate kinase |
| AT1G12940 | nitrate transporter2 |
| AT4G37790 | Homeobox-leucine zipper protein family |

TABLE 5-continued

SCR direct targets identified by ChIP-chip

| Arabidopsis Genome Initiative (AGI) identification number | Description |
|---|---|
| AT5G28620 | protein kinase C-related |
| AT5G08130 | basic helix-loop-helix (bHLH) DNA-binding superfamily protein |
| AT5G65230 | myb domain protein 53 |
| AT2G45770 | signal recognition particle receptor protein, chloroplast (FTSY) |
| AT3G27570 | Sucrase/ferredoxin-like family protein |
| AT1G15550 | gibberellin 3-oxidase 1 |
| AT3G30820 | Arabidopsis retrotransposon ORF-1 protein |
| AT1G01140 | CBL-interacting protein kinase 9 |
| AT5G28020 | cysteine synthase D2 |
| AT1G07540 | TRF-like 2 |
| AT5G36870 | glucan synthase-like 9 |
| AT2G47190 | myb domain protein 2 |
| AT4G14500 | Polyketide cyclase/dehydrase and lipid transport superfamily protein |
| AT5G18610 | Protein kinase superfamily protein |
| AT2G39380 | exocyst subunit exo70 family protein H2 |
| AT5G25930 | Protein kinase family protein with leucine-rich repeat domain |
| AT1G43890 | RAB GTPASE HOMOLOG B18 |
| AT3G14450 | CTC-interacting domain 9 |
| AT1G02450 | NIM1-interacting 1 |
| AT1G35350 | EXS (ERD1/XPR1/SYG1) family protein |
| AT1G47128 | Granulin repeat cysteine protease family protein |
| AT4G16110 | response regulator 2 |
| AT2G15695 | Protein of unknown function DUF829, transmembrane 53 |
| AT3G49590 | Autophagy-related protein 13 |
| AT4G13810 | receptor like protein 47 |
| AT2G26260 | 3beta-hydroxysteroid-dehydrogenase/decarboxylase isoform 2 |
| AT1G01260 | basic helix-loop-helix (bHLH) DNA-binding superfamily protein |
| AT1G12430 | armadillo repeat kinesin 3 |
| AT1G60060 | Serine/threonine-protein kinase WNK (With No Lysine)-related |
| AT3G57950 | unknown protein |
| AT3G27260 | global transcription factor group E8 |
| AT2G40690 | NAD-dependent glycerol-3-phosphate dehydrogenase family protein |
| AT5G27700 | Ribosomal protein S21e |
| AT5G04590 | sulfite reductase |
| AT2G24740 | SET domain group 21 |
| AT4G35930 | F-box family protein |
| AT5G12990 | CLAVATA3/ESR-RELATED 40 |
| AT5G02640 | unknown protein |
| AT3G61470 | photosystem I light harvesting complex gene 2 |
| AT3G13890 | myb domain protein 26 |
| AT1G19835 | Plant protein of unknown function (DUF869) |
| AT2G14110 | Haloacid dehalogenase-like hydrolase (HAD) superfamily protein |
| AT2G45970 | cytochrome P450, family 86, subfamily A, polypeptide 8 |
| AT4G04210 | plant UBX domain containing protein 4 |
| AT5G59650 | Leucine-rich repeat protein kinase family protein |
| AT2G28690 | Protein of unknown function (DUF1635) |
| AT2G18960 | H(+)-ATPase 1 |
| AT3G21670 | Major facilitator superfamily protein |
| AT1G06400 | Ras-related small GTP-binding family protein |
| AT2G29670 | Tetratricopeptide repeat (TPR)-like superfamily protein |
| AT5G20250 | Raffinose synthase family protein |
| AT1G18710 | myb domain protein 47 |
| AT4G38950 | ATP binding microtubule motor family protein |
| AT4G14230 | CBS domain-containing protein with a domain of unknown function (DUF21) |
| AT4G11330 | MAP kinase 5 |
| AT2G39950 | unknown protein |
| AT3G63010 | alpha/beta-Hydrolases superfamily protein |
| AT4G39400 | Leucine-rich receptor-like protein kinase family protein |
| AT5G43680 | unknown protein |
| AT3G44330 | unknown protein |
| AT5G37790 | Protein kinase superfamily protein |
| AT3G29780 | ralf-like 27 |
| AT3G23240 | ethylene response factor 1 |
| AT2G34720 | nuclear factor Y, subunit A4 |
| AT2G17120 | lysm domain GPI-anchored protein 2 precursor |
| AT1G10180 | unknown protein |
| AT4G30020 | PA-domain containing subtilase family protein |
| AT1G30360 | Early-responsive to dehydration stress protein (ERD4) |
| AT2G14060 | S-adenosyl-L-methionine-dependent methyltransferases superfamily protein |
| AT2G23300 | Leucine-rich repeat protein kinase family protein |
| AT4G37470 | alpha/beta-Hydrolases superfamily protein |

TABLE 5-continued

SCR direct targets identified by ChIP-chip

| Arabidopsis Genome Initiative (AGI) identification number | Description |
|---|---|
| AT3G47500 | cycling DOF factor 3 |
| AT4G35920 | PLAC8 family protein |
| AT5G63580 | flavonol synthase 2 |
| AT1G76420 | NAC (No Apical Meristem) domain transcriptional regulator superfamily protein |
| AT2G33320 | Calcium-dependent lipid-binding (CaLB domain) family protein |
| AT4G37630 | cyclin d5; 1 |
| AT1G50310 | sugar transporter 9 |
| AT4G12480 | Bifunctional inhibitor/lipid-transfer protein/seed storage 2S albumin superfamily protein |
| AT4G20010 | plastid transcriptionally active 9 |
| AT4G27980 | Domain of unknown function (DUF3444) |
| AT5G51770 | Protein kinase superfamily protein |
| AT3G50300 | HXXXD-type acyl-transferase family protein |
| AT1G36000 | LOB domain-containing protein 5 |
| AT2G22490 | Cyclin D2; 1 |
| AT1G50730 | unknown protein |
| AT1G77750 | Ribosomal protein S13/S18 family |
| AT3G14050 | RELA/SPOT homolog 2 |
| AT1G76510 | ARID/BRIGHT DNA-binding domain-containing protein |
| AT2G13810 | AGD2-like defense response protein 1 |
| AT1G23860 | RS-containing zinc finger protein 21 |
| AT5G47280 | ADR1-like 3 |
| AT3G07190 | B-cell receptor-associated protein 31-like |
| AT3G52780 | Purple acid phosphatases superfamily protein |
| AT5G05690 | Cytochrome P450 superfamily protein |
| AT3G26130 | Cellulase (glycosyl hydrolase family 5) protein |
| AT1G43810 | unknown protein |
| AT5G55120 | galactose-1-phosphate guanylyltransferase (GDP)s; GDP-D-glucose phosphorylases; quercetin 4'-O-glucosyltransferases |
| AT5G67440 | Phototropic-responsive NPH3 family protein |
| AT3G20370 | TRAF-like family protein |
| AT5G35460 | unknown protein |
| AT1G41830 | SKU5-similar 6 |
| AT3G57940 | Domain of unknown function (DUF1726); Putative ATPase (DUF699) |
| AT3G14440 | nine-cis-epoxycarotenoid dioxygenase 3 |
| AT4G19440 | Tetratricopeptide repeat (TPR)-like superfamily protein |
| AT2G15090 | 3-ketoacyl-CoA synthase 8 |
| AT3G47370 | Ribosomal protein S10p/S20e family protein |
| AT1G26620 | Plant protein of unknown function (DUF863) |
| AT4G14490 | SMAD/FHA domain-containing protein |
| AT3G11980 | Jojoba acyl CoA reductase-related male sterility protein |
| AT2G31820 | Ankyrin repeat family protein |
| AT2G22560 | Kinase interacting (KIP1-like) family protein |
| AT3G52480 | unknown protein |
| AT3G12840 | unknown protein |
| AT5G25830 | GATA transcription factor 12 |
| AT2G01900 | DNAse I-like superfamily protein |
| AT4G12990 | unknown protein |
| AT4G27400 | Late embryogenesis abundant (LEA) protein-related |
| AT2G36960 | TSL-kinase interacting protein 1 |
| AT1G69420 | DHHC-type zinc finger family protein |
| AT3G57370 | Cyclin family protein |
| AT1G30140 | unknown protein |
| AT5G51500 | Plant invertase/pectin methylesterase inhibitor superfamily |
| AT2G45700 | sterile alpha motif (SAM) domain-containing protein |
| AT3G48640 | unknown protein |
| AT2G36090 | F-box family protein |
| AT1G76620 | Protein of unknown function, DUF547 |
| AT2G46620 | P-loop containing nucleoside triphosphate hydrolases superfamily protein |
| AT3G27380 | succinate dehydrogenase 2-1 |
| AT4G36520 | Chaperone DnaJ-domain superfamily protein |
| AT3G05800 | AtBS1 (activation-tagged BRI1 suppressor 1)-interacting factor 1 |
| AT3G58890 | RNI-like superfamily protein |
| AT5G66390 | Peroxidase superfamily protein |
| AT1G07795 | unknown protein |
| AT4G39000 | glycosyl hydrolase 9B17 |
| AT1G78260 | RNA-binding (RRM/RBD/RNP motifs) family protein |
| AT1G51110 | Plastid-lipid associated protein PAP/fibrillin family protein |
| AT5G28040 | DNA-binding storekeeper protein-related transcriptional regulator |
| AT3G27360 | Histone superfamily protein |
| AT1G72700 | ATPase E1-E2 type family protein/haloacid dehalogenase-like hydrolase family protein |
| AT3G06200 | P-loop containing nucleoside triphosphate hydrolases superfamily protein |

TABLE 5-continued

SCR direct targets identified by ChIP-chip

| Arabidopsis Genome Initiative (AGI) identification number | Description |
|---|---|
| AT4G33770 | Inositol 1,3,4-trisphosphate 5/6-kinase family protein |
| AT3G61910 | NAC domain protein 66 |
| AT3G51430 | Calcium-dependent phosphotriesterase superfamily protein |
| AT2G25270 | unknown protein |
| AT4G35730 | Regulator of Vps4 activity in the MVB pathway protein |
| AT5G23610 | unknown protein |
| AT5G40480 | embryo defective 3012 |
| AT4G36110 | SAUR-like auxin-responsive protein family |
| AT1G69750 | cytochrome c oxidase 19-2 |
| AT2G20110 | Tesmin/TSO1-like CXC domain-containing protein |
| AT1G24490 | OxaA/YidC-like membrane insertion protein |
| AT3G13810 | indeterminate(ID)-domain 11 |
| AT5G41180 | leucine-rich repeat transmembrane protein kinase family protein |
| AT5G10140 | K-box region and MADS-box transcription factor family protein |
| AT1G53325 | F-box associated ubiquitination effector family protein |
| AT5G01020 | Protein kinase superfamily protein |
| AT4G39680 | SAP domain-containing protein |
| AT2G37210 | lysine decarboxylase family protein |
| AT5G11040 | TRS120 |
| AT2G44830 | Protein kinase superfamily protein |
| AT1G61900 | unknown protein |
| AT3G63050 | unknown protein |
| AT4G28080 | Tetratricopeptide repeat (TPR)-like superfamily protein |
| AT2G02520 | RNA-directed DNA polymerase (reverse transcriptase)-related family protein |
| AT1G71890 | Major facilitator superfamily protein |
| AT3G48000 | aldehyde dehydrogenase 2B4 |
| AT1G77870 | membrane-anchored ubiquitin-fold protein 5 precursor |
| AT2G42610 | Protein of unknown function (DUF640) |
| AT4G24780 | Pectin lyase-like superfamily protein |
| AT4G34138 | UDP-glucosyl transferase 73B1 |
| AT5G54510 | Auxin-responsive GH3 family protein |
| AT1G79430 | Homeodomain-like superfamily protein |
| AT1G54130 | RELA/SPOT homolog 3 |
| AT1G23440 | Peptidase C15, pyroglutamyl peptidase I-like |
| AT5G55970 | RING/U-box superfamily protein |
| AT1G59780 | NB-ARC domain-containing disease resistance protein |
| AT3G50770 | calmodulin-like 41 |
| AT3G63210 | Protein of unknown function (DUF581) |
| AT2G46610 | RNA-binding (RRM/RBD/RNP motifs) family protein |
| AT5G22640 | MORN (Membrane Occupation and Recognition Nexus) repeat-containing protein |
| AT5G64980 | unknown protein |
| AT1G56160 | myb domain protein 72 |
| AT5G21100 | Plant L-ascorbate oxidase |
| AT3G46570 | Glycosyl hydrolase superfamily protein |
| AT1G49490 | Leucine-rich repeat (LRR) family protein |
| AT1G23090 | sulfate transporter 91 |
| AT3G50500 | SNF1-related protein kinase 2 |
| AT3G20980 | Gag-Pol-related retrotransposon family protein |
| AT2G41190 | Transmembrane amino acid transporter family protein |
| AT1G17420 | lipoxygenase 3 |
| AT4G12330 | cytochrome P450, family 706, subfamily A, polypeptide 7 |
| AT2G36950 | Heavy metal transport/detoxification superfamily protein |
| AT3G05050 | Protein kinase superfamily protein |
| AT3G08620 | RNA-binding KH domain-containing protein |
| AT1G20580 | Small nuclear ribonucleoprotein family protein |
| AT4G29810 | MAP kinase kinase 2 |
| AT3G27660 | oleosin 4 |
| AT1G73490 | RNA-binding (RRM/RBD/RNP motifs) family protein |
| AT1G44835 | YbaK/aminoacyl-tRNA synthetase-associated domain |
| AT5G15960 | stress-responsive protein (KIN1)/stress-induced protein (KIN1) |
| AT5G13560 | unknown protein |
| AT4G32760 | ENTH/VHS/GAT family protein |
| AT4G23890 | unknown protein |
| AT1G18190 | golgin candidate 2 |
| AT2G35230 | VQ motif-containing protein |
| AT1G73050 | Glucose-methanol-choline (GMC) oxidoreductase family protein |
| AT1G71330 | non-intrinsic ABC protein 5 |
| AT2G27090 | Protein of unknown function (DUF630 and DUF632) |
| AT5G03690 | Aldolase superfamily protein |
| AT5G47820 | P-loop containing nucleoside triphosphate hydrolases superfamily protein |
| AT5G10020 | Leucine-rich receptor-like protein kinase family protein |

TABLE 5-continued

SCR direct targets identified by ChIP-chip

| Arabidopsis Genome Initiative (AGI) identification number | Description |
|---|---|
| AT1G27000 | Protein of unknown function (DUF1664) |
| AT2G21390 | Coatomer, alpha subunit |
| AT5G50400 | purple acid phosphatase 27 |
| AT1G02300 | Cysteine proteinases superfamily protein |
| AT5G12330 | Lateral root primordium (LRP) protein-related |
| AT5G46250 | RNA-binding protein |
| AT1G06225 | CLAVATA3/ESR-RELATED 3 |
| AT1G75460 | ATP-dependent protease La (LON) domain protein |
| AT5G62940 | Dof-type zinc finger DNA-binding family protein |
| AT5G24470 | pseudo-response regulator 5 |
| AT1G53050 | Protein kinase superfamily protein |
| AT4G33560 | Wound-responsive family protein |
| AT1G14690 | microtubule-associated protein 65-7 |
| AT1G49940 | unknown protein |
| AT1G02330 | unknown protein |
| AT1G51100 | unknown protein |
| AT3G30350 | unknown protein |
| AT1G76880 | Duplicated homeodomain-like superfamily protein |
| AT2G17390 | ankyrin repeat-containing 2B |
| AT4G36010 | Pathogenesis-related thaumatin superfamily protein |
| AT1G65580 | Endonuclease/exonuclease/phosphatase family protein |
| AT1G23870 | trehalose-phosphatase/synthase 9 |
| AT4G12360 | Bifunctional inhibitor/lipid-transfer protein/seed storage 2S albumin superfamily protein |
| AT5G56070 | unknown protein |
| AT5G53540 | P-loop containing nucleoside triphosphate hydrolases superfamily protein |
| AT2G41330 | Glutaredoxin family protein |
| AT1G52690 | Late embryogenesis abundant protein (LEA) family protein |
| AT5G02590 | Tetratricopeptide repeat (TPR)-like superfamily protein |
| AT1G67720 | Leucine-rich repeat protein kinase family protein |
| AT5G01190 | laccase 10 |
| AT2G41660 | Protein of unknown function, DUF617 |
| AT1G76520 | Auxin efflux carrier family protein |
| AT3G04060 | NAC domain containing protein 46 |
| AT1G31300 | TRAM, LAG1 and CLN8 (TLC) lipid-sensing domain containing protein |
| AT2G17260 | glutamate receptor 2 |
| AT2G41760 | unknown protein |
| AT4G22010 | SKU5 similar 4 |
| AT3G20810 | 2-oxoglutarate (2OG) and Fe(II)-dependent oxygenase superfamily protein |
| AT1G70430 | Protein kinase superfamily protein |
| AT5G52110 | Protein of unknown function (DUF2930) |
| AT4G08850 | Leucine-rich repeat receptor-like protein kinase family protein |
| AT2G30020 | Protein phosphatase 2C family protein |
| AT1G27980 | dihydrosphingosine phosphate lyase |
| AT5G08590 | SNF1-related protein kinase 2.1 |
| AT3G09920 | phosphatidyl inositol monophosphate 5 kinase |
| AT2G07050 | cycloartenol synthase 1 |
| AT1G48470 | glutamine synthetase 1; 5 |
| AT1G70060 | SIN3-like 4 |
| AT3G20340 | unknown protein |
| AT2G28360 | SIT4 phosphatase-associated family protein |
| AT2G20970 | unknown protein |
| AT1G09160 | Protein phosphatase 2C family protein |
| AT2G34710 | Homeobox-leucine zipper family protein/lipid-binding START domain-containing protein |
| AT1G66860 | Class I glutamine amidotransferase-like superfamily protein |
| AT5G45390 | CLP protease P4 |
| AT5G18130 | unknown protein |
| AT5G18130 | unknown protein |
| AT2G16950 | transportin 1 |
| AT2G02070 | indeterminate(ID)-domain 5 |
| AT5G18490 | Plant protein of unknown function (DUF946) |
| AT1G09390 | GDSL-like Lipase/Acylhydrolase superfamily protein |
| AT2G47410 | WD40/YVTN repeat-like-containing domain; Bromodomain |
| AT2G34700 | Pollen Ole e 1 allergen and extensin family protein |
| AT1G68530 | 3-ketoacyl-CoA synthase 6 |
| AT4G34590 | G-box binding factor 6 |
| AT2G26880 | AGAMOUS-like 41 |
| AT2G32540 | cellulose synthase-like B4 |
| AT4G36810 | geranylgeranyl pyrophosphate synthase 1 |
| AT3G51830 | SAC domain-containing protein 8 |
| AT2G46690 | SAUR-like auxin-responsive protein family |
| AT3G12290 | Amino acid dehydrogenase family protein |

TABLE 5-continued

SCR direct targets identified by ChIP-chip

| Arabidopsis Genome Initiative (AGI) identification number | Description |
|---|---|
| AT3G27110 | Peptidase family M48 family protein |
| AT3G56100 | meristematic receptor-like kinase |
| AT3G53460 | chloroplast RNA-binding protein 29 |
| AT1G07870 | Protein kinase superfamily protein |
| AT3G51860 | cation exchanger 3 |
| AT2G26510 | Xanthine/uracil permease family protein |
| AT5G03290 | isocitrate dehydrogenase V |
| AT1G04620 | coenzyme F420 hydrogenase family/dehydrogenase, beta subunit family |
| AT3G28480 | Oxoglutarate/iron-dependent oxygenase |
| AT1G17700 | prenylated RAB acceptor 1.F1 |
| AT1G35560 | TCP family transcription factor |
| AT2G35075 | unknown protein |
| AT5G60750 | CAAX amino terminal protease family protein |
| AT3G14067 | Subtilase family protein |
| AT2G33380 | Caleosin-related family protein |
| AT2G33380 | Caleosin-related family protein |
| AT5G41100 | unknown protein |
| AT1G22530 | PATELLIN 2 |
| AT5G43360 | phosphate transporter 1; 3 |
| AT4G08920 | cryptochrome 1 |
| AT1G78080 | related to AP2 4 |
| AT5G24530 | 2-oxoglutarate (2OG) and Fe(II)-dependent oxygenase superfamily protein |
| AT1G20330 | sterol methyltransferase 2 |
| AT3G44990 | xyloglucan endo-transglycosylase-related 8 |
| AT5G66570 | PS II oxygen-evolving complex 1 |
| AT3G24590 | plastidic type i signal peptidase 1 |
| AT2G19190 | FLG22-induced receptor-like kinase 1 |
| AT1G23780 | F-box family protein |
| AT5G44230 | Pentatricopeptide repeat (PPR) superfamily protein |
| AT3G10550 | Myotubularin-like phosphatases II superfamily |
| AT1G68680 | unknown protein |
| AT2G39230 | LATERAL ORGAN JUNCTION |
| AT4G14000 | Putative methyltransferase family protein |
| AT5G09760 | Plant invertase/pectin methylesterase inhibitor superfamily |
| AT1G53645 | hydroxyproline-rich glycoprotein family protein |
| AT4G11980 | nudix hydrolase homolog 14 |
| AT1G79080 | Pentatricopeptide repeat (PPR) superfamily protein |
| AT1G43000 | PLATZ transcription factor family protein |
| AT1G58370 | glycosyl hydrolase family 10 protein/carbohydrate-binding domain-containing protein |
| AT3G15150 | RING/U-box superfamily protein |
| AT5G10290 | leucine-rich repeat transmembrane protein kinase family protein |
| AT5G16640 | Pentatricopeptide repeat (PPR) superfamily protein |
| AT1G73500 | MAP kinase kinase 9 |
| AT3G51120 | DNA binding; zinc ion binding; nucleic acid binding; nucleic acid binding |
| AT1G62800 | aspartate aminotransferase 4 |
| AT3G15880 | WUS-interacting protein 2 |
| AT5G64560 | magnesium transporter 9 |
| AT1G62830 | LSD1-like 1 |
| AT1G69920 | glutathione S-transferase TAU 12 |
| AT2G17600 | Cysteine/Histidine-rich C1 domain family protein |
| AT4G00630 | K+ efflux antiporter 2 |
| AT4G32390 | Nucleotide-sugar transporter family protein |
| AT3G60510 | ATP-dependent caseinolytic (Clp) protease/crotonase family protein |
| AT2G24810 | Pathogenesis-related thaumatin superfamily protein |
| AT3G49560 | Mitochondrial import inner membrane translocase subunit Tim17/Tim22/Tim23 family protein |
| AT3G14670 | unknown protein |
| AT1G07890 | ascorbate peroxidase 1 |
| AT4G38760 | Protein of unknown function (DUF3414) |
| AT2G30210 | laccase 3 |
| AT1G73910 | actin-related proteins 4A |
| AT3G57380 | Glycosyltransferase family 61 protein |
| AT4G20800 | FAD-binding Berberine family protein |
| AT1G29400 | MEI2-like protein 5 |
| AT5G53290 | cytokinin response factor 3 |
| AT1G71010 | FORMS APLOID AND BINUCLEATE CELLS 1C |
| AT4G32750 | unknown protein |
| AT2G23360 | Plant protein of unknown function (DUF869) |
| AT5G08580 | Calcium-binding EF hand family protein |
| AT5G61340 | unknown protein |
| AT1G05850 | Chitinase family protein |
| AT2G02810 | UDP-galactose transporter 1 |

TABLE 5-continued

SCR direct targets identified by ChIP-chip

| Arabidopsis Genome Initiative (AGI) identification number | Description |
| --- | --- |
| AT1G13950 | eukaryotic elongation factor 5A-1 |
| AT2G02950 | phytochrome kinase substrate 1 |
| AT1G63850 | BTB/POZ domain-containing protein |
| AT2G28070 | ABC-2 type transporter family protein |
| AT1G42470 | Patched family protein |
| AT1G45616 | receptor like protein 6 |
| AT1G61500 | S-locus lectin protein kinase family protein |
| AT3G23090 | TPX2 (targeting protein for Xklp2) protein family |
| AT4G01730 | DHHC-type zinc finger family protein |
| AT5G35730 | EXS (ERD1/XPR1/SYG1) family protein |
| AT4G18600 | SCAR family protein |
| AT4G18610 | Protein of unknown function (DUF640) |
| AT5G07010 | sulfotransferase 2A |
| AT5G65210 | bZIP transcription factor family protein |
| AT3G24503 | aldehyde dehydrogenase 2C4 |
| AT3G16850 | Pectin lyase-like superfamily protein |
| AT4G13450 | Adenine nucleotide alpha hydrolases-like superfamily protein |
| AT3G04230 | Ribosomal protein S5 domain 2-like superfamily protein |
| AT4G29700 | Alkaline-phosphatase-like family protein |
| AT5G67190 | DREB and EAR motif protein 2 |
| AT5G65310 | homeobox protein 5 |
| AT4G01120 | G-box binding factor 2 |
| AT5G04400 | NAC domain containing protein 77 |
| AT5G49400 | zinc knuckle (CCHC-type) family protein |
| AT3G51680 | NAD(P)-binding Rossmann-fold superfamily protein |
| AT2G46370 | Auxin-responsive GH3 family protein |
| AT3G08600 | Protein of unknown function (DUF1191) |
| AT1G74670 | Gibberellin-regulated family protein |
| AT5G06700 | Plant protein of unknown function (DUF828) |
| AT5G45070 | phloem protein 2-A8 |
| AT1G26730 | EXS (ERD1/XPR1/SYG1) family protein |
| AT3G12110 | actin-11 |
| AT3G15530 | S-adenosyl-L-methionine-dependent methyltransferases superfamily protein |
| AT5G03680 | Duplicated homeodomain-like superfamily protein |
| AT3G25480 | Rhodanese/Cell cycle control phosphatase superfamily protein |
| AT3G05630 | phospholipase D P2 |
| AT3G11670 | UDP-Glycosyltransferase superfamily protein |
| AT2G16710 | Iron-sulphur cluster biosynthesis family protein |
| AT3G60570 | expansin B5 |
| AT3G21090 | ABC-2 type transporter family protein |
| AT5G03880 | Thioredoxin family protein |
| AT4G29010 | Enoyl-CoA hydratase/isomerase family |
| AT5G17570 | TatD related DNase |
| AT5G66730 | C2H2-like zinc finger protein |
| AT4G39840 | unknown protein |
| AT1G71720 | Nucleic acid-binding proteins superfamily |
| AT2G06850 | xyloglucan endotransglucosylase/hydrolase 4 |
| AT1G08180 | unknown protein |
| AT5G53410 | unknown protein |
| AT5G07630 | lipid transporters |
| AT1G58340 | MATE efflux family protein |
| AT3G21770 | Peroxidase superfamily protein |
| AT1G10030 | homolog of yeast ergosterol28 |
| AT2G03020 | Heat shock protein HSP20/alpha crystallin family |
| AT2G19760 | profilin 1 |
| AT4G15310 | cytochrome P450, family 702, subfamily A, polypeptide 3 |
| AT2G43510 | trypsin inhibitor protein 1 |
| AT1G13250 | galacturonosyltransferase-like 3 |
| AT1G34130 | staurosporin and temperature sensitive 3-like b |
| AT3G22630 | 20S proteasome beta subunit D1 |
| AT4G20740 | Pentatricopeptide repeat (PPR-like) superfamily protein |
| AT1G19090 | receptor-like serine/threonine kinase 2 |
| AT4G37870 | phosphoenolpyruvate carboxykinase 1 |
| AT2G20240 | Protein of unknown function (DUF3741) |
| AT3G52960 | Thioredoxin superfamily protein |
| AT1G27320 | histidine kinase 3 |
| AT5G28560 | unknown protein |
| AT4G25630 | fibrillarin 2 |
| AT4G37550 | Acetamidase/Formamidase family protein |
| AT1G07680 | unknown protein |
| AT5G15540 | PHD finger family protein |

TABLE 5-continued

SCR direct targets identified by ChIP-chip

| Arabidopsis Genome Initiative (AGI) identification number | Description |
|---|---|
| AT5G51830 | pfkB-like carbohydrate kinase family protein |
| AT2G33500 | B-box type zinc finger protein with CCT domain |
| AT3G12640 | RNA binding (RRM/RBD/RNP motifs) family protein |
| AT3G13320 | cation exchanger 2 |
| AT5G42110 | unknown protein |
| AT2G34180 | CBL-interacting protein kinase 13 |
| AT5G56870 | beta-galactosidase 4 |
| AT1G26960 | homeobox protein 23 |
| AT5G30520 | unknown protein |
| AT1G30250 | unknown protein |
| AT5G11160 | adenine phosphoribosyltransferase 5 |
| AT3G06520 | agenet domain-containing protein |
| AT2G05600 | F-box associated ubiquitination effector family protein |
| AT4G01130 | GDSL-like Lipase/Acylhydrolase superfamily protein |
| AT1G21410 | F-box/RNI-like superfamily protein |
| AT1G20980 | squamosa promoter binding protein-like 14 |
| AT1G69780 | Homeobox-leucine zipper protein family |
| AT4G03510 | RING membrane-anchor 1 |
| AT4G25380 | stress-associated protein 10 |
| AT4G31720 | TBP-associated factor II 15 |
| AT4G04730 | unknown protein |
| AT4G20270 | Leucine-rich receptor-like protein kinase family protein |
| AT5G35410 | Protein kinase superfamily protein |
| AT1G61890 | MATE efflux family protein |
| AT1G12270 | stress-inducible protein, putative |
| AT2G24550 | unknown protein |
| AT4G22570 | adenine phosphoribosyl transferase 3 |
| AT1G70490 | Ras-related small GTP-binding family protein |
| AT5G09800 | ARM repeat superfamily protein |
| AT5G62620 | Galactosyltransferase family protein |
| AT2G23410 | cis-prenyltransferase |
| AT1G56210 | Heavy metal transport/detoxification superfamily protein |
| AT2G32740 | galactosyltransferase 13 |
| AT3G05860 | MADS-box transcription factor family protein |
| AT3G45620 | Transducin/WD40 repeat-like superfamily protein |
| AT1G21060 | Protein of unknown function, DUF547 |
| AT1G66390 | myb domain protein 90 |
| AT2G34555 | gibberellin 2-oxidase 3 |
| AT1G01630 | Sec14p-like phosphatidylinositol transfer family protein |
| AT2G46360 | unknown protein |
| AT3G01480 | cyclophilin 38 |
| AT3G62790 | NADH-ubiquinone oxidoreductase-related |
| AT1G09250 | basic helix-loop-helix (bHLH) DNA-binding superfamily protein |
| AT1G10150 | Carbohydrate-binding protein |
| AT3G07310 | Protein of unknown function (DUF760) |
| AT2G27590 | S-adenosyl-L-methionine-dependent methyltransferases superfamily protein |
| AT1G06010 | unknown protein |
| AT3G22530 | unknown protein |
| AT4G25350 | EXS (ERD1/XPR1/SYG1) family protein |
| AT1G28050 | B-box type zinc finger protein with CCT domain |
| AT5G05060 | Cystatin/monellin superfamily protein |
| AT3G15220 | Protein kinase superfamily protein |
| AT4G05100 | myb domain protein 74 |
| AT1G26770 | expansin A10 |
| AT2G35900 | unknown protein |
| AT2G43150 | Proline-rich extensin-like family protein |
| AT4G12300 | cytochrome P450, family 706, subfamily A, polypeptide 4 |
| AT1G20693 | high mobility group B2 |
| AT5G51940 | RNA polymerase Rpb6 |
| AT5G66360 | Ribosomal RNA adenine dimethylase family protein |
| AT5G06320 | NDR1/HIN1-like 3 |
| AT5G57800 | Fatty acid hydroxylase superfamily |
| AT5G55680 | glycine-rich protein |
| AT4G25560 | myb domain protein 18 |
| AT2G40800 | unknown protein |
| AT3G61920 | unknown protein |
| AT5G16720 | Protein of unknown function, DUF593 |
| AT2G16810 | F-box and associated interaction domains-containing protein |
| AT1G26970 | Protein kinase superfamily protein |
| AT1G32930 | Galactosyltransferase family protein |
| AT1G65920 | Regulator of chromosome condensation (RCC1) family with FYVE zinc finger domain |

TABLE 5-continued

SCR direct targets identified by ChIP-chip

| Arabidopsis Genome Initiative (AGI) identification number | Description |
|---|---|
| AT5G43270 | squamosa promoter binding protein-like 2 |
| AT1G67210 | Proline-rich spliceosome-associated (PSP) family protein/zinc knuckle (CCHC-type) family protein |
| AT1G76040 | calcium-dependent protein kinase 29 |
| AT4G31860 | Protein phosphatase 2C family protein |
| AT5G46900 | Bifunctional inhibitor/lipid-transfer protein/seed storage 2S albumin superfamily protein |
| AT5G56600 | profilin 3 |
| AT1G62850 | Class I peptide chain release factor |
| AT4G38680 | glycine rich protein 2 |
| AT5G09810 | actin 7 |
| AT2G43160 | ENTH/VHS family protein |
| AT3G12360 | Ankyrin repeat family protein |
| AT1G70750 | Protein of unknown function, DUF593 |
| AT1G64290 | F-box protein-related |
| AT1G21090 | Cupredoxin superfamily protein |
| AT4G11000 | Ankyrin repeat family protein |
| AT5G64310 | arabinogalactan protein 1 |
| AT2G37820 | Cysteine/Histidine-rich C1 domain family protein |
| AT1G26270 | Phosphatidylinositol 3- and 4-kinase family protein |
| AT1G62570 | flavin-monooxygenase glucosinolate S-oxygenase 4 |
| AT3G46480 | 2-oxoglutarate (2OG) and Fe(II)-dependent oxygenase superfamily protein |
| AT5G14700 | NAD(P)-binding Rossmann-fold superfamily protein |
| AT2G25080 | glutathione peroxidase 1 |
| AT3G28910 | myb domain protein 30 |
| AT2G04038 | basic leucine-zipper 48 |
| AT1G22275 | Myosin heavy chain-related protein |
| AT2G36750 | UDP-glucosyl transferase 73C1 |
| AT1G19390 | Wall-associated kinase family protein |
| AT3G08940 | light harvesting complex photosystem II |
| AT5G18870 | Inosine-uridine preferring nucleoside hydrolase family protein |
| AT1G18070 | Translation elongation factor EF1A/initiation factor IF2gamma family protein |
| AT3G04920 | Ribosomal protein S24e family protein |
| AT2G07760 | Zinc knuckle (CCHC-type) family protein |
| AT4G24960 | HVA22 homologue D |
| AT2G27860 | UDP-D-apiose/UDP-D-xylose synthase 1 |
| AT5G43920 | transducin family protein/WD-40 repeat family protein |
| AT1G49430 | long-chain acyl-CoA synthetase 2 |
| AT1G53300 | tetratricopetide-repeat thioredoxin-like 1 |
| AT3G26110 | Anther-specific protein agp1-like |
| AT4G25450 | non-intrinsic ABC protein 8 |
| AT3G14060 | unknown protein |
| AT3G47620 | TEOSINTE BRANCHED, cycloidea and PCF (TCP) 14 |
| AT5G03840 | PEBP (phosphatidylethanolamine-binding protein) family protein |
| AT1G67090 | ribulose bisphosphate carboxylase small chain 1A |
| AT1G10710 | poor homologous synapsis 1 |
| AT3G11650 | NDR1/HIN1-like 2 |
| AT3G22970 | Protein of unknown function (DUF506) |
| AT5G22510 | alkaline/neutral invertase |
| AT5G06250 | AP2/B3-like transcriptional factor family protein |
| AT5G20730 | Transcriptional factor B3 family protein/auxin-responsive factor AUX/IAA-related |
| AT3G45160 | Putative membrane lipoprotein |
| AT4G17460 | Homeobox-leucine zipper protein 4 (HB-4)/HD-ZIP protein |
| AT3G59190 | F-box/RNI-like superfamily protein |
| AT4G23060 | IQ-domain 22 |
| AT1G72140 | Major facilitator superfamily protein |
| AT1G22030 | unknown protein |
| AT1G64970 | gamma-tocopherol methyltransferase |
| AT5G27810 | MADS-box transcription factor family protein |
| AT1G71000 | Chaperone DnaJ-domain superfamily protein |
| AT5G58590 | RAN binding protein 1 |
| AT4G18710 | Protein kinase superfamily protein |
| AT3G55880 | Alpha/beta hydrolase related protein |
| AT4G11890 | Protein kinase superfamily protein |
| AT4G34200 | D-3-phosphoglycerate dehydrogenase |
| AT5G17610 | unknown protein |
| AT1G49710 | fucosyltransferase 12 |
| AT2G39980 | HXXXD-type acyl-transferase family protein |
| AT2G20580 | 26S proteasome regulatory subunit S2 1A |
| AT4G29900 | autoinhibited Ca(2+)-ATPase 10 |
| AT1G47720 | Primosome PriB/single-strand DNA-binding |
| AT4G37480 | Chaperone DnaJ-domain superfamily protein |
| AT3G15850 | fatty acid desaturase 5 |

TABLE 5-continued

SCR direct targets identified by ChIP-chip

| Arabidopsis Genome Initiative (AGI) identification number | Description |
|---|---|
| AT3G61490 | Pectin lyase-like superfamily protein |
| AT3G03040 | F-box/RNI-like superfamily protein |
| AT1G66090 | Disease resistance protein (TIR-NBS class) |
| AT2G01540 | Calcium-dependent lipid-binding (CaLB domain) family protein |
| AT2G17730 | NEP-interacting protein 2 |
| AT4G29190 | Zinc finger C-x8-C-x5-C-x3-H type family protein |
| AT2G35750 | unknown protein |
| AT2G27760 | tRNAisopentenyltransferase 2 |
| AT4G18840 | Pentatricopeptide repeat (PPR-like) superfamily protein |
| AT1G68050 | flavin-binding, kelch repeat, fbox 1 |
| AT2G39030 | Acyl-CoA N-acyltransferases (NAT) superfamily protein |
| AT3G54990 | Integrase-type DNA-binding superfamily protein |
| AT2G38800 | Plant calmodulin-binding protein-related |
| AT3G47050 | Glycosyl hydrolase family protein |
| AT4G22370 | unknown protein |
| AT1G28490 | syntaxin of plants 61 |
| AT5G07830 | glucuronidase 2 |
| AT1G59650 | Protein of unknown function (DUF1336) |
| AT3G60580 | C2H2-like zinc finger protein |
| AT5G28910 | unknown protein |
| AT4G15930 | Dynein light chain type 1 family protein |
| AT1G78110 | unknown protein |
| AT1G04250 | AUX/IAA transcriptional regulator family protein |
| AT4G14930 | Survival protein SurE-like phosphatase/nucleotidase |
| AT4G14940 | amine oxidase 1 |
| AT3G13682 | LSD1-like2 |
| AT5G62220 | glycosyltransferase 18 |
| AT4G01720 | WRKY family transcription factor |
| AT4G14680 | Pseudouridine synthase/archaeosine transglycosylase-like family protein |
| AT4G18290 | potassium channel in Arabidopsis thaliana 2 |
| AT1G55120 | beta-fructofuranosidase 5 |
| AT4G13460 | SU(VAR)3-9 homolog 9 |
| AT4G37610 | BTB and TAZ domain protein 5 |
| AT5G54530 | Protein of unknown function, DUF538 |
| AT5G24810 | ABC1 family protein |
| AT5G54250 | cyclic nucleotide-gated cation channel 4 |
| AT2G27750 | Surfeit locus protein 6 |
| AT4G02320 | Plant invertase/pectin methylesterase inhibitor superfamily |
| AT2G05160 | CCCH-type zinc fingerfamily protein with RNA-binding domain |
| AT3G25640 | Protein of unknown function, DUF617 |
| AT1G31940 | unknown protein |
| AT1G48095 | unknown protein |
| AT2G01180 | phosphatidic acid phosphatase 1 |
| AT1G23390 | Kelch repeat-containing F-box family protein |
| AT1G27990 | unknown protein |
| AT1G66140 | zinc finger protein 4 |
| AT1G77510 | PD1-like 1-2 |
| AT4G35410 | Clathrin adaptor complex small chain family protein |
| AT3G23540 | alpha/beta-Hydrolases superfamily protein |
| AT3G62170 | VANGUARD 1 homolog 2 |
| AT4G16563 | Eukaryotic aspartyl protease family protein |
| AT5G12460 | Protein of unknown function (DUF604) |
| AT5G65100 | Ethylene insensitive 3 family protein |
| AT5G65070 | K-box region and MADS-box transcription factor family protein |
| AT5G67420 | LOB domain-containing protein 37 |
| AT3G07160 | glucan synthase-like 10 |
| AT5G06710 | homeobox from Arabidopsis thaliana |
| AT5G27600 | long-chain acyl-CoA synthetase 7 |
| AT2G24150 | heptahelical protein 3 |
| AT1G51990 | O-methyltransferase family protein |
| AT5G05780 | RP non-ATPase subunit 8A |
| AT5G18690 | arabinogalactan protein 25 |
| AT5G43880 | Protein of unknown function (DUF3741) |
| AT5G64790 | O-Glycosyl hydrolases family 17 protein |
| AT4G12860 | EF hand calcium-binding protein family |
| AT2G41390 | Pollen Ole e 1 allergen and extensin family protein |
| AT5G43030 | Cysteine/Histidine-rich C1 domain family protein |
| AT3G14310 | pectin methylesterase 3 |
| AT2G32510 | mitogen-activated protein kinase kinase kinase 17 |
| AT3G62010 | unknown protein |
| AT4G17910 | transferases, transferring acyl groups |

TABLE 5-continued

SCR direct targets identified by ChIP-chip

| Arabidopsis Genome Initiative (AGI) identification number | Description |
|---|---|
| AT1G11720 | starch synthase 3 |
| AT2G01820 | Leucine-rich repeat protein kinase family protein |
| AT3G57610 | adenylosuccinate synthase |
| AT5G24140 | squalene monooxygenase 2 |
| AT1G33790 | jacalin lectin family protein |
| AT4G25360 | TRICHOME BIREFRINGENCE-LIKE 18 |
| AT3G21970 | Domain of unknown function (DUF26) |
| AT4G33010 | glycine decarboxylase P-protein 1 |
| AT4G12690 | Plant protein of unknown function (DUF868) |
| AT4G28250 | expansin B3 |
| AT5G07560 | glycine-rich protein 20 |
| AT2G31470 | F-box and associated interaction domains-containing protein |
| AT5G62150 | peptidoglycan-binding LysM domain-containing protein |
| AT2G45900 | Phosphatidylinositol N-acetyglucosaminlytransferase subunit P-related |
| AT5G18310 | unknown protein |
| AT5G17860 | calcium exchanger 7 |
| AT5G52680 | Copper transport protein family |
| AT5G49520 | WRKY DNA-binding protein 48 |
| AT1G44478 | Cyclophilin |
| AT3G24190 | Protein kinase superfamily protein |
| AT5G37560 | RING/U-box superfamily protein |
| AT3G17120 | unknown protein |
| AT4G24010 | cellulose synthase like G1 |
| AT4G36960 | RNA-binding (RRM/RBD/RNP motifs) family protein |
| AT2G04690 | Pyridoxamine 5'-phosphate oxidase family protein |
| AT4G37750 | Integrase-type DNA-binding superfamily protein |
| AT3G13800 | Metallo-hydrolase/oxidoreductase superfamily protein |
| AT3G07570 | Cytochrome b561/ferric reductase transmembrane with DOMON related domain |
| AT1G32090 | early-responsive to dehydration stress protein (ERD4) |
| AT2G02620 | Cysteine/Histidine-rich C1 domain family protein |
| AT4G23960 | F-box family protein |
| AT3G15160 | unknown protein |
| AT3G12560 | TRF-like 9 |
| AT4G25990 | CCT motif family protein |
| AT3G12820 | myb domain protein 10 |
| AT1G34370 | C2H2 and C2HC zinc fingers superfamily protein |
| AT1G65190 | Protein kinase superfamily protein |
| AT2G31400 | genomes uncoupled 1 |
| AT4G07380 | unknown protein |
| AT2G41140 | CDPK-related kinase 1 |
| AT3G53040 | late embryogenesis abundant protein, putative/LEA protein, putative |
| AT5G67480 | BTB and TAZ domain protein 4 |
| AT4G00810 | 60S acidic ribosomal protein family |
| AT1G33950 | Avirulence induced gene (AIG1) family protein |
| AT2G20610 | Tyrosine transaminase family protein |
| AT1G02580 | SET domain-containing protein |
| AT5G55620 | unknown protein |
| AT2G30860 | glutathione S-transferase PHI 9 |
| AT5G53370 | pectin methylesterase PCR fragment F |
| AT3G59580 | Plant regulator RWP-RK family protein |
| AT1G16500 | unknown protein |
| AT2G28170 | Cation/hydrogen exchanger family protein |
| AT1G75810 | unknown protein |
| AT5G40420 | oleosin 2 |
| AT3G53410 | RING/U-box superfamily protein |
| AT3G45130 | lanosterol synthase 1 |
| AT3G51370 | Protein phosphatase 2C family protein |
| AT5G07580 | Integrase-type DNA-binding superfamily protein |
| AT5G52160 | Bifunctional inhibitor/lipid-transfer protein/seed storage 2S albumin superfamily protein |
| AT3G48140 | B12D protein |
| AT1G54210 | Ubiquitin-like superfamily protein |
| AT5G57620 | myb domain protein 36 |
| AT1G36640 | unknown protein |
| AT4G32800 | Integrase-type DNA-binding superfamily protein |
| AT4G34110 | poly(A) binding protein 2 |
| AT3G45700 | Major facilitator superfamily protein |
| AT1G48760 | delta-adaptin |
| AT4G21910 | MATE efflux family protein |
| AT1G20400 | Protein of unknown function (DUF1204) |
| AT4G35830 | aconitase 1 |
| AT5G24030 | SLAC1 homologue 3 |

TABLE 5-continued

SCR direct targets identified by ChIP-chip

| Arabidopsis Genome Initiative (AGI) identification number | Description |
|---|---|
| AT2G03890 | phosphoinositide 4-kinase gamma 7 |
| AT2G23290 | myb domain protein 70 |
| AT2G41890 | curculin-like (mannose-binding) lectin family protein/PAN domain-containing protein |
| AT5G22600 | FBD/Leucine Rich Repeat domains containing protein |
| AT4G32190 | Myosin heavy chain-related protein |
| AT1G66450 | Cysteine/Histidine-rich C1 domain family protein |
| AT1G28375 | unknown protein |
| AT1G13680 | PLC-like phosphodiesterases superfamily protein |
| AT1G34640 | peptidases |
| AT1G30620 | NAD(P)-binding Rossmann-fold superfamily protein |
| AT5G47530 | Auxin-responsive family protein |
| AT1G54040 | epithiospecifier protein |
| AT2G16500 | arginine decarboxylase 1 |
| AT5G07250 | RHOMBOID-like protein 3 |
| AT1G08340 | Rho GTPase activating protein with PAK-box/P21-Rho-binding domain |
| AT1G71980 | Protease-associated (PA) RING/U-box zinc finger family protein |
| AT1G60940 | SNF1-related protein kinase 2.10 |
| AT2G03500 | Homeodomain-like superfamily protein |
| AT3G62550 | Adenine nucleotide alpha hydrolases-like superfamily protein |
| AT2G46140 | Late embryogenesis abundant protein |
| AT4G08840 | pumilio 11 |
| AT3G19140 | RING/U-box superfamily protein |
| AT3G29010 | Biotin/lipoate A/B protein ligase family |
| AT3G44550 | fatty acid reductase 5 |
| AT3G44100 | MD-2-related lipid recognition domain-containing protein |
| AT4G26620 | Sucrase/ferredoxin-like family protein |
| AT5G04020 | calmodulin binding |
| AT1G13940 | Plant protein of unknown function (DUF863) |
| AT1G23030 | ARM repeat superfamily protein |
| AT3G43270 | Plant invertase/pectin methylesterase inhibitor superfamily |
| AT1G69310 | WRKY DNA-binding protein 57 |
| AT3G23130 | C2H2 and C2HC zinc fingers superfamily protein |
| AT4G37250 | Leucine-rich repeat protein kinase family protein |
| AT2G26490 | Transducin/WD40 repeat-like superfamily protein |
| AT1G77690 | like AUX1 3 |
| AT3G55000 | tonneau family protein |
| AT1G18740 | Protein of unknown function (DUF793) |
| AT3G12280 | retinoblastoma-related 1 |
| AT3G56720 | unknown protein |
| AT1G43970 | unknown protein |
| AT3G57040 | response regulator 9 |
| AT3G47510 | unknown protein |
| AT1G16750 | Protein of unknown function, DUF547 |
| AT1G47370 | Toll-Interleukin-Resistance (TIR) domain family protein |
| AT1G56040 | HEAT/U-box domain-containing protein |
| AT4G18140 | SCP1-like small phosphatase 4b |
| AT1G04120 | multidrug resistance-associated protein 5 |
| AT3G03680 | C2 calcium/lipid-binding plant phosphoribosyltransferase family protein |
| AT1G34510 | Peroxidase superfamily protein |
| AT2G30750 | cytochrome P450, family 71, subfamily A, polypeptide 12 |
| AT5G01180 | peptide transporter 5 |
| AT3G44735 | PHYTOSULFOKINE 3 PRECURSOR |
| AT1G17230 | Leucine-rich receptor-like protein kinase family protein |
| AT2G38970 | Zinc finger (C3HC4-type RING finger) family protein |
| AT1G29660 | GDSL-like Lipase/Acylhydrolase superfamily protein |
| AT5G22850 | Eukaryotic aspartyl protease family protein |
| AT5G54800 | glucose 6-phosphate/phosphate translocator 1 |
| AT1G13590 | phytosulfokine 1 precursor |
| AT5G46830 | NACL-inducible gene 1 |
| AT5G28630 | glycine-rich protein |
| AT4G30530 | Class I glutamine amidotransferase-like superfamily protein |
| AT1G78360 | glutathione S-transferase TAU 21 |
| AT4G28100 | unknown protein |
| AT5G25290 | F-box family protein with a domain of unknown function (DUF295) |
| AT1G75390 | basic leucine-zipper 44 |
| AT3G58970 | magnesium transporter 6 |
| AT2G17550 | unknown protein |
| AT3G03380 | DegP protease 7 |
| AT1G64260 | MuDR family transposase |
| AT1G43900 | Protein phosphatase 2C family protein |
| AT3G44370 | Membrane insertion protein, OxaA/YidC with tetratricopeptide repeat domain |

TABLE 5-continued

SCR direct targets identified by ChIP-chip

| Arabidopsis Genome Initiative (AGI) identification number | Description |
|---|---|
| AT3G28920 | homeobox protein 34 |
| AT1G58100 | TCP family transcription factor |
| AT1G09940 | Glutamyl-tRNA reductase family protein |
| AT1G31240 | Bromodomain transcription factor |
| AT5G11960 | Protein of unknown function (DUF803) |
| AT2G28560 | DNA repair (Rad51) family protein |
| AT4G14730 | Bax inhibitor-1 family protein |
| AT1G76990 | ACT domain repeat 3 |
| AT4G17150 | alpha/beta-Hydrolases superfamily protein |
| AT4G36050 | endonuclease/exonuclease/phosphatase family protein |
| AT3G45430 | Concanavalin A-like lectin protein kinase family protein |
| AT5G62070 | IQ-domain 23 |
| AT1G16530 | ASYMMETRIC LEAVES 2-like 9 |
| AT2G04220 | Plant protein of unknown function (DUF868) |
| AT1G49620 | Cyclin-dependent kinase inhibitor family protein |
| AT4G37540 | LOB domain-containing protein 39 |
| AT3G17730 | NAC domain containing protein 57 |
| AT4G31250 | Leucine-rich repeat protein kinase family protein |
| AT4G13610 | DNA (cytosine-5-)-methyltransferase family protein |
| AT1G31220 | Formyl transferase |
| AT2G40440 | BTB/POZ domain-containing protein |
| AT1G35670 | calcium-dependent protein kinase 2 |
| AT5G24010 | Protein kinase superfamily protein |
| AT5G49660 | Leucine-rich repeat transmembrane protein kinase family protein |
| AT4G04900 | ROP-interactive CRIB motif-containing protein 10 |
| AT1G67350 | unknown protein |
| AT5G47990 | cytochrome P450, family 705, subfamily A, polypeptide 5 |
| AT1G59600 | ZCW7 |
| AT2G23700 | Protein of unknown function, DUF547 |
| AT5G42170 | SGNH hydrolase-type esterase superfamily protein |
| AT2G17710 | unknown protein |
| AT4G23180 | cysteine-rich RLK (RECEPTOR-like protein kinase) 10 |
| AT2G26760 | Cyclin B1; 4 |
| AT5G10190 | Major facilitator superfamily protein |
| AT3G27240 | Cytochrome C1 family |
| AT5G46680 | Pentatricopeptide repeat (PPR-like) superfamily protein |
| AT5G01600 | ferretin 1 |
| AT2G28890 | poltergeist like 4 |
| AT4G36550 | ARM repeat superfamily protein |
| AT5G39950 | thioredoxin 2 |
| AT4G32020 | unknown protein |
| AT3G08020 | PHD finger family protein |
| AT4G35040 | Basic-leucine zipper (bZIP) transcription factor family protein |
| AT5G59760 | Protein of unknown function (DUF1635) |
| AT1G44830 | Integrase-ripe DNA-binding superfamily protein |
| AT4G26940 | Galactosyltransferase family protein |
| AT5G53190 | Nodulin MtN3 family protein |
| AT1G51950 | indole-3-acetic acid inducible 18 |
| AT2G46940 | unknown protein |
| AT5G55050 | GDSL-like Lipase/Acylhydrolase superfamily protein |
| AT3G04810 | NIMA-related kinase 2 |
| AT3G18560 | unknown protein |
| AT1G07430 | highly ABA-induced PP2C gene 2 |
| AT5G03870 | Glutaredoxin family protein |
| AT1G30780 | F-box associated ubiquitination effector family protein |
| AT4G12430 | Haloacid dehalogenase-like hydrolase (HAD) superfamily protein |
| AT4G38570 | probable CDP-diacylglycerol--inositol 3-phosphatidyltransferase 2 |
| AT3G48510 | unknown protein |
| AT3G52000 | serine carboxypeptidase-like 36 |
| AT1G52990 | thioredoxin family protein |
| AT4G13520 | small acidic protein 1 |
| AT1G75830 | low-molecular-weight cysteine-rich 67 |
| AT5G27730 | Protein of unknown function (DUF1624) |
| AT1G33110 | MATE efflux family protein |
| AT1G02670 | P-loop containing nucleoside triphosphate hydrolases superfamily protein |
| AT3G24480 | Leucine-rich repeat (LRR) family protein |
| AT3G60560 | unknown protein |
| AT5G13870 | xyloglucan endotransglucosylase/hydrolase 5 |
| AT4G34135 | UDP-glucosyltransferase 73B2 |
| AT4G31460 | Ribosomal L28 family |
| AT5G38780 | S-adenosyl-L-methionine-dependent methyltransferases superfamily protein |

TABLE 5-continued

SCR direct targets identified by ChIP-chip

| Arabidopsis Genome Initiative (AGI) identification number | Description |
|---|---|
| AT5G38195 | Bifunctional inhibitor/lipid-transfer protein/seed storage 2S albumin superfamily protein |
| AT1G73680 | alpha dioxygenase |
| AT1G75450 | cytokinin oxidase 5 |
| AT1G51310 | transferases; RNA (5-methylaminomethyl-2-thiouridylate)-methyltransferases |
| AT3G15730 | phospholipase D alpha 1 |
| AT5G11900 | Translation initiation factor SUI1 family protein |
| AT1G77790 | Glycosyl hydrolase superfamily protein |
| AT1G31650 | RHO guanyl-nucleotide exchange factor 14 |
| AT1G02060 | Tetratricopeptide repeat (TPR)-like superfamily protein |
| AT1G63840 | RING/U-box superfamily protein |
| AT1G31120 | K+ uptake permease 10 |
| AT4G38900 | Basic-leucine zipper (bZIP) transcription factor family protein |
| AT2G18520 | Tetratricopeptide repeat (TPR)-like superfamily protein |
| AT5G57810 | tetraspanin15 |
| AT3G13880 | Tetratricopeptide repeat (TPR)-like superfamily protein |
| AT5G58680 | ARM repeat superfamily protein |
| AT4G35620 | Cyclin B2; 2 |
| AT1G67060 | unknown protein |
| AT1G68190 | B-box zinc finger family protein |
| AT5G43700 | AUX/IAA transcriptional regulator family protein |
| AT3G02180 | SPIRAL1-like3 |
| AT2G14850 | unknown protein |
| AT1G10740 | alpha/beta-Hydrolases superfamily protein |
| AT5G03040 | IQ-domain 2 |
| AT3G25870 | unknown protein |
| AT4G25030 | unknown protein |
| AT1G28610 | GDSL-like Lipase/Acylhydrolase superfamily protein |
| AT4G24970 | Histidine kinase-, DNA gyrase B-, and HSP90-like ATPase family protein |
| AT1G20640 | Plant regulator RWP-RK family protein |
| AT1G49380 | cytochrome c biogenesis protein family |
| AT1G68720 | tRNA arginine adenosine deaminase |
| AT5G47370 | Homeobox-leucine zipper protein 4 (HB-4)/HD-ZIP protein |
| AT5G56980 | unknown protein |
| AT3G61010 | Ferritin/ribonucleotide reductase-like family protein |
| AT4G30580 | Phospholipid/glycerol acyltransferase family protein |
| AT5G09450 | Tetratricopeptide repeat (TPR)-like superfamily protein |
| AT2G38310 | PYR1-like 4 |
| AT4G11790 | Pleckstrin homology (PH) domain superfamily protein |
| AT1G31230 | aspartate kinase-homoserine dehydrogenase i |
| AT5G39250 | F-box family protein |
| AT1G10640 | Pectin lyase-like superfamily protein |
| AT3G19450 | GroES-like zinc-binding alcohol dehydrogenase family protein |
| AT1G10490 | Domain of unknown function (DUF1726); Putative ATPase (DUF699) |
| AT1G68510 | LOB domain-containing protein 42 |
| AT5G25810 | Integrase-type DNA-binding superfamily protein |
| AT1G33560 | Disease resistance protein (CC-NBS-LRR class) family |
| AT1G32540 | lsd one like 1 |
| AT4G26140 | beta-galactosidase 12 |
| AT2G02180 | tobamovirus multiplication protein 3 |
| AT1G23310 | glutamate: glyoxylate aminotransferase |
| AT5G25560 | CHY-type/CTCHY-type/RING-type Zinc finger protein |
| AT2G45340 | Leucine-rich repeat protein kinase family protein |
| AT1G51300 | alpha/beta-Hydrolases superfamily protein |
| AT3G12670 | CTP synthase family protein |
| AT1G10560 | plant U-box 18 |
| AT5G02580 | Plant protein 1589 of unknown function |
| AT1G25550 | myb-like transcription factor family protein |
| AT5G51460 | Haloacid dehalogenase-like hydrolase (HAD) superfamily protein |
| AT5G29050 | Protein of unknown function (DUF3287) |
| AT1G04130 | Tetratricopeptide repeat (TPR)-like superfamily protein |
| AT1G28760 | Uncharacterized conserved protein (DUF2215) |
| AT1G04150 | C2 calcium/lipid-binding plant phosphoribosyltransferase family protein |
| AT5G10130 | Pollen Ole e 1 allergen and extensin family protein |
| AT1G65480 | PEBP (phosphatidylethanolamine-binding protein) family protein |
| AT3G04110 | glutamate receptor 1.1 |
| AT1G76550 | Phosphofructokinase family protein |
| AT2G21870 | copper ion binding; cobalt ion binding; zinc ion binding |
| AT4G05370 | BCS1 AAA-type ATPase |
| AT3G03270 | Adenine nucleotide alpha hydrolases-like superfamily protein |
| AT1G13270 | methionine aminopeptidase 1B |
| AT3G19860 | basic helix-loop-helix (bHLH) DNA-binding superfamily protein |

TABLE 5-continued

SCR direct targets identified by ChIP-chip

| Arabidopsis Genome Initiative (AGI) identification number | Description |
|---|---|
| AT1G37140 | MEI2 C-terminal RRM only like 1 |
| AT3G30210 | myb domain protein 121 |
| AT3G50080 | VIER F-box proteine 2 |
| AT2G04795 | unknown protein |
| AT1G76410 | RING/U-box superfamily protein |
| AT2G21910 | cytochrome P450, family 96, subfamily A, polypeptide 5 |
| AT5G40750 | FBD/Leucine Rich Repeat domains containing protein |
| AT1G45110 | Tetrapyrrole (Corrin/Porphyrin) Methylases |
| AT5G39910 | Pectin lyase-like superfamily protein |
| AT3G23730 | xyloglucan endotransglucosylase/hydrolase 16 |
| AT1G31360 | RECQ helicase L2 |
| AT2G24070 | Family of unknown function (DUF566) |
| AT4G11160 | Translation initiation factor 2, small GTP-binding protein |
| AT5G02730 | CAP (Cysteine-rich secretory proteins, Antigen 5, and Pathogenesis-related 1 protein) superfamily protein |
| AT1G01110 | IQ-domain 18 |
| AT3G43840 | 3-oxo-5-alpha-steroid 4-dehydrogenase family protein |
| AT2G30540 | Thioredoxin superfamily protein |
| AT4G11310 | Papain family cysteine protease |
| AT3G14200 | Chaperone DnaJ-domain superfamily protein |
| AT1G11260 | sugar transporter 1 |
| AT5G35750 | histidine kinase 2 |
| AT1G53460 | unknown protein |
| AT2G30520 | Phototropic-responsive NPH3 family protein |
| AT4G13550 | triglyceride lipases; triglyceride lipases |
| AT1G79780 | Uncharacterised protein family (UPF0497) |
| AT2G28740 | histone H4 |
| AT4G14130 | xyloglucan endotransglucosylase/hydrolase 15 |
| AT5G02220 | unknown protein |
| AT4G09000 | general regulatory factor 1 |
| AT5G53160 | regulatory components of ABA receptor 3 |
| AT5G38260 | Protein kinase superfamily protein |
| AT1G28327 | unknown protein |
| AT5G24580 | Heavy metal transport/detoxification superfamily protein |
| AT1G10550 | xyloglucan: xyloglucosyl transferase 33 |
| AT2G28950 | expansin A6 |
| AT4G16970 | Protein kinase superfamily protein |
| AT4G16980 | arabinogalactan-protein family |
| AT2G32350 | Ubiquitin-like superfamily protein |
| AT3G57930 | unknown protein |
| AT2G14890 | arabinogalactan protein 9 |
| AT3G02875 | Peptidase M20/M25/M40 family protein |
| AT1G05010 | ethylene-forming enzyme |
| AT5G61650 | CYCLIN P4; 2 |
| AT2G20930 | SNARE-like superfamily protein |
| AT5G02030 | POX (plant homeobox) family protein |
| AT1G64060 | respiratory burst oxidase protein F |
| AT1G63420 | Arabidopsis thaliana protein of unknown function (DUF821) |
| AT4G23580 | Galactose oxidase/kelch repeat superfamily protein |
| AT5G60910 | AGAMOUS-like 8 |
| AT5G59380 | methyl-CPG-binding domain 6 |
| AT1G62750 | Translation elongation factor EFG/EF2 protein |
| AT1G23340 | Protein of Unknown Function (DUF239) |
| AT1G20440 | cold-regulated 47 |
| AT3G45060 | high affinity nitrate transporter 2.6 |
| AT5G63520 | unknown protein |
| AT2G38530 | lipid transfer protein 2 |
| AT4G29100 | basic helix-loop-helix (bHLH) DNA-binding superfamily protein |
| AT4G11150 | vacuolar ATP synthase subunit El |
| AT5G28010 | Polyketide cyclase/dehydrase and lipid transport superfamily protein |
| AT3G27280 | prohibitin 4 |
| AT2G17480 | Seven transmembrane MLO family protein |
| AT3G62000 | S-adenosyl-L-methionine-dependent methyltransferases superfamily protein |
| AT3G50760 | galacturonosyltransferase-like 2 |
| AT2G05840 | 20S proteasome subunit PAA2 |
| AT4G17010 | unknown protein |
| AT1G80330 | gibberellin 3-oxidase 4 |
| AT1G03090 | methylcrotonyl-CoA carboxylase alpha chain, mitochondrial/3-methylcrotonyl-CoA carboxylase 1 (MCCA) |
| AT5G07760 | formin homology 2 domain-containing protein/FH2 domain-containing protein |
| AT3G23290 | Protein of unknown function (DUF640) |

TABLE 5-continued

SCR direct targets identified by ChIP-chip

| Arabidopsis Genome Initiative (AGI) identification number | Description |
|---|---|
| AT5G38760 | Late embryogenesis abundant protein (LEA) family protein |
| AT5G58960 | Plant protein of unknown function (DUF641) |
| AT5G06790 | unknown protein |
| AT5G15750 | Alpha-L RNA-binding motif/Ribosomal protein S4 family protein |
| AT3G51610 | unknown protein |
| AT4G13030 | P-loop containing nucleoside triphosphate hydrolases superfamily protein |
| AT1G76930 | extensin 4 |
| AT2G32580 | Protein of unknown function (DUF1068) |
| AT3G23000 | CBL-interacting protein kinase 7 |
| AT5G62350 | Plant invertase/pectin methylesterase inhibitor superfamily protein |
| AT1G35515 | high response to osmotic stress 10 |
| AT5G14210 | Leucine-rich repeat protein kinase family protein |
| AT5G16990 | Zinc-binding dehydrogenase family protein |
| AT2G29450 | glutathione S-transferase tau 5 |
| AT2G04070 | MATE efflux family protein |
| AT3G46130 | myb domain protein 48 |
| AT4G18010 | myo-inositol polyphosphate 5-phosphatase 2 |
| AT2G23040 | unknown protein |
| AT5G18650 | CHY-type/CTCHY-type/RING-type Zinc finger protein |
| AT2G28830 | PLANT U-BOX 12 |
| AT1G44000 | unknown protein |
| AT3G24100 | Uncharacterised protein family SERF |
| AT1G30840 | purine permease 4 |
| AT3G03900 | adenosine-5'-phosphosulfate (APS) kinase 3 |
| AT1G17500 | ATPase E1-E2 type family protein/haloacid dehalogenase-like hydrolase family protein |
| AT3G10210 | SEC14 cytosolic factor family protein/ phosphoglyceride transfer family protein |
| AT2G17770 | basic region/leucine zipper motif 27 |
| AT5G24165 | unknown protein |
| AT1G04160 | myosin XIB |
| AT5G44610 | microtubule-associated protein 18 |
| AT1G14840 | microtubule-associated proteins 70-4 |
| AT4G37780 | myb domain protein 87 |
| AT3G11820 | syntaxin of plants 121 |
| AT3G05220 | Heavy metal transport/detoxification superfamily protein |
| AT5G27920 | F-box family protein |
| AT3G28860 | ATP binding cassette subfamily B19 |
| AT5G50130 | NAD(P)-binding Rossmann-fold superfamily protein |
| AT5G18940 | Mo25 family protein |
| AT2G46060 | transmembrane protein-related |
| AT5G49060 | Heat shock protein DnaJ, N-terminal with domain of unknown function (DUF1977) |
| AT3G21420 | 2-oxoglutarate (2OG) and Fe(II)-dependent oxygenase superfamily protein |
| AT1G75880 | SGNH hydrolase-type esterase superfamily protein |
| AT5G17240 | SET domain group 40 |
| AT1G18470 | Transmembrane Fragile-X-F-associated protein |
| AT5G26230 | unknown protein |
| AT5G04820 | ovate family protein 13 |
| AT4G22070 | WRKY DNA-binding protein 31 |
| AT3G07910 | unknown protein |
| AT5G62420 | NAD(P)-linked oxidoreductase superfamily protein |
| AT4G29940 | pathogenesis related homeodomain protein A |
| AT4G38170 | FAR1-related sequence 9 |
| AT5G24050 | Domain of unknown function (DUF313) |
| AT2G39710 | Eukaryotic aspartyl protease family protein |
| AT3G28940 | AIG2-like (avirulence induced gene) family protein |
| AT3G03840 | SAUR-like auxin-responsive protein family |
| AT4G36930 | basic helix-loop-helix (bHLH) DNA-binding superfamily protein |
| AT5G60620 | glycerol-3-phosphate acyltransferase 9 |
| AT5G04600 | RNA-binding (RRM/RBD/RNP motifs) family protein |
| AT3G17130 | Plant invertase/pectin methylesterase inhibitor superfamily protein |
| AT5G59880 | actin depolymerizing factor 3 |
| AT1G52300 | Zinc-binding ribosomal protein family protein |
| AT3G11420 | Protein of unknown function (DUF604) |
| AT4G02860 | Phenazine biosynthesis PhzC/PhzF protein |
| AT4G34970 | actin depolymerizing factor 9 |
| AT5G48240 | unknown protein |
| AT4G22650 | unknown protein |
| AT1G05500 | Calcium-dependent lipid-binding (CaLB domain) family protein |
| AT2G15860 | unknown protein |
| AT5G06800 | myb-like HTH transcriptional regulator family protein |
| AT5G58650 | plant peptide containing sulfated tyrosine 1 |
| AT1G67820 | Protein phosphatase 2C family protein |

TABLE 5-continued

SCR direct targets identified by ChIP-chip

| Arabidopsis Genome Initiative (AGI) identification number | Description |
|---|---|
| AT2G28160 | FER-like regulator of iron uptake |
| AT3G21070 | NAD kinase 1 |
| AT2G43880 | Pectin lyase-like superfamily protein |
| AT2G33540 | C-terminal domain phosphatase-like 3 |
| AT4G22960 | Protein of unknown function (DUF544) |
| AT4G17810 | C2H2 and C2HC zinc fingers superfamily protein |
| AT1G56500 | haloacid dehalogenase-like hydrolase family protein |
| AT1G61740 | Sulfite exporter TauE/SafE family protein |
| AT4G26680 | Tetratricopeptide repeat (TPR)-like superfamily protein |
| AT1G63200 | Cystatin/monellin superfamily protein |
| AT5G21170 | 5'-AMP-activated protein kinase beta-2 subunit protein |
| AT4G14920 | Acyl-CoA N-acyltransferase with RING/FYVE/PHD-type zinc finger protein |
| AT4G16370 | oligopeptide transporter |
| AT5G05180 | unknown protein |
| AT1G30090 | Galactose oxidase/kelch repeat superfamily protein |
| AT2G02450 | NAC domain containing protein 35 |
| AT1G68570 | Major facilitator superfamily protein |
| AT3G24650 | AP2/B3-like transcriptional factor family protein |
| AT4G16640 | Matrixin family protein |
| AT5G19870 | Family of unknown function (DUF716) |
| AT1G63870 | Disease resistance protein (TER-NBS-LRR class) family |
| AT3G29370 | unknown protein |
| AT4G18820 | AAA-type ATPase family protein |
| AT2G13570 | nuclear factor Y, subunit B7 |
| AT4G22770 | AT hook motif DNA-binding family protein |
| AT5G47060 | Protein of unknown function (DUF581) |
| AT1G80050 | adenine phosphoribosyl transferase 2 |
| AT1G35470 | SPla/RYanodine receptor (SPRY) domain-containing protein |
| AT3G29796 | unknown protein |
| AT4G40040 | Histone superfamily protein |
| AT5G19130 | GPI transamidase component family protein/Gaal-like family protein |
| AT1G31530 | DNAse I-like superfamily protein |
| AT2G19380 | RNA recognition motif (RRM)-containing protein |
| AT3G15770 | unknown protein |
| AT3G30380 | alpha/beta-Hydrolases superfamily protein |
| AT5G25350 | EIN3-binding F box protein 2 |
| AT3G15630 | unknown protein |
| AT4G34770 | SAUR-like auxin-responsive protein family |
| AT4G30520 | Leucine-rich repeat protein kinase family protein |
| AT1G26630 | Eukaryotic translation initiation factor 5A-1 (eIF-5A 1) protein |
| AT4G22190 | unknown protein |
| AT3G43810 | calmodulin 7 |
| AT1G48880 | TRICHOME BIREFRINGENCE-LIKE 7 |
| AT5G44290 | Protein kinase superfamily protein |
| AT3G26230 | cytochrome P450, family 71, subfamily B, polypeptide 24 |
| AT2G02820 | myb domain protein 88 |
| AT5G49540 | Rab5-interacting family protein |
| AT1G13410 | Tetratricopeptide repeat (TPR)-like superfamily protein |
| AT2G20750 | expansin B1 |
| AT2G30100 | pentatricopeptide (PPR) repeat-containing protein |
| AT5G24270 | Calcium-binding EF-hand family protein |
| AT2G44210 | Protein of Unknown Function (DUF239) |
| AT3G47020 | F-box and associated interaction domains-containing protein |
| AT1G22480 | Cupredoxin superfamily protein |
| AT1G14890 | Plant invertase/pectin methylesterase inhibitor superfamily protein |
| AT3G15790 | methyl-CPG-binding domain 11 |
| AT5G15950 | Adenosylmethionine decarboxylase family protein |
| AT1G48870 | Transducin/WD40 repeat-like superfamily protein |
| AT5G44820 | Nucleotide-diphospho-sugar transferase family protein |
| AT5G12440 | CCCH-type zinc fingerfamily protein with RNA-binding domain |
| AT2G24762 | glutamine dumper 4 |
| AT3G61880 | cytochrome p450 78a9 |
| AT1G20960 | U5 small nuclear ribonucleoprotein helicase, putative |
| AT1G58270 | TRAF-like family protein |
| AT1G18540 | Ribosomal protein L6 family protein |
| AT3G19050 | phragmoplast orienting kinesin 2 |
| AT1G55360 | Protein of Unknown Function (DUF239) |
| AT5G65370 | ENTH/ANTH/VHS superfamily protein |
| AT2G03040 | emp24/gp25L/p24 family/GOLD family protein |
| AT5G13220 | jasmonate-zim-domain protein 10 |
| AT5G11060 | KNOTTED1-like homeobox gene 4 |

TABLE 5-continued

| SCR direct targets identified by ChIP-chip | |
|---|---|
| Arabidopsis Genome Initiative (AGI) identification number | Description |
| AT3G18850 | lysophosphatidyl acyltransferase 5 |
| AT1G06410 | trehalose-phosphatase/synthase 7 |
| AT1G05470 | DNAse I-like superfamily protein |
| AT1G34670 | myb domain protein 93 |
| AT1G34540 | cytochrome P450, family 94, subfamily D, polypeptide 1 |
| AT3G25660 | Amidase family protein |
| AT1G47610 | Transducin/WD40 repeat-like superfamily protein |
| AT4G39900 | unknown protein |
| AT3G29400 | exocyst subunit exo70 family protein E1 |
| AT4G39040 | RNA-binding CRS1/YhbY (CRM) domain protein |
| AT2G18840 | Integral membrane Yip1 family protein |
| AT4G16990 | disease resistance protein (TER-NBS class), putative |
| AT1G47840 | hexokinase 3 |
| AT4G07515 | Protein of unknown function (DUF784) |
| AT1G56230 | Protein of unknown function (DUF1399) |
| AT3G13620 | Amino acid permease family protein |
| AT3G13240 | unknown protein |
| AT2G18160 | basic leucine-zipper 2 |
| AT5G20790 | unknown protein |
| AT1G50620 | RING/FYVE/PHD zinc finger superfamily protein |
| AT3G20830 | AGC (cAMP-dependent, cGMP-dependent and protein kinase C) kinase family protein |
| AT5G10650 | RING/U-box superfamily protein |
| AT1G62660 | Glycosyl hydrolases family 32 protein |
| AT1G47410 | unknown protein |
| AT1G22430 | GroES-like zinc-binding dehydrogenase family protein |
| AT4G10170 | SNARE-like superfamily protein |
| AT3G44830 | Lecithin: cholesterol acyltransferase family protein |
| AT2G39970 | Mitochondrial substrate carrier family protein |
| AT3G61220 | NAD(P)-binding Rossmann-fold superfamily protein |
| AT1G69970 | CLAVATA3/ESR-RELATED 26 |
| AT1G30820 | CTP synthase family protein |
| AT5G14430 | S-adenosyl-L-methionine-dependent methyltransferases superfamily protein |
| AT5G63410 | Leucine-rich repeat protein kinase family protein |
| AT1G74650 | myb domain protein 31 |
| AT4G15050 | Protein of Unknown Function (DUF239) |
| AT3G15260 | Protein phosphatase 2C family protein |
| AT1G80580 | Integrase-type DNA-binding superfamily protein |
| AT3G44380 | Late embryogenesis abundant (LEA) hydroxyproline-rich glycoprotein family |
| AT2G18120 | SHI-related sequence 4 |
| AT4G05340 | P-loop containing nucleoside triphosphate hydrolases superfamily protein |
| AT4G27820 | beta glucosidase 9 |
| AT3G23300 | S-adenosyl-L-methionine-dependent methyltransferases superfamily protein |
| AT1G36510 | Nucleic acid-binding proteins superfamily |
| AT1G49780 | plant U-box 26 |
| AT5G05140 | Transcription elongation factor (TFIIS) family protein |
| AT5G16490 | ROP-interactive CRIB motif-containing protein 4 |
| AT1G73780 | Bifunctional inhibitor/lipid-transfer protein/seed storage 2S albumin superfamily protein |
| AT3G07270 | GTP cyclohydrolase I |
| AT1G30210 | TEOSINTE BRANCHED 1, cycloidea, and PCF family 24 |
| AT5G26650 | AGAMOUS-like 36 |
| AT3G62620 | sucrose-phosphatase-related |
| AT3G57850 | unknown protein |
| AT3G25810 | Terpenoid cyclases/Protein prenyltransferases superfamily protein |
| AT1G26090 | P-loop containing nucleoside triphosphate hydrolases superfamily protein |
| AT3G57520 | seed imbibition 2 |
| AT5G28530 | FARl-related sequence 10 |

TABLE 6

| SHR direct targets identified by ChIP-chip | |
|---|---|
| Arabidopsis Genome Initiative (AGI) identification number | Short_description |
| AT1G78090 | trehalose-6-phosphate phosphatase |
| AT4G01960 | unknown protein |
| AT2G40008 | other RNA |
| AT3G19020 | Leucine-rich repeat (LRR) family protein |
| AT2G45190 | Plant-specific transcription factor YABBY family protein |
| AT3G19030 | unknown protein |
| AT4G36040 | Chaperone DnaJ-domain superfamily protein |
| AT5G35698 | Plant thionin family protein |
| AT4G01720 | WRKY family transcription factor |
| AT4G01120 | G-box binding factor 2 |
| AT3G61460 | brassinosteroid-responsive RING-H2 |
| AT4G39800 | myo-inositol-1-phosphate synthase 1 |
| AT3G63052 | This gene encodes a small protein and has either evidence of transcription or purifying selection. |
| AT3G49960 | Peroxidase superfamily protein |
| AT2G23140 | RING/U-box superfamily protein with ARM repeat domain |
| AT5G49750 | Leucine-rich repeat (LRR) family protein |
| AT1G67195 | MIR414 (MICRORNA 414) |
| AT1G20320 | Haloacid dehalogenase-like hydrolase (HAD) superfamily protein |
| AT1G23010 | Cupredoxin superfamily protein |
| AT1G29920 | chlorophyll A/B-binding protein 2 |
| AT3G30775 | Methylenetetrahydrofolate reductase family protein |
| AT5G64310 | arabinogalactan protein 1 |
| AT1G68680 | unknown protein, LOCATED IN: chloroplast |
| AT2G23148 | Plant self-incompatibility protein S1 family |
| AT1G49510 | embryo defective 1273 |
| AT1G61740 | Sulfite exporter TauE/SafE family protein |
| AT2G30070 | potassium transporter 1 |
| AT3G49820 | unknown protein |
| AT1G71880 | sucrose-proton symporter 1 |
| AT1G21590 | Protein kinase protein with adenine nucleotide alpha hydrolases-like domain |
| AT5G03210 | Encodes a small polypeptide contributing to resistance to potyvirus |
| AT5G13740 | zinc induced facilitator 1 |
| AT5G62060 | F-box and associated interaction domains-containing protein |
| AT1G70550 | Protein of Unknown Function (DUF239) |
| AT4G16447 | unknown protein |
| AT4G08950 | Phosphate-responsive 1 family protein |
| AT2G23142 | Plant self-incompatibility protein S1 family |
| AT5G01810 | CBL-interacting protein kinase 15 |
| AT4G19700 | SBP (S-ribonuclease binding protein) family protein |
| AT1G77765 | unknown protein |
| AT2G29490 | glutathione S-transferase TAU 1 |
| AT5G54300 | Protein of unknown function (DUF761) |
| AT4G32480 | Protein of unknown function (DUF506) |
| AT2G23300 | Leucine-rich repeat protein kinase family protein |
| AT5G14920 | Gibberellin-regulated family protein |
| AT3G13000 | Protein of unknown function, DUF547 |
| AT3G03770 | Leucine-rich repeat protein kinase family protein |
| AT5G51490 | Plant invertase/pectin methylesterase inhibitor superfamily |
| AT5G11740 | arabinogalactan protein 15 |
| AT2G46530 | auxin response factor 11 |
| AT1G64380 | Integrase-type DNA-binding superfamily protein |
| AT3G07360 | plant U-box 9 |
| AT2G28570 | unknown protein |
| AT1G70370 | polygalacturonase 2 |
| AT3G19380 | plant U-box 25 |
| AT1G13260 | related to ABI3/VP1 1 |
| AT5G14120 | Major facilitator superfamily protein |
| AT5G20250 | Raffinose synthase family protein |
| AT2G28070 | ABC-2 type transporter family protein |
| AT5G47940 | unknown protein |
| AT3G52490 | Double Clp-N motif-containing P-loop nucleoside triphosphate hydrolases superfamily protein |
| AT5G53420 | CCT motif family protein |
| AT1G11260 | sugar transporter 1 |
| AT4G34131 | UDP-glucosyl transferase 73B3 |
| AT5G67350 | |
| AT1G13245 | ROTUNDIFOLIA like 17 |
| AT3G50660 | Cytochrome P450 superfamily protein |
| AT3G19390 | Granulin repeat cysteine protease family protein |
| AT4G16444 | molecular_function unknown |
| AT1G25560 | AP2/B3 transcription factor family protein |
| AT1G72630 | ELF4-like 2 |

TABLE 6-continued

SHR direct targets identified by ChIP-chip

| Arabidopsis Genome Initiative (AGI) identification number | Short_description |
|---|---|
| AT1G66170 | RING/FYVE/PHD zinc finger superfamily protein |
| AT2G26740 | soluble epoxide hydrolase |
| AT2G38120 | Transmembrane amino acid transporter family protein |
| AT3G02580 | sterol 1 |
| AT5G59780 | myb domain protein 59 |
| AT5G57020 | myristoyl-CoA: protein N-myristoyltransferase |
| AT3G50770 | calmodulin-like 41 |
| AT5G65340 | Protein of unknown function, DUF617 |
| AT4G36920 | Integrase-type DNA-binding superfamily protein |
| AT5G11750 | Ribosomal protein L19 family protein |
| AT1G32928 | unknown protein |
| AT3G61470 | photosystem I light harvesting complex gene 2 |
| AT5G21940 | unknown protein |
| AT3G23000 | CBL-interacting protein kinase 7 |
| AT3G15200 | Tetratricopeptide repeat (TPR)-like superfamily protein |
| AT1G79130 | SAUR-like auxin-responsive protein family |
| AT2G22520 | unknown protein |
| AT1G30110 | nudix hydrolase homolog 25 |
| AT1G03840 | C2H2 and C2HC zinc fingers superfamily protein |
| AT5G25280 | serine-rich protein-related |
| AT4G31550 | WRKY DNA-binding protein 11 |
| AT4G13830 | DNAJ-like 20 |
| AT5G56610 | Phosphotyrosine protein phosphatases superfamily protein |
| AT4G01250 | WRKY family transcription factor |
| AT1G03610 | Protein of unknown function (DUF789) |
| AT1G05010 | ethylene-forming enzyme |
| AT1G15750 | Transducin family protein/WD-40 repeat family protein |
| AT4G16370 | oligopeptide transporter |
| AT1G03457 | RNA-binding (RRM/RBD/RNP motifs) family protein |
| AT3G20340 | Expression of the gene is downregulated in the presence of paraquat, an inducer of photoxidative stress. |
| AT5G27030 | TOPLESS-related 3 |
| AT5G25290 | F-box family protein with a domain of unknown function (DUF295) |
| AT5G62410 | structural maintenance of chromosomes 2 |
| AT3G02150 | plastid transcription factor 1 |
| AT3G02140 | AFP2 (ABI five-binding protein 2) family protein |
| AT5G39620 | RAB GTPase homolog G1 |
| AT2G31750 | UDP-glucosyl transferase 74D1 |
| AT3G06080 | Plant protein of unknown function (DUF828) |
| AT1G05710 | basic helix-loop-helix (bHLH) DNA-binding superfamily protein |
| AT1G69760 | unknown protein |
| AT3G16240 | delta tonoplast integral protein |
| AT1G13210 | autoinhibited Ca2+/ATPase II |
| AT1G13950 | eukaryotic elongation factor 5A-1 |
| AT1G19180 | jasmonate-zim-domain protein 1 |
| AT1G01550 | Protein of unknown function (DUF793) |
| AT3G48630 | unknown protein |
| AT3G19850 | Phototropic-responsive NPH3 family protein |
| AT1G15670 | Galactose oxidase/kelch repeat superfamily protein |
| AT5G52690 | Copper transport protein family |
| AT1G13250 | galacturonosyltransferase-like 3 |
| AT1G06400 | Ras-related small GTP-binding family protein |
| AT1G21000 | PLATZ transcription factor family protein |
| AT1G32920 | unknown protein, LOCATED IN: endomembrane system |
| AT4G37780 | myb domain protein 87 |
| AT4G30490 | AFG1-like ATPase family protein |
| AT3G06070 | unknown protein |
| AT5G62400 | unknown protein |
| AT3G53450 | Putative lysine decarboxylase family protein |
| AT2G45970 | cytochrome P450, family 86, subfamily A, polypeptide 8 |
| AT3G17120 | unknown protein |
| AT1G21835 | Plant thionin family protein |
| AT3G25717 | ROTUNDIFOLIA like 16 |
| AT3G05690 | nuclear factor Y, subunit A2 |
| AT3G04732 | unknown protein |
| AT1G21810 | Plant protein of unknown function (DUF869) |
| AT4G29700 | Alkaline-phosphatase-like family protein |
| AT4G27740 | Yippee family putative zinc-binding protein |
| AT1G30590 | RNA polymerase I specific transcription initiation factor RRN3 protein |
| AT3G16830 | TOPLESS-related 2 |
| AT4G33080 | AGC (cAMP-dependent, cGMP-dependent and protein kinase C) kinase family protein |
| AT5G11530 | embryonic flower 1 (EMF1) |

TABLE 6-continued

SHR direct targets identified by ChIP-chip

| Arabidopsis Genome Initiative (AGI) identification number | Short_description |
|---|---|
| AT5G67070 | ralf-like 34 |
| AT4G32020 | unknown protein |
| AT3G13810 | indeterminate(ID)-domain 11 |
| AT3G03990 | alpha/beta-Hydrolases superfamily protein |
| AT3G47660 | Regulator of chromosome condensation (RCC1) family protein |
| AT5G56075 | Domain of unknown function (DUF2431) |
| AT3G15095 | Encodes HCF243 (high chlorophyll fluorescence), a chloroplast-localized protein involved in the D1 protein stability of the photosystem II complex1 |
| AT1G78050 | phosphoglycerate/bisphosphoglycerate mutase |
| AT1G53170 | ethylene response factor 8 |
| AT4G38470 | ACT-like protein tyrosine kinase family protein |
| AT4G37260 | myb domain protein 73 |
| AT1G80450 | VQ motif-containing protein |
| AT5G13181 | This gene encodes a small protein and has either evidence of transcription or purifying selection. |
| AT1G78240 | S-adenosyl-L-methionine-dependent methyltransferases superfamily protein |
| AT1G20330 | sterol methyltransferase 2 |
| AT1G18075 | MIR159/MIR159B; miRNA |
| AT3G05490 | ralf-like 22 |
| AT1G62510 | Bifunctional inhibitor/lipid-transfer protein/seed storage 2S albumin superfamily protein |
| AT5G13730 | sigma factor 4 |
| AT1G18740 | Protein of unknown function (DUF793) |
| AT2G36420 | unknown protein |
| AT1G02350 | protoporphyrinogen oxidase-related |
| AT4G36870 | BEL1-like homeodomain 2 |
| AT5G52930 | Protein of unknown function (DUF295) |
| AT3G56850 | ABA-responsive element binding protein 3 |
| AT4G36030 | armadillo repeat only 3 |
| AT5G42110 | unknown protein |
| AT2G25480 | TPX2 (targeting protein for Xklp2) protein family |
| AT1G67740 | photosystem II BY |
| AT3G03773 | HSP20-like chaperones superfamily protein |
| AT3G23030 | indole-3-acetic acid inducible 2 |
| AT5G62050 | homolog of yeast oxidase assembly 1 (OXA1) |
| AT3G16800 | Protein phosphatase 2C family protein |
| AT2G31620 | Receptor-like protein kinase-related family protein |
| AT1G55120 | beta-fructofuranosidase 5 |
| AT3G02550 | LOB domain-containing protein 41 |
| AT2G20680 | Glycosyl hydrolase superfamily protein |
| AT2G28060 | 5'-AMP-activated protein kinase beta-2 subunit protein |
| AT3G23020 | Tetratricopeptide repeat (TPR)-like superfamily protein |
| AT3G05110 | Domain of unknown function (DUF3444) |
| AT4G36860 | LIM domain-containing protein |
| AT3G14310 | pectin methylesterase 3 |
| AT3G02570 | Mannose-6-phosphate isomerase, type I |
| AT5G40440 | mitogen-activated protein kinase kinase 3 |
| AT1G12440 | A20/AN1-like zinc finger family protein |
| AT4G24120 | YELLOW STRIPE like 1 |
| AT5G67450 | zinc-finger protein 1 |
| AT1G22400 | UDP-Glycosyltransferase superfamily protein |
| AT3G63050 | unknown protein |
| AT2G20613 | DNA-binding storekeeper protein-related transcriptional regulator |
| AT2G35960 | NDR1/HIN1-like 12 |
| AT3G18080 | B-S glucosidase 44 |
| AT1G75500 | Walls Are Thin 1 |
| AT4G27730 | oligopeptide transporter 1 |
| AT1G02420 | Pentatricopeptide repeat (PPR) superfamily protein |
| AT1G23030 | ARM repeat superfamily protein |
| AT3G25770 | allene oxide cyclase 2 |
| AT3G04730 | indoleacetic acid-induced protein 16 |
| AT5G03290 | isocitrate dehydrogenase V |
| AT2G30550 | alpha/beta-Hydrolases superfamily protein |
| AT1G02065 | squamosa promoter binding protein-like 8 |
| AT4G13340 | Leucine-rich repeat (LRR) family protein |
| AT1G78020 | Protein of unknown function (DUF581) |
| AT4G25500 | arginine/serine-rich splicing factor 35 |
| AT5G05440 | Polyketide cyclase/dehydrase and lipid transport superfamily protein |
| AT1G22190 | Integrase-type DNA-binding superfamily protein |
| AT5G01720 | RNI-like superfamily protein |
| AT1G02340 | basic helix-loop-helix (bHLH) DNA-binding superfamily protein |
| AT5G64690 | neurofilament triplet H protein-related |
| AT1G68530 | 3-ketoacyl-CoA synthase 6 |

TABLE 6-continued

SHR direct targets identified by ChIP-chip

| Arabidopsis Genome Initiative (AGI) identification number | Short_description |
|---|---|
| AT5G67460 | O-Glycosyl hydrolases family 17 protein |
| AT1G01140 | CBL-interacting protein kinase 9 |
| AT3G06760 | Drought-responsive family protein |
| AT1G22180 | Sec14p-like phosphatidylinositol transfer family protein |
| AT3G22380 | time for coffee |
| AT3G07460 | Protein of unknown function, DUF538 |
| AT4G32410 | cellulose synthase 1 |
| AT5G05590 | phosphoribosylanthranilate isomerase 2 |
| AT3G50820 | photosystem II subunit O-2 |
| AT2G27240 | Aluminium activated malate transporter family protein |
| AT1G68450 | VQ motif-containing protein |
| AT5G65207 | unknown protein |
| AT4G27260 | Auxin-responsive GH3 family protein |
| AT1G30330 | auxin response factor 6 |
| AT3G45230 | hydroxyproline-rich glycoprotein family protein |
| AT4G15430 | ERD (early-responsive to dehydration stress) family protein |
| AT5G43060 | Granulin repeat cysteine protease family protein |
| AT5G03140 | Concanavalin A-like lectin protein kinase family protein |
| AT1G04120 | multidrug resistance-associated protein 5 |
| AT3G12920 | SBP (S-ribonuclease binding protein) family protein |
| AT1G19835 | Plant protein of unknown function (DUF869) |
| AT1G45976 | S-ribonuclease binding protein 1 |
| AT5G01850 | Protein kinase superfamily protein |
| AT3G48350 | Cysteine proteinases superfamily protein |
| AT1G71980 | Protease-associated (PA) RING/U-box zinc finger family protein |
| AT2G45340 | Leucine-rich repeat protein kinase family protein |
| AT5G62390 | BCL-2-associated athanogene 7 |
| AT2G34720 | nuclear factor Y, subunit A4 |
| AT4G36850 | PQ-loop repeat family protein/transmembrane family protein |
| AT4G30270 | xyloglucan endotransglucosylase/hydrolase 24 |
| AT5G25190 | Integrase-type DNA-binding superfamily protein |
| AT3G14205 | Phosphoinositide phosphatase family protein |
| AT3G19580 | zinc-finger protein 2 |
| AT3G11700 | FASCICLIN-like arabinogalactan protein 18 precursor |
| AT4G22980 | Pyridoxal phosphate (PLP)-dependent transferases superfamily protein |
| AT1G24170 | Nucleotide-diphospho-sugar transferases superfamily protein |
| AT1G24540 | cytochrome P450, family 86, subfamily C, polypeptide 1 |
| AT3G04120 | glyceraldehyde-3-phosphate dehydrogenase C subunit 1 |
| AT4G37608 | unknown protein |
| AT1G19490 | Basic-leucine zipper (bZIP) transcription factor family protein |
| AT3G04000 | NAD(P)-binding Rossmann-fold superfamily protein |
| AT5G09490 | Ribosomal protein S19 family protein |
| AT4G38670 | Pathogenesis-related thaumatin superfamily protein |
| AT1G17380 | jasmonate-zim-domain protein 5 |
| AT4G23060 | IQ-domain 22 |
| AT4G18710 | Protein kinase superfamily protein |
| AT2G22460 | Protein of unknown function, DUF617 |
| AT5G40430 | myb domain protein 22 |
| AT1G51300 | alpha/beta-Hydrolases superfamily protein |
| AT5G65210 | bZIP transcription factor family protein |
| AT4G17453 | This gene encodes a small protein and has either evidence of transcription or purifying selection |
| AT1G30410 | multidrug resistance-associated protein 13 |
| AT1G51950 | indole-3-acetic acid inducible 18 |
| AT1G23100 | GroES-like family protein |
| AT2G27510 | ferredoxin 3 |
| AT2G37200 | Uncharacterised protein family (UPF0497) |
| AT3G12560 | TRF-like 9 |
| AT3G23750 | Leucine-rich repeat protein kinase family protein |
| AT2G35980 | Late embryogenesis abundant (LEA) hydroxyproline-rich glycoprotein family |
| AT5G42170 | SGNH hydrolase-type esterase superfamily protein |
| AT1G68550 | Integrase-type DNA-binding superfamily protein |
| AT1G68552 | conserved peptide upstream open reading frame 53 |
| AT2G40750 | WRKY DNA-binding protein 54 |
| AT1G47870 | winged-helix DNA-binding transcription factor family protein |
| AT1G44350 | IAA-leucine resistant (ILR)-like gene 6 |
| AT5G10310 | unknown protein |
| AT4G26690 | PLC-like phosphodiesterase family protein |
| AT4G37550 | Acetamidase/Formamidase family protein |
| AT1G16510 | SAUR-like auxin-responsive protein family |
| AT5G14820 | Pentatricopeptide repeat (PPR) superfamily protein |
| AT5G19190 | unknown protein |

TABLE 6-continued

SHR direct targets identified by ChIP-chip

| Arabidopsis Genome Initiative (AGI) identification number | Short_description |
|---|---|
| AT4G17500 | ethylene responsive element binding factor 1 |
| AT3G48640 | unknown protein |
| AT1G27290 | unknown protein |
| AT1G77510 | PDI-like 1-2 |
| AT5G16030 | unknown protein |
| AT1G19350 | Brassinosteroid signalling positive regulator (BZR1) family protein |
| AT4G40050 | Protein of unknown function (DUF3550/UPF0682) |
| AT1G20440 | cold-regulated 47 |
| AT3G63040 | unknown protein |
| AT4G30020 | PA-domain containing subtilase family protein |
| AT2G15640 | F-box family protein |
| AT4G29905 | unknown protein |
| AT1G20340 | Cupredoxin superfamily protein |
| AT5G62430 | cycling DOF factor 1 |
| AT5G07580 | Integrase-type DNA-binding superfamily protein |
| AT4G15800 | ralf-like 33 |
| AT2G29980 | fatty acid desaturase 3 |
| AT2G28755 | UDP-D-glucuronate carboxy-lyase-related |
| AT5G09440 | EXORDIUM like 4 |
| AT3G12320 | unknown protein |
| AT3G52480 | unknown protein |
| AT3G48390 | MA3 domain-containing protein |
| AT4G18010 | myo-inositol polyphosphate 5-phosphatase 2 |
| AT3G28920 | homeobox protein 34 |
| AT1G64385 | unknown protein, LOCATED IN: endomembrane |
| AT2G01850 | endoxyloglucan transferase A3 |
| AT3G57840 | Plant self-incompatibility protein S1 family |
| AT4G37590 | Phototropic-responsive NPH3 family protein |
| AT4G37250 | Leucine-rich repeat protein kinase family protein |
| AT4G18890 | BES1/BZR1 homolog 3 |
| AT5G19900 | PRLI-interacting factor, putative |
| AT5G54365 | pre-tRNA |
| AT4G17900 | PLATZ transcription factor family protein |
| AT5G39630 | Vesicle transport v-SNARE family protein |
| AT4G00630 | K+ efflux antiporter 2 |
| AT1G76190 | SAUR-like auxin-responsive protein family |
| AT1G04400 | cryptochrome 2 |
| AT5G45470 | Protein of unknown function (DUF594) |
| AT1G04130 | Tetratricopeptide repeat (TPR)-like superfamily protein |
| AT5G42790 | proteasome alpha subunit F1 |
| AT5G17847 | unknown protein |
| AT4G03210 | xyloglucan endotransglucosylase/hydrolase 9 |
| AT1G09260 | Chaperone DnaJ-domain superfamily protein |
| AT1G28310 | Dof-type zinc finger DNA-binding family protein |
| AT5G46730 | glycine-rich protein |
| AT5G44160 | C2H2-like zinc finger protein |
| AT4G20930 | 6-phosphogluconate dehydrogenase family protein |
| AT2G39180 | CRINKLY4 related 2 |
| AT1G01040 | dicer-like 1 |
| AT1G01046 | MIR838a; miRNA |
| AT5G11090 | serine-rich protein-related |
| AT3G13080 | multidrug resistance-associated protein 3 |
| AT5G54200 | Transducin/WD40 repeat-like superfamily protein |
| AT4G13395 | ROTUNDIFOLIA like 12 |
| AT1G14770 | RING/FYVE/PHD zinc finger superfamily protein |
| AT1G07010 | Calcineurin-like metallo-phosphoesterase superfamily protein |
| AT4G14730 | Bax inhibitor-1 family protein |
| AT5G03370 | acylphosphatase family |
| AT1G72520 | PLAT/LH2 domain-containing lipoxygenase family protein |
| AT4G01080 | TRICHOME BIREFRINGENCE-LIKE 26 |
| AT5G59880 | actin depolymerizing factor 3 |
| AT5G49740 | ferric reduction oxidase 7 |
| AT5G49540 | Rab5-interacting family protein |
| AT1G14720 | xyloglucan endotransglucosylase/hydrolase 28 |
| AT2G42885 | Defensin-like (DEFL) family protein |
| AT4G00140 | Calcium-binding EF-hand family protein |
| AT5G67340 | ARM repeat superfamily protein |
| AT1G25540 | phytochrome and flowering time regulatory protein (PFT1) |
| AT1G76900 | tubby like protein 1 |
| AT5G10550 | global transcription factor group E2 |
| AT3G26511 | unknown protein |

TABLE 6-continued

SHR direct targets identified by ChIP-chip

| Arabidopsis Genome Initiative (AGI) identification number | Short_description |
|---|---|
| AT5G56100 | glycine-rich protein/oleosin |
| AT5G49410 | unknown protein |
| AT4G20780 | calmodulin like 42 |
| AT5G01710 | methyltransferases |
| AT5G01712 | conserved peptide upstream open reading frame 48 |
| AT1G61260 | Protein of unknown function (DUF761) |
| AT4G32160 | Phox (PX) domain-containing protein |
| AT2G35490 | Plastid-lipid associated protein PAP/fibrillin family protein |
| AT2G35500 | shikimate kinase like 2 |
| AT1G21830 | unknown protein |
| AT3G60570 | expansin B5 |
| AT1G73600 | S-adenosyl-L-methionine-dependent methyltransferases superfamily protein |
| AT1G73602 | conserved peptide upstream open reading frame 32 |
| AT1G14330 | Galactose oxidase/kelch repeat superfamily protein |
| AT2G45900 | Phosphatidylinositol N-acetyglucosaminlytransferase subunit P-related |
| AT5G03380 | Heavy metal transport/detoxification superfamily protein |
| AT1G63430 | Leucine-rich repeat protein kinase family protein |
| AT1G30825 | Arp2/3 complex, 34 kD subunit p34-Arc |
| AT1G01580 | ferric reduction oxidase 2 |
| AT2G38325 | MIR390A; miRNA |
| AT1G78080 | related to AP2 4 |
| AT5G03520 | RAB GTPase homolog 8C |
| AT5G46140 | Protein of unknown function (DUF295) |
| AT1G80470 | F-box/RNI-like/FBD-like domains-containing protein |
| AT5G65683 | Zinc finger (C3HC4-type RING finger) family protein |
| AT4G28230 | unknown protein |
| AT4G28240 | Wound-responsive family protein |
| AT4G08949 | This gene encodes a small protein and has either evidence of transcription or purifying selection. |
| AT2G36090 | F-box family protein |
| AT5G07710 | Polynucleotidyl transferase, ribonuclease H-like superfamily protein |
| AT1G61890 | MATE efflux family protein |
| AT1G32190 | alpha/beta-Hydrolases superfamily protein |
| AT5G41460 | Protein of unknown function (DUF604) |
| AT1G67510 | Leucine-rich repeat protein kinase family protein |
| AT2G46330 | arabinogalactan protein 16 |
| AT5G53910 | RING/U-box superfamily protein |
| AT4G39403 | polaris |
| AT1G18710 | myb domain protein 47 |
| AT1G63090 | phloem protein 2-A11 |
| AT1G72060 | serine-type endopeptidase inhibitors |
| AT1G10410 | Protein of unknown function (DUF1336) |
| AT3G50080 | VIER F-box proteine 2 |
| AT5G19120 | Eukaryotic aspartyl protease family protein |
| AT3G05120 | alpha/beta-Hydrolases superfamily protein |
| AT1G32230 | WWE protein-protein interaction domain protein family |
| AT5G49520 | WRKY DNA-binding protein 48 |
| AT5G24890 | unknown protein |
| AT1G17620 | Late embryogenesis abundant (LEA) hydroxyproline-rich glycoprotein family |
| AT1G14920 | GRAS family transcription factor family protein |
| AT4G38520 | Protein phosphatase 2C family protein |
| AT4G39404 | other RNA |
| AT5G01849 | This gene encodes a small protein and has either evidence of transcription or purifying selection. |
| AT1G76880 | Duplicated homeodomain-like superfamily protein |
| AT2G27850 | pre-tRNA |
| AT4G37790 | Homeobox-leucine zipper protein family |
| AT1G67210 | Proline-rich spliceosome-associated (PSP) family protein/zinc knuckle (CCHC-type) family protein |
| AT3G27960 | Tetratricopeptide repeat (TPR)-like superfamily protein |
| AT1G07090 | Protein of unknown function (DUF640) |
| AT2G28950 | expansin A6 |
| AT4G38860 | SAUR-like auxin-responsive protein family |
| AT5G41470 | Nuclear transport factor 2 (NTF2) family protein |
| AT5G65700 | Leucine-rich receptor-like protein kinase family protein |
| AT4G34760 | SAUR-like auxin-responsive protein family |
| AT3G50760 | galacturonosyltransferase-like 2 |
| AT5G18610 | Protein kinase superfamily protein |
| AT2G18750 | Calmodulin-binding protein |
| AT5G16010 | 3-oxo-5-alpha-steroid 4-dehydrogenase family protein |
| AT4G28720 | Flavin-binding monooxygenase family protein |
| AT3G19590 | Transducin/WD40 repeat-like superfamily protein |
| AT3G05840 | Protein kinase superfamily protein |
| AT1G64625 | Serine/threonine-protein kinase WNK (With No Lysine)-related |

TABLE 6-continued

SHR direct targets identified by ChIP-chip

| Arabidopsis Genome Initiative (AGI) identification number | Short_description |
|---|---|
| AT1G36060 | Integrase-type DNA-binding superfamily protein |
| AT4G23190 | cysteine-rich RLK (RECEPTOR-like protein kinase) 11 |
| AT1G01490 | Heavy metal transport/detoxification superfamily protein |
| AT4G25640 | detoxifying efflux carrier 35 |
| AT4G21680 | NITRATE TRANSPORTER 1.8 |
| AT2G01570 | GRAS family transcription factor family protein |
| AT5G58680 | ARM repeat superfamily protein |
| AT3G16860 | COBRA-like protein 8 precursor |
| AT5G40930 | translocase of outer membrane 20-4 |
| AT3G18485 | iaa-leucine resistant 2 |
| AT5G66816 | unknown protein |
| AT3G13750 | beta galactosidase 1 |
| AT5G17300 | Homeodomain-like superfamily protein |
| AT2G39675 | TAS1C; other RNA |
| AT5G10290 | leucine-rich repeat transmembrane protein kinase family protein |
| AT5G57510 | unknown protein |
| AT2G16630 | Pollen Ole e 1 allergen and extensin family protein |
| AT2G34355 | Major facilitator superfamily protein |
| AT5G07290 | MEI2-like 4 |
| AT5G05860 | UDP-glucosyl transferase 76C2 |
| AT5G08330 | TCP family transcription factor |
| AT5G10840 | Endomembrane protein 70 protein family |
| AT3G02315 | pre-tRNA |
| AT1G72200 | RING/U-box superfamily protein |
| AT5G14110 | Protein of unknown function (DUF 3339) |
| AT5G04560 | HhH-GPD base excision DNA repair family protein |
| AT2G46630 | unknown protein; LOCATED IN: chloroplast |
| AT4G36770 | UDP-Glycosyltransferase superfamily protein |
| AT2G25470 | receptor like protein 21 |
| AT4G23760 | Cox19-like CHCH family protein |
| AT1G13350 | Protein kinase superfamily protein |
| AT2G31751 | unknown gene |
| AT5G67440 | Phototropic-responsive NPH3 family protein |
| AT2G41340 | RNA polymerase II fifth largest subunit, D |
| AT4G27510 | unknown protein |
| AT3G17230 | invertase/pectin methylesterase inhibitor family protein |
| AT5G64770 | unknown protein |
| AT3G50920 | Phosphatidic acid phosphatase (PAP2) family protein |
| AT5G24870 | RING/U-box superfamily protein |
| AT1G01260 | basic helix-loop-helix (bHLH) DNA-binding superfamily protein |
| AT2G22770 | basic helix-loop-helix (bHLH) DNA-binding superfamily protein |
| AT4G05060 | PapD-like superfamily protein |
| AT3G11590 | unknown protein |
| AT2G39030 | Acyl-CoA N-acyltransferases (NAT) superfamily protein |
| AT1G21010 | unknown protein |
| AT3G10530 | Transducin/WD40 repeat-like superfamily protein |
| AT2G30040 | mitogen-activated protein kinase kinase kinase 14 |
| AT5G15160 | BANQUO 2 |
| AT3G48425 | DNAse I-like superfamily protein |
| AT1G30810 | Transcription factor jumonji (jmj) family protein/zinc finger (C5HC2 type) family protein |
| AT2G45620 | Nucleotidyltransferase family protein |
| AT4G17615 | calcineurin B-like protein 1 |
| AT5G66780 | unknown protein |
| AT1G74950 | TIFY domain/Divergent CCT motif family protein |
| AT5G56080 | nicotianamine synthase 2 |
| AT1G09520 | BEST Arabidopsis thaliana protein match is: PHD finger family protein (TAIR: AT3G17460.1) |
| AT4G00650 | FRIGIDA-like protein |
| AT3G54826 | Zim17-type zinc finger protein |
| AT1G28330 | dormancy-associated protein-like 1 |
| AT2G42880 | MAP kinase 20 |
| AT4G00440 | Protein of unknown function (DUF3741) |
| AT5G12010 | unknown protein |
| AT3G51990 | Protein kinase superfamily protein |
| AT2G23700 | Protein of unknown function, DUF547 |
| AT4G25470 | C-repeat/DRE binding factor 2 |
| AT5G58950 | Protein kinase superfamily protein |
| AT4G25480 | dehydration response element B1A |
| AT5G56840 | myb-like transcription factor family protein |
| AT4G35940 | unknown protein |
| AT4G20010 | plastid transcriptionally active 9 |
| AT3G04855 | unknown protein |

TABLE 6-continued

SHR direct targets identified by ChIP-chip

| Arabidopsis Genome Initiative (AGI) identification number | Short_description |
|---|---|
| AT2G36590 | proline transporter 3 |
| AT5G18670 | beta-amylase 3 |
| AT1G24120 | ARG1-like 1 |
| AT1G72180 | Leucine-rich receptor-like protein kinase family protein |
| AT1G68570 | Major facilitator superfamily protein |
| AT5G15350 | early nodulin-like protein 17 |
| AT1G76580 | Squamosa promoter-binding protein-like (SBP domain) transcription factor family protein |
| AT5G56090 | cytochrome c oxidase 15 |
| AT5G02020 | Encodes a protein involved in salt tolerance, names SIS (Salt Induced Serine rich). |
| AT1G73560 | Bifunctional inhibitor/lipid-transfer protein/seed storage 2S albumin superfamily protein |
| AT4G23920 | UDP-D-glucose/UDP-D-galactose 4-epimerase 2 |
| AT1G24265 | Protein of unknown function (DUF1664) |
| AT1G03870 | FASCICLIN-like arabinoogalactan 9 |
| AT2G44500 | O-fucosyltransferase family protein |
| AT1G21050 | Protein of unknown function, DUF617 |
| AT4G37080 | Protein of unknown function, DUF547 |
| AT2G22510 | hydroxyproline-rich glycoprotein family protein |
| AT3G05800 | AtBS1 (activation-tagged BRI1 suppressor l)-interacting factor 1 |
| AT1G23710 | Protein of unknown function (DUF1645) |
| AT3G19100 | Protein kinase superfamily protein |
| AT5G24030 | SLAC1 homologue 3 |
| AT4G37320 | cytochrome P450, family 81, subfamily D, polypeptide 5 |
| AT1G12380 | unknown protein |
| AT3G02170 | longifolia2 |
| AT2G01680 | Ankyrin repeat family protein |
| AT4G17460 | Homeobox-leucine zipper protein 4 (HB-4)/HD-ZIP protein |
| AT4G05071 | This gene encodes a small protein and has either evidence of transcription or purifying selection. |
| AT4G18900 | Transducin/WD40 repeat-like superfamily protein |
| AT5G45360 | F-box family protein |
| AT1G09070 | soybean gene regulated by cold-2 |
| AT1G73840 | hydroxyproline-rich glycoprotein family protein |
| AT5G23280 | TCP family transcription factor |
| AT5G13100 | unknown protein |
| AT3G07350 | Protein of unknown function (DUF506) |
| AT5G43810 | Stabilizer of iron transporter SufD/Polynucleotidyl transferase |
| AT3G56000 | cellulose synthase like A14 |
| AT1G66140 | zinc finger protein 4 |
| AT3G27170 | chloride channel B |
| AT1G71890 | Major facilitator superfamily protein |
| AT4G23750 | cytokinin response factor 2 |
| AT5G52260 | myb domain protein 19 |
| AT5G44090 | Calcium-binding EF-hand family protein |
| AT4G40060 | homeobox protein 16 |
| AT3G24050 | GATA transcription factor 1 |
| AT5G06865 | other RNA |
| AT5G06870 | polygalacturonase inhibiting protein 2 |
| AT3G15770 | unknown protein |
| AT4G36780 | BES1/BZR1 homolog 2 |
| AT1G72430 | SAUR-like auxin-responsive protein family |
| AT5G15210 | homeobox protein 30 |
| AT1G30380 | photosystem I subunit K |
| AT1G13360 | unknown protein |
| AT5G46740 | ubiquitin-specific protease 21 |
| AT5G06390 | FASCICLIN-like arabinogalactan protein 17 precursor |
| AT5G56010 | heat shock protein 81-3 |
| AT2G35940 | BEL1-like homeodomain 1 |
| AT1G03860 | prohibitin 2 |
| AT1G04000 | unknown protein; BEST Arabidopsis thaliana protein match is: unknown protein (TAIR: AT5G44060.1); Has 62 Blast hits to 62 prot . . . |
| AT1G68845 | unknown protein |
| AT2G34450 | HMG-box (high mobility group) DNA-binding family protein |
| AT4G37610 | BTB and TAZ domain protein 5 |
| AT3G62200 | Putative endonuclease or glycosyl hydrolase |
| AT4G38680 | glycine rich protein 2 |
| AT5G57690 | diacylglycerol kinase 4 |
| AT4G27310 | B-box type zinc finger family protein |
| AT3G61480 | Quinoprotein amine dehydrogenase, beta chain-like; RIC1-like guanyl-nucleotide exchange factor |
| AT2G02070 | indeterminate(ID)-domain 5 |
| AT3G02910 | AIG2-like (avirulence induced gene) family protein |
| AT1G35560 | TCP family transcription factor |
| AT1G70710 | glycosyl hydrolase 9B1 |

TABLE 6-continued

SHR direct targets identified by ChIP-chip

| Arabidopsis Genome Initiative (AGI) identification number | Short_description |
|---|---|
| AT3G19680 | Protein of unknown function (DUF1005) |
| AT4G03400 | Auxin-responsive GH3 family protein |
| AT1G30360 | Early-responsive to dehydration stress protein (ERD4) |
| AT3G05200 | RING/U-box superfamily protein |
| AT5G67240 | small RNA degrading nuclease 3 |
| AT5G66815 | unknown protein |
| AT2G06520 | photosystem II subunit X |
| AT3G48530 | SNF1-related protein kinase regulatory subunit gamma 1 |
| AT3G49970 | Phototropic-responsive NPH3 family protein |
| AT5G09620 | Octicosapeptide/Phox/Bem1p family protein |
| AT3G52740 | unknown protein |
| AT4G17250 | unknown protein |
| AT4G39100 | PHD finger family protein/bromo-adjacent homology (BAH) domain-containing protein |
| AT1G70100 | unknown protein |
| AT5G25220 | KNOTTED1-like homeobox gene 3 |
| AT5G25350 | EIN3-binding F box protein 2 |
| AT4G36648 | other RNA |
| AT3G25905 | CLAVATA3/ESR-RELATED 27 |
| AT4G16780 | homeobox protein 2 |
| AT5G13180 | NAC domain containing protein 83 |
| AT1G03040 | basic helix-loop-helix (bHLH) DNA-binding superfamily protein |
| AT4G00310 | Putative membrane lipoprotein |
| AT3G15210 | ethylene responsive element binding factor 4 |
| AT1G32640 | Basic helix-loop-helix (bHLH) DNA-binding family protein |
| AT4G16980 | arabinogalactan-protein family |
| AT3G14067 | Subtilase family protein |
| AT4G35800 | RNA polymerase II large subunit |
| AT2G48030 | DNAse I-like superfamily protein |
| AT4G08920 | cryptochrome 1 |
| AT5G51590 | AT hook motif DNA-binding family protein |
| AT1G80460 | Actin-like ATPase superfamily protein |
| AT5G52940 | Protein of unknown function (DUF295) |
| AT5G05250 | unknown protein |
| AT5G65660 | hydroxyproline-rich glycoprotein family protein |
| AT3G05910 | Pectinacetylesterase family protein |
| AT2G43360 | Radical SAM superfamily protein |
| AT2G43370 | RNA-binding (RRM/RBD/RNP motifs) family protein |
| AT5G58690 | phosphatidylinositol-speciwc phospholipase C5 |
| AT3G12700 | Eukaryotic aspartyl protease family protein |
| AT5G15340 | Pentatricopeptide repeat (PPR) superfamily protein |
| AT3G24480 | Leucine-rich repeat (LRR) family protein |
| AT5G45370 | nodulin MtN21/EamA-like transporter family protein |
| AT4G29190 | Zinc finger C-x8-C-x5-C-x3-H type family protein |
| AT1G02640 | beta-xylosidase 2 |
| AT4G29780 | unknown protein |
| AT1G59750 | auxin response factor 1 |
| AT2G23350 | poly(A) binding protein 4 |
| AT1G10020 | Protein of unknown function (DUF1005) |
| AT3G46660 | UDP-glucosyl transferase 76E12 |
| AT5G54360 | C2H2-like zinc finger protein |
| AT3G47500 | cycling DOF factor 3 |
| AT3G21890 | B-box type zinc finger family protein |
| AT2G39880 | myb domain protein 25 |
| AT5G60890 | myb domain protein 34 |
| AT4G04640 | ATPase, F1 complex, gamma subunit protein |
| AT4G25490 | C-repeat/DRE binding factor 1 |
| AT5G23850 | Arabidopsis thaliana protein of unknown function (DUF821) |
| AT1G75820 | Leucine-rich receptor-like protein kinase family protein |
| AT4G39070 | B-box zinc finger family protein |
| AT4G11300 | Protein of unknown function (DUF793) |
| AT3G23820 | UDP-D-glucuronate 4-epimerase 6 |
| AT2G36020 | HVA22-like protein J |
| AT2G47180 | galactinol synthase 1 |
| AT4G30960 | SOS3-interacting protein 3 |
| AT4G38620 | myb domain protein 4 |
| AT5G55970 | RING/U-box superfamily protein |
| AT5G57700 | BNR/Asp-box repeat family protein |
| AT5G59490 | Haloacid dehalogenase-like hydrolase (HAD) superfamily protein |
| AT5G01820 | serine/threonine protein kinase 1 |
| AT1G70944 | unknown protein |
| AT3G60410 | Protein of unknown function (DUF1639) |

TABLE 6-continued

SHR direct targets identified by ChIP-chip

| Arabidopsis Genome Initiative (AGI) identification number | Short_description |
|---|---|
| AT1G10150 | Carbohydrate-binding protein |
| AT2G01490 | phytanoyl-CoA dioxygenase (PhyH) family protein |
| AT2G35610 | xyloglucanase 113 |
| AT1G10470 | response regulator 4 |
| AT3G57785 | unknown protein |
| AT1G06070 | Basic-leucine zipper (bZIP) transcription factor family protein |
| AT1G19380 | Protein of unknown function (DUF1195) |
| AT1G06680 | photosystem II subunit P-1 |
| AT5G21960 | Integrase-type DNA-binding superfamily protein |
| AT1G69850 | nitrate transporter 1: 2 |
| AT1G33240 | GT-2-like 1 |
| AT5G62040 | PEBP (phosphatidylethanolamine-binding protein) family protein |
| AT4G16380 | Heavy metal transport/detoxification superfamily protein |
| AT5G12050 | unknown protein |
| AT3G05220 | Heavy metal transport/detoxification superfamily protein |
| AT1G11330 | S-locus lectin protein kinase family protein |
| AT1G02080 | transcription regulators |
| AT1G09940 | Glutamyl-tRNA reductase family protein |
| AT5G60700 | glycosyltransferase family protein 2 |
| AT5G15850 | CONSTANS-like 1 |
| AT1G15820 | light harvesting complex photosystem II subunit 6 |
| AT5G18310 | unknown protein |
| AT3G18830 | polyol/monosaccharide transporter 5 |
| AT2G43040 | tetratricopeptide repeat (TPR)-containing protein |
| AT3G11410 | protein phosphatase 2CA |
| AT5G67360 | Subtilase family protein |
| AT2G47090 | zinc ion binding; nucleic acid binding |
| AT5G56070 | unknown protein |
| AT1G29930 | chlorophyll A/B binding protein 1 |
| AT5G67330 | natural resistance associated macrophage protein 4 |
| AT2G03240 | EXS (ERD1/XPR1/SYG1) family protein |
| AT3G25910 | Protein of unknown function (DUF1644) |
| AT4G38550 | Arabidopsis phospholipase-like protein (PEARLI 4) family |
| AT3G04470 | Ankyrin repeat family protein |
| AT2G41910 | Protein kinase superfamily protein |
| AT3G15530 | S-adenosyl-L-methionine-dependent methyltransferases superfamily protein |
| AT3G08940 | light harvesting complex photosystem II |
| AT5G11970 | Protein of unknown function (DUF3511) |
| AT1G01430 | TRICHOME BIREFRINGENCE-LIKE 25 |
| AT4G05320 | polyubiquitin 10 |
| AT1G75540 | salt tolerance homolog2 |
| AT5G40480 | embryo defective 3012 |
| AT1G31835 | unknown protein |
| AT5G61670 | unknown protein |
| AT4G32030 | unknown protein |
| AT5G04830 | Nuclear transport factor 2 (NTF2) family protein |
| AT2G27710 | 60S acidic ribosomal protein family |
| AT1G03600 | photosystem II family protein |
| AT5G52050 | MATE efflux family protein |
| AT5G21280 | hydroxyproline-rich glycoprotein family protein |
| AT5G52100 | Dihydrodipicolinate reductase, bacterial/plant |
| AT5G05140 | Transcription elongation factor (TFIIS) family protein |
| AT1G68585 | unknown protein |
| AT1G28190 | unknown protein |
| AT1G20980 | squamosa promoter binding protein-like 14 |
| AT1G03730 | unknown protein; BEST Arabidopsis thaliana protein match is: unknown protein (TAIR: AT4G03600.1); Has 50 Blast hits to 50 prot . . . |
| AT3G16610 | pentatricopeptide (PPR) repeat-containing protein |
| AT1G50020 | unknown protein |
| AT5G40380 | cysteine-rich RLK (RECEPTOR-like protein kinase) 42 |
| AT1G80930 | MIF4G domain-containing protein/MA3 domain-containing protein |
| AT3G51690 | PIF1 helicase |
| AT1G26580 | molecular function unknown |
| AT1G58110 | Basic-leucine zipper (bZIP) transcription factor family protein |
| AT1G80200 | unknown protein, LOCATED IN: endomembrane |
| AT4G24570 | dicarboxylate carrier 2 |
| AT1G72700 | ATPase E1-E2 type family protein/haloacid dehalogenase-like hydrolase family protein |
| AT3G11690 | unknown protein |
| AT5G25360 | unknown protein |
| AT4G34050 | S-adenosyl-L-methionine-dependent methyltransferases superfamily protein |
| AT1G07870 | Protein kinase superfamily protein |

TABLE 6-continued

SHR direct targets identified by ChIP-chip

| Arabidopsis Genome Initiative (AGI) identification number | Short_description |
|---|---|
| AT5G15780 | Pollen Ole e 1 allergen and extensin family protein |
| AT3G59090 | tobamovirus multiplication 1 |
| AT4G17870 | Polyketide cyclase/dehydrase and lipid transport superfamily protein |
| AT4G24960 | HVA22 homologue D |
| AT1G66260 | RNA-binding (RRM/RBD/RNP motifs) family protein |
| AT1G30200 | F-box family protein |
| AT4G03010 | RNI-like superfamily protein |
| AT3G13110 | serine acetyltransferase 2; 2 |
| AT3G13784 | cell wall invertase 5 |
| AT1G01620 | plasma membrane intrinsic protein 1C |
| AT1G15810 | S15/NS1, RNA-binding protein |
| AT4G39840 | unknown protein |
| AT1G29910 | chlorophyll A/B binding protein 3 |
| AT1G62390 | Octicosapeptide/Phox/Bem1p (PB1) domain-containing protein/tetratricopeptide repeat (TPR)-containing protein |
| AT4G29890 | choline monooxygenase, putative (CMO-like) |
| AT1G27730 | salt tolerance zinc finger |
| AT2G45630 | D-isomer specific 2-hydroxyacid dehydrogenase family protein |
| AT3G19970 | alpha/beta-Hydrolases superfamily protein |
| AT4G16563 | Eukaryotic aspartyl protease family protein |
| AT5G10980 | Histone superfamily protein |
| AT1G08315 | ARM repeat superfamily protein |
| AT3G22968 | conserved peptide upstream open reading frame 59 |
| AT3G22970 | Protein of unknown function (DUF506) |
| AT5G03285 | other RNA |
| AT4G28750 | Photosystem I reaction centre subunit IV/PsaE protein |
| AT3G08610 | unknown protein |
| AT1G34000 | one-helix protein 2 |
| AT3G17040 | high chlorophyll fluorescent 107 |
| AT4G03110 | RNA-binding protein-defense related 1 |
| AT1G37130 | nitrate reductase 2 |
| AT3G28860 | ATP binding cassette subfamily B19 |
| AT3G14440 | nine-cis-epoxycarotenoid dioxygenase 3 |
| AT4G20860 | FAD-binding Berberine family protein |
| AT1G12240 | Glycosyl hydrolases family 32 protein |
| AT1G71040 | Cupredoxin superfamily protein |
| AT4G31800 | WRKY DNA-binding protein 18 |
| AT3G49290 | ABL interactor-like protein 2 |
| AT5G03890 | unknown protein |
| AT2G44798 | other RNA |
| AT1G46264 | heat shock transcription factor B4 |
| AT1G12110 | nitrate transporter 1.1 |
| AT1G70530 | cysteine-rich RLK (RECEPTOR-like protein kinase) 3 |
| AT4G04850 | K+ efflux antiporter 3 |
| AT2G45850 | AT hook motif DNA-binding family protein |
| AT1G78110 | unknown protein, LOCATED IN: plasma membrane |
| AT5G05600 | 2-oxoglutarate (2OG) and Fe(II)-dependent oxygenase superfamily protein |
| AT5G45113 | mitochondrial transcription termination factor-related/mTERF-related |
| AT4G29735 | unknown protein |
| AT2G26750 | alpha/beta-Hydrolases superfamily protein |
| AT4G30350 | Double Clp-N motif-containing P-loop nucleoside triphosphate hydrolases superfamily protein |
| AT4G30190 | H(+)-ATPase 2 |
| AT3G17130 | Plant invertase/pectin methylesterase inhibitor superfamily protein |
| AT5G42150 | Glutathione S-transferase family protein |
| AT4G39780 | Integrase-type DNA-binding superfamily protein |
| AT5G17760 | P-loop containing nucleoside triphosphate hydrolases superfamily protein |
| AT4G23740 | Leucine-rich repeat protein kinase family protein |
| AT3G57790 | Pectin lyase-like superfamily protein |
| AT1G01120 | 3-ketoacyl-CoA synthase 1 |
| AT1G01180 | S-adenosyl-L-methionine-dependent methyltransferases superfamily protein |
| AT1G01570 | Protein of unknown function (DLF604) |
| AT1G02090 | Proteasome component (PCI) domain protein |
| AT1G02110 | Protein of unknown function (DUF630 and DUF632) |
| AT1G02360 | Chitinase family protein |
| AT1G02660 | alpha/beta-Hydrolases superfamily protein |
| AT1G04830 | Ypt/Rab-GAP domain of gyp1p superfamily protein |
| AT1G05370 | Sec14p-like phosphatidylinositol transfer family protein |
| AT1G05805 | basic helix-loop-helix (bHLH) DNA-binding superfamily protein |
| AT1G06040 | B-box zinc finger family protein |
| AT1G07250 | UDP-glucosyl transferase 71C4 |
| AT1G08510 | fatty acyl-ACP thioesterases B |

TABLE 6-continued

SHR direct targets identified by ChIP-chip

| Arabidopsis Genome Initiative (AGI) identification number | Short_description |
|---|---|
| AT1G09250 | basic helix-loop-helix (bHLH) DNA-binding superfamily protein |
| AT1G12090 | extensin-like protein |
| AT1G13080 | cytochrome P450, family 71, subfamily B, polypeptide 2 |
| AT1G13700 | 6-phosphogluconolactonase 1 |
| AT1G13880 | ELM2 domain-containing protein |
| AT1G14280 | phytochrome kinase substrate 2 |
| AT1G14540 | Peroxidase superfamily protein |
| AT1G14780 | MAC/Perforin domain-containing protein |
| AT1G15700 | ATPase, F1 complex, gamma subunit protein |
| AT1G15800 | unknown protein |
| AT1G17420 | lipoxygenase 3 |
| AT1G18010 | Major facilitator superfamily protein |
| AT1G19210 | Integrase-type DNA-binding superfamily protein |
| AT1G19720 | Pentatricopeptide repeat (PPR-like) superfamily protein |
| AT1G21400 | Thiamin diphosphate-binding fold (THDP-binding) superfamily protein |
| AT1G21600 | plastid transcriptionally active 6 |
| AT1G21920 | Histone H3 K4-specific methyltransferase SET7/9 family protein |
| AT1G22360 | UDP-glucosyl transferase 85A2 |
| AT1G27200 | Domain of unknown function (DUF23) |
| AT1G27930 | Protein of unknown function (DUF579) |
| AT1G28280 | VQ motif-containing protein |
| AT1G29300 | Plant protein of unknown function (DUF641) |
| AT1G34010 | unknown protein |
| AT1G48970 | NagB/RpiA/CoA transferase-like superfamily protein |
| AT1G49790 | F-box associated ubiquitination effector family protein |
| AT1G50300 | TBP-associated factor 15 |
| AT1G50430 | Ergosterol biosynthesis ERG4/ERG24 family |
| AT1G50640 | ethylene responsive element binding factor 3 |
| AT1G51690 | protein phosphatase 2A 55 kDa regulatory subunit B alpha isoform |
| AT1G51710 | ubiquitin-specific protease 6 |
| AT1G52240 | RHO guanyl-nucleotide exchange factor 11 |
| AT1G53530 | Peptidase S24/S26A/S26B/S26C family protein |
| AT1G53850 | 20S proteasome alpha subunit E1 |
| AT1G54080 | oligouridylate-binding protein 1A |
| AT1G55230 | Family of unknown function (DUF716) |
| AT1G55340 | Protein of unknown function (DUF1639) |
| AT1G55680 | Transducin/WD40 repeat-like superfamily protein |
| AT1G56230 | Protein of unknown function (DUF1399) |
| AT1G56290 | CwfJ-like family protein |
| AT1G56590 | Clathrin adaptor complexes medium subunit family protein |
| AT1G60110 | Mannose-binding lectin superfamily protein |
| AT1G60160 | Potassium transporter family protein |
| AT1G60970 | SNARE-like superfamily protein |
| AT1G61750 | Receptor-like protein kinase-related family protein |
| AT1G62050 | Ankyrin repeat family protein |
| AT1G63020 | nuclear RNA polymerase D1A |
| AT1G65410 | non-intrinsic ABC protein 11 |
| AT1G66150 | transmembrane kinase 1 |
| AT1G66950 | pleiotropic drug resistance 11 |
| AT1G67855 | unknown protein |
| AT1G67856 | RING/U-box superfamily protein |
| AT1G67900 | Phototropic-responsive NPH3 family protein |
| AT1G67950 | RNA-binding (RRM/RBD/RNP motifs) family protein |
| AT1G68850 | Peroxidase superfamily protein |
| AT1G69870 | nitrate transporter 1.7 |
| AT1G70250 | receptor serine/threonine kinase, putative |
| AT1G70290 | trehalose-6-phosphatase synthase S8 |
| AT1G70300 | K+ uptake permease 6 |
| AT1G70610 | transporter associated with antigen processing protein 1 |
| AT1G71528 | other RNA |
| AT1G71530 | Protein kinase superfamily protein |
| AT1G72440 | CCAAT-binding factor |
| AT1G72460 | Leucine-rich repeat protein kinase family protein |
| AT1G72510 | Protein of unknown function (DUF1677) |
| AT1G72640 | NAD(P)-binding Rossmann-fold superfamily protein |
| AT1G72760 | Protein kinase superfamily protein |
| AT1G73480 | alpha/beta-Hydrolases superfamily protein |
| AT1G73530 | RNA-binding (RRM/RBD/RNP motifs) family protein |
| AT1G74960 | fatty acid biosynthesis 1 |
| AT1G75470 | purine permease 15 |
| AT1G76170 | 2-thiocytidine tRNA biosynthesis protein, TtcA |

TABLE 6-continued

| SHR direct targets identified by ChIP-chip | |
|---|---|
| Arabidopsis Genome Initiative (AGI) identification number | Short_description |
| AT1G76400 | Ribophorin I |
| AT1G77460 | Armadillo/beta-catenin-like repeat; C2 calcium/lipid-binding domain (CaLB) protein |
| AT1G78280 | transferases, transferring glycosyl groups |
| AT1G78580 | trehalose-6-phosphate synthase |
| AT1G79080 | Pentatricopeptide repeat (PPR) superfamily protein |
| AT1G79350 | RING/FYVE/PHD zinc finger superfamily protein |
| AT1G79430 | Homeodomain-like superfamily protein |
| AT1G79890 | RAD3-like DNA-binding helicase protein |
| AT1G80190 | partner of SLD five 1 |
| AT1G80300 | nucleotide transporter 1 |
| AT1G80310 | sulfate transmembrane transporters |
| AT1G80325 | other RNA |
| AT2G01420 | Auxin efflux carrier family protein |
| AT2G01670 | nudix hydrolase homolog 17 |
| AT2G01735 | RING-finger protein for embryogenesis |
| AT2G05790 | O-Glycosyl hydrolases family 17 protein |
| AT2G08986 | unknown protein |
| AT2G18100 | Protein of unknown function (DUF726) |
| AT2G18800 | xyloglucan endotransglucosylase/hydrolase 21 |
| AT2G18969 | Encodes a atypical member of the bHLH (basic helix-loop-helix) family transcriptional factors |
| AT2G18970 | unknown protein |
| AT2G19830 | SNF7 family protein |
| AT2G20550 | HSP40/DnaJ peptide-binding protein |
| AT2G20616 | Family of unknown function (DUF566) |
| AT2G21540 | SEC14-like 3 |
| AT2G22120 | RING/FYVE/PHD zinc finger superfamily protein |
| AT2G22480 | phosphofructokinase 5 |
| AT2G22870 | P-loop containing nucleoside triphosphate hydrolases superfamily protein |
| AT2G24390 | AIG2-like (avirulence induced gene) family protein |
| AT2G24810 | Pathogenesis-related thaumatin superfamily protein |
| AT2G25270 | unknown protein; LOCATED IN: plasma membrane |
| AT2G26130 | RING/U-box protein with C6HC-type zinc finger |
| AT2G26550 | heme oxygenase 2 |
| AT2G28350 | auxin response factor 10 |
| AT2G28900 | outer plastid envelope protein 16-1 |
| AT2G30250 | WRKY DNA-binding protein 25 |
| AT2G30520 | Phototropic-responsive NPH3 family protein |
| AT2G30580 | DREB2A-interacting protein 2 |
| AT2G30890 | Cytochrome b561/fetric reductase transmembrane protein family |
| AT2G31350 | glyoxalase 2-5 |
| AT2G32170 | S-adenosyl-L-methionine-dependent methyltransferases superfamily protein |
| AT2G32730 | 26S proteasome regulatory complex, non-ATPase subcomplex, Rpn2/Psmd1 subunit |
| AT2G34090 | maternal effect embryo arrest 18 |
| AT2G34110 | forkhead-associated (FHA) domain-containing protein |
| AT2G34460 | NAD(P)-binding Rossmann-fold superfamily protein |
| AT2G34470 | urease accessory protein G |
| AT2G35880 | TPX2 (targeting protein for Xklp2) protein family |
| AT2G36060 | MMS ZWEI homologue 3 |
| AT2G36250 | Tubulin/FtsZ family protein |
| AT2G36340 | DNA-binding storekeeper protein-related transcriptional regulator |
| AT2G36840 | ACT-like superfamily protein |
| AT2G37210 | lysine decarboxylase family protein |
| AT2G38320 | TRICHOME BIREFRINGENCE-LIKE 34 |
| AT2G39020 | Acyl-CoA N-acyltransferases (NAT) superfamily protein |
| AT2G39040 | Peroxidase superfamily protein |
| AT2G39380 | exocyst subunit exo70 family protein H2 |
| AT2G40010 | Ribosomal protein L10 family protein |
| AT2G40160 | Plant protein of unknown function (DUF828) |
| AT2G40990 | DHHC-type zinc finger family protein |
| AT2G41330 | Glutaredoxin family protein |
| AT2G41590 | unknown protein |
| AT2G41945 | unknown protein |
| AT2G42710 | Ribosomal protein L1p/L10e family |
| AT2G42780 | molecular_function unknow |
| AT2G42790 | citrate synthase 3 |
| AT2G42980 | Eukaryotic aspartyl protease family protein |
| AT2G43070 | SIGNAL PEPTIDE PEPTIDASE-LIKE 3 |
| AT2G43080 | P4H isoform 1 |
| AT2G44520 | cytochrome c oxidase 10 |
| AT2G44950 | histone mono-ubiquitination 1 |
| AT2G45180 | Bifunctional inhibitor/lipid-transfer protein/seed storage 2S albumin superfamily protein |

TABLE 6-continued

| SHR direct targets identified by ChIP-chip | |
|---|---|
| Arabidopsis Genome Initiative (AGI) identification number | Short_description |
| AT2G45500 | AAA-type ATPase family protein |
| AT2G45700 | sterile alpha motif (SAM) domain-containing protein |
| AT2G45880 | beta-amylase 7 |
| AT2G45980 | unknown protein |
| AT2G46290 | Transducin/WD40 repeat-like superfamily protein |
| AT2G46430 | cyclic nucleotide gated channel 3 |
| AT2G46840 | DOMAIN OF UNKNOWN FUNCTION 724 4 |
| AT2G48060 | unknown protein |
| AT3G01430 | NHL domain-containing protein |
| AT3G01640 | glucuronokinase G |
| AT3G02880 | Leucine-rich repeat protein kinase family protein |
| AT3G03470 | cytochrome P450, family 87, subfamily A, polypeptide 9 |
| AT3G03980 | NAD(P)-binding Rossmann-fold superfamily protein |
| AT3G05670 | RING/U-box protein |
| AT3G07390 | auxin-responsive family protein |
| AT3G07470 | Protein of unknown function, DUF538 |
| AT3G08580 | ADP/ATP carrier 1 |
| AT3G09630 | Ribosomal protein L4/L1 family |
| AT3G10985 | senescence associated gene 20 |
| AT3G11850 | Protein of unknown function, DUF593 |
| AT3G13790 | Glycosyl hydrolases family 32 protein |
| AT3G14840 | Leucine-rich repeat transmembrane protein kinase |
| AT3G14870 | Plant protein of unknown function (DUF641) |
| AT3G17100 | sequence-specific DNA binding transcription factors |
| AT3G17800 | Protein of unknown function (DUF760) |
| AT3G18050 | unknown protein |
| AT3G20310 | ethylene response factor 7 |
| AT3G23450 | unknown protein |
| AT3G24520 | heat shock transcription factor C1 |
| AT3G25700 | Eukaryotic aspartyl protease family protein |
| AT3G25760 | allene oxide cyclase 1 |
| AT3G27831 | Gamma-thionin family protein |
| AT3G45300 | isovaleryl-CoA-dehydrogenase |
| AT3G46658 | other RNA |
| AT3G46668 | other RNA |
| AT3G46670 | UDP-glucosyl transferase 76E11 |
| AT3G47360 | hydroxysteroid dehydrogenase 3 |
| AT3G47460 | Structural maintenance of chromosomes (SMC) family protein |
| AT3G47675 | Protein of unknown function |
| AT3G47680 | DNA binding |
| AT3G47990 | SUGAR-INSENSITIVE 3 |
| AT3G49810 | ARM repeat superfamily protein |
| AT3G51070 | S-adenosyl-L-methionine-dependent methyltransferases superfamily protein |
| AT3G51075 | other RNA |
| AT3G51580 | unknown protein |
| AT3G51700 | PIF1 helicase |
| AT3G51860 | cation exchanger 3 |
| AT3G53280 | cytochrome p450 71b5 |
| AT3G54060 | unknown protein |
| AT3G54230 | suppressor of abi3-5 |
| AT3G54440 | glycoside hydrolase family 2 protein |
| AT3G54950 | patatin-like protein 6 |
| AT3G55590 | Glucose-1-phosphate adenylyltransferase family protein |
| AT3G56920 | DHHC-type zinc finger family protein |
| AT3G57060 | binding |
| AT3G57110 | unknown protein |
| AT3G57470 | Insulinase (Peptidase family M16) family protein |
| AT3G58640 | Mitogen activated protein kinase kinase kinase-related |
| AT3G58840 | Tropomyosin-related |
| AT3G58890 | RNI-like superfamily protein |
| AT3G59420 | crinkly4 |
| AT3G59970 | methylenetetrahydrofolate reductase 1 |
| AT3G59980 | Nucleic acid-binding, OB-fold-like protein |
| AT3G60140 | Glycosyl hydrolase superfamily protein |
| AT3G60440 | Phosphoglycerate mutase family protein |
| AT3G60660 | unknown protein |
| AT3G60800 | DHHC-type zinc finger family protein |
| AT3G61780 | embryo defective 1703 |
| AT3G62660 | galacturonosyltransferase-like 7 |
| AT3G63060 | EID1-like 3 |
| AT3G63070 | Tudor/PWWP/MBT domain-containing protein |

TABLE 6-continued

SHR direct targets identified by ChIP-chip

| Arabidopsis Genome Initiative (AGI) identification number | Short_description |
|---|---|
| AT3G63460 | transducin family protein/WD-40 repeat family protein |
| AT4G00150 | GRAS family transcription factor |
| AT4G00335 | RING-H2 finger B1A |
| AT4G00430 | plasma membrane intrinsic protein 1; 4 |
| AT4G01400 | Pentatricopeptide repeat (PPR) superfamily protein ( |
| AT4G01970 | stachyose synthase |
| AT4G02100 | Heat shock protein DnaJ with tetratricopeptide repeat |
| AT4G02770 | photosystem I subunit D-1 |
| AT4G05018 | unknown protein |
| AT4G05070 | Wound-responsive family protein |
| AT4G05150 | Octicosapeptide/Phox/Bem1p family protein |
| AT4G08850 | Leucine-rich repeat receptor-like protein kinase family protein |
| AT4G09000 | general regulatory factor 1 |
| AT4G09010 | ascorbate peroxidase 4 |
| AT4G12230 | alpha/beta-Hydrolases superfamily protein |
| AT4G12730 | FASCICLIN-like arabinogalactan 2 |
| AT4G14620 | Protein of unknown function (DUF506) |
| AT4G14622 | conserved peptide upstream open reading frame 60 |
| AT4G15560 | Deoxyxylulose-5-phosphate synthase |
| AT4G15920 | Nodulin MtN3 family protein |
| AT4G16140 | proline-rich family protein |
| AT4G16490 | ARM repeat superfamily protein |
| AT4G17090 | chloroplast beta-amylase |
| AT4G17430 | O-fucosyltransferase family protein |
| AT4G17895 | ubiquitin-specific protease 20 |
| AT4G18020 | CheY-like two-component responsive regulator family protein |
| AT4G18570 | Tetratricopeptide repeat (TPR)-like superfamily protein |
| AT4G18670 | Leucine-rich repeat (LRR) family protein |
| AT4G19160 | unknown protein |
| AT4G19190 | zinc knuckle (CCHC-type) family protein |
| AT4G20830 | FAD-binding Berberine family protein |
| AT4G21210 | PPDK regulatory protein |
| AT4G22010 | SKU5 similar 4 |
| AT4G22360 | SWIB complex BAF60b domain-containing protein |
| AT4G23205 | other RNA |
| AT4G23630 | VIRB2-interacting protein 1 |
| AT4G23810 | WRKY family transcription factor |
| AT4G24240 | WRKY DNA-binding protein 7 |
| AT4G24805 | S-adenosyl-L-methionine-dependent methyltransferases superfamily protein |
| AT4G24920 | secE/sec61-gamma protein transport protein |
| AT4G26400 | RING/U-box superfamily protein |
| AT4G26850 | mannose-1-phosphate guanylyltransferase (GDP)s; GDP-galactose: mannose-1-phosphate guanylyltransferases; GDP-galactose: glucose-1-phosphate guanylyltransferases; GDP-galactose: myoinositol-1-phosphate guanylyltransferases; glucose-1-phosphate guanylyltransferase |
| AT4G27280 | Calcium-binding EF-hand family protein |
| AT4G27500 | proton pump interactor 1 |
| AT4G27520 | early nodulin-like protein 2 |
| AT4G27700 | Rhodanese/Cell cycle control phosphatase superfamily protein |
| AT4G28290 | unknown protein |
| AT4G28760 | Protein of unknown function (DUF3741) |
| AT4G29840 | Pyridoxal-5'-phosphate-dependent enzyme family protein |
| AT4G30440 | UDP-D-glucuronate 4-epimerase 1 |
| AT4G31500 | cytochrome P450, family 83, subfamily B, polypeptide 1 |
| AT4G32290 | Core-2/I-branching beta-1,6-N-acetylglucosaminyltransferase family protein |
| AT4G33670 | NAD(P)-linked oxidoreductase superfamily protein |
| AT4G34135 | UDP-glucosyltransferase 73B2 |
| AT4G35750 | SEC14 cytosolic factor family protein/phosphoglyceride transfer family protein |
| AT4G36500 | unknown protein |
| AT4G36970 | Remorin family protein |
| AT4G36988 | conserved peptide upstream open reading frame 49 |
| AT4G36990 | heat shock factor 4 |
| AT4G37040 | methionine aminopeptidase 1D |
| AT4G39270 | Leucine-rich repeat protein kinase family protein |
| AT5G01210 | HXXXD-type acyl-transferase family protein |
| AT5G01215 | other RNA |
| AT5G01530 | light harvesting complex photosystem II |
| AT5G01750 | Protein of unknown function (DUF567) |
| AT5G01790 | unknown protein |
| AT5G02190 | Eukaryotic aspartyl protease family protein |
| AT5G03230 | Protein of unknown function, DUF584 |
| AT5G03730 | Protein kinase superfamily protein |

TABLE 6-continued

SHR direct targets identified by ChIP-chip

| Arabidopsis Genome Initiative (AGI) identification number | Short_description |
|---|---|
| AT5G03760 | Nucleotide-diphospho-sugar transferases superfamily protein |
| AT5G04170 | Calcium-binding EF-hand family protein |
| AT5G04610 | S-adenosyl-L-methionine-dependent methyltransferases superfamily protein |
| AT5G04770 | cationic amino acid transporter 6 |
| AT5G06320 | NDR1/HIN1-like 3 |
| AT5G06860 | polygalacturonase inhibiting protein 1 |
| AT5G09850 | Transcription elongation factor (TFIIS) family protein |
| AT5G11000 | Plant protein of unknown function (DUF868) |
| AT5G14565 | MIR398C; miRNA |
| AT5G14570 | high affinity nitrate transporter 2.7 |
| AT5G15845 | other RNA |
| AT5G15970 | stress-responsive protein (KIN2)/stress-induced protein (KIN2)/cold-responsive protein (COR6.6)/ cold-regulated protein (COR6.6) |
| AT5G17490 | RGA-like protein 3 |
| AT5G17980 | C2 calcium/lipid-binding plant phosphoribosyltransferase family protein |
| AT5G19140 | Aluminium induced protein with YGL and LRDR motifs |
| AT5G19150 | pfkB-like carbohydrate kinase family protein |
| AT5G20110 | Dynein light chain type 1 family protein |
| AT5G21482 | cytokinin oxidase 7 |
| AT5G23100 | Protein of unknown function, DUF617 |
| AT5G23240 | DNAJ heat shock N-terminal domain-containing protein |
| AT5G24530 | 2-oxoglutarate (2OG) and Fe(II)-dependent oxygenase superfamily protein |
| AT5G24930 | CONSTANS-like 4 |
| AT5G35695 | unknown protein |
| AT5G37590 | Tetratricopeptide repeat (TPR)-like superfamily protein |
| AT5G38910 | RmlC-like cupins superfamily protein |
| AT5G39710 | Tetratricopeptide repeat (TPR)-like superfamily protein |
| AT5G40820 | Ataxia telangiectasia-mutated and RAD3-related |
| AT5G42120 | Concanavalin A-like lectin protein kinase family protein |
| AT5G44180 | Homeodomain-like transcriptional regulator |
| AT5G44230 | Pentatricopeptide repeat (PPR) superfamily protein |
| AT5G44310 | Late embryogenesis abundant protein (LEA) family protein |
| AT5G45110 | NPR1-like protein 3 |
| AT5G45840 | Leucine-rich repeat protein kinase family protein |
| AT5G47260 | ATP binding; GTP binding; nucleotide binding; nucleoside-triphosphatases |
| AT5G47300 | F-box and associated interaction domains-containing protein |
| AT5G47430 | DWNN domain, a CCHC-type zinc finger |
| AT5G47440 | Plant protein of unknown function (DUF828) with plant pleckstrin homology-like region |
| AT5G47690 | binding |
| AT5G47700 | 60S acidic ribosomal protein family |
| AT5G49400 | zinc knuckle (CCHC-type) family protein |
| AT5G49470 | PAS domain-containing protein tyrosine kinase family protein |
| AT5G49550 | Putative homolog of mammalian BLOC-1 Subunit 2. Protein - protein interaction with BLOS1. |
| AT5G49555 | FAD/NAD(P)-binding oxidoreductase family protein |
| AT5G51500 | Plant invertase/pectin methylesterase inhibitor superfamily |
| AT5G51600 | Microtubule associated protein (MAP65/ASE1) family protein |
| AT5G53310 | myosin heavy chain-related |
| AT5G54510 | Auxin-responsive GH3 family protein |
| AT5G55070 | Dihydrolipoamide succinyltransferase |
| AT5G56270 | WRKY DNA-binding protein 2 |
| AT5G56510 | pumilio 12 |
| AT5G56690 | FBD, F-box and Leucine Rich Repeat domains containing protein |
| AT5G56880 | unknown protein |
| AT5G57015 | casein kinase I-like 12 |
| AT5G57770 | Plant protein of unknown function (DUF828) with plant pleckstrin homology-like region |
| AT5G57970 | DNA glycosylase superfamily protein |
| AT5G58170 | SHV3-like 5 |
| AT5G59120 | subtilase 4.13 |
| AT5G59830 | unknown protein |
| AT5G60530 | late embryogenesis abundant protein-related/LEA protein-related |
| AT5G60900 | receptor-like protein kinase 1 |
| AT5G61000 | Replication factor-A protein 1-related |
| AT5G61140 | U5 small nuclear ribonucleoprotein helicase |
| AT5G62600 | ARM repeat superfamily protein |
| AT5G63200 | tetratricopeptide repeat (TPR)-containing protein |
| AT5G63470 | nuclear factor Y, subunit C4 |
| AT5G63580 | flavonol synthase 2 |
| AT5G64080 | Bifunctional inhibitor/lipid-transfer protein/seed storage 2S albumin superfamily protein |
| AT5G64670 | Ribosomal protein L18e/L15 superfamily protein |
| AT5G65200 | plant U-box 38 |
| AT5G65950 | unknown protein |

TABLE 6-continued

| SHR direct targets identified by ChIP-chip | |
|---|---|
| Arabidopsis Genome Initiative (AGI) identification number | Short_description |
| AT5G66610 | DA1-related protein 7 |
| AT5G66620 | DA1-related protein 6 |
| AT5G66770 | GRAS family transcription factor |
| AT5G67385 | Phototropic-responsive NPH3 family protein |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,962,028
U.S. Pat. No. 5,034,322
U.S. Pat. No. 5,106,739
U.S. Pat. No. 5,589,610
U.S. Pat. No. 5,625,136
U.S. Pat. No. 5,639,948
U.S. Pat. No. 5,661,017
U.S. Pat. No. 6,455,760
U.S. Pat. No. 6,462,185
U.S. Pat. No. 6,610,840
U.S. Pat. No. 6,696,623
U.S. Published Application No. 20030084486
U.S. Published Application No. 20030177536
U.S. Published Application No. 20040019934
U.S. Published Application No. 20040067506
U.S. Published Application No. 20040078841
U.S. Published Application No. 20040123349
European Application No. EP1528104

Altschul, S. F. et al. (1990) "Basic Local Alignment Search Tool" *J. Mol. Biol.* 215:402-410.

Altschul, S. F. et al. (1997) "Gapped BLAST and PSI-BLAST: A New Generation of Protein Database Search Programs" *Nucl. Acids Res.* 25:3389-3402.

Bolle, C., The role of GRAS proteins in plant signal transduction and development. *Planta* 218, 683 (2004).

Bosabalidis, A., R. F. Evert, W. A. Russin, Ontogeny of the vascular bundles and contiguous tissues in the maize leaf blade1. *Am. J Bot.* 81, 745 (1984).

Brown, N. J. et al., Independent and parallel recruitment of preexisting mechanisms underlying C photosynthesis. *Science* 331, 1436 (2011).

Brutnell, T. P., R. J. Sawers, A. Mant, J. A. Langdale, BUNDLE SHEATH DEFECTIVE2, a novel protein required for post-translational regulation of the rbcL gene of maize. *Plant Cell* 11, 849 (1999).

Cermak, T., Doyle, E. L., Christian, M., Wang, L., Zhang, Y., Schmidt, C., Baller, J. A., Somia, N. V., Bogdanove, A. J. and Voytas, D. F. (2011) Efficient design and assembly of custom TALEN and other TAL effector-based constructs for DNA targeting. *Nucleic Acids Res.* 39, e82.

Clancy, M. and Hannah, L. C. (2002) "Splicing of the maize Sh1 first intron is essential for enhancement of gene expression, and a T-rich motif increases expression without affecting splicing" *Plant Physiol.* 130(2):918-29.

Clough, S. J. and Bent, A. F. (1998) Floral dip: a simplified method for *Agrobacterium*-mediated transformation of *Arabidopsis thaliana. Plant J.* 16, 735-743.

Cruz-Ramirez, A., Diaz-Trivino, S., Blilou, I. et al. (2012) A bistable circuit involving SCARECROW-RETINOBLASTOMA integrates cues to inform asymmetric stem cell division. *Cell,* 150, 1002-1015.

Cui, H. et al., An evolutionarily conserved mechanism delimiting SHR movement defines a single layer of endodermis in plants. *Science* 316, 421 (2007).

Cui, H. et al., Genome-Wide Direct Target Analysis Reveals a Role for SHORT-ROOT in Root Vascular Patterning through Cytokinin Homeostasis. *Plant Physiol.* 157, 1221 (2011).

Cui, H., P. N. Benfey, Interplay between SCARECROW, GA and LIKE HETEROCHROMATIN PROTEIN 1 in ground tissue patterning in the *Arabidopsis* root. *Plant J.* 58, 1016 (2009).

Cui, H., Y. Hao, D. Kong, SCARECROW has a SHORT-ROOT-independent role in modulating the sugar response. *Plant Physiol.* 158, 1769 (2012).

Dhondt, S. et al., SHORT-ROOT and SCARECROW regulate leaf growth in *Arabidopsis* by stimulating S-phase progression of the cell cycle. *Plant Physiol.* 154, 1183 (2010).

Di Laurenzio, L. et al., The SCARECROW gene regulates an asymmetric cell division that is essential for generating the radial organization of the *Arabidopsis* root. *Cell* 86, 423 (1996).

Fukaki, H., Wysocka-Diller, J., Kato, T., Fujisawa, H., Benfey, P. N. and Tasaka, M. (1998) Genetic evidence that the endodermis is essential for shoot gravitropism in *Arabidopsis thaliana. Plant J.* 14, 425-430.

Furtado, A. et al. (2002) "Tools for Use in the Genetic Engineering of Barley" *Proceedings of the* $10^{th}$ *Australian Barley Technical Symposium, Canberra, ACT, Australia.*

Gardiner, J., T. J. Donner, E. Scarpella, Simultaneous activation of SHR and ATHB8 expression defines switch to preprocambial cell state in Arabidopsis leaf development. *Dev. Dyn.* 240, 261 (2010).

Gendrel, A. V., Lippman, Z., Martienssen, R. and Colot, V. Profiling histone modification patterns in plants using genomic tiling microarrays. *Nat. Methods,* 2, 213-218 (2005).

Good, X. et al. (1994) "Reduced ethylene synthesis by transgenic tomatoes expressing S-adenosylmethionine hydrolase" *Plant Molec. Biol.* 26:781-790.

Hall, L. N., L. Rossini, L. Cribb, J. A. Langdale, GOLDEN 2: a novel transcriptional regulator of cellular differentiation in the maize leaf. *Plant Cell* 10, 925 (1998).

Haritatos, E., R. Medville, R. Turgeon, Minor vein structure and sugar transport in *Arabidopsis thaliana. Planta* 211, 105 (2000).

Helariutta, Y. et al., The SHORT-ROOT gene controls radial patterning of the Arabidopsis root through radial signaling. *Cell* 101, 555 (2000).

Hibberd, J. M., J. E. Sheehy, J. A. Langdale, Using C4 photosynthesis to increase the yield of rice-rationale and feasibility. *Curr. Opin. Plant Biol.* 11, 228 (2008).

Hirner, A., Ladwig, F., Stransky, H., Okumoto, S., Keinath, M., Harms, A., Frommer, W. B., and Koch, W. (2006). Arabidopsis LHT1 is a high-affinity transporter for cellular amino acid uptake in both root epidermis and leaf mesophyll. The Plant cell 18, 1931-1946.

Hwang, Y-S. et al. (2002) "Analysis of the Rice Endosperm-Specific Globulin Promoter in Transformed Rice Cells" *Plant Cell Rep.* 20:842-847.

Jankovsky, J. P., Smith, L. G. and Nelson, T. (2001) Specification of bundle sheath cell fates during maize leaf development: roles of lineage and positional information evaluated through analysis of the tangled1 mutant. *Development,* 128, 2747-2753.

Kajala, K. et al., Strategies for engineering a two-celled C(4) photosynthetic pathway into rice. *J. Exp. Bot.* 62, 3001 (2011).

Kamiya, N., Itoh, J., Morikami, A., Nagato, Y. and Matsuoka, M. (2003) The SCARECROW gene's role in asymmetric cell divisions in rice plants. *Plant J.* 36, 45-54.

Kangasjarvi, S., Nurmi, M., Tikkanen, M. and Aro, E. M. (2009) Cell-specific mechanisms and systemic signalling as emerging themes in light acclimation of C3 plants. *Plant, Cell Environ.* 32, 1230-1240.

Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.

Karlin S. and Altschul, S. F. (1993) "Applications and Statistics for Multiple High-Scoring Segments in Molecular Sequences" *Proc. Natl. Acad. Sci. USA* 90:5873-5877.

Kausch, A. P., Owen, T. P., Jr., Zachwieja, S. J., Flynn, A. R., and Sheen, J. (2001). Mesophyll-specific, light and metabolic regulation of the C4 PPCZm1 promoter in transgenic maize. Plant molecular biology 45, 1-15.

Kinsman, E. A., K. A. Pyke, Bundle sheath cells and cell-specific plastid development in Arabidopsis leaves. *Development* 125, 1815 (1998).

Laajanen, K., Vuorinen, I., Salo, V., Juuti, J. and Raudaskoski, M. (2007) Cloning of *Pinus sylvestris* SCARECROW gene and its expression pattern in the pine root system, mycorrhiza and NPA-treated short roots. *New Phytol.* 175, 230-243.

Langdale, J. A. C4 cycles: past, present, and future research on C4 photosynthesis. *Plant Cell* 23, 3879 (2011).

Langdale, J. A., Taylor, W. C. and Nelson, T. (1991) Cell-specific accumulation of maize phospho enolpyruvate carboxylase is correlated with demethylation at a specific site>3 kb upstream of the gene. *Mol. Gen. Genet.,* 225, 49-55.

Langdale, J. A., Zelitch, I., Miller, E. and Nelson, T. (1988) Cell position and light influence C4 versus C3 patterns of photosynthetic gene expression in maize. *The EMBO J.* 7, 3643-3651.

Leegood, R. C., Roles of the bundle sheath cells in leaves of C3 plants. *J Exp. Bot.* 59, 1663 (2008).

Levesque, M. P. et al., Whole-genome analysis of the SHORT-ROOT developmental pathway in Arabidopsis. *PLoS Biol.* 4, e143 (2006).

Lewin, B. (1985) *Genes II*, John Wiley & Sons, Inc., p. 96.

Lim, J., Helariutta, Y., Specht, C. D., Jung, J., Sims, L., Bruce, W. B., Diehn, S. and Benfey, P. N. (2000) Molecular analysis of the SCARECROW gene in maize reveals a common basis for radial patterning in diverse meristems. *Plant Cell,* 12, 1307-1318.

Nakajima, K., G. Sena, T. Nawy, P. N. Benfey, Intercellular movement of the putative transcription factor SHR in root patterning. *Nature* 413, 307 (2001).

Nelson, T., The grass leaf developmental gradient as a platform for a systems understanding of the anatomical specialization of C(4) leaves. *J. Exp. Bot.* 62, 3039 (2011).

Nomura M, Katayama K, Nishimura A, Ishida Y, Ohta S, Komari T, Miyao-Tokutomi M, Tajima S, Matsuoka M. (2000) The promoter of rbcS in a C3 plant (rice) directs organ-specific, light-dependent expression in a C4 plant (maize), but does not confer bundle sheath cell-specific expression. *Plant Mol Biol.* 44(1):99-106.

Petricka, J. J., N. K. Clay, T. M. Nelson, Vein patterning screens and the defectively organized tributaries mutants in *Arabidopsis thaliana. Plant J.* 56, 251 (2008).

Pysh, L. D., J. W. Wysocka-Diller, C. Camilleri, D. Bouchez, P. N. Benfey, The GRAS gene family in Arabidopsis: sequence characterization and basic expression analysis of the SCARECROW-LIKE genes. *Plant J.* 18, 111 (1999).

Rossini, L., L. Cribb, D. J. Martin, J. A. Langdale, The maize golden2 gene defines a novel class of transcriptional regulators in plants. *Plant Cell* 13, 1231 (2001).

Sage, R. F., X. G. Zhu, Exploiting the engine of C(4) photosynthesis. *J. Exp. Bot.* 62, 2989 (2011).

Sakamoto et al. (1991) *Plant Cell Physiology,* 32:385-393.

Sassa, N., Matsushita, Y., Nakamura, T. and Nyunoya, H. (2001) The molecular characterization and in situ expression pattern of pea SCARECROW gene. *Plant Cell Physiol.* 42, 385-394.

Schäffner, A. R. and Sheen, J. (1991) *The Plant Cell,* 3:997-1012.

Slewinski, T. L., A. A. Anderson, C. Zhang, R. Turgeon, Scarecrow plays a role in establishing kranz anatomy in maize leaves. *Plant Cell Physiol.* 53, 2030 (2012).

Sole, A., Sanchez, C., Vielba, J. M., Valladares, S., Abarca, D. and Diaz-Sala, C. (2008) Characterization and expression of a *Pinus radiata* putative ortholog to the Arabidopsis SHORT-ROOT gene. *Tree Physiol.* 28, 1629-1639.

Spreitzer, R. J., M. E. Salvucci, (2002) Rubisco: structure, regulatory interactions, and possibilities for a better enzyme. *Ann. Rev. Plant Biol.* 53, 449.

Stockhaus, J., Schlue, U., Koczor, M., Chitty, J. A., Taylor, W. C., and Westhoff, P. (1997). The Promoter of the Gene Encoding the C4 Form of Phosphoenolpyruvate Carboxylase Directs Mesophyll-Specific Expression in Transgenic C4 Flaveria spp. The Plant cell 9, 479-489.

Sun, X., Xue, B., Jones, W. T., Rikkerink, E., Dunker, A. K. and Uversky, V. N. (2011) A functionally required unfoldome from the plant kingdom: intrinsically disordered N-terminal domains of GRAS proteins are involved in molecular recognition during plant development. *Plant Mol. Biol.* 77, 205-223.

Takahashi, H. et al., The roles of three functional sulphate transporters involved in uptake and translocation of sulphate in *Arabidopsis thaliana. Plant J.* 23, 171 (2000).

Taniguchi, Y. et al., Overproduction of C4 photosynthetic enzymes in transgenic rice plants: an approach to introduce the C4-like photosynthetic pathway into rice. *J. Exp. Bot.* 59, 1799 (2008).

von Caemmerer, S., Quick, W. P. and Furbank, R. T. (2012) The Development of C4 Rice: Current Progress and Future Challenges. *Science,* 336, 1671-1672.

Wang, L., R. B. Peterson, T. P. Brutnell, Regulatory mechanisms underlying C(4) photosynthesis. *New Phytol.* 190, 1 (2011).

Weigel, D., J. Glazebrook, Arabidopsis: A Laboratory Manual. CSHL press, New York (2002). Pp 241-248.

Welch, D., Hassan, H., Blilou, I., Immink, R., Heidstra, R. and Scheres, B. (2007) Arabidopsis JACKDAW and MAGPIE zinc finger proteins delimit asymmetric cell division and stabilize tissue boundaries by restricting SHORT-ROOT action. *Genes Dev.* 21, 2196-2204.

Wu, C-L. et al. (1998) "Promoters of Rice Seed Storage Protein Genes Direct Endosperm-Specific Gene Expression in Transgenic Rice" *Plant and Cell Physiology,* 39(8):885-889.

Wysocka-Diller, J. W., Y. Helariutta, H. Fukaki, J. E. Malamy, P. N. Benfey, Molecular analysis of SCARECROW function reveals a radial patterning mechanism common to root and shoot. *Development* 127, 595 (2000).

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

We claim:

1. A plant that exhibits increased expression or ectopic expression or altered expression of a SHORT-ROOT (SHR), wherein a polynucleotide encodes said SHR comprising the amino acid sequence shown in SEQ ID NO:9, 11, 19, 21, 27, 29, 31, or 37, and said polynucleotide is operably linked to a polynucleotide promoter sequence comprising the nucleotide sequence of SEQ ID NO:49.

2. The plant according to claim 1, wherein said plant is a C3 plant.

3. The plant according to claim 1, wherein said plant is rice, barley, thale cress, wheat, rye, oat, fescue, sunflower, tomato, cucumber, potato, peanut, cotton, sugar beet, tobacco, soybean, spinach, or a tree.

4. The plant according to claim 1, wherein said polynucleotide is stably incorporated into the genome of said plant.

5. The plant according to claim 1, wherein said polynucleotide comprises the nucleotide sequence shown in SEQ ID NO:10, 12, 20, 22, 28, 30, 32, or 38, or a nucleotide sequence that has at least 90% sequence identity with said SEQ ID NO.

6. The plant according to claim 1, wherein said polynucleotide is heterologous to said plant.

7. A cell transformed with a polynucleotide encoding a SHORT-ROOT (SHR) comprising the amino acid sequence shown in SEQ ID NO:9, 11, 19, 21, 27, 29, 31, or 37, and said polynucleotide is operably linked to a polynucleotide promoter sequence, wherein said promoter sequence comprises the nucleotide sequence of SEQ ID NO:49.

8. The transformed cell according to claim 7, wherein said cell is a C3 plant cell.

9. The transformed cell according to claim 7, wherein said cell is a plant cell from rice, barley, thale cress, wheat, rye, oat, fescue, sunflower, tomato, cucumber, potato, peanut, cotton, sugar beet, tobacco, soybean, spinach, or a tree.

10. The transformed cell according to claim 7, wherein said polynucleotide is stably incorporated into the genome of said cell.

11. The transformed cell according to claim 7, wherein said polynucleotide comprises the nucleotide sequence shown in SEQ ID NO:10, 12, 20, 22, 28, 30, 32, or 38, or a nucleotide sequence that has at least 90% sequence identity with said SEQ ID NO.

12. The transformed cell according to claim 7, wherein said polynucleotide is heterologous to said cell.

* * * * *

SEQUENCE LISTING

```
<160> NUMBER OF SEQ ID NOS: 77

<210> SEQ ID NO 1
<211> LENGTH: 653
<212> TYPE: PRT
<213> ORGANISM: Arabidopsis thaliana

<400> SEQUENCE: 1

Met Ala Glu Ser Gly Asp Phe Asn Gly Gly Gln Pro Pro Pro His Ser
1               5                   10                  15

Pro Leu Arg Thr Thr Ser Ser Gly Ser Ser Ser Ser Asn Asn Arg Gly
            20                  25                  30

Pro Pro Pro Pro Pro Pro Pro Pro Leu Val Met Val Arg Lys Arg Leu
        35                  40                  45

Ala Ser Glu Met Ser Ser Asn Pro Asp Tyr Asn Asn Ser Ser Arg Pro
    50                  55                  60

Pro Arg Arg Val Ser His Leu Leu Asp Ser Asn Tyr Asn Thr Val Thr
65                  70                  75                  80

Pro Gln Gln Pro Pro Ser Leu Thr Ala Ala Ala Thr Val Ser Ser Gln
                85                  90                  95

Pro Asn Pro Pro Leu Ser Val Cys Gly Phe Ser Gly Leu Pro Val Phe
            100                 105                 110

Pro Ser Asp Arg Gly Gly Arg Asn Val Met Met Ser Val Gln Pro Met
        115                 120                 125

Asp Gln Asp Ser Ser Ser Ser Ser Ala Ser Pro Thr Val Trp Val Asp
    130                 135                 140

Ala Ile Ile Arg Asp Leu Ile His Ser Ser Thr Ser Val Ser Ile Pro
145                 150                 155                 160

Gln Leu Ile Gln Asn Val Arg Asp Ile Ile Phe Pro Cys Asn Pro Asn
                165                 170                 175

Leu Gly Ala Leu Leu Glu Tyr Arg Leu Arg Ser Leu Met Leu Leu Asp
            180                 185                 190

Pro Ser Ser Ser Ser Asp Pro Ser Pro Gln Thr Phe Glu Pro Leu Tyr
        195                 200                 205

Gln Ile Ser Asn Asn Pro Ser Pro Pro Gln Gln Gln Gln Gln His Gln
    210                 215                 220

Gln Gln Gln Gln Gln His Lys Pro Pro Pro Pro Pro Ile Gln Gln Gln
225                 230                 235                 240

Glu Arg Glu Asn Ser Ser Thr Asp Ala Pro Pro Gln Pro Glu Thr Val
```

```
                245                 250                 255

Thr Ala Thr Val Pro Ala Val Gln Thr Asn Thr Ala Glu Ala Leu Arg
            260                 265                 270

Glu Arg Lys Glu Glu Ile Lys Arg Gln Lys Gln Asp Glu Glu Gly Leu
        275                 280                 285

His Leu Leu Thr Leu Leu Leu Gln Cys Ala Glu Ala Val Ser Ala Asp
    290                 295                 300

Asn Leu Glu Glu Ala Asn Lys Leu Leu Leu Glu Ile Ser Gln Leu Ser
305                 310                 315                 320

Thr Pro Tyr Gly Thr Ser Ala Gln Arg Val Ala Ala Tyr Phe Ser Glu
                325                 330                 335

Ala Met Ser Ala Arg Leu Leu Asn Ser Cys Leu Gly Ile Tyr Ala Ala
            340                 345                 350

Leu Pro Ser Arg Trp Met Pro Gln Thr His Ser Leu Lys Met Val Ser
        355                 360                 365

Ala Phe Gln Val Phe Asn Gly Ile Ser Pro Leu Val Lys Phe Ser His
    370                 375                 380

Phe Thr Ala Asn Gln Ala Ile Gln Glu Ala Phe Glu Lys Glu Asp Ser
385                 390                 395                 400

Val His Ile Ile Asp Leu Asp Ile Met Gln Gly Leu Gln Trp Pro Gly
                405                 410                 415

Leu Phe His Ile Leu Ala Ser Arg Pro Gly Gly Pro Pro His Val Arg
            420                 425                 430

Leu Thr Gly Leu Gly Thr Ser Met Glu Ala Leu Gln Ala Thr Gly Lys
        435                 440                 445

Arg Leu Ser Asp Phe Thr Asp Lys Leu Gly Leu Pro Phe Glu Phe Cys
    450                 455                 460

Pro Leu Ala Glu Lys Val Gly Asn Leu Asp Thr Glu Arg Leu Asn Val
465                 470                 475                 480

Arg Lys Arg Glu Ala Val Ala Val His Trp Leu Gln His Ser Leu Tyr
                485                 490                 495

Asp Val Thr Gly Ser Asp Ala His Thr Leu Trp Leu Leu Gln Arg Leu
            500                 505                 510

Ala Pro Lys Val Val Thr Val Val Glu Gln Asp Leu Ser His Ala Gly
        515                 520                 525

Ser Phe Leu Gly Arg Phe Val Glu Ala Ile His Tyr Tyr Ser Ala Leu
    530                 535                 540

Phe Asp Ser Leu Gly Ala Ser Tyr Gly Glu Glu Ser Glu Glu Arg His
545                 550                 555                 560

Val Val Glu Gln Gln Leu Leu Ser Lys Glu Ile Arg Asn Val Leu Ala
                565                 570                 575

Val Gly Gly Pro Ser Arg Ser Gly Glu Val Lys Phe Glu Ser Trp Arg
            580                 585                 590

Glu Lys Met Gln Gln Cys Gly Phe Lys Gly Ile Ser Leu Ala Gly Asn
        595                 600                 605

Ala Ala Thr Gln Ala Thr Leu Leu Leu Gly Met Phe Pro Ser Asp Gly
    610                 615                 620

Tyr Thr Leu Val Asp Asp Asn Gly Thr Leu Lys Leu Gly Trp Lys Asp
625                 630                 635                 640

Leu Ser Leu Leu Thr Ala Ser Ala Trp Thr Pro Arg Ser
                645                 650
```

<210> SEQ ID NO 2

<211> LENGTH: 2163
<212> TYPE: DNA
<213> ORGANISM: Arabidopsis thaliana

<400> SEQUENCE: 2

```
ccttatttat aaccatgcaa tctcacgacc aacaaccctt caatctccat ggcggaatcc      60
ggcgatttca acggtggtca acctcctcct catagtcctc tgagaacaac ttcttccggt     120
agtagcagca gcaacaaccg tggtcctcct cctcctcctc ctcctccttt agtgatggtg     180
agaaaaagat tagcttccga gatgtcttct aaccctgact acaacaactc ctctcgtcct     240
cctcgccgtg tctctcacct tcttgactcc aactacaata ctgtcacacc acaacaacca     300
ccgtctctta cggcggcggc tactgtatct tctcaaccaa acccaccact ctctgtttgt     360
ggcttctctg gtcttcccgt ttttccttca gaccgtggtg gtcggaatgt tatgatgtcc     420
gtacaaccaa tggatcaaga ctcttcatct tcttctgctt cacctactgt atgggttgac     480
gccattatca gagaccttat ccattcctca acttcagtct ctattcctca acttatccaa     540
aacgttagag acattatctt cccttgtaac ccaaatctcg gtgctcttct tgaatacagg     600
ctccgatctc tcatgctcct tgatccttcc tcttcctctg acccttctcc tcaaactttc     660
gaacctctct atcagatctc caacaatcct tctcctccac aacagcaaca gcagcaccaa     720
caacaacaac aacagcataa gcctcctcct cctccgattc agcagcaaga aagagaaaat     780
tcttctaccg atgcaccacc gcaaccagag acagtgacgg ccactgttcc cgccgtccaa     840
acaaatacgg cggaggcttt aagagagagg aaggaagaga ttaagaggca gaagcaagac     900
gaagaaggat tacaccttct cacattgctg ctacagtgtg ctgaagctgt ctctgctgat     960
aatctcgaag aagcaaacaa gcttcttctt gagatctctc agttatcaac tccttacggg    1020
acctcagcgc agagagtagc tgcttacttc tcggaagcta tgtcagcgag attactcaac    1080
tcgtgtctcg gaatttacgc ggctttgcct tcacggtgga tgcctcaaac gcatagcttg    1140
aaaatggtct ctgcgtttca ggtctttaat gggataagcc ctttagtgaa attctcacac    1200
tttacagcga atcaggcgat tcaagaagca tttgagaaag aagacagtgt acacatcatt    1260
gacttggaca tcatgcaggg acttcaatgg cctggtttat tccacattct tgcttctaga    1320
cctggaggac ctccacacgt gcgactcacg ggacttggta cttccatgga agctcttcag    1380
gctacaggga aacgtctttc ggatttcaca gataagcttg gcctgccttt tgagttctgc    1440
cctttagctg agaaagttgg aaacttggac actgagagac tcaatgtgag gaaaagggaa    1500
gctgtggctg ttcactggct tcaacattct ctttatgatg tcactggctc tgatgcacac    1560
actctctggt tactccaaag gtaaaataaa cattaccttt taatcactct ttatctataa    1620
attattttaa gattatatag gaaagatatg ttctaaaaag ctggcttttt tggttaatga    1680
ttggggaatg aacagattag ctcctaaagt tgtgacagta gtggagcaag atttgagcca    1740
cgctggttct ttcttaggaa gatttgtaga ggcaatacat tactactctg cactctttga    1800
ctcactggga gcaagctacg gcgaagagag tgaagagaga catgtcgtgg aacagcagct    1860
attatcgaaa gagatacgga atgtattagc ggttggagga ccatcgagaa gcggtgaagt    1920
gaagtttgag agctggaggg agaaaatgca acaatgtggg tttaaaggta tatctttagc    1980
tggaaatgca gctacacaag cgactctact gttgggaatg tttccttcgg atggttacac    2040
tttggttgat gataatggta cacttaagct tggatggaaa gatctttcgt tactcactgc    2100
ttcagcttgg acgcctcgtt cttagttttc ttctcctttt tcacaaacaa tgtgcccata    2160
aat                                                                  2163
```

<210> SEQ ID NO 3
<211> LENGTH: 660
<212> TYPE: PRT
<213> ORGANISM: Oryza sativa

<400> SEQUENCE: 3

```
Met Gly Ser Ser Ser Leu Leu Leu Phe Pro Ser Ser Ser Ser Ser Ala
1               5                   10                  15

Thr His Ser Ser Tyr Ser Pro Ser Ser Ser Ser His Ala Ile Thr Ser
            20                  25                  30

Leu Leu Pro Pro Leu Pro Ser Asp His His Leu Leu Leu Tyr Leu Asp
        35                  40                  45

His Gln Glu Gln His His Leu Ala Ala Ala Met Val Arg Lys Arg Pro
    50                  55                  60

Ala Ser Asp Met Asp Leu Pro Pro Pro Arg Arg His Val Thr Gly Asp
65                  70                  75                  80

Leu Ser Asp Val Thr Ala Ala Ala Ala Gly Ala Pro Thr Leu Ser Ala
                85                  90                  95

Ser Ala Gln Leu Pro Ala Leu Pro Thr Gln Leu Pro Ala Phe His His
            100                 105                 110

Thr Asp Met Asp Leu Ala Ala Pro Ala Pro Pro Ala Pro Gln Gln Val
        115                 120                 125

Ala Ala Gly Glu Gly Gly Pro Pro Ser Thr Ala Trp Val Asp Gly Ile
    130                 135                 140

Ile Arg Asp Ile Ile Ala Ser Ser Gly Ala Ala Val Ser Val Ala Gln
145                 150                 155                 160

Leu Ile His Asn Val Arg Glu Ile Ile Arg Pro Cys Asn Pro Asp Leu
                165                 170                 175

Ala Ser Ile Leu Glu Leu Arg Leu Arg Ser Leu Leu Asn Ser Asp Pro
            180                 185                 190

Ala Pro Pro Pro Pro Pro Pro Ser His Pro Ala Leu Leu Pro Pro Asp
        195                 200                 205

Ala Thr Ala Pro Pro Pro Pro Pro Thr Ser Val Ala Ala Leu Pro Pro
    210                 215                 220

Pro Pro Pro Ala Gln Pro Asp Lys Arg Arg Arg Glu Pro Gln Cys Gln
225                 230                 235                 240

Glu Gln Glu Pro Asn Gln Pro Gln Ser Pro Lys Pro Pro Thr Ala Glu
                245                 250                 255

Glu Thr Ala Ala Ala Ala Ala Ala Ala Ala Ala Ala Ala Ala Ala Ala
            260                 265                 270

Ala Lys Glu Arg Lys Glu Glu Gln Arg Arg Lys Gln Arg Asp Glu Glu
        275                 280                 285

Gly Leu His Leu Leu Thr Leu Leu Leu Gln Cys Ala Glu Ser Val Asn
    290                 295                 300

Ala Asp Asn Leu Asp Glu Ala His Arg Ala Leu Leu Glu Ile Ala Glu
305                 310                 315                 320

Leu Ala Thr Pro Phe Gly Thr Ser Thr Gln Arg Val Ala Ala Tyr Phe
                325                 330                 335

Ala Glu Ala Met Ser Ala Arg Leu Val Ser Ser Cys Leu Gly Leu Tyr
            340                 345                 350

Ala Pro Leu Pro Asn Pro Ser Pro Ala Ala Ala Arg Leu His Gly Arg
        355                 360                 365

Val Ala Ala Ala Phe Gln Val Phe Asn Gly Ile Ser Pro Phe Val Lys
```

```
    370                 375                 380

Phe Ser His Phe Thr Ala Asn Gln Ala Ile Gln Glu Ala Phe Glu Arg
385                 390                 395                 400

Glu Glu Arg Val His Ile Ile Asp Leu Asp Ile Met Gln Gly Leu Gln
                405                 410                 415

Trp Pro Gly Leu Phe His Ile Leu Ala Ser Arg Pro Gly Gly Pro Pro
            420                 425                 430

Arg Val Arg Leu Thr Gly Leu Gly Ala Ser Met Glu Ala Leu Glu Ala
        435                 440                 445

Thr Gly Lys Arg Leu Ser Asp Phe Ala Asp Thr Leu Gly Leu Pro Phe
    450                 455                 460

Glu Phe Cys Pro Val Ala Asp Lys Ala Gly Asn Leu Asp Pro Glu Lys
465                 470                 475                 480

Leu Gly Val Thr Arg Arg Glu Ala Val Ala Val His Trp Leu Arg His
                485                 490                 495

Ser Leu Tyr Asp Val Thr Gly Ser Asp Ser Asn Thr Leu Trp Leu Ile
            500                 505                 510

Gln Arg Leu Ala Pro Lys Val Val Thr Met Val Glu Gln Asp Leu Ser
        515                 520                 525

His Ser Gly Ser Phe Leu Ala Arg Phe Val Glu Ala Ile His Tyr Tyr
    530                 535                 540

Ser Ala Leu Phe Asp Ser Leu Asp Ala Ser Tyr Ser Glu Asp Ser Pro
545                 550                 555                 560

Glu Arg His Val Val Glu Gln Gln Leu Leu Ser Arg Glu Ile Arg Asn
                565                 570                 575

Val Leu Ala Val Gly Gly Pro Ala Arg Thr Gly Asp Val Lys Phe Gly
            580                 585                 590

Ser Trp Arg Glu Lys Leu Ala Gln Ser Gly Phe Arg Val Ser Ser Leu
        595                 600                 605

Ala Gly Ser Ala Ala Ala Gln Ala Val Leu Leu Leu Gly Met Phe Pro
    610                 615                 620

Ser Asp Gly Tyr Thr Leu Ile Glu Glu Asn Gly Ala Leu Lys Leu Gly
625                 630                 635                 640

Trp Lys Asp Leu Cys Leu Leu Thr Ala Ser Ala Trp Arg Pro Ile Gln
                645                 650                 655

Ala Ser Gly Arg
            660


<210> SEQ ID NO 4
<211> LENGTH: 2398
<212> TYPE: DNA
<213> ORGANISM: Oryza sativa
<220> FEATURE:
<221> NAME/KEY: misc_feature
<222> LOCATION: (1446)..(1446)
<223> OTHER INFORMATION: n is a, c, g, or t

<400> SEQUENCE: 4

cctctcggcc tcttcctctt tactccccct tcgcgccatc gcctcgcttg cgccgcgcca     60

aattccataa aaattccacc caacacaagc gttaggcctc ccgcgcacgc ccgtccgctc    120

gccatgccca cggcctcttc cccttggcgt ttgtagatgg gctcctcctc cctcctcctc    180

ttcccctcct cttcctcctc cgccacccac tcctcttatt ctccctcctc ctcctctcat    240

gccatcacct ccttgctgcc tcctctcccc tccgaccacc atctcctcct ctacctagac    300

caccaagaac aacaccacct cgccgccgcc atggtccgca agcgccccgc ctccgacatg    360
```

```
gacctgccac cgccgcgccg ccatgtcacc ggcgacctgt ccgatgtcac ggccgccgcg    420
gcgggcgcgc cgacgttgtc tgccagcgcg cagctccccg cgctgcccac gcagctcccg    480
gcgttccacc acacggacat ggacctcgcc gcgcccgcgc cgccggcgcc gcaacaggtg    540
gcggcgggtg agggtgggcc gcccagcacg gcttgggtgg atggcatcat ccgtgacatc    600
atcgccagca gcggcgccgc ggtctccgtc gcgcagctca tccacaacgt gcgtgagatc    660
atccggccat gtaaccccga cctcgcgtcc atcctcgagc tccgcctccg ctctctcctc    720
aactccgacc ccgcgccgcc gccgccgccg ccgtcgcatc ctgctctcct ccctcccgac    780
gccacggcgc caccgccacc acccacgtcg gtcgccgcgc tccctccccc tccgccagcg    840
cagcccgaca agcggcgtcg cgagcctcag tgtcaggagc aggagcccaa ccagccgcag    900
tcgccgaagc cccccaccgc ggaggaaacc gccgccgccg ccgcggccgc cgcagcggcg    960
gctgccgcgg ccgccaagga gcggaaggag gagcagcggc ggaagcagcg cgacgaggag   1020
ggcctccacc tgctgacgct gctgctccag tgcgcggagt cggtgaacgc ggacaacctc   1080
gacgaggcgc accgcgcgct gctggagatc gcggagcttg ccacgccgtt cggcacatcc   1140
acgcagcgcg tcgccgccta cttcgcggag gccatgtcgg cgcggctggt gagctcgtgc   1200
ctggggctgt acgcgccgct ccccaacccg tccccggcgg cggcgcgtct ccacgggcgc   1260
gtcgccgcgg cgttccaggt gttcaacggc atcagcccgt tcgtgaagtt ctcgcacttc   1320
acggcgaacc aggcgatcca ggaggcgttc gagagggagg agagggtgca catcatcgac   1380
ctggacatca tgcaggggct ccaatggccg ggcttgttcc acatcctggc gtcgaggccg   1440
gggggnccgc cgagggtgag gctgaccggg ctgggggcgt ccatggaggc gctggaggcg   1500
acggggaaga ggctatcgga cttcgcggac acgctgggat tgccattcga gttctgcccg   1560
gtggctgaca aggccgggaa tcttgacccg gagaagctag gcgtcacgcg ccgcgaggcc   1620
gtcgccgtcc actggctgcg ccactccctc tacgatgtca ccggctccga ctccaacacg   1680
ctctggctca tccagaggtt ggcgccaaag gttgtaacaa tggtggagca ggatctgagc   1740
cactcaggct ccttcctggc acgttttgtg gaggccatcc actactattc ggcactgttc   1800
gactcgcttg atgcgagtta cagcgaggat agcccggagc ggcatgtcgt ggagcaacaa   1860
ctcttgtcac gggagatccg caatgtgcta gccgtgggcg gtccagcacg caccggcgat   1920
gttaagtttg ggagctggcg cgagaagctt gcgcagtcgg gcttccgtgt gtcgtcgctt   1980
gctggaagtg ccgctgctca ggccgtgctg ctgcttggga tgttcccttc cgatgggtac   2040
acgctcattg aggagaatgg cgccctgaag cttggatgga aggatctgtg ccttctcact   2100
gcctctgctt ggcgcccaat tcaggcttcg ggacgttagt actgaggggg aatttataga   2160
gctgaagtat cacttgatct tacttaggtg caattaccta gtccttttgc ttcttttagc   2220
tgctcaattt ggtcaattct gagaaaagaa aaataaaaaa aattctgatc actaattgcc   2280
agatctccac acggtggtag ttactgatgt gcagcttagc tttagctttt attctgttca   2340
tgctccagtt aaccattctg tccagtttag tttattttgc acggacgcgt gggtcgac     2398
```

<210> SEQ ID NO 5
<211> LENGTH: 668
<212> TYPE: PRT
<213> ORGANISM: Zea mays

<400> SEQUENCE: 5

```
Met Pro Pro Pro Pro Pro Pro Pro Pro Leu Thr Pro Tyr Cys Arg Arg
1               5                   10                  15
```

```
Cys Pro Pro Pro His Leu Pro Pro Pro Pro Pro Ser Ser Pro Asn His
            20                  25                  30

Phe Leu Leu His Tyr Leu His Gln Leu Asp His Gln Glu Ala Ala Ala
        35                  40                  45

Ala Ala Met Val Arg Lys Arg Pro Ala Ser Asp Met Asp Leu Pro Pro
    50                  55                  60

Pro Arg Arg His Val Thr Gly Asp Leu Ser Asp Val Thr Ala Ala Ala
65                  70                  75                  80

Ala Ala Gly Val Gly Gly Ser Gly Ala Pro Ser Ser Ala Ser Ala Gln
                85                  90                  95

Leu Pro Ala Leu Pro Thr Gln Leu His Gln Leu Pro Pro Ala Phe Gln
            100                 105                 110

His His Ala Pro Glu Val Asp Val Pro Ala His Pro Ala Pro Ala Ala
        115                 120                 125

His Ala Gln Ala Gly Gly Glu Ala Thr Ala Ser Thr Thr Ala Trp Val
    130                 135                 140

Asp Gly Ile Ile Arg Asp Ile Ile Gly Ser Ser Gly Gly Ala Ala Val
145                 150                 155                 160

Ser Ile Thr Gln Leu Ile His Asn Val Arg Glu Ile Ile His Pro Cys
                165                 170                 175

Asn Pro Gly Leu Ala Ser Leu Leu Glu Leu Arg Leu Arg Ser Leu Leu
            180                 185                 190

Ala Ala Asp Pro Ala Pro Leu Pro Pro Pro Pro Gln Pro Gln Gln His
        195                 200                 205

Ala Leu Leu His Gly Ala Pro Ala Ala Ala Pro Ala Gly Leu Thr Leu
    210                 215                 220

Pro Pro Pro Pro Pro Leu Pro Asp Lys Arg Arg His Glu His Pro Pro
225                 230                 235                 240

Pro Cys Gln Gln Gln Gln Gln Glu Glu Pro His Pro Ala Pro Gln Ser
                245                 250                 255

Pro Lys Ala Pro Thr Ala Glu Glu Thr Ala Ala Ala Ala Ala Ala Ala
            260                 265                 270

Gln Ala Ala Ala Ala Ala Ala Ala Lys Glu Arg Lys Glu Glu Gln Arg
        275                 280                 285

Arg Lys Gln Arg Asp Glu Glu Gly Leu His Leu Leu Thr Leu Leu Leu
    290                 295                 300

Gln Cys Ala Glu Ala Val Asn Ala Asp Asn Leu Asp Asp Ala His Gln
305                 310                 315                 320

Thr Leu Leu Glu Ile Ala Glu Leu Ala Thr Pro Phe Gly Thr Ser Thr
                325                 330                 335

Gln Arg Val Ala Ala Tyr Phe Ala Glu Ala Met Ser Ala Arg Leu Val
            340                 345                 350

Ser Ser Cys Leu Gly Leu Tyr Ala Pro Leu Pro Pro Gly Ser Pro Ala
        355                 360                 365

Ala Ala Arg Leu His Gly Arg Val Ala Ala Ala Phe Gln Val Phe Asn
    370                 375                 380

Gly Ile Ser Pro Phe Val Lys Phe Ser His Phe Thr Ala Asn Gln Ala
385                 390                 395                 400

Ile Gln Glu Ala Phe Glu Arg Glu Glu Arg Val His Ile Ile Asp Leu
                405                 410                 415

Asp Ile Met Gln Gly Leu Gln Trp Pro Gly Leu Phe His Ile Leu Ala
            420                 425                 430
```

```
Ser Arg Pro Gly Gly Pro Pro Arg Val Arg Leu Thr Gly Leu Gly Ala
        435                 440                 445

Ser Met Glu Ala Leu Glu Ala Thr Gly Lys Arg Leu Ser Asp Phe Ala
    450                 455                 460

Asp Thr Leu Gly Leu Pro Phe Glu Phe Cys Ala Val Ala Glu Lys Ala
465                 470                 475                 480

Gly Asn Val Asp Pro Glu Lys Leu Gly Val Thr Arg Arg Glu Ala Val
                485                 490                 495

Ala Val His Trp Leu His His Ser Leu Tyr Asp Val Thr Gly Ser Asp
            500                 505                 510

Ser Asn Thr Leu Trp Leu Ile Gln Arg Leu Ala Pro Lys Val Val Thr
        515                 520                 525

Met Val Glu Gln Asp Leu Ser His Ser Gly Ser Phe Leu Ala Arg Phe
    530                 535                 540

Val Glu Ala Ile His Tyr Tyr Ser Ala Leu Phe Asp Ser Leu Asp Ala
545                 550                 555                 560

Ser Tyr Gly Glu Asp Ser Pro Glu Arg His Val Val Glu Gln Gln Leu
                565                 570                 575

Leu Ser Arg Glu Ile Arg Asn Val Leu Ala Val Gly Gly Pro Ala Arg
            580                 585                 590

Thr Gly Asp Val Lys Phe Gly Ser Trp Arg Glu Lys Leu Ala Gln Ser
        595                 600                 605

Gly Phe Arg Ala Ala Ser Leu Ala Gly Ser Ala Ala Ala Gln Ala Ser
    610                 615                 620

Leu Leu Leu Gly Met Phe Pro Ser Asp Gly Tyr Thr Leu Val Glu Glu
625                 630                 635                 640

Asn Gly Ala Leu Lys Leu Gly Trp Lys Asp Leu Cys Leu Leu Thr Ala
                645                 650                 655

Ser Ala Trp Arg Pro Ile Gln Val Pro Pro Cys Arg
            660                 665


<210> SEQ ID NO 6
<211> LENGTH: 3100
<212> TYPE: DNA
<213> ORGANISM: Zea mays

<400> SEQUENCE: 6

atgccaccgc caccgcctcc gcctcctctc actccttatt gccgccgctg ccctccccca      60

cacctccctc cgcctcctcc ttcttcccca aaccacttcc tcctccacta cctccatcag     120

ctagaccacc aagaagccgc cgccgccgcc atggtccgca agcgccccgc gtccgacatg     180

gacctcccgc cgccgcgccg ccacgtcacg ggcgacctct ccgacgtcac ggcggccgct     240

gccgccggtg ttggtggtag tggcgcgccg tcctccgcca gcgcgcagct gcccgcgctg     300

cccacccagc tccaccagct gccccccgcg ttccagcacc acgcgccgga ggtggacgtg     360

cccgcgcacc cggccccggc cgcccacgcg caggcgggcg gcgaggcaac cgcgtccacg     420

accgcgtggg tggacggcat catccgcgac atcatcggga gcagcggcgg cgccgcggtc     480

tccatcacgc agctcatcca caacgtccgc gagatcatcc acccctgcaa ccccggcctc     540

gcgtcgctcc tggagctccg cctccgctcc ctcctcgcag ccgacccggc cccactgccg     600

ccgccgccgc agccgcagca gcatgctctc ctgcacggcg ctccggccgc cgctcccgcg     660

gggctgacgc tccctccccc gccaccgctt ccggacaagc gccgccacga gcatccaccg     720

ccgtgccagc agcaacagca ggaggaaccg catccggcgc cgcagtcgcc caaggccccg     780
```

-continued

```
accgcggaag agaccgcagc ggcggccgcc gccgcacaag cagcagctgc tgcggccgcc    840
aaggagcgga aggaggagca gcggcggaag cagcgcgacg aggagggcct ccacctgctg    900
acgctgctgc tgcagtgcgc cgaggccgtg aacgcggaca acctggacga cgcgcaccag    960
acgctgctgg agatcgcgga gctagcgacg ccgttcggca cctcgacgca gcgcgtggcc   1020
gcctacttcg cggaggccat gtcggcgcgg ctcgtcagct cctgcctggg cctgtacgcg   1080
ccgctgccgc cgggctcccc cgccgcggcg cgcctccacg gccgcgtcgc cgccgcgttc   1140
caggtgttca acggcatcag ccccttcgtc aagttctcgc acttcaccgc caaccaggcc   1200
atccaggagg cgttcgagcg ggaggagcgc gtgcacatca tcgacctcga catcatgcag   1260
gggctgcagt ggccggggct cttccacatc cttgcctccc gccccggggg cccgcccagg   1320
gtgaggctca ccggcctcgg ggcgtccatg gaggcgctcg aggccacggg gaagcgcctc   1380
tccgatttcg ccgacacgct cggcctgccc ttcgagttct gcgccgtcgc cgagaaggcc   1440
ggcaatgttg acccggagaa gctaggggtc acgaggcggg aggccgtcgc cgtccactgg   1500
ctgcaccact cgctctacga cgtcactggc tccgactcca acacgctctg gctcatccaa   1560
aggtaggaag gagtacacca tctctcgatc ctgacttcct tgctaccatg tcaaatcttg   1620
atgcaatcat ggccactttt cagctactaa cactttagtt tagccaatgc gacatccagt   1680
acaactaatc taaaaaaata atcttcagag gtttcctagt aaaaaaaccg cgtttttgga   1740
gctcaaaaag cttgtcatta tgaccaacca actttctagg cttaaaaagg ttgaatcttg   1800
gcaatgcttt tgagacgatg ctgtactgaa gtactggtag agagagtatc ctccatggcc   1860
tttgttgatc ccagaaccac aaaagatagt atttcgctcg catttggtta gtggaggtgt   1920
tctgatcatc acttggagga tggagctgaa agttcctatc atcatgacca actttccatg   1980
gcaaaaggtt tctagttcca agtggcagga cgatgattac tgagtgactg aatggagtaa   2040
ctgtcatctt ctaccactaa ccatcattta ttaatacata aatcatcatc cggagcctaa   2100
actcagaaag gctaatcaaa agtgcaatct ttctcaaatg gctgccatat gccagtggta   2160
catgcctggc cattgtactt tttcggtgaa ccatctcgtc tcaagcatga gatgaaggcc   2220
tgaactgcaa tgtccttgat ttgatgcaac cattattaga agaaacgcta agcgatgccg   2280
gtcctggcaa gggcaatgcc atatcgtcag acagacaggg attcggaatc gaatggctag   2340
ctggtgacaa atcgcacggg gattaataaa ctacattggt cattgattcc atcccccaca   2400
cacctgcagg ctggccccca aggtggtgac aatggtggag caggacctga gccactcggg   2460
ctccttcctg gcgcgcttcg tggaggccat ccactactac tcggcgctgt tcgactcgct   2520
ggacgcgagc tacggcgagg acagccccga gcggcacgtc gtggagcagc agctgctgtc   2580
gcgggagatc cgcaacgtgc tggccgtggg cgggccggcc cgcaccggcg acgtcaagtt   2640
cggcagctgg cgcgagaagc tggcgcagtc cgggttccgc gccgcctcgc tcgccggcag   2700
cgccgcggcg caggcgtccc tgctgctcgg catgttcccc tccgacgggt acacgctggt   2760
ggaggagaac ggcgcgctga agctcgggtg gaaggacctc tgcctgctca ccgcgtcggc   2820
ctggcgcccc atccaggtgc cgccgtgccg ttgatgagac ctctgcctgc tcctgcttgc   2880
gttgagaggc cgccactcca cttgttttgc atctgtagct gctcggtttg gtcatcagct   2940
gggagataag aaaagcggaa acgtactaat tgctctggag tagatccatc cattcacagt   3000
gatagttact gatgtactaa gctttaatta gttcaatgct agatcgttct tgttcaggtg   3060
tcgatcgcgt atccttgtcc ttggtctcct tttcattttg                         3100
```

```
<210> SEQ ID NO 7
<211> LENGTH: 531
<212> TYPE: PRT
<213> ORGANISM: Arabidopsis thaliana

<400> SEQUENCE: 7

Met Asp Thr Leu Phe Arg Leu Val Ser Leu Gln Gln Gln Gln Gln Ser
1               5                   10                  15

Asp Ser Ile Ile Thr Asn Gln Ser Ser Leu Ser Arg Thr Ser Thr Thr
            20                  25                  30

Thr Thr Gly Ser Pro Gln Thr Ala Tyr His Tyr Asn Phe Pro Gln Asn
        35                  40                  45

Asp Val Val Glu Glu Cys Phe Asn Phe Phe Met Asp Glu Glu Asp Leu
    50                  55                  60

Ser Ser Ser Ser Ser His His Asn His His Asn His Asn Asn Pro Asn
65                  70                  75                  80

Thr Tyr Tyr Ser Pro Phe Thr Thr Pro Thr Gln Tyr His Pro Ala Thr
                85                  90                  95

Ser Ser Thr Pro Ser Ser Thr Ala Ala Ala Ala Ala Leu Ala Ser Pro
            100                 105                 110

Tyr Ser Ser Ser Gly His His Asn Asp Pro Ser Ala Phe Ser Ile Pro
        115                 120                 125

Gln Thr Pro Pro Ser Phe Asp Phe Ser Ala Asn Ala Lys Trp Ala Asp
    130                 135                 140

Ser Val Leu Leu Glu Ala Ala Arg Ala Phe Ser Asp Lys Asp Thr Ala
145                 150                 155                 160

Arg Ala Gln Gln Ile Leu Trp Thr Leu Asn Glu Leu Ser Ser Pro Tyr
                165                 170                 175

Gly Asp Thr Glu Gln Lys Leu Ala Ser Tyr Phe Leu Gln Ala Leu Phe
            180                 185                 190

Asn Arg Met Thr Gly Ser Gly Glu Arg Cys Tyr Arg Thr Met Val Thr
        195                 200                 205

Ala Ala Ala Thr Glu Lys Thr Cys Ser Phe Glu Ser Thr Arg Lys Thr
    210                 215                 220

Val Leu Lys Phe Gln Glu Val Ser Pro Trp Ala Thr Phe Gly His Val
225                 230                 235                 240

Ala Ala Asn Gly Ala Ile Leu Glu Ala Val Asp Gly Glu Ala Lys Ile
                245                 250                 255

His Ile Val Asp Ile Ser Ser Thr Phe Cys Thr Gln Trp Pro Thr Leu
            260                 265                 270

Leu Glu Ala Leu Ala Thr Arg Ser Asp Asp Thr Pro His Leu Arg Leu
        275                 280                 285

Thr Thr Val Val Val Ala Asn Lys Phe Val Asn Asp Gln Thr Ala Ser
    290                 295                 300

His Arg Met Met Lys Glu Ile Gly Asn Arg Met Glu Lys Phe Ala Arg
305                 310                 315                 320

Leu Met Gly Val Pro Phe Lys Phe Asn Ile Ile His His Val Gly Asp
                325                 330                 335

Leu Ser Glu Phe Asp Leu Asn Glu Leu Asp Val Lys Pro Asp Glu Val
            340                 345                 350

Leu Ala Ile Asn Cys Val Gly Ala Met His Gly Ile Ala Ser Arg Gly
        355                 360                 365

Ser Pro Arg Asp Ala Val Ile Ser Ser Phe Arg Arg Leu Arg Pro Arg
    370                 375                 380
```

```
Ile Val Thr Val Val Glu Glu Glu Ala Asp Leu Val Gly Glu Glu Glu
385                 390                 395                 400

Gly Gly Phe Asp Asp Glu Phe Leu Arg Gly Phe Gly Glu Cys Leu Arg
                405                 410                 415

Trp Phe Arg Val Cys Phe Glu Ser Trp Glu Glu Ser Phe Pro Arg Thr
            420                 425                 430

Ser Asn Glu Arg Leu Met Leu Glu Arg Ala Ala Gly Arg Ala Ile Val
        435                 440                 445

Asp Leu Val Ala Cys Glu Pro Ser Asp Ser Thr Glu Arg Arg Glu Thr
    450                 455                 460

Ala Arg Lys Trp Ser Arg Arg Met Arg Asn Ser Gly Phe Gly Ala Val
465                 470                 475                 480

Gly Tyr Ser Asp Glu Val Ala Asp Asp Val Arg Ala Leu Leu Arg Arg
                485                 490                 495

Tyr Lys Glu Gly Val Trp Ser Met Val Gln Cys Pro Asp Ala Ala Gly
            500                 505                 510

Ile Phe Leu Cys Trp Arg Asp Gln Pro Val Val Trp Ala Ser Ala Trp
        515                 520                 525

Arg Pro Thr
    530


<210> SEQ ID NO 8
<211> LENGTH: 2825
<212> TYPE: DNA
<213> ORGANISM: Arabidopsis thaliana

<400> SEQUENCE: 8

atcgattaag agaaaataga gttttcatgc accagtgttg atagtaacgt agtcgcggaa     60

tgtctaaaac gattatgagt ttggtgtttt gattggttag aattggtatt agtaggacat    120

tctaactttt ttgttagtct gttgatttag gatgcgtaaa gagtcttttt attttacacc    180

agttgagact tgggatcgat agtacttgaa acacttggtt ggtttcatgt atttggccta    240

tatataaaca aacatcgtaa ttatatacgg attttttcg gaattttacg ccatatctgt    300

aagtatatat aacatgcatg tcgttttcaa attcatatga tgaacgatcc acgtaagtgc    360

tactactcct acaatattgc atgagagaga tatgtattta taaattttat tttgaagaag    420

aaataagagg gaaggttact tgggtggatc gatgtgaaaa caaaagaaga aaaagcgaaa    480

cccactaagc cattacatga tatcgacctt cttatctttt tcctctttat tttatttttc    540

tcaggacttt tttctactta atgaaacctc caaactatct aactaataca ctcccatgta    600

gaataaagaa aattatataa gatattgttg atattttgta actagaaaat atatttgctc    660

tgtaattttt cgtaagttaa atcaacattt ttcagtagaa acaaatatta ctgcaaaaag    720

taggatcatt atttttgtcc aaaatctcag ttagctatag ggttgtagta aaaacaaaac    780

acattcttga tttgccccaa aaaataaaga gagagaagaa tattgttcaa aagtggtctc    840

ttctctctct aattatgttt tcactaaacc caattagatt caaacagtct acaaagtcca    900

aaagataaac atgggacaac aattcgatgc aaaaaatcct cttttcatgc tcttttttta    960

ttctctagtc ttttaaatta ctaataaaaa ctcacaaatc caccaaaccc attctctaca   1020

actcaccttc atctagattt acccactccc accgagaaac acaagaaaaa aaatatacat   1080

atataaatat acaagacaac acatgatgct gatgcaatat acacaacaaa gtattaaatc   1140

ttagatattg tgggtctccc tttcttctat tcattttctt attcattaaa aaaaaaaaat   1200

ggatactctc tttagactag tcagtctcca acaacaacaa caatccgata gtatcattac   1260
```

```
aaatcaatct tcgttaagca gaacttccac caccactact ggctctccac aaactgctta   1320

tcactacaac tttccacaaa acgacgtcgt cgaagaatgc ttcaactttt tcatggatga   1380

agaagacctt tcctcttctt cttctcacca caaccatcac aaccacaaca atcctaatac   1440

ttactactct cctttcacta ctcccaccca ataccatccc gccacatcat caaccccttc   1500

ctccaccgcc gcagccgcag ctttagcctc gccttactcc tcctccggcc accataatga   1560

cccttccgcg ttctccatac ctcaaactcc tccgtccttc gacttctcag ccaatgccaa   1620

gtgggcagac tcggtccttc ttgaagcggc acgtgccttc tccgacaaag acactgcacg   1680

tgcgcaacaa atcctatgga cgctcaacga gctctcttct ccgtacggag acaccgagca   1740

aaaactggct tcttacttcc tccaagctct cttcaaccgc atgaccggtt caggcgaacg   1800

atgctaccga accatggtaa cagctgcagc cacagagaag acttgctcct tcgagtcaac   1860

gcgaaaaact gtactaaagt tccaagaagt tagcccctgg gccacgtttg gacacgtggc   1920

ggcaaacgga gcaatcttgg aagcagtaga cggagaggca aagatccaca tcgttgacat   1980

aagctccacg ttttgcactc aatggccgac tcttctagaa gctttagcca caagatcaga   2040

cgacacgcct cacctaaggc taaccacagt tgtcgtggcc aacaagtttg tcaacgatca   2100

aacggcgtcg catcggatga tgaaagagat cggaaaccga atggagaaat tcgctaggct   2160

tatgggagtt cctttcaaat ttaacattat tcatcacgtt ggagatttat ctgagtttga   2220

tctcaacgaa ctcgacgtta aaccagacga agtcttggcc attaactgcg taggcgcgat   2280

gcatgggatc gcttcacgtg gaagccctag agacgctgtg atatcgagtt tccgacggtt   2340

aagaccgagg attgtgacgg tcgtagaaga agaagctgat cttgtcggag aagaagaagg   2400

tggctttgat gatgagttct tgagagggtt tggagaatgt ttacgatggt ttagggtttg   2460

cttcgagtca tgggaagaga gttttccaag gacgagcaac gagaggttga tgctagagcg   2520

tgcagcggga cgtgcgatcg ttgatcttgt ggcttgtgag ccgtcggatt ccacggagag   2580

gcgagagaca gcgaggaagt ggtcgaggag gatgaggaat agtgggtttg gagcggtggg   2640

gtatagtgat gaggtggcgg atgatgtcag agctttgttg aggagatata aagaaggtgt   2700

ttggtcgatg gtacagtgtc ctgatgccgc cggaatattc ctttgttgga gagatcagcc   2760

ggtggtttgg gctagtgcgt ggcggccaac gtaaagggtt gtttttattt tttcataagg   2820

aattc                                                               2825
```

```
<210> SEQ ID NO 9
<211> LENGTH: 602
<212> TYPE: PRT
<213> ORGANISM: Oryza sativa

<400> SEQUENCE: 9

Met Asp Thr Leu Phe Arg Leu Val Ser Leu Gln Ala Ala Ser Glu Gln
1               5                   10                  15

Gln Gln Gln Gln Gln Gln Ser Ala Ser Tyr Asn Ser Arg Ser Thr Thr
            20                  25                  30

Ser Ser Gly Ser Arg Ser Ser Ser His Gln Thr Asn Ala Ser Tyr Ser
        35                  40                  45

Tyr Tyr His His Ser Ser Asn Ser Gly Gly Gly Gly Gly Gly Gly Gly
    50                  55                  60

Gly Tyr Tyr Tyr Gly Gly Gln Gln Pro Pro Pro Ser Gln Tyr Tyr Tyr
65                  70                  75                  80

Leu Glu Pro Tyr Gln Glu Glu Cys Gly Asn Ala Pro His His Gln Leu
```

```
                85                  90                  95

Tyr Met Asp Glu Asp Phe Ser Ser Ser Ser Ser Ser Arg His Phe His
            100                 105                 110

His Gly Ala Arg Val Gln Gln Gln Gln Pro Pro Ala Ser Ser Thr Pro
        115                 120                 125

Thr Gly Thr Ala Pro Thr Pro Pro Leu Ser Thr Ser Ser Thr Ala Ala
    130                 135                 140

Gly Ala Gly His Gly Leu Phe Glu Ala Ala Asp Leu Ser Phe Pro Pro
145                 150                 155                 160

Asp Leu Asn Leu Asp Phe Ser Ser Pro Ala Ser Ser Ser Gly Gly Gly
                165                 170                 175

Thr Ala Ser Ser Gly Ala Val Gly Gly Gly Gly Gly Gly Arg Trp Ala
            180                 185                 190

Ser Gln Leu Leu Leu Glu Cys Ala Arg Ser Val Ala Ala Arg Asp Ser
        195                 200                 205

Gln Arg Val Gln Gln Leu Met Trp Met Leu Asn Glu Leu Ala Ser Pro
    210                 215                 220

Tyr Gly Asp Val Glu Gln Lys Leu Ala Ser Tyr Phe Leu Gln Gly Leu
225                 230                 235                 240

Phe Ala Arg Leu Thr Ala Ser Gly Pro Arg Thr Leu Arg Thr Leu Ala
                245                 250                 255

Ala Ala Ser Asp Arg Asn Thr Ser Phe Asp Ser Thr Arg Arg Thr Ala
            260                 265                 270

Leu Arg Phe Gln Glu Leu Ser Pro Trp Ser Ser Phe Gly His Val Ala
        275                 280                 285

Ala Asn Gly Ala Ile Leu Glu Ser Phe Leu Glu Val Ala Ala Ala Ala
    290                 295                 300

Ser Ser Glu Thr Gln Arg Phe His Ile Leu Asp Leu Ser Asn Thr Phe
305                 310                 315                 320

Cys Thr Gln Trp Pro Thr Leu Leu Glu Ala Leu Ala Thr Arg Ser Ala
                325                 330                 335

Asp Glu Thr Pro His Leu Ser Ile Thr Thr Val Val Ser Ala Ala Pro
            340                 345                 350

Ser Ala Pro Thr Ala Ala Val Gln Arg Val Met Arg Glu Ile Gly Gln
        355                 360                 365

Arg Met Glu Lys Phe Ala Arg Leu Met Gly Val Pro Phe Arg Phe Arg
    370                 375                 380

Ala Val His His Ser Gly Asp Leu Ala Glu Leu Asp Leu Asp Ala Leu
385                 390                 395                 400

Asp Leu Arg Glu Gly Gly Ala Thr Thr Ala Leu Ala Val Asn Cys Val
                405                 410                 415

Asn Ser Leu Arg Gly Val Val Pro Gly Arg Ala Arg Arg Arg Asp Ala
            420                 425                 430

Phe Ala Ala Ser Leu Arg Arg Leu Asp Pro Arg Val Val Thr Val Val
        435                 440                 445

Glu Glu Glu Ala Asp Leu Val Ala Ser Asp Pro Asp Ala Ser Ser Ala
    450                 455                 460

Thr Glu Glu Gly Gly Asp Thr Glu Ala Ala Phe Leu Lys Val Phe Gly
465                 470                 475                 480

Glu Gly Leu Arg Phe Phe Ser Ala Tyr Met Asp Ser Leu Glu Glu Ser
                485                 490                 495

Phe Pro Lys Thr Ser Asn Glu Arg Leu Ala Leu Glu Arg Gly Ala Gly
            500                 505                 510
```

```
Arg Ala Ile Val Asp Leu Val Ser Cys Pro Ala Ser Glu Ser Met Glu
        515                 520                 525

Arg Arg Glu Thr Ala Ala Ser Trp Ala Arg Arg Met Arg Ser Ala Gly
    530                 535                 540

Phe Ser Pro Val Ala Phe Ser Glu Asp Val Ala Asp Asp Val Arg Ser
545                 550                 555                 560

Leu Leu Arg Arg Tyr Arg Glu Gly Trp Ser Met Arg Glu Ala Gly Thr
                565                 570                 575

Asp Asp Ser Ala Ala Gly Ala Gly Val Phe Leu Ala Trp Lys Glu Gln
            580                 585                 590

Pro Leu Val Trp Ala Ser Ala Trp Arg Pro
        595                 600


<210> SEQ ID NO 10
<211> LENGTH: 2279
<212> TYPE: DNA
<213> ORGANISM: Oryza sativa

<400> SEQUENCE: 10

tagatggata cgctgtttag gttggttagc ctccaagccg cctccgagca gcagcagcag      60

cagcagcagt cggcgtccta caactcgagg agcacgacgt cgagcgggtc caggtcgtcg     120

tcgcaccaga cgaacgcgtc ctacagctac taccaccaca gcagcaacag cggcggcggc     180

ggcggaggcg gcggagggta ctactacggc ggccagcagc cgccgccgtc gcagtactac     240

tacctggagc cgtaccaaga agaatgcggc aacgccccac accaccagct ttacatggat     300

gaagacttct cctcctcgtc gtcgtcgagg cacttccacc acggcgcgcg ggtgcagcag     360

cagcagccgc cggcgtcgtc cacgcccacg gggacggcgc cgacgccgcc gctgtcgacc     420

tcgtccaccg cggcgggcgc cgggcacggc ctgttcgagg cggcggacct gtcgttcccg     480

ccggacctca acctcgactt ctcgtccccg gcgtcgtcgt ccggcggcgg gacagcgtcg     540

tcgggcgcgg ttgggggcgg cggcggcggg aggtgggcta gccagctgct gctggagtgc     600

gcgcggtcgg tggccgcccg cgacagccag cgcgtgcagc agctcatgtg gatgctcaac     660

gagctcgcgt cgccgtacgg cgacgtggag cagaagctgg cttcctactt cttgcagggg     720

ctgttcgctc ggctcacggc gtccgggccg cgcacgctgc gcacgctcgc cgcggcgtcc     780

gaccggaaca cgtcgttcga ctcgacgcgg cgcacggcgc tgcggttcca ggagctcagc     840

ccctggtcct cgtttgggca cgtcgccgcc aatggcgcca tcctcgagtc cttcctggag     900

gtcgccgccg cggcgtcgtc ggagacgcag cggttccaca tcctcgacct gagcaacacg     960

ttctgcacgc agtggccgac gctgctggag gcgctggcca cgcggtccgc cgacgagacg    1020

ccgcacctct cgatcaccac cgtggtgtcc gccgcgccgt ccgcgcccac ggcggcggtg    1080

cagcgcgtca tgcgggagat cgggcagcgc atggagaagt tcgcgcggct catgggcgtg    1140

cccttccgct tccgcgccgt gcaccactcc ggggacctcg cggagctcga cctcgacgcg    1200

ctcgacctcc gcgagggcgg cgccaccacc gcgctcgccg tcaactgcgt caactcgctg    1260

cgcggcgtgg ttcccggcag ggcccgccgg cgcgacgcgt tcgcggcgtc gctccgccgg    1320

ctggacccgc gggtcgtcac cgtcgtcgag gaggaggcgg acctggtggc gtccgatccc    1380

gacgcgtcgt cggcgacgga ggaaggcggc gacacggagg cggcgttcct caaggtgttc    1440

ggcgagggct tgcgcttctt ctcggcgtac atggattcgc tcgaggagag cttccccaag    1500

acgagcaacg agaggctggc attggagagg ggagcagggc gcgccatcgt cgacttggtc    1560
```

```
tcgtgcccgg cgtcggagtc gatggagcgg cgggagacgg cggcgtcgtg ggcgcggcgc   1620

atgcggtcgg ccgggttctc tccggtggca ttcagcgagg acgtcgccga cgacgtgcga   1680

tcgctgctgc gccggtacag ggaagggtgg tcgatgcgcg aggccggcac ggacgactcg   1740

gcggccggag ccggcgtctt cctcgcgtgg aaggagcagc ctctggtgtg ggcaagcgcg   1800

tggcggccat gatcggatcg tcgtgatcga tggatcaaag ctcaccggtg agtggaacag   1860

catggaagaa aagagctcca tagctaagca agcacgcatg catatccacc atgcatgggg   1920

taagctagca agctctctcg tgtgtgtcac gatcgacatt aatggcggct cacacaaagg   1980

catgtagggt tttgaaacag cgtaggaagc tacagaaatg gatcacgtac gtacgtacac   2040

attgggttgc agcgatcgag gagggagatg atagttttag ttcctagatt tgcatccatt   2100

tttattcatc gatcgccaac aagttcttgg cgagaagatg attttgattt gcttgcttcc   2160

atcttcttgt ttatttttcc ccctttcgtt tgtgtttctt cttaatttgt aagggttaac   2220

gacatttttc ttcactctgg agaaatttta cgtgcatggt ttttatcatg cgtacctgc    2279
```

```
<210> SEQ ID NO 11
<211> LENGTH: 449
<212> TYPE: PRT
<213> ORGANISM: Malus domestica

<400> SEQUENCE: 11

Met Leu Gln Ser Leu Val Pro Gln Ser Pro Ile Thr Ala Ala Thr Pro
1               5                   10                  15

Asn Asn Asn Asn Pro Thr Ser Ser Ser Ser Ser Met Lys Thr Lys Arg
            20                  25                  30

Val Asp Arg Asp Leu Ala Gly Ser Gly Ser Gly Asp Ser Asp Ala Glu
        35                  40                  45

Asp Pro Ser Phe Thr Lys Arg Pro Asn Ser Gly Arg Asn Phe Arg Glu
    50                  55                  60

Arg Thr Ala Asp Asp Arg Asp Thr Glu Pro Val Ala Glu Gly Glu Ser
65                  70                  75                  80

Asp Gly Leu Arg Leu Leu Gly Leu Leu Leu Gln Cys Ala Glu Phe Val
                85                  90                  95

Ala Met Asp Ser Leu Asp Asp Ala Ser Asp Leu Leu Pro Glu Ile Ala
            100                 105                 110

Glu Leu Ser Ser Pro Phe Gly Ser Ser Pro Glu Arg Val Gly Ala Tyr
        115                 120                 125

Phe Ser His Ala Leu Gln Thr Arg Val Ile Ser Ser Cys Leu Gly Thr
    130                 135                 140

Tyr Ser Pro Leu Thr Asn Arg Thr Leu Thr Leu Ala Gln Ser Gln Arg
145                 150                 155                 160

Ile Phe Asn Ala Leu Gln Ser Tyr Asn Ser Ile Ser Pro Leu Val Lys
                165                 170                 175

Phe Ser His Phe Thr Ser Asn Gln Ala Ile Phe Gln Ala Leu Asp Gly
            180                 185                 190

Glu Asp His Val His Val Ile Asp Leu Asp Ile Met Gln Gly Leu Gln
        195                 200                 205

Trp Pro Gly Leu Phe His Ile Leu Ala Ser Arg Ser Lys Lys Ile Arg
    210                 215                 220

Ser Met Arg Ile Thr Gly Phe Gly Ser Ser Ser Glu Leu Leu Glu Ser
225                 230                 235                 240

Thr Gly Arg Arg Leu Ala Asp Phe Ala Ser Ser Leu Gly Leu Pro Phe
                245                 250                 255
```

```
Glu Phe Gln Pro Leu Glu Gly Lys Ile Gly Ser Ile Thr Asp Leu Ser
            260                 265                 270

Gln Leu Gly Ile Arg Pro Ser Glu Ala Thr Val Val His Trp Met His
        275                 280                 285

His Cys Leu Tyr Asp Val Thr Gly Ser Asp Leu Ala Thr Leu Arg Leu
    290                 295                 300

Leu Gly Ser Leu Arg Pro Lys Leu Ile Thr Ile Ala Glu Gln Asp Leu
305                 310                 315                 320

Ser His Ser Gly Ser Phe Leu Ser Arg Phe Val Glu Ala Leu His Tyr
                325                 330                 335

Tyr Ser Ala Leu Phe Asp Ala Leu Gly Asp Gly Leu Gly Ala Asp Ser
            340                 345                 350

Leu Glu Arg His Met Val Glu Gln Gln Leu Phe Gly Tyr Glu Ile Arg
        355                 360                 365

Asn Ile Leu Ala Val Gly Gly Pro Lys Arg Thr Gly Glu Val Lys Val
    370                 375                 380

Glu Arg Trp Gly Asp Glu Leu Lys Arg Val Gly Phe Gly Pro Val Ser
385                 390                 395                 400

Leu Gly Gly Asn Pro Ala Ala Gln Ala Ser Leu Leu Leu Gly Met Phe
                405                 410                 415

Pro Trp Lys Gly Tyr Thr Leu Val Glu Glu Asn Gly Cys Leu Lys Leu
            420                 425                 430

Gly Trp Lys Asp Leu Ser Leu Leu Thr Ala Ser Ala Trp Gln Pro Leu
        435                 440                 445

Asp
```

<210> SEQ ID NO 12
<211> LENGTH: 1823
<212> TYPE: DNA
<213> ORGANISM: Malus domestica

<400> SEQUENCE: 12

```
ctctaaccaa acagttttct ctctctactc tctctcctct ctctctgaca aagctttctg     60

caaaactctc actgtacatg cgtttggttg tctttctcgc ttttctttgt cgctttccgc    120

ccgaaggctt ccgagctttt tatattctct ctatcgacaa tcacacactt cctccttcct    180

cctcctcctc ctcctctacc agtcatgctt cagagcttag ttcctcaatc cccaatcacc    240

gccgccaccc ctaacaataa caaccctacc tcctcctcct cctccatgaa gaccaagcgc    300

gtcgaccgcg accttgccgg cagtggaagc ggcgattccg acgccgaaga cccctccttc    360

accaaacgcc ccaattccgg cagaaatttc cgcgaaagaa ctgccgacga tcgtgacacc    420

gaaccggtgg cggagggcga atcggacggg ttgagactgt tggggcttct gctacaatgc    480

gccgagttcg tcgccatgga cagcctcgac gacgccagcg acctgttacc tgagatcgcg    540

gaactatcat cgccgttcgg gtcgtcgccg gagcgagtag gtgcttattt ctcgcacgcg    600

cttcagactc gcgtgatcag ctcctgctta ggtacctact ctccgctcac caacagaacc    660

ctaacgcttg ctcagtcgca gcggatcttc aacgctctcc aatcctacaa ctccatcagt    720

ccgctagtca aattctcaca cttcacgtcc aatcaggcga ttttccaggc gctggacggc    780

gaggatcacg tccacgtcat cgatttggat ataatgcaag gcctccagtg gccaggattg    840

ttccacatcc ttgcatcgcg gtcgaagaag atccgatcaa tgcggataac cgggttcggg    900

tcctcctcgg agctcctcga gtcgaccggg cggagactcg ctgatttcgc gagctcgctc    960
```

```
ggcctgccct tcgagttcca gccgctggag ggcaaaatcg ggagcataac cgacctaagt   1020

caactcggaa tcagaccgag cgaggccacc gtggtccact ggatgcacca ttgcttgtac   1080

gacgtcaccg gcagcgattt ggcgacgctg agattgctgg gctcgctgag accgaagctg   1140

atcacgatcg ccgagcagga tttgagccac agcggcagct tcctgagtag gtttgtggag   1200

gccttgcatt actacagcgc gctgtttgat gcgctcgggg acggattggg cgccgacagc   1260

ctggagaggc atatggtgga gcagcagctg ttcggctacg agattaggaa tatcctcgcg   1320

gtgggcgggc cgaagagaac cggggaggtg aaggtggaga ggtgggggga tgagttgaag   1380

cgggtcgggt ttgggcccgt ttcgcttggc gggaacccgg cggcgcaggc tagcttgttg   1440

cttgggatgt ttccgtggaa ggggtacact ttggtggagg agaatgggtg cttgaagttg   1500

ggttggaagg acctctcctt gcttacagcc tctgcctggc agcctttgga ttgaaatact   1560

ttgaccagca tgatacggtg gggaggagga cttgtttttc acttggctgt aattctttga   1620

aggagaaaaa cattgtagtt aggttttttt cggttccttg ttatatgttt aaagaaaaga   1680

agagagcggt gctgtctacg tatctatttt tacttatcac atatttcttg ttaatttttg   1740

ttctttgaat ttttgtgatt tattaaattc gacggtgaaa actgaaatgg gtgtgtagat   1800

aacatcatcc gaaaaaaaaa aaa                                           1823
```

<210> SEQ ID NO 13
<211> LENGTH: 457
<212> TYPE: PRT
<213> ORGANISM: Oryza sativa

<400> SEQUENCE: 13

```
Met Leu Gln Gly Val Leu Ser Arg Ala Pro Gly Ala Asp Ala Ala Ala
1               5                   10                  15

Met Lys Ala Lys Arg Ala Ala Asp Asp Glu Glu Glu Gly Gly Glu Arg
            20                  25                  30

Glu Arg Ala Arg Gly Lys Arg Leu Ala Ala Glu Gly Lys Gln Gly Leu
        35                  40                  45

Val Val Val Ser Thr Gly Glu Glu Glu Glu Ala Ala Ala Glu Thr Arg
    50                  55                  60

Gly Leu Arg Leu Leu Ser Leu Leu Leu Arg Cys Ala Glu Ala Val Ala
65                  70                  75                  80

Met Asp Gln Leu Pro Glu Ala Arg Asp Leu Leu Pro Glu Ile Ala Glu
                85                  90                  95

Leu Ala Ser Pro Phe Gly Ser Ser Pro Glu Arg Val Ala Ala Tyr Phe
            100                 105                 110

Gly Asp Ala Leu Cys Ala Arg Val Leu Ser Ser Tyr Leu Gly Ala Tyr
        115                 120                 125

Ser Pro Leu Ala Leu Arg Pro Leu Ala Ala Ala Gln Ser Arg Arg Ile
    130                 135                 140

Ser Gly Ala Phe Gln Ala Tyr Asn Ala Leu Ser Pro Leu Val Lys Phe
145                 150                 155                 160

Ser His Phe Thr Ala Asn Gln Ala Ile Phe Gln Ala Leu Asp Gly Glu
                165                 170                 175

Asp Arg Val His Val Ile Asp Leu Asp Ile Met Gln Gly Leu Gln Trp
            180                 185                 190

Pro Gly Leu Phe His Ile Leu Ala Ser Arg Pro Thr Lys Pro Arg Ser
        195                 200                 205

Leu Arg Ile Thr Gly Leu Gly Ala Ser Leu Asp Val Leu Glu Ala Thr
    210                 215                 220
```

```
Gly Arg Arg Leu Ala Asp Phe Ala Ala Ser Leu Gly Leu Pro Phe Glu
225                 230                 235                 240

Phe Arg Pro Ile Glu Gly Lys Ile Gly His Val Ala Asp Ala Ala Ala
                245                 250                 255

Leu Leu Gly Pro Arg His His Gly Glu Ala Thr Val Val His Trp Met
            260                 265                 270

His His Cys Leu Tyr Asp Val Thr Gly Ser Asp Ala Gly Thr Val Arg
        275                 280                 285

Leu Leu Lys Ser Leu Arg Pro Lys Leu Ile Thr Ile Val Glu Gln Asp
    290                 295                 300

Leu Gly His Ser Gly Asp Phe Leu Gly Arg Phe Val Glu Ala Leu His
305                 310                 315                 320

Tyr Tyr Ser Ala Leu Phe Asp Ala Leu Gly Asp Gly Ala Gly Ala Ala
                325                 330                 335

Glu Glu Glu Ala Ala Glu Arg His Ala Val Glu Arg Gln Leu Leu Gly
            340                 345                 350

Ala Glu Ile Arg Asn Ile Val Ala Val Gly Gly Pro Lys Arg Thr Gly
        355                 360                 365

Glu Val Arg Val Glu Arg Trp Gly Asp Glu Leu Arg Arg Ala Gly Phe
    370                 375                 380

Arg Pro Val Thr Leu Ala Gly Ser Pro Ala Ala Gln Ala Arg Leu Leu
385                 390                 395                 400

Leu Gly Met Tyr Pro Trp Lys Gly Tyr Thr Leu Val Glu Glu Asp Gly
                405                 410                 415

Cys Leu Lys Leu Gly Trp Lys Asp Leu Ser Leu Leu Thr Ala Ser Ser
            420                 425                 430

Trp Glu Pro Thr Asp Gly Asp Ala Asp Ala Asp Val Ala Val Ala Gly
        435                 440                 445

Asp Thr His His Glu Ser His Asp Ser
    450                 455
```

<210> SEQ ID NO 14
<211> LENGTH: 1679
<212> TYPE: DNA
<213> ORGANISM: Oryza sativa

<400> SEQUENCE: 14

```
atgcttgctt gttgcagtgg ttttgccacg gagaagggtc accgggaaat tattgtttag      60

gctgacgtga tgctccaggg agtcctgtcg cgagctcccg gcgccgacgc ggcagcgatg     120

aaggcgaagc gcgcggccga cgacgaggag gaaggcggcg agcgggagcg cgcgcgtggg     180

aagcggctgg ctgctgaggg gaagcaaggg ttagtggtgg tgagtacggg ggaggaggag     240

gaggcggcgg cggagacgcg tgggctgcgg ctgcttagtt tgttgctgag gtgtgcggag     300

gcggtggcga tggaccagct gccggaggcg cgggacctgc tgccggagat cgccgagctg     360

gcgtcgccgt tcgggtcgtc gcccgagcgc gtcgcggcct acttcgggga cgcgctgtgc     420

gcgcgcgtgc tgagctccta cctgggggcc tactcgccgc tggcgctccg cccgctcgcc     480

gccgcgcaga gccgccgcat ctccggcgcg ttccaggcgt acaacgcgct gtcgccgctc     540

gtcaagttct cgcacttcac ggccaaccag gccatcttcc aggcgctcga cggcgaggac     600

cgcgtccacg tgatcgacct cgacatcatg caggggctgc agtggccggg cctcttccac     660

atcctcgcct cccgccccac caagccgcgc tcgctccgga tcaccggcct cggcgcgtcg     720

ctcgacgtcc tcgaggccac cggccgccgc ctcgccgact tcgccgcgtc gctcggcttg     780
```

```
ccccttcgagt tccggcccat cgaggggaag atcgggcacg tcgccgacgc cgccgcgctc    840
ctcggcccgc gccaccacgg ggaggccacc gttgtgcact ggatgcacca ctgcctctac    900
gacgtgacgg gctccgacgc cggcacggtg cgcctgctca agagcctccg gccgaagctg    960
atcaccatcg tggagcagga cctcggccac agcggcgact tcctgggccg cttcgtggag   1020
gcgctgcact actactcggc gctgttcgac gcgctgggcg acggcgcggg ggccgccgag   1080
gaggaggcgg cggagcggca cgcggtggag cgtcagctcc tcggcgcgga gatacggaac   1140
atcgtcgccg tcgggggccc caagcgcacc ggcgaggtgc gcgtcgagcg gtggggcgac   1200
gagctgcggc gagcggggtt ccggccggtg accctggccg gcagccccgc cgcgcaggcg   1260
aggctgcttc ttggcatgta cccatggaag ggctacactc tcgtcgaaga ggacggctgc   1320
ctcaagctcg ggtggaagga cctgtccctg ctcaccgcct cgtcgtggga gccgacagac   1380
ggcgacgccg acgccgacgt cgccgtcgcc ggcgataccc accatgagag ccacgattct   1440
tgatcacatg atcgcagtag cagccaggtc gattcacctg tcgcagcttt tcttggtcat   1500
attcattatc ctctttctgc tagctacttc attcgatcgt tcttcctcct gtgagtagta   1560
ttttggccga tgattaagct tgtaatataa tcgtataggc ttcatcattc gttccctctc   1620
caggttgcca tgaacaacac catttcaatt acaaaataga actcttctac ctccaaaaa    1679
```

<210> SEQ ID NO 15
<211> LENGTH: 651
<212> TYPE: PRT
<213> ORGANISM: Oryza sativa

<400> SEQUENCE: 15

```
Met Gly Ser Ser Ser Leu Leu Leu Phe Pro Ser Ser Ser Ser Ser Ala
1               5                   10                  15

Thr His Ser Ser Tyr Ser Pro Ser Ser Ser Ser His Ala Ile Thr Ser
            20                  25                  30

Leu Leu Pro Pro Leu Pro Ser Asp His His Leu Leu Leu Tyr Leu Asp
        35                  40                  45

His Gln Glu Gln His His Leu Ala Ala Ala Met Val Arg Lys Arg Pro
    50                  55                  60

Ala Ser Asp Met Asp Leu Pro Pro Pro Arg Arg His Val Thr Gly Asp
65                  70                  75                  80

Leu Ser Asp Val Thr Ala Ala Ala Ala Pro Ser Ser Ala Ser Ala Gln
                85                  90                  95

Leu Pro Ala Leu Pro Thr Gln Leu Pro Ala Phe His His Thr Asp Met
            100                 105                 110

Asp Leu Ala Ala Pro Ala Pro Pro Pro Pro Gln Gln Gln Val Ala Ala
        115                 120                 125

Gly Glu Gly Gly Pro Pro Ser Thr Ala Trp Val Asp Gly Ile Ile Arg
    130                 135                 140

Asp Ile Ile Ala Ser Ser Gly Ala Ala Val Ser Val Ala Gln Leu Ile
145                 150                 155                 160

His Asn Val Arg Glu Ile Ile Arg Pro Cys Asn Pro Asp Leu Ala Ser
                165                 170                 175

Ile Leu Glu Leu Arg Leu Arg Ser Leu Leu Thr Ser Asp Pro Ala Pro
            180                 185                 190

Pro Pro Pro Pro Pro Pro Ser His Pro Ala Leu Leu Pro Pro Asp Ala
        195                 200                 205

Thr Ala Pro Pro Pro Pro Pro Thr Ser Val Ala Ala Leu Pro Pro Pro
```

```
    210                 215                 220

Pro Pro Pro Gln Pro Asp Lys Arg Arg Arg Glu Pro Gln Cys Gln Glu
225                 230                 235                 240

Gln Glu Pro Asn Gln Pro Gln Ser Pro Lys Pro Pro Thr Ala Glu Glu
                245                 250                 255

Thr Ala Ala Ala Ala Ala Ala Ala Lys Glu Arg Lys Glu Glu Gln Arg
            260                 265                 270

Arg Lys Gln Arg Asp Glu Glu Gly Leu His Leu Leu Thr Leu Leu Leu
        275                 280                 285

Gln Cys Ala Glu Ser Val Asn Ala Asp Asn Leu Asp Glu Ala His Arg
    290                 295                 300

Ala Leu Leu Glu Ile Ala Glu Leu Ala Thr Pro Phe Gly Thr Ser Thr
305                 310                 315                 320

Gln Arg Val Ala Ala Tyr Phe Ala Glu Ala Met Ser Ala Arg Leu Val
                325                 330                 335

Ser Ser Cys Leu Gly Leu Tyr Ala Pro Leu Pro Asn Pro Ser Pro Ala
            340                 345                 350

Ala Ala Arg Leu His Gly Arg Val Ala Ala Ala Phe Gln Val Phe Asn
        355                 360                 365

Gly Ile Ser Pro Phe Val Lys Phe Ser His Phe Thr Ala Asn Gln Ala
    370                 375                 380

Ile Gln Glu Ala Phe Glu Arg Glu Glu Arg Val His Ile Ile Asp Leu
385                 390                 395                 400

Asp Ile Met Gln Gly Leu Gln Trp Pro Gly Leu Phe His Ile Leu Ala
                405                 410                 415

Ser Arg Pro Gly Gly Pro Pro Arg Val Arg Leu Thr Gly Leu Gly Ala
            420                 425                 430

Ser Met Glu Ala Leu Glu Ala Thr Gly Lys Arg Leu Ser Asp Phe Ala
        435                 440                 445

Asp Thr Leu Gly Leu Pro Phe Glu Phe Cys Pro Val Ala Asp Lys Ala
    450                 455                 460

Gly Asn Leu Asp Pro Glu Lys Leu Gly Val Thr Arg Arg Glu Ala Val
465                 470                 475                 480

Ala Val His Trp Leu Arg His Ser Leu Tyr Asp Val Thr Gly Ser Asp
                485                 490                 495

Ser Asn Thr Leu Trp Leu Ile Gln Arg Leu Ala Pro Lys Val Val Thr
            500                 505                 510

Met Val Glu Gln Asp Leu Ser His Ser Gly Ser Phe Leu Ala Arg Phe
        515                 520                 525

Val Glu Ala Ile His Tyr Tyr Ser Ala Leu Phe Asp Ser Leu Asp Ala
    530                 535                 540

Ser Tyr Ser Glu Asp Ser Pro Glu Arg His Val Val Glu Gln Gln Leu
545                 550                 555                 560

Leu Ser Arg Glu Ile Arg Asn Val Leu Ala Val Gly Gly Pro Ala Arg
                565                 570                 575

Thr Gly Asp Val Lys Phe Gly Ser Trp Arg Glu Lys Leu Ala Gln Ser
            580                 585                 590

Gly Phe Arg Val Ser Ser Leu Ala Gly Ser Ala Ala Ala Gln Ala Val
        595                 600                 605

Leu Leu Leu Gly Met Phe Pro Ser Asp Gly Tyr Thr Leu Ile Glu Glu
    610                 615                 620

Asn Gly Ala Leu Lys Leu Gly Trp Lys Asp Leu Cys Leu Leu Thr Ala
625                 630                 635                 640
```

```
Ser Ala Trp Arg Pro Ile Gln Ala Ser Gly Arg
                645                 650
```

<210> SEQ ID NO 16
<211> LENGTH: 2924
<212> TYPE: DNA
<213> ORGANISM: Oryza sativa

<400> SEQUENCE: 16

```
atgctcctgc taacctctcc ctcttggtct cctcctctcg gcctcttcct ctttactccg     60
cttcccccctt cgcgccatcg cctcgcttgc gccgcgccaa atcccataaa aattccaccc    120
aacacaagcg ttaggcctcc cgcgcgcgcc cgtccgctcg ccatgctcgc ggccgcttcc    180
ccttggcgtt tgtagatggg ctcctcctcc ctcctcctct tcccctcctc ttcctcctcc    240
gccacccact cctcttattc tccctcctcc tcctctcatg ccatcacctc cttgctgcct    300
cctctcccct ccgaccacca tctcctcctc tacctagacc accaagaaca acaccacctc    360
gccgccgcca tggtccgcaa gcgccccgcc tccgacatgg acctgccacc gccgcgccgc    420
catgtcaccg gcgacctgtc cgatgtcacg gccgccgcgg cgccgtcgtc tgccagcgcg    480
cagctccccg cgctgcccac gcagctcccg gcgttccacc acacggacat ggacctcgcc    540
gcgcccgcgc cgccgccgcc gcagcagcag gtggcggcgg gtgagggtgg gccgcctagt    600
acggcttggg tggatggtat catccgtgac atcatcgcca gcagcggcgc cgcggtctcc    660
gtcgcgcagc tcatccacaa cgtgcgtgag atcatccgac cttgtaaccc cgacctcgcg    720
tccatcctcg agctccgcct ccgctctctc ctcacctccg accctgcgcc gccgccgccg    780
ccgccgccgt cgcatcctgc tctcctccct cccgacgcca cggcgccacc gccaccccccc    840
acgtcggtcg ccgcgcttcc tccccctccg ccgccgcagc ccgacaagcg gcgccgcgag    900
cctcagtgtc aggagcagga gcccaaccag ccgcagtcgc cgaagccccc caccgcggag    960
gaaaccgccg ccgctgccgc ggccgccaag gagcggaagg aggagcagcg gcggaagcag   1020
cgcgacgagg agggcctcca cctgctgacg ctgctgctcc agtgcgcgga gtcggtgaac   1080
gcggacaacc tcgacgaggc gcaccgcgcg ctgctggaga tcgcggagct tgccacgccg   1140
ttcggcacat ccacgcagcg cgtcgccgcc tacttcgcgg aggccatgtc ggcgcggctg   1200
gtgagctcgt gcctggggct gtacgcgccg ctcccccaacc cgtccccggc ggcggcgcgt   1260
ctccacgggc gcgtcgccgc ggcgttccag gtgttcaacg gcatcagccc gttcgtgaag   1320
ttctcgcact tcacggcgaa ccaggcgatc caggaggcgt tcgagaggga ggagagggtg   1380
cacatcatcg acctggacat catgcagggg ctccaatggc cggggctgtt ccacatcctg   1440
gcgtcgaggc cggggggggcc gccgagggtg aggctgaccg ggctgggggc gtccatggag   1500
gcgctggagg cgacggggaa gaggctatcg gacttcgcgg acacgctggg attgccattc   1560
gagttctgcc cggtggctga caaggccggg aatcttgacc cggagaagct aggcgtcacg   1620
cgccgcgagg ccgtcgccgt ccactggctg cgccactccc tctacgatgt caccggctcc   1680
gactccaaca cgctctggct catccagagg ttggcgccaa aggttgtaac aatggtggag   1740
caggatctga gccactcagg ctccttcctg gcacgttttg tggaggccat ccactactat   1800
tcggcactgt tcgactcgct tgatgcgagt tacagcgagg atagcccgga gcggcatgtc   1860
gtggagcaac aactcttgtc acgggagatc cgcaatgtgc tagccgtggg cggtccagca   1920
cgcaccggcg atgttaagtt tgggagctgg cgcgagaagc ttgcgcagtc gggcttccgt   1980
gtgtcgtcgc ttgctggaag tgccgctgct caggccgtgc tgctgcttgg gatgttccct   2040
```

```
tccgatgggt acacgctcat tgaggagaat ggcgccctga agcttggatg gaaggatctg   2100

tgccttctca ctgcctctgc ttggcgccca attcaggctt cgggacgtta gtactgaggg   2160

ggaatttata gagctgaagt atcacttgat cttacttagg tgcaattacc tagtcctttt   2220

gcttctttta gctgctcaat ttggtcaatt ctgagaaaag aaaaataaaa aaaattctga   2280

tcactaattg ccagatctcc acacggtggt agttactgat gtgcagctta gctttagctt   2340

ttattctgtt catgctccag ttaaccattc tgtccagttt agtttatttt gcaattttgt   2400

agtgcttaat ccttgctgac attgttttgg gggaacacgc aaaaggatcc ttactgacat   2460

tagagatgca gttcttatcg tatgatcatt gatcacaaaa tgaaatatct ggtggttagt   2520

gagctcaatt agattgttga tagtgtagca ttgtcaatga tcaccaaata atattgttag   2580

tgtccatcta ctatgagaat ttacatgtac atttaagtta atgttcctaa ttttctccag   2640

aaaatgactt agggttgatc tgaatgccaa attatcagca atgaactaat gatgggtagc   2700

acatgagttg tgtactagaa agtcaggatg ttagtggttt taattcatgc catctaaatc   2760

ctgctaattc ttttcttctg aaatatttga aaccactgac ctacactgct catttagaca   2820

ttggtgtatc acttttctaa catttttgca ttacaataat cttattatgt aattcactta   2880

ttcctgtatc cggcatctac tggatataca tggttttact tttt                    2924
```

<210> SEQ ID NO 17
<211> LENGTH: 660
<212> TYPE: PRT
<213> ORGANISM: Oryza sativa

<400> SEQUENCE: 17

```
Met Gly Ser Ser Ser Leu Leu Leu Phe Pro Ser Ser Ser Ser Ser Ala
1               5                   10                  15

Thr His Ser Ser Tyr Ser Pro Ser Ser Ser Ser His Ala Ile Thr Ser
            20                  25                  30

Leu Leu Pro Pro Leu Pro Ser Asp His His Leu Leu Leu Tyr Leu Asp
        35                  40                  45

His Gln Glu Gln His His Leu Ala Ala Ala Met Val Arg Lys Arg Pro
    50                  55                  60

Ala Ser Asp Met Asp Leu Pro Pro Pro Arg Arg His Val Thr Gly Asp
65                  70                  75                  80

Leu Ser Asp Val Thr Ala Ala Ala Ala Gly Ala Pro Thr Leu Ser Ala
                85                  90                  95

Ser Ala Gln Leu Pro Ala Leu Pro Thr Gln Leu Pro Ala Phe His His
            100                 105                 110

Thr Asp Met Asp Leu Ala Ala Pro Ala Pro Pro Ala Pro Gln Gln Val
        115                 120                 125

Ala Ala Gly Glu Gly Gly Pro Pro Ser Thr Ala Trp Val Asp Gly Ile
    130                 135                 140

Ile Arg Asp Ile Ile Ala Ser Ser Gly Ala Ala Val Ser Val Ala Gln
145                 150                 155                 160

Leu Ile His Asn Val Arg Glu Ile Ile Arg Pro Cys Asn Pro Asp Leu
                165                 170                 175

Ala Ser Ile Leu Glu Leu Arg Leu Arg Ser Leu Leu Asn Ser Asp Pro
            180                 185                 190

Ala Pro Pro Pro Pro Pro Pro Ser His Pro Ala Leu Leu Pro Pro Asp
        195                 200                 205

Ala Thr Ala Pro Pro Pro Pro Pro Thr Ser Val Ala Ala Leu Pro Pro
```

```
    210                 215                 220

Pro Pro Pro Ala Gln Pro Asp Lys Arg Arg Arg Glu Pro Gln Cys Gln
225                 230                 235                 240

Glu Gln Glu Pro Asn Gln Pro Gln Ser Pro Lys Pro Pro Thr Ala Glu
                245                 250                 255

Glu Thr Ala Ala Ala Ala Ala Ala Ala Ala Ala Ala Ala Ala Ala Ala
            260                 265                 270

Ala Lys Glu Arg Lys Glu Glu Gln Arg Arg Lys Gln Arg Asp Glu Glu
        275                 280                 285

Gly Leu His Leu Leu Thr Leu Leu Leu Gln Cys Ala Glu Ser Val Asn
    290                 295                 300

Ala Asp Asn Leu Asp Glu Ala His Arg Ala Leu Leu Glu Ile Ala Glu
305                 310                 315                 320

Leu Ala Thr Pro Phe Gly Thr Ser Thr Gln Arg Val Ala Ala Tyr Phe
                325                 330                 335

Ala Glu Ala Met Ser Ala Arg Leu Val Ser Ser Cys Leu Gly Leu Tyr
            340                 345                 350

Ala Pro Leu Pro Ser Pro Ser Pro Ala Gly Ala Arg Val His Gly Arg
        355                 360                 365

Val Ala Ala Ala Phe Gln Val Phe Asn Gly Ile Ser Pro Phe Val Lys
    370                 375                 380

Phe Ser His Phe Thr Ala Asn Gln Ala Ile Gln Glu Ala Phe Glu Arg
385                 390                 395                 400

Glu Glu Arg Val His Ile Ile Asp Leu Asp Ile Met Gln Gly Leu Gln
                405                 410                 415

Trp Pro Gly Leu Phe His Ile Leu Ala Ser Arg Pro Gly Gly Pro Pro
            420                 425                 430

Arg Val Arg Leu Thr Gly Leu Gly Ala Ser Met Glu Ala Leu Glu Ala
        435                 440                 445

Thr Gly Lys Arg Leu Ser Asp Phe Ala Asp Thr Leu Gly Leu Pro Phe
    450                 455                 460

Glu Phe Cys Pro Val Ala Asp Lys Ala Gly Asn Leu Asp Pro Glu Lys
465                 470                 475                 480

Leu Gly Val Thr Arg Arg Glu Ala Val Ala Val His Trp Leu Arg His
                485                 490                 495

Ser Leu Tyr Asp Val Thr Gly Ser Asp Ser Asn Thr Leu Trp Leu Ile
            500                 505                 510

Gln Arg Leu Ala Pro Lys Val Val Thr Met Val Glu Gln Asp Leu Ser
        515                 520                 525

His Ser Gly Ser Phe Leu Ala Arg Phe Val Glu Ala Ile His Tyr Tyr
    530                 535                 540

Ser Ala Leu Phe Asp Ser Leu Asp Ala Ser Tyr Ser Glu Asp Ser Pro
545                 550                 555                 560

Glu Arg His Val Val Glu Gln Gln Leu Leu Ser Arg Glu Ile Arg Asn
                565                 570                 575

Val Leu Ala Val Gly Gly Pro Ala Arg Thr Gly Asp Val Lys Phe Gly
            580                 585                 590

Ser Trp Arg Glu Lys Leu Ala Gln Ser Gly Phe Arg Val Ser Ser Leu
        595                 600                 605

Ala Gly Ser Ala Ala Ala Gln Ala Ala Leu Leu Leu Gly Met Phe Pro
    610                 615                 620

Ser Asp Gly Tyr Thr Leu Ile Glu Glu Asn Gly Ala Leu Lys Leu Gly
625                 630                 635                 640
```

```
Trp Lys Asp Leu Cys Leu Leu Thr Ala Ser Ala Trp Arg Pro Ile Gln
                645                 650                 655

Ala Ser Gly Arg
            660


<210> SEQ ID NO 18
<211> LENGTH: 2474
<212> TYPE: DNA
<213> ORGANISM: Oryza sativa

<400> SEQUENCE: 18

tgctaacctc tccttcttgg tctcctcctc tcggcctctt cctctttact ccccccttcgc     60

gccatcgcct cgcttgcgcc gcgccaaatt ccataaaaat tccacccaac acaagcgtta    120

ggcctcccgc gcacgcccgt ccgctcgcca tgcccacggc ctcttcccct tggcgtttgt    180

agatgggctc ctcctccctc ctcctcttcc cctcctcttc ctcctccgcc acccactcct    240

cttattctcc ctcctcctcc tctcatgcca tcacctcctt gctgcctcct ctcccctccg    300

accaccatct cctcctctac ctagaccacc aagaacaaca ccacctcgcc gccgccatgg    360

tccgcaagcg ccccgcctcc gacatggacc tgccaccgcc gcgccgccat gtcaccggcg    420

acctgtccga tgtcacggcc gccgcggcgg gcgcgccgac gttgtctgcc agcgcgcagc    480

tccccgcgct gcccacgcag ctcccggcgt tccaccacac ggacatggac ctcgccgcgc    540

ccgcgccgcc ggcgccgcag caggtggcgg cgggtgaggg tgggccgccc agcacggctt    600

gggtggatgg catcatccgt gacatcatcg ccagcagcgg cgccgcggtc tccgtcgcgc    660

agctcatcca caacgtgcgt gagatcatcc ggccatgtaa ccccgacctc gcgtccatcc    720

tcgagctccg cctccgctct ctcctcaact ccgaccccgc gccgccgccg ccgccgccgt    780

cgcatcctgc tctcctccct cccgacgcca cggcgccacc gccaccaccc acgtcggtcg    840

ccgcgctccc tccccctccg ccagcgcagc ccgacaagcg gcgtcgcgag cctcagtgtc    900

aggagcagga gcccaaccag ccgcagtcgc cgaagccccc caccgcggag gaaaccgccg    960

ccgccgccgc ggccgccgca gcggcggctg ccgcggccgc caaggagcgt aaggaggagc   1020

agcggcggaa gcagcgcgac gaggagggcc tccacttgct gacgctgctg ctccagtgcg   1080

cggagtcggt gaacgcggac aacctggacg aggcgcaccg cgcgctgctg gagatcgcgg   1140

agctcgccac gccgttcggc acctcgacgc agcgcgtggc ggcctacttc gcggaggcca   1200

tgtcggcgcg gctggtgagc tcgtgcctgg ggctgtacgc gccgctcccg agcccgtccc   1260

cggcgggcgc gcgggtccac gggcgcgtgg cggcggcgtt ccaggtgttc aacgggatca   1320

gcccgttcgt gaagttctcg cacttcacgg cgaaccaggc gatccaggag gcgttcgaga   1380

gggaggagag ggtgcacatc atcgacctgg acatcatgca ggggctccaa tggccggggc   1440

tgttccacat cctggcgtcg cggccggggg ggccgcccga ggtgaggctg accgggctgg   1500

gggcgtccat ggaggcgctg gaggcgacgg ggaagaggct gtcggacttc gcggacacgc   1560

tgggattgcc gttcgagttc tgcccggtgg ctgacaaggc cgggaatctg gacccggaga   1620

agctgggcgt cacgcgccgc gaggccgtcg ccgtccactg gctgcgccac tccctctacg   1680

atgtcaccgg ctccgactcc aacacgctct ggctcatcca gaggttggcg ccaaaggttg   1740

taacaatggt ggagcaggat ctgagccact caggctcctt cctggcacgt tttgtggagg   1800

ccatccacta ctattcggca ctgttcgact cgcttgatgc gagttacagc gaggatagcc   1860

cggagcggca tgtcgtggag caacaactct tgtcgcggga gatccgcaat gtgctagccg   1920
```

```
tgggcggtcc agcacgcacc ggcgatgtta agtttgggag ctggcgcgaa aagcttgcgc   1980

agtcgggctt ccgtgtgtcg tcgcttgctg gaagcgctgc tgctcaggct gcactgctgc   2040

ttgggatgtt cccttccgat ggatacacgc ttattgagga gaatggcgct ctgaagctcg   2100

gatggaagga tctgtgcctt ctcactgcct ctgcttggcg cccaattcag gcttcgggac   2160

gttagtattg agggggaatt tatagagctg aagtatcact tgatcttact taggtgcaat   2220

tacctagtcc ttttgcttct tttagctgct caatttggtc aattctgaga aaagaaaaat   2280

aaaaaaaaat tctgatcact aattttcaga tctccacaca gtggtagtta ctaatgtgca   2340

acttagcttt agcttttatt ctgttcatgc tccagttaac cattctgtcc aatttagttt   2400

attttgcaat tttgtagtgc ttaatccttg ctgacattgt tttgggggaa cacgcaaaag   2460

gatccttact gaca                                                     2474


<210> SEQ ID NO 19
<211> LENGTH: 602
<212> TYPE: PRT
<213> ORGANISM: Oryza sativa

<400> SEQUENCE: 19

Met Asp Thr Leu Phe Arg Leu Val Ser Leu Gln Ala Ala Ser Glu Gln
1               5                   10                  15

Gln Gln Gln Gln Gln Gln Ser Ala Ser Tyr Asn Ser Arg Ser Thr Thr
            20                  25                  30

Ser Ser Gly Ser Arg Ser Ser Ser His Gln Thr Asn Ala Ser Tyr Ser
        35                  40                  45

Tyr Tyr His His Ser Ser Asn Ser Gly Gly Gly Gly Gly Gly Gly Gly
    50                  55                  60

Gly Tyr Tyr Tyr Gly Gly Gln Gln Pro Pro Pro Ser Gln Tyr Tyr Tyr
65                  70                  75                  80

Leu Glu Pro Tyr Gln Glu Glu Cys Gly Asn Ala Pro His His Gln Leu
                85                  90                  95

Tyr Met Asp Glu Asp Phe Ser Ser Ser Ser Ser Ser Arg His Phe His
            100                 105                 110

His Gly Ala Arg Val Gln Gln Gln Gln Pro Pro Ala Ser Ser Thr Pro
        115                 120                 125

Thr Gly Thr Ala Pro Thr Pro Pro Leu Ser Thr Ser Ser Thr Ala Ala
    130                 135                 140

Gly Ala Gly His Gly Leu Phe Glu Ala Ala Asp Leu Ser Phe Pro Pro
145                 150                 155                 160

Asp Leu Asn Leu Asp Phe Ser Ser Pro Ala Ser Ser Ser Gly Gly Gly
                165                 170                 175

Thr Ala Ser Ser Gly Ala Val Gly Gly Gly Gly Gly Gly Arg Trp Ala
            180                 185                 190

Ser Gln Leu Leu Leu Glu Cys Ala Arg Ser Val Ala Ala Arg Asp Ser
        195                 200                 205

Gln Arg Val Gln Gln Leu Met Trp Met Leu Asn Glu Leu Ala Ser Pro
    210                 215                 220

Tyr Gly Asp Val Glu Gln Lys Leu Ala Ser Tyr Phe Leu Gln Gly Leu
225                 230                 235                 240

Phe Ala Arg Leu Thr Ala Ser Gly Pro Arg Thr Leu Arg Thr Leu Ala
                245                 250                 255

Ala Ala Ser Asp Arg Asn Thr Ser Phe Asp Ser Thr Arg Arg Thr Ala
            260                 265                 270
```

```
Leu Arg Phe Gln Glu Leu Ser Pro Trp Ser Ser Phe Gly His Val Ala
        275                 280                 285

Ala Asn Gly Ala Ile Leu Glu Ser Phe Leu Glu Val Ala Ala Ala Ala
    290                 295                 300

Ser Ser Glu Thr Gln Arg Phe His Ile Leu Asp Leu Ser Asn Thr Phe
305                 310                 315                 320

Cys Thr Gln Trp Pro Thr Leu Leu Glu Ala Leu Ala Thr Arg Ser Ala
                325                 330                 335

Asp Glu Thr Pro His Leu Ser Ile Thr Thr Val Val Ser Ala Ala Pro
            340                 345                 350

Ser Ala Pro Thr Ala Ala Val Gln Arg Val Met Arg Glu Ile Gly Gln
        355                 360                 365

Arg Met Glu Lys Phe Ala Arg Leu Met Gly Val Pro Phe Arg Phe Arg
    370                 375                 380

Ala Val His His Ser Gly Asp Leu Ala Glu Leu Asp Leu Asp Ala Leu
385                 390                 395                 400

Asp Leu Arg Glu Gly Gly Ala Thr Thr Ala Leu Ala Val Asn Cys Val
                405                 410                 415

Asn Ser Leu Arg Gly Val Val Pro Gly Arg Ala Arg Arg Arg Asp Ala
            420                 425                 430

Phe Ala Ala Ser Leu Arg Arg Leu Asp Pro Arg Val Val Thr Val Val
        435                 440                 445

Glu Glu Glu Ala Asp Leu Val Ala Ser Asp Pro Asp Ala Ser Ser Ala
    450                 455                 460

Thr Glu Glu Gly Gly Asp Thr Glu Ala Ala Phe Leu Lys Val Phe Gly
465                 470                 475                 480

Glu Gly Leu Arg Phe Phe Ser Ala Tyr Met Asp Ser Leu Glu Glu Ser
                485                 490                 495

Phe Pro Lys Thr Ser Asn Glu Arg Leu Ala Leu Glu Arg Gly Ala Gly
            500                 505                 510

Arg Ala Ile Val Asp Leu Val Ser Cys Pro Ala Ser Glu Ser Met Glu
        515                 520                 525

Arg Arg Glu Thr Ala Ala Ser Trp Ala Arg Arg Met Arg Ser Ala Gly
    530                 535                 540

Phe Ser Pro Val Ala Phe Ser Glu Asp Val Ala Asp Asp Val Arg Ser
545                 550                 555                 560

Leu Leu Arg Arg Tyr Arg Glu Gly Trp Ser Met Arg Glu Ala Gly Thr
                565                 570                 575

Asp Asp Ser Ala Ala Gly Ala Gly Val Phe Leu Ala Trp Lys Glu Gln
            580                 585                 590

Pro Leu Val Trp Ala Ser Ala Trp Arg Pro
        595                 600
```

<210> SEQ ID NO 20
<211> LENGTH: 2729
<212> TYPE: DNA
<213> ORGANISM: Oryza sativa

<400> SEQUENCE: 20

```
aaaaggcgcc cacacccact gccgctgcct gctgctgctg cccccggtaa atttaaagaa     60

cccctccaat cagagcgagg catcatcgat ccccctccct ctcatcctct ccctctccac    120

cctcctctcc ttctctcatc gatccggcca aaagctactc aaatgttatc gatctcacca    180

aaagagaagc aaagagaaag agagcatcaa aagcacaaac accaagccac tcaccacacc    240
```

```
tcgcaattta catggctcct actaggttgt gtagctgcta ctagctagct cagctcggct    300
cggctcggct cgccattaaa atccccttgt taccgcgcgt tgtttggttg taccgcgcca    360
tatgttgccg cctcctcctc gtcgccgttg cttagatgga tacgctgttt aggttggtta    420
gcctccaagc cgcctccgag cagcagcagc agcagcagca gtcggcgtcc tacaactcga    480
ggagcacgac gtcgagcggg tccaggtcgt cgtcgcacca gacgaacgcg tcctacagct    540
actaccacca cagcagcaac agcggcggcg gcggcggagg cggcggaggg tactactacg    600
gcggccagca gccgccgccg tcgcagtact actacctgga gccgtaccaa gaagaatgcg    660
gcaacgcccc acaccaccag ctttacatgg atgaagactt ctcctcctcg tcgtcgtcga    720
ggcacttcca ccacggcgcg cgggtgcagc agcagcagcc gccggcgtcg tccacgccca    780
cggggacggc gccgacgccg ccgctgtcga cctcgtccac cgcggcgggc gccgggcacg    840
gcctgttcga ggcggcggac ctgtcgttcc cgccggacct caacctcgac ttctcgtccc    900
cggcgtcgtc gtccggcggc gggacagcgt cgtcgggcgc ggttgggggc ggcggcggcg    960
ggaggtgggc tagccagctg ctgctggagt gcgcgcggtc ggtggccgcc cgcgacagcc   1020
agcgcgtgca gcagctcatg tggatgctca acgagctcgc gtcgccgtac ggcgacgtgg   1080
agcagaagct ggcttcctac ttcttgcagg ggctgttcgc tcggctcacg gcgtccgggc   1140
cgcgcacgct gcgcacgctc gccgcggcgt ccgaccggaa cacgtcgttc gactcgacgc   1200
ggcgcacggc gctgcggttc caggagctca gcccctggtc ctcgtttggg cacgtcgccg   1260
ccaatggcgc catcctcgag tccttcctgg aggtcgccgc cgcggcgtcg tcggagacgc   1320
agcggttcca catcctcgac ctgagcaaca cgttctgcac gcagtggccg acgctgctgg   1380
aggcgctggc cacgcggtcc gccgacgaga cgccgcacct ctcgatcacc accgtggtgt   1440
ccgccgcgcc gtccgcgccc acggcggcgg tgcagcgcgt catgcgggag atcgggcagc   1500
gcatggagaa gttcgcgcgg ctcatgggcg tgcccttccg cttccgcgcc gtgcaccact   1560
ccggggacct cgcggagctc gacctcgacg cgctcgacct ccgcgagggc ggcgccacca   1620
ccgcgctcgc cgtcaactgc gtcaactcgc tgcgcggcgt ggttcccggc agggcccgcc   1680
ggcgcgacgc gttcgcggcg tcgctccgcc ggctggaccc gcgggtcgtc accgtcgtcg   1740
aggaggaggc ggacctggtg gcgtccgatc ccgacgcgtc gtcggcgacg gaggaaggcg   1800
gcgacacgga ggcggcgttc ctcaaggtgt tcggcgaggg cttgcgcttc ttctcggcgt   1860
acatggattc gctcgaggag agcttcccca agacgagcaa cgagaggctg gcattggaga   1920
ggggagcagg gcgcgccatc gtcgacttgg tctcgtgccc ggcgtcggag tcgatggagc   1980
ggcgggagac ggcggcgtcg tgggcgcggc gcatgcggtc ggccgggttc tctccggtgg   2040
cattcagcga ggacgtcgcc gacgacgtgc gatcgctgct gcgccggtac agggaagggt   2100
ggtcgatgcg cgaggccggc acggacgact cggcggccgg agccggcgtc ttcctcgcgt   2160
ggaaggagca gcctctggtg tgggcaagcg cgtggcggcc atgatcggat cgtcgtgatc   2220
gatggatcaa agctcaccgg tgagtggaac agcatggaag aaaagagctc catagctaag   2280
caagcacgca tgcatatcca ccatgcatgg ggtaagctag caagctctct cgtgtgtgtc   2340
acgatcgaca ttaatggcgg ctcacacaaa ggcatgtagg gttttgaaac agcgtaggaa   2400
gctacagaaa tggatcacgt acgtacgtac acattgggtt gcagcgatcg aggagggaga   2460
tgatagtttt agttcctaga tttgcatcca tttttattca tcgatcgcca acaagttctt   2520
ggcgagaaga tgattttgat ttgcttgctt ccatcttctt gtttattttt ccccctttcg   2580
tttgtgtttc ttcttaattt gtaagggtta acgacatttt tcttcactct ggagaaattt   2640
```

```
tacgtgcatg gtttttatca tgcgtacctg catcgatctg atcataccta tatatattca   2700

tctagctagt agctagcatc ttgcaaaca                                     2729


<210> SEQ ID NO 21
<211> LENGTH: 603
<212> TYPE: PRT
<213> ORGANISM: Oryza sativa

<400> SEQUENCE: 21

Met Asp Thr Leu Phe Arg Leu Val Ser Leu His His His His His His
1               5                   10                  15

Gln His Ala Ala Ser Pro Ser Pro Pro Asp Gln Pro His Lys Ser Tyr
            20                  25                  30

Pro Ser Ser Arg Gly Ser Thr Ser Ser Pro Ser Ser His His Thr His
        35                  40                  45

Asn His Thr Tyr Tyr His His Ser His Ser His Tyr Asn Asn Asn Ser
    50                  55                  60

Asn Thr Asn Tyr Tyr Tyr Gln Gly Gly Gly Gly Gly Gly Gly Gly Tyr
65                  70                  75                  80

Tyr Tyr Ala Glu Glu Gln Gln Pro Ala Ala Tyr Leu Glu Glu Cys Gly
                85                  90                  95

Asn Gly His Gln Phe Tyr Met Asp Glu Asp Phe Ser Ser Ser Ser Ser
            100                 105                 110

Ser Arg Gln Phe His Ser Gly Thr Gly Ala Pro Ser Ser Ala Pro Val
        115                 120                 125

Pro Pro Pro Pro Ser Ala Thr Thr Ser Ser Ala Gly Gly His Gly Leu
    130                 135                 140

Phe Glu Ala Ala Asp Phe Ser Phe Pro Gln Val Asp Ile Ser Leu Asp
145                 150                 155                 160

Phe Gly Gly Ser Pro Ala Val Pro Ser Ser Ser Gly Ala Gly Ala Gly
                165                 170                 175

Ala Gly Ala Ala Pro Ser Ser Ser Gly Arg Trp Ala Ala Gln Leu Leu
            180                 185                 190

Met Glu Cys Ala Arg Ala Val Ala Gly Arg Asp Ser Gln Arg Val Gln
        195                 200                 205

Gln Leu Met Trp Met Leu Asn Glu Leu Ala Ser Pro Tyr Gly Asp Val
    210                 215                 220

Asp Gln Lys Leu Ala Ser Tyr Phe Leu Gln Gly Leu Phe Ala Arg Leu
225                 230                 235                 240

Thr Thr Ser Gly Pro Arg Thr Leu Arg Thr Leu Ala Thr Ala Ser Asp
                245                 250                 255

Arg Asn Ala Ser Phe Asp Ser Thr Arg Arg Thr Ala Leu Lys Phe Gln
            260                 265                 270

Glu Leu Ser Pro Trp Thr Pro Phe Gly His Val Ala Ala Asn Gly Ala
        275                 280                 285

Ile Leu Glu Ser Phe Leu Glu Ala Ala Ala Ala Gly Ala Ala Ala Ser
    290                 295                 300

Ser Ser Ser Ser Ser Ser Ser Ser Thr Pro Pro Thr Arg Leu His Ile
305                 310                 315                 320

Leu Asp Leu Ser Asn Thr Phe Cys Thr Gln Trp Pro Thr Leu Leu Glu
                325                 330                 335

Ala Leu Ala Thr Arg Ser Ser Asp Asp Thr Pro His Leu Ser Ile Thr
            340                 345                 350
```

```
Thr Val Val Pro Thr Ala Ala Pro Ser Ala Ala Ala Gln Arg Val Met
        355                 360                 365

Arg Glu Ile Gly Gln Arg Leu Glu Lys Phe Ala Arg Leu Met Gly Val
    370                 375                 380

Pro Phe Ser Phe Arg Ala Val His His Ser Gly Asp Leu Ala Asp Leu
385                 390                 395                 400

Asp Leu Ala Ala Leu Asp Leu Arg Glu Gly Gly Ala Thr Ala Ala Leu
                405                 410                 415

Ala Val Asn Cys Val Asn Ala Leu Arg Gly Val Ala Arg Gly Arg Asp
            420                 425                 430

Ala Phe Val Ala Ser Leu Arg Arg Leu Glu Pro Arg Val Val Thr Val
        435                 440                 445

Val Glu Glu Glu Ala Asp Leu Ala Ala Pro Glu Ala Asp Ala Ser Ser
    450                 455                 460

Glu Ala Asp Thr Asp Ala Ala Phe Val Lys Val Phe Gly Glu Gly Leu
465                 470                 475                 480

Arg Phe Phe Ser Ala Tyr Met Asp Ser Leu Glu Glu Ser Phe Pro Lys
                485                 490                 495

Thr Ser Asn Glu Arg Leu Ser Leu Glu Arg Ala Val Gly Arg Ala Ile
            500                 505                 510

Val Asp Leu Val Ser Cys Pro Ala Ser Gln Ser Ala Glu Arg Arg Glu
        515                 520                 525

Thr Ala Ala Ser Trp Ala Arg Arg Met Arg Ser Ala Gly Phe Ser Pro
    530                 535                 540

Ala Ala Phe Ser Glu Asp Val Ala Asp Asp Val Arg Ser Leu Leu Arg
545                 550                 555                 560

Arg Tyr Lys Glu Gly Trp Ser Met Arg Asp Ala Gly Gly Ala Thr Asp
                565                 570                 575

Asp Ala Ala Gly Ala Ala Ala Ala Gly Ala Phe Leu Ala Trp Lys Glu
            580                 585                 590

Gln Pro Val Val Trp Ala Ser Ala Trp Lys Pro
        595                 600
```

<210> SEQ ID NO 22
<211> LENGTH: 2475
<212> TYPE: DNA
<213> ORGANISM: Oryza sativa

<400> SEQUENCE: 22

```
cacaactagc tagtttagat ccccttttgca tccatcgatg atcagttgtt gcaggacagt     60

gtagtgaggt gagaaagatt gttgtagtag ctgctgtgct gtatggtggt agccagtgag    120

tagctactac actgcactgc agtttgcacc ccggccatat gttggctact actactgcag    180

gtgtcttagg tctagatgga taccctcttc aggttggtta gcctccacca ccatcaccac    240

caccagcacg cggcctcacc gtcgccgccg gaccagccgc acaagtcgta cccctcctcg    300

cgagggagca ccagctcccc ctcctcccac cacacccaca accacaccta ctaccaccac    360

tcccactccc actacaacaa taatagcaac accaactact attaccaggg tggtggaggc    420

ggcggcggag ggtactacta cgcggaggag cagcagccgg cggcgtacct agaagaatgc    480

ggcaacggcc accagtttta catggatgaa gacttctcct cctcgtcttc ctcccgccag    540

ttccactcgg gaacgggcgc gccgtcgtcg gcgccggtgc ctcctcctcc gtcggcgacg    600

acgtcgtccg cgggcgggca cgggctgttt gaggcggcgg acttctcgtt cccgcaggtt    660

gatatcagcc tcgacttcgg cggctctccg gccgttccgt cgtcgtccgg tgctggcgcc    720
```

```
ggcgccgggg cagcgccgtc gtcgtcgggg aggtgggcgg cgcagctgct gatggagtgc    780

gcgcgcgcgg tggcggggcg cgacagccag cgcgtgcagc agctcatgtg gatgctcaac    840

gagctggcct cgccgtacgg cgacgtcgac cagaagctgg cctcctactt cctgcagggc    900

ctcttcgcgc ggctcaccac ctccggcccg cgcacgctgc ggacgctcgc caccgcgtcg    960

gaccggaacg cgtcgttcga ctccacgcgc cgcacggcgc tcaagttcca ggagctcagc   1020

ccgtggacgc cgttcgggca cgtcgccgcc aacggcgcca tactcgagtc gttcctggag   1080

gccgcggcgg cgggcgccgc cgcctcctcc tcctcgtcgt cttcatcgtc gacgccgccg   1140

acgcggctgc acatcctcga cctgagcaac acgttctgca cgcagtggcc gaccctcctg   1200

gaggcgctgg ccacccggtc ctcggacgac acgccgcacc tgtccatcac caccgtcgtg   1260

cccacggcgg cgccgtcggc ggccgcgcag cgcgtgatgc gggagatcgg gcagcgcctc   1320

gagaagttcg cgcggctgat gggcgtcccg ttcagcttcc gcgccgtgca ccactcgggg   1380

gacctggccg acctcgacct cgccgcgctg gacctccgcg agggcggcgc caccgccgcg   1440

ctcgccgtca actgcgtaaa cgcgctgcgc ggggtcgcgc gggggcgcga cgcgttcgtg   1500

gcgtcgctcc ggcgcctgga gccgcgcgtg gtcaccgtcg tggaggagga ggccgacctg   1560

gcggcgccgg aggcggacgc gtcgtcggag gccgacaccg acgccgcgtt cgtcaaggtg   1620

ttcggcgagg gcctccgctt cttctcggcg tacatggact cgctggagga gagcttcccc   1680

aagacaagca acgagaggct gtcactggag agggcggtcg gccgtgccat cgtcgacctc   1740

gtgtcatgcc cggcctccca gtccgccgag cgccgggaga ccgccgcgtc gtgggcgcgg   1800

cgcatgcggt cggcggggtt ctcgccggcg gcattcagcg aggacgtcgc cgacgacgtg   1860

cggtcgcttc tccggcggta caaggagggc tggtcgatgc gggacgccgg cggtgccacg   1920

gacgacgccg ccggcgccgc tgctgccgga gcgttccttg cgtggaagga gcagcctgtc   1980

gtgtgggcga gcgcgtggaa gccatgagat cgatcgatcc aacaagtcca aatccgccat   2040

tgctgcaaat catcgagcct gcgatgcatc gtgcatgcaa tacacaatat ggatcatgca   2100

tatcgcacgt gcgggttgaa tgggaagagg aagcagcgcg cgcgtgtacg tacttagggt   2160

ttttcagcca gcaacgtacg tgtgtagtag ggagaggagg tagcaaaaca catcagatgg   2220

attaagttaa tcaatcacca gttattacta gaaaattaat ttggaggaat taattggcat   2280

ttattgttct tgcattacat gtttattaat tattagatgc ttcctctgat tattaacttt   2340

gtgaattcag gtgtgttcaa tttaatttta gctagctagt agatatatcg atcctcaggt   2400

gatttatttg tagatctgaa tattccatga cttgtatagg agctactaat agtttatttg   2460

ttttaccggt taaca                                                    2475
```

<210> SEQ ID NO 23
<211> LENGTH: 668
<212> TYPE: PRT
<213> ORGANISM: Zea mays

<400> SEQUENCE: 23

```
Met Pro Pro Pro Pro Pro Pro Pro Pro Leu Thr Pro Tyr Cys Arg Arg
1               5                   10                  15

Cys Pro Pro Pro His Leu Pro Pro Pro Pro Pro Ser Ser Pro Asn His
            20                  25                  30

Phe Leu Leu His Tyr Leu His Gln Leu Asp His Gln Glu Ala Ala Ala
        35                  40                  45

Ala Ala Met Val Arg Lys Arg Pro Ala Ser Asp Met Asp Leu Pro Pro
```

```
    50                  55                  60

Pro Arg Arg His Val Thr Gly Asp Leu Ser Asp Val Thr Ala Ala Ala
65                  70                  75                  80

Ala Ala Gly Val Gly Gly Ser Gly Ala Pro Ser Ser Ala Ser Ala Gln
                85                  90                  95

Leu Pro Ala Leu Pro Thr Gln Leu His Gln Leu Pro Pro Ala Phe Gln
            100                 105                 110

His His Ala Pro Glu Val Asp Val Pro Ala His Pro Ala Pro Ala Ala
        115                 120                 125

His Ala Gln Ala Gly Gly Glu Ala Thr Ala Ser Thr Thr Ala Trp Val
    130                 135                 140

Asp Gly Ile Ile Arg Asp Ile Ile Gly Ser Ser Gly Gly Ala Ala Val
145                 150                 155                 160

Ser Ile Thr Gln Leu Ile His Asn Val Arg Glu Ile Ile His Pro Cys
                165                 170                 175

Asn Pro Gly Leu Ala Ser Leu Leu Glu Leu Arg Leu Arg Ser Leu Leu
            180                 185                 190

Ala Ala Asp Pro Ala Pro Leu Pro Pro Pro Pro Gln Pro Gln Gln His
        195                 200                 205

Ala Leu Leu His Gly Ala Pro Ala Ala Ala Pro Ala Gly Leu Thr Leu
    210                 215                 220

Pro Pro Pro Pro Pro Leu Pro Asp Lys Arg Arg His Glu His Pro Pro
225                 230                 235                 240

Pro Cys Gln Gln Gln Gln Gln Glu Glu Pro His Pro Ala Pro Gln Ser
                245                 250                 255

Pro Lys Ala Pro Thr Ala Glu Glu Thr Ala Ala Ala Ala Ala Ala Ala
            260                 265                 270

Gln Ala Ala Ala Ala Ala Ala Ala Lys Glu Arg Lys Glu Glu Gln Arg
        275                 280                 285

Arg Lys Gln Arg Asp Glu Glu Gly Leu His Leu Leu Thr Leu Leu Leu
    290                 295                 300

Gln Cys Ala Glu Ala Val Asn Ala Asp Asn Leu Asp Asp Ala His Gln
305                 310                 315                 320

Thr Leu Leu Glu Ile Ala Glu Leu Ala Thr Pro Phe Gly Thr Ser Thr
                325                 330                 335

Gln Arg Val Ala Ala Tyr Phe Ala Glu Ala Met Ser Ala Arg Leu Val
            340                 345                 350

Ser Ser Cys Leu Gly Leu Tyr Ala Pro Leu Pro Pro Gly Ser Pro Ala
        355                 360                 365

Ala Ala Arg Leu His Gly Arg Val Ala Ala Ala Phe Gln Val Phe Asn
    370                 375                 380

Gly Ile Ser Pro Phe Val Lys Phe Ser His Phe Thr Ala Asn Gln Ala
385                 390                 395                 400

Ile Gln Glu Ala Phe Glu Arg Glu Glu Arg Val His Ile Ile Asp Leu
                405                 410                 415

Asp Ile Met Gln Gly Leu Gln Trp Pro Gly Leu Phe His Ile Leu Ala
            420                 425                 430

Ser Arg Pro Gly Gly Pro Pro Arg Val Arg Leu Thr Gly Leu Gly Ala
        435                 440                 445

Ser Met Glu Ala Leu Glu Ala Thr Gly Lys Arg Leu Ser Asp Phe Ala
    450                 455                 460

Asp Thr Leu Gly Leu Pro Phe Glu Phe Cys Ala Val Ala Glu Lys Ala
465                 470                 475                 480
```

```
Gly Asn Val Asp Pro Glu Lys Leu Gly Val Thr Arg Arg Glu Ala Val
                485                 490                 495

Ala Val His Trp Leu His His Ser Leu Tyr Asp Val Thr Gly Ser Asp
            500                 505                 510

Ser Asn Thr Leu Trp Leu Ile Gln Arg Leu Ala Pro Lys Val Val Thr
        515                 520                 525

Met Val Glu Gln Asp Leu Ser His Ser Gly Ser Phe Leu Ala Arg Phe
    530                 535                 540

Val Glu Ala Ile His Tyr Tyr Ser Ala Leu Phe Asp Ser Leu Asp Ala
545                 550                 555                 560

Ser Tyr Gly Glu Asp Ser Pro Glu Arg His Val Val Glu Gln Gln Leu
                565                 570                 575

Leu Ser Arg Glu Ile Arg Asn Val Leu Ala Val Gly Gly Pro Ala Arg
            580                 585                 590

Thr Gly Asp Val Lys Phe Gly Ser Trp Arg Glu Lys Leu Ala Gln Ser
        595                 600                 605

Gly Phe Arg Ala Ala Ser Leu Ala Gly Ser Ala Ala Ala Gln Ala Ser
    610                 615                 620

Leu Leu Leu Gly Met Phe Pro Ser Asp Gly Tyr Thr Leu Val Glu Glu
625                 630                 635                 640

Asn Gly Ala Leu Lys Leu Gly Trp Lys Asp Leu Cys Leu Leu Thr Ala
                645                 650                 655

Ser Ala Trp Arg Pro Ile Gln Val Pro Pro Cys Arg
            660                 665
```

<210> SEQ ID NO 24
<211> LENGTH: 2449
<212> TYPE: DNA
<213> ORGANISM: Zea mays

<400> SEQUENCE: 24

```
ctcttgtgct tacgcccttg ttcgtctccc ggcggcgtct tcctctttac tcctcccgct      60

ctccctccct cgcaccgtcc gtctgctagc tcagcctact cactccactc aactcacccc     120

caactccact ccgctcccga gcccggactg actgactgac tgtggtggtg gtggtgcatc     180

agcagcccgc gcggcgccaa aacacgcaaa ctgctccctc cctcactcac ccctatcccc     240

cgcgctgggt cgcccgatcg ccatgcgcgc ggcggcttcc tcttggcgtt tctagatggg     300

ctcctcctcc tccctcctct tctcctcgtc ctcctccgcc gcatccaccg ccccccactc     360

ctttccccac tctcatgcca ccgccaccgc ctccgcctcc tctcactcct tattgccgcc     420

gctgccctcc cccacacctc cctccgcctc ctccttcttc cccaaaccac ttcctcctcc     480

actacctcca tcagctagac caccaagaag ccgccgccgc cgccatggtc cgcaagcgcc     540

ccgcgtccga catggacctc ccgccgccgc gccgccacgt cacgggcgac ctctccgacg     600

tcacggcggc cgctgccgcc ggtgttggtg gtagtggcgc gccgtcctcc gccagcgcgc     660

agctgcccgc gctgcccacc cagctccacc agctgccccc cgcgttccag caccacgcgc     720

cggaggtgga cgtgcccgcg cacccggccc cggccgccca cgcgcaggcg ggcggcgagg     780

caaccgcgtc cacgaccgcg tgggtggacg gcatcatccg cgacatcatc gggagcagcg     840

gcggcgccgc ggtctccatc acgcagctca tccacaacgt ccgcgagatc atccacccct     900

gcaaccccgg cctcgcgtcg ctcctggagc tccgcctccg ctccctcctc gcagccgacc     960

cggccccact gccgccgccg ccgcagccgc agcagcatgc tctcctgcac ggcgctccgg    1020
```

```
ccgccgctcc cgcggggctg acgctccctc ccccgccacc gcttccggac aagcgccgcc   1080
acgagcatcc accgccgtgc cagcagcaac agcaggagga accgcatccg gcgccgcagt   1140
cgcccaaggc cccgaccgcg gaagagaccg cagcggcggc cgccgccgca caagcagcag   1200
ctgctgcggc cgccaaggag cggaaggagg agcagcggcg gaagcagcgc gacgaggagg   1260
gcctccacct gctgacgctg ctgctgcagt gcgccgaggc cgtgaacgcg gacaacctgg   1320
acgacgcgca ccagacgctg ctggagatcg cggagctagc gacgccgttc ggcacctcga   1380
cgcagcgcgt ggccgcctac ttcgcggagg ccatgtcggc gcggctcgtc agctcctgcc   1440
tgggcctgta cgcgccgctg ccgccgggct cccccgccgc ggcgcgcctc cacggccgcg   1500
tcgccgccgc gttccaggtg ttcaacggca tcagcccctt cgtcaagttc tcgcacttca   1560
ccgccaacca ggccatccag gaggcgttcg agcgggagga gcgcgtgcac atcatcgacc   1620
tcgacatcat gcaggggctg cagtggccgg ggctcttcca catccttgcc tcccgccccg   1680
ggggcccgcc cagggtgagg ctcaccggcc tcggggcgtc catggaggcg ctcgaggcca   1740
cggggaagcg cctctccgat ttcgccgaca cgctcggcct gcccttcgag ttctgcgccg   1800
tcgccgagaa ggccggcaat gttgacccgg agaagctagg ggtcacgagg cgggaggccg   1860
tcgccgtcca ctggctgcac cactcgctct acgacgtcac tggctccgac tccaacacgc   1920
tctggctcat ccaaaggctg gcccccaagg tggtgacaat ggtggagcag gacctgagcc   1980
actcgggctc cttcctggcg cgcttcgtgg aggccatcca ctactactcg gcgctgttcg   2040
actcgctgga cgcgagctac ggcgaggaca gccccgagcg gcacgtcgtg gagcagcagc   2100
tgctgtcgcg ggagatccgc aacgtgctgg ccgtgggcgg gccggcccgc accggcgacg   2160
tcaagttcgg cagctggcgc gagaagctgg cgcagtccgg gttccgcgcc gcctcgctcg   2220
ccggcagcgc cgcggcgcag gcgtccctgc tgctcggcat gttcccctcc gacgggtaca   2280
cgctggtgga ggagaacggc gcgctgaagc tcgggtggaa ggacctctgc ctgctcaccg   2340
cgtcggcctg gcgccccatc caggtgccgc cgtgccgttg atgagacctc tgcctgctcc   2400
tgcttgcgtt gagaggccgc cactccactt gttttgcatc tgtagctgc              2449
```

```
<210> SEQ ID NO 25
<211> LENGTH: 678
<212> TYPE: PRT
<213> ORGANISM: Zea mays

<400> SEQUENCE: 25

Met Gly Ser Ser Ser Val Leu Leu Phe Pro Ser Ser Ser Ser Ala Ala
1               5                   10                  15

Pro Ser Ala Pro His Ser Phe Pro His Ser His Ala Thr Ala Ile Ala
            20                  25                  30

Ser Ser His Ser Leu Leu Pro Pro Leu Pro Cys Ser Asn Pro Pro Pro
        35                  40                  45

Pro Leu Ser Ser Gln Asp His Val Leu Ile His Tyr Ile His Gln Leu
    50                  55                  60

Asp Glu Gln Glu Ala Ala Thr Met Val Arg Lys Arg Pro Ala Pro Asp
65                  70                  75                  80

Met Asp Leu Pro Pro Pro Arg Arg His Val Thr Gly Asp Leu Ser Asp
                85                  90                  95

Val Thr Ala Ala Ala Ala Ala Gly Gly Gly Pro Gly Ala Pro Ser Ser
            100                 105                 110

Ala Ser Ala Gln Leu Pro Ala Leu Pro Thr Gln Leu His Gln Leu Pro
        115                 120                 125
```

```
Pro Ala Phe Gln His His Ala Ala Glu Val Asp Val Pro Pro Gln Pro
    130                 135                 140

His Pro Pro Ala His Ser Gln Ala Gly Gly Glu Ala Pro Ala Ser Thr
145                 150                 155                 160

Thr Ala Trp Val Asp Gly Ile Ile Arg Asp Ile Ile Gly Ser Ser Gly
                165                 170                 175

Gly Gly Ala Val Ser Ile Thr Gln Leu Ile His Asn Val Arg Glu Ile
            180                 185                 190

Ile His Pro Cys Asn Pro Gly Leu Ala Ser Leu Leu Glu Leu Arg Leu
        195                 200                 205

Arg Ser Leu Leu Ala Ala Asp Pro Ala Pro Leu Pro Gln Gln Gln Arg
    210                 215                 220

Ala Leu Leu His Gly Ala Pro Ala Ala Ala Ala Gly Leu Ala Leu Pro
225                 230                 235                 240

Leu Pro Pro Pro Leu Pro Asp Lys Arg Arg His Glu Pro Ala Pro Arg
                245                 250                 255

Cys Gln Gln Gln Gln Gln Glu Glu Pro His Pro Ala Pro Gln Ser Pro
            260                 265                 270

Lys Val Pro Thr Ala Glu Glu Thr Ala Ala Ala Ser Ala Ala Ala Ala
        275                 280                 285

Lys Glu Arg Lys Glu Val Gln Arg Arg Lys Gln Arg Asp Glu Glu Gly
    290                 295                 300

Leu His Leu Leu Thr Leu Leu Leu Gln Cys Ala Glu Ala Val Asn Ala
305                 310                 315                 320

Asp Asn Leu Asp Asp Ala His Gln Thr Leu Leu Glu Ile Ala Glu Leu
                325                 330                 335

Ala Thr Pro Phe Gly Thr Ser Thr Gln Arg Val Ala Ala Tyr Phe Ala
            340                 345                 350

Glu Ala Met Ser Ala Arg Val Val Ser Ser Cys Leu Gly Leu Tyr Ala
        355                 360                 365

Pro Leu Pro Pro Gly Ser Pro Ala Ala Ala Arg Leu His Gly Arg Val
    370                 375                 380

Ala Ala Ala Phe Gln Val Phe Asn Gly Ile Ser Pro Phe Val Lys Phe
385                 390                 395                 400

Ser His Phe Thr Ala Asn Gln Ala Ile Gln Glu Ala Phe Glu Arg Glu
                405                 410                 415

Glu Arg Val His Ile Ile Asp Leu Asp Ile Met Gln Gly Leu Gln Trp
            420                 425                 430

Pro Gly Leu Phe His Ile Leu Ala Ser Arg Pro Gly Gly Pro Pro Arg
        435                 440                 445

Val Arg Leu Thr Gly Leu Gly Ala Ser Met Glu Ala Leu Glu Ala Thr
    450                 455                 460

Gly Lys Arg Leu Ser Asp Phe Ala Asp Thr Leu Gly Leu Pro Phe Glu
465                 470                 475                 480

Phe Cys Ala Val Asp Glu Lys Val Gly Asn Val Asp Pro Gln Lys Leu
                485                 490                 495

Gly Val Thr Arg Arg Glu Ala Val Ala Val His Trp Leu His His Ser
            500                 505                 510

Leu Tyr Asp Val Thr Gly Ser Asp Ser Asn Thr Leu Arg Leu Ile Gln
        515                 520                 525

Arg Leu Ala Pro Lys Val Val Thr Met Val Glu Gln Asp Leu Ser Gln
    530                 535                 540
```

```
Ser Gly Ser Phe Leu Ala Arg Phe Val Asp Ala Ile His Tyr Tyr Ser
545                 550                 555                 560

Ala Leu Phe Asp Ser Leu Asp Ala Ser Tyr Gly Glu Asp Ser Pro Glu
                565                 570                 575

Arg His Val Val Glu Gln Gln Leu Leu Ala Arg Glu Ile Arg Asn Val
            580                 585                 590

Leu Ala Val Gly Gly Pro Ala Arg Ala Gly Ala Gly Gly Ala Arg Phe
        595                 600                 605

Gly Ser Trp Arg Glu Glu Leu Ala Arg Ser Gly Phe Arg Ala Ala Ser
    610                 615                 620

Leu Ala Gly Gly Ala Ala Ala Gln Ala Ser Leu Leu Leu Gly Met Phe
625                 630                 635                 640

Pro Ser Asp Gly Tyr Thr Leu Val Glu Glu Lys Gly Ala Leu Arg Leu
                645                 650                 655

Gly Trp Lys Asp Leu Cys Leu Leu Thr Ala Ser Ala Trp Arg Pro Val
            660                 665                 670

Gln Thr Pro Pro Cys Arg
        675


<210> SEQ ID NO 26
<211> LENGTH: 2727
<212> TYPE: DNA
<213> ORGANISM: Zea mays

<400> SEQUENCE: 26

cttgttcctg tctcggcggc gtcttcttct ttactcccgg tttccctccc tcgtcgccgt     60

ccatctgcta tctcaggcgc tcagccaact gactccactg acccccaact ccgctgccga    120

ctgccgagcc cggactggct gactgggtgc gcgcggcgcg gtggtgcatc agcagcccgc    180

gcggcgccaa aacacacaaa ctgctccctc cctccatcct atccccccac gctgggtcgc    240

ccgatctgca tgcgcacggc ggcttcctct tggcgtttct agatgggctc ctcctccgtc    300

ctcctcttcc cctcgtcctc ctccgccgca ccctccgccc cccattcctt tccccactct    360

catgccaccg ccatcgcctc ctcccactcc ttattgccgc cgctgccctg ctccaacccc    420

ccgcctcctc tttcctcgca agaccacgtc ctcatccact acatccacca gctagacgag    480

caagaagccg ccaccatggt ccgcaagcgc cccgcgcccg acatggacct cccgccgccg    540

cgccgtcacg tcacgggcga cctctccgac gttacggccg cagccgccgc cggtggtggt    600

cctggcgcgc cgtcctccgc tagcgcgcag ctacccgcgc tgcccaccca gctccaccag    660

ctgccccccg cgttccagca ccacgcggcg gaggtggacg tgcccccgca accgcacccg    720

ccggcccatt cgcaggcggg cggcgaggcg cccgcgtcca cgaccgcgtg ggtggacggc    780

atcatccgcg acatcatcgg gagcagcggc ggcggcgctg tctccatcac gcagctcatc    840

cacaacgtcc gcgagatcat ccacccctgc aacccaggcc tcgcgtccct cctcgagctc    900

cgcctccgtt cccttctcgc cgccgacccc gccccgctgc cgcagcagca gcgcgctctc    960

ctgcacggcg ctccggccgc cgccgcgggg ctggcgctcc ctctcccgcc accgcttcct   1020

gacaagcgcc gccacgagcc tgcgccgcgg tgccagcagc aacagcagga ggagccgcat   1080

ccggcgccgc agtcgcccaa ggtcccgacc gccgaggaga ccgccgcggc ctcggccgcc   1140

gcggccaagg agcggaagga ggtgcagcgg cggaagcagc gcgacgagga gggcctccac   1200

ctgctgacgc tgctgctgca gtgcgcggag gccgtgaacg cggacaacct cgacgacgcg   1260

caccagacgc tgctggagat cgcggagctg gccacgccgt tcggcacctc gacgcagcgc   1320
```

```
gtggccgcct acttcgccga ggccatgtcg gcgcgcgtcg tcagctcctg cctaggcctg   1380
tacgcgccgc tgccgccggg ctcccccgcc gcggcgcgcc tccacggccg cgtggccgcc   1440
gcgttccagg tgttcaacgg catcagcccc ttcgtcaagt tctcgcactt caccgccaac   1500
caggccatcc aggaggcgtt cgagcgggag gagcgcgtgc acatcatcga cctcgacatc   1560
atgcagggcc tgcagtggcc gggcctcttc cacatcctcg cctcccgccc cggcggcccg   1620
cccagggtca ggctcaccgg cctgggggcg tccatggagg cgctcgaggc gacggggaag   1680
cgcctctccg acttcgccga cacgctcggc ctgcccttcg agttctgcgc cgtcgacgag   1740
aaggtcggca acgttgaccc gcagaagctg ggcgtcacgc ggcgggaggc cgtcgccgtc   1800
cactggctgc accactcgct ttacgacgtg accggctccg actccaacac gctccggctc   1860
atccaaaggc tggcccccaa ggtggtgacg atggtggagc aggacctgag ccagtcgggg   1920
tcgttcctgg cgcgcttcgt ggacgccatc cactactact cggcgctgtt cgactcgctg   1980
gacgcgagct acggcgagga cagccccgag cggcacgtgg tggagcagca gctgctggcg   2040
cgggagatcc gcaacgtgct ggccgtgggc gggccggccc gcgccggcgc cggcggcgcc   2100
aggttcggca gctggcgcga agagctcgcg cggtctgggt tccgcgccgc ctcgctcgcc   2160
ggcggcgccg ccgcgcaggc gtcgctgctg ctcggcatgt tcccctccga cgggtacacg   2220
ctggtggagg agaagggcgc gctcaggctc gggtggaagg acctctgcct gctcaccgcg   2280
tcggcgtggc ggcccgtcca gacgccgccg tgccgttgag agctgaaatc gttgttggtt   2340
acccagccag tggtagatct tcttcgtact atactcctgc ttgagtttct tgtgccactt   2400
cttttgcatc tgtagctagc tagctggctg ctcgatttgg tcgtcagttc cgagatggga   2460
aaacgaaaac atctcttctc gtcactaatc gctagatcca ttcacagtga tagttactga   2520
tgtaagccta ctaattagtt taatggcaga tcaaccttgt ttagcctaat tagttacttg   2580
gtactactgt tctttatttg gtggagttcc accatttcat atgtgggcat gagctgaggt   2640
caaggctgtc tacaacagct attctatttt agctcgtatc atatcttcta ttttaattta   2700
aacgctgcat tctacagtat aaaacaa                                       2727
```

<210> SEQ ID NO 27
<211> LENGTH: 592
<212> TYPE: PRT
<213> ORGANISM: Zea mays

<400> SEQUENCE: 27

```
Met Asp Thr Leu Phe Arg Leu Val Ser Leu Gln Ala Ser Glu Gln Gln
1               5                   10                  15

Gln Gln Gln Ser Ala Ser Tyr Asn Ser Arg Ser Thr Thr Ser Ser Gly
            20                  25                  30

Ser Arg Ser Ser Ser His Gln Thr Asn Ala Ser Tyr Asn Tyr Tyr Tyr
        35                  40                  45

His Ser Asn Ser Ser Gly Gly Gly Gly Gly Gln Tyr Tyr Tyr Gly Gln
    50                  55                  60

Gln His Pro His Gln His Gln His Gln Gln Tyr Tyr Leu Glu Pro Tyr
65                  70                  75                  80

Gln Gln Glu Glu Cys Gly Asn Thr His His Leu Tyr Met Asp Glu Asp
                85                  90                  95

Phe Ser Ser Ser Ser Ser Ser Arg Gln His Phe His Ser His Gly Ala
            100                 105                 110

Val Val Gln Pro Pro Thr Ser Ser Thr Ala Thr Pro Thr Ala Pro Thr
        115                 120                 125
```

```
Pro Ser Leu Ser Thr Ser Ser Thr Ala Ala Gly Ala Ala His Ala Leu
    130                 135                 140

Phe Glu Ala Ala Asp Leu Ser Phe Pro Pro Asp Leu Asn Leu Asp Phe
145                 150                 155                 160

Ser Ser Pro Ala Ser Ser Ser Gly Gly Gly Ala Ala Ser Ser Ala Ala
                165                 170                 175

Val Gly Gly Gly Gly Gly Gly Arg Trp Ala Ser Gln Leu Leu Leu Glu
            180                 185                 190

Cys Ala Arg Ala Val Ala Gly Arg Asp Ser Gln Arg Val Gln Gln Leu
        195                 200                 205

Met Trp Met Leu Asn Glu Leu Ala Ser Pro Tyr Gly Asp Val Glu Gln
    210                 215                 220

Lys Leu Ala Ser Tyr Phe Leu Gln Gly Leu Phe Ala Arg Leu Thr Ala
225                 230                 235                 240

Ser Gly Pro Arg Thr Leu Arg Thr Leu Ala Ala Ala Ser Asp Arg Asn
                245                 250                 255

Thr Ser Phe Asp Ser Thr Arg Arg Thr Ala Leu Arg Phe Gln Glu Leu
            260                 265                 270

Ser Pro Trp Ser Ser Phe Gly His Val Ala Ala Asn Gly Ala Ile Leu
        275                 280                 285

Glu Ser Phe Leu Glu Ala Ala Ala Ala Ser Pro Glu Pro Gln Arg Leu
    290                 295                 300

His Ile Leu Asp Leu Ser Asn Thr Phe Cys Thr Gln Trp Pro Thr Leu
305                 310                 315                 320

Leu Glu Ala Leu Ala Thr Arg Ser Ala Asp Asp Thr Pro His Leu Ser
                325                 330                 335

Ile Thr Thr Val Val Ser Ser Ala Pro Ser Ala Pro Thr Ala Ala Val
            340                 345                 350

Gln Arg Val Met Arg Glu Ile Gly Gln Arg Met Glu Lys Phe Ala Arg
        355                 360                 365

Leu Met Gly Val Pro Phe Ser Phe Arg Ala Val His His Ala Gly Asp
    370                 375                 380

Leu Ala Gly Leu Asp Leu Asp Ala Leu Asp Leu Arg Asp Gly Gly Ala
385                 390                 395                 400

Thr Thr Ala Leu Ala Ile Asn Cys Val Asn Ser Leu Arg Gly Val Val
                405                 410                 415

Pro Gly Gly Ala Arg Arg Arg Asp Ala Phe Ala Ala Ser Leu Arg Arg
            420                 425                 430

Leu Asp Pro Arg Val Val Thr Val Val Glu Glu Glu Ala Asp Leu Val
        435                 440                 445

Ala Phe Asp Pro Gly Ala Pro Glu Glu Ser Gly Asp Thr Glu Ala Ala
    450                 455                 460

Phe Leu Lys Val Phe Gly Glu Gly Leu Arg Phe Phe Ser Ala Tyr Met
465                 470                 475                 480

Asp Ser Leu Glu Glu Ser Phe Pro Lys Thr Ser Asn Glu Arg Leu Ala
                485                 490                 495

Leu Glu Arg Gly Ala Gly Arg Ala Ile Val Asp Leu Val Ser Cys Pro
            500                 505                 510

Ala Ser Glu Ser Met Glu Arg Arg Glu Thr Ala Ala Ser Trp Ala Arg
        515                 520                 525

Arg Met Arg Ser Ser Gly Phe Ser Pro Val Ala Phe Ser Glu Asp Val
    530                 535                 540
```

```
Ala Asp Asp Val Arg Ser Leu Leu Arg Arg Tyr Arg Glu Gly Trp Ser
545                 550                 555                 560

Met Arg Asp Ala Gly Leu Asp Asp Ser Ala Ala Gly Ala Gly Val Phe
                565                 570                 575

Leu Ala Trp Lys Glu Gln Pro Leu Val Trp Ala Ser Ala Trp Arg Pro
            580                 585                 590


<210> SEQ ID NO 28
<211> LENGTH: 2456
<212> TYPE: DNA
<213> ORGANISM: Zea mays

<400> SEQUENCE: 28

cgcgtaggta gccacactta gaattggatt gctgccactc acaattccct ctcatagcct     60

ggcatcgtag ctatagctgg ctagcttcct cctcctggct gctacccttc ccggttctca    120

ccgcgctgcc attaaaaacc cccttccttg ttaccacttc gaccttgagc aagcgcactc    180

ttcatgttgc cgcctcgccg cagtagcagc ttacatggat acgctgttta ggttggttag    240

ccttcaagcc tccgagcagc agcagcagca atcggcgtcc tacaactcga ggagcaccac    300

gtcgagcggc tccaggtcgt cgtcgcacca gaccaacgca tcctacaact actactacca    360

cagcaacagc agcggcggcg gcggcgggca gtactactac ggtcagcagc acccacacca    420

gcaccagcac cagcagtact acctggagcc gtaccagcaa gaagaatgcg gcaacaccca    480

ccacctttac atggatgaag acttctcctc ctcgtcctcg tcgaggcagc atttccactc    540

gcacggcgcg gtggtgcagc cgccgacgtc gtccacggcc acgcccacgg cgccgacgcc    600

ctcgctgtcc acgtcgtcca cggccgcggg ggcggcgcac gcgctgttcg aggcggccga    660

cctgtcgttc ccgcctgacc tcaacctcga cttctcgtcc ccggcctcgt cgtccggcgg    720

gggcgcggcc tcgtcggcgg cggtcggggg aggtggcggg ggaaggtggg cgagccagct    780

gctgctggag tgcgcgcgcg cggtggcggg ccgcgacagc cagcgcgtgc agcagctgat    840

gtggatgctc aacgagctgg cctcgccgta cggggacgtc gagcagaagc tggcgtccta    900

cttcctccag ggcgcttcg cgcgcctcac ggcgtccgga ccgcggacgc tgcgcacgct    960

cgctgcggcg tccgaccgga acacgtcctt cgactccacg cggcgcacgg cgctgcggtt   1020

ccaggagctc agcccgtggt cgtcgtttgg gcacgtggcc gccaacggcg ccatcctgga   1080

gtcgttcctg gaggccgccg cggcgtcgcc ggagccccag aggctccaca tcctcgacct   1140

cagcaacacg ttctgcacgc agtggcccac gctgctcgag gcgctcgcca cgcggtccgc   1200

cgacgacacg ccgcacctgt cgatcaccac ggtggtctcc tccgcgccgt ccgcgccgac   1260

ggccgccgtg cagcgcgtga tgcgggagat cgggcagcgg atggaaaagt tcgcgcggct   1320

gatgggcgtg cccttcagct tccgcgcagt gcaccacgcc ggggaccttg cggggctcga   1380

cctcgacgcg ctcgacctgc gcgacggcgg cgccaccacc gcgctcgcca tcaactgcgt   1440

caactcgctg cgcggcgtgg tgccgggcgg tgcgcggaga cgggacgcgt tcgccgcgtc   1500

cctccggcgt ctcgatccgc gggttgttac tgtcgtcgag gaggaggccg atctcgtggc   1560

ttttgacccc ggcgcgcccg aggaaagcgg cgacacggag gcagcgttcc tgaaggtgtt   1620

cggcgagggc ttgcggttct tctcggctta catggactcg ctggaagaga gcttccccaa   1680

gactagcaac gagaggctgg cgctggagag gggagccgga cgtgccattg tagacttggt   1740

ctcgtgcccg gcgtcggagt ccatggagcg gcgggagacg gcggcttcat gggcgcgccg   1800

catgcggtct tccggcttct ctccggtggc gttcagcgag gacgtcgccg acgacgtgcg   1860
```

```
gtcgttgctc cgtcggtatc gggaaggctg gtcgatgcgg gacgccggtt tagacgactc   1920

ggcagccgga gcaggcgtct tcctggcgtg gaaggaacag cctctcgtgt gggcgagcgc   1980

gtggaggcca tgatagagat ccccgtcgac gcaagatgca agctcggtga gtacgcgcgt   2040

acgtggaaca tcatgaacca caggagaagc aagggcgcca tccgccatac ctagccggcg   2100

cgtggatgca atgatccatg cagtggatcg ggcgcacgtg catgtgtatg gcgagctgaa   2160

tggcgcaacg catctagggt tttggagcag tggtagggat tgctagttca cgcacacatg   2220

gttgtatgca gcaaggtgat ccaggaggag gtatggtcga tggttttagg ttttagactt   2280

gcatctattt caaatttgga tcatcgatcg ccacaagctt ttggcgtgat gattccgatt   2340

ttcttgcttc tttttttttg tcacatttct ctgtgtttct tcatgtaatt caatgttaac   2400

aactttcttc cctctggagg gatttacgtg catggttttg tcatactttc tctcat       2456


<210> SEQ ID NO 29
<211> LENGTH: 586
<212> TYPE: PRT
<213> ORGANISM: Zea mays

<400> SEQUENCE: 29

Met Asp Thr Leu Phe Arg Ser Val Ser Leu Gln Ala Ser Glu Gln Gln
1               5                   10                  15

Gln Gln Gln Gln Ser Ala Ser Tyr Asn Ser Arg Ser Thr Thr Ser Ser
            20                  25                  30

Gly Ser Arg Ser Ser Ser His Gln Thr Asp Ala Ser Tyr Asn Tyr Tyr
        35                  40                  45

Tyr His Ser Asn Ser Gly Val Gly Gly Val Gly Gln Tyr Tyr Tyr Gly
    50                  55                  60

Gln Gln Asn Gln Gln Tyr Tyr Gln Glu Pro Tyr Gln Gln Glu Glu Cys
65                  70                  75                  80

Gly Asn Ala His Arg Leu Tyr Met Asp Glu Asp Phe Ser Ser Ser Ser
                85                  90                  95

Ser Ser Arg Gln His Phe His Ser His Gly Ala Ala Val Gln Pro Ala
            100                 105                 110

Thr Ser Ser Ala Val Thr Ala Thr Ala Pro Thr Pro Pro Leu Ser Thr
        115                 120                 125

Ser Ser Thr Ala Ala Gly Ala Ala His Ala Leu Phe Glu Ala Ala Asp
    130                 135                 140

Leu Ser Phe Pro Pro Asp Leu Asn Leu Asp Phe Ser Ser Pro Ala Ser
145                 150                 155                 160

Ser Ser Gly Gly Cys Val Ala Ser Ser Ala Ala Val Gly Gly Arg Trp
                165                 170                 175

Ala Ser Gln Leu Leu Leu Glu Cys Ala Arg Ala Val Ala Ala Arg Asp
            180                 185                 190

Ser Gln Arg Val Gln Gln Leu Met Trp Met Leu Asn Glu Leu Ala Ser
        195                 200                 205

Pro Tyr Gly Asp Val Glu Gln Lys Leu Ala Ser Tyr Phe Leu Gln Gly
    210                 215                 220

Leu Phe Ala Arg Leu Thr Ala Ser Gly Pro Gln Thr Leu Arg Thr Leu
225                 230                 235                 240

Ala Ala Ala Ser Asp Arg Asn Thr Ser Phe Asp Ser Thr Arg Arg Thr
                245                 250                 255

Ala Leu Arg Phe Gln Glu Leu Ser Pro Trp Ser Ser Phe Gly His Val
            260                 265                 270
```

```
Ala Ala Asn Gly Ala Ile Leu Glu Ser Phe Leu Glu Ala Ala Ala Ala
        275                 280                 285

Ser Ser Glu Pro Gln Arg Phe His Ile Leu Asp Leu Ser Asn Thr Phe
    290                 295                 300

Cys Thr Gln Trp Pro Thr Leu Leu Glu Ala Leu Ala Thr Arg Ser Thr
305                 310                 315                 320

Asp Asp Thr Pro His Leu Ser Ile Thr Thr Val Val Ser Ala Ala Pro
                325                 330                 335

Ser Ala Pro Thr Val Ala Val Gln Arg Arg Gln Arg Val Met Arg Glu
            340                 345                 350

Ile Gly Gln Arg Ile Glu Lys Phe Ala Arg Leu Met Gly Val Pro Phe
        355                 360                 365

Ser Phe Arg Ala Val His His Ala Gly Asp Leu Ala Glu Leu Asp Leu
    370                 375                 380

Asp Ala Leu Asp Leu Arg Asp Gly Gly Ala Thr Thr Ala Leu Ala Ile
385                 390                 395                 400

Asn Cys Leu Asn Ser Leu Arg Gly Val Val Pro Gly Gly Val Arg Arg
                405                 410                 415

Arg Asp Ala Phe Gly Ala Ser Leu Arg Arg Leu Asp Pro Arg Val Val
            420                 425                 430

Thr Val Val Glu Glu Glu Ala Asp Leu Val Ala Phe Asp Pro Asp Ala
        435                 440                 445

Ser Glu Glu Ser Gly Asp Thr Glu Ala Ala Phe Leu Lys Val Phe Gly
    450                 455                 460

Glu Gly Leu Arg Phe Phe Ser Ala Tyr Met Asp Ser Leu Glu Glu Ser
465                 470                 475                 480

Phe Pro Lys Thr Ser Asn Glu Arg Leu Ala Leu Glu Arg Gly Ala Gly
                485                 490                 495

Arg Ala Ile Val Asp Leu Val Ser Cys Pro Pro Ser Lys Ser Met Glu
            500                 505                 510

Arg Arg Glu Thr Ala Val Ser Trp Ala Arg Arg Met Arg Ser Ala Gly
        515                 520                 525

Phe Ser Pro Val Ala Phe Ser Glu Asp Val Ala Asp Asp Val Arg Ser
    530                 535                 540

Leu Leu Arg Arg Tyr Arg Glu Gly Trp Ser Met Arg Asp Thr Gly Leu
545                 550                 555                 560

Asp Asp Ser Ala Ala Gly Ala Gly Ile Phe Leu Ala Trp Lys Glu Gln
                565                 570                 575

Pro Leu Val Trp Ala Ser Ala Trp Arg Pro
            580                 585
```

<210> SEQ ID NO 30
<211> LENGTH: 2093
<212> TYPE: DNA
<213> ORGANISM: Zea mays

<400> SEQUENCE: 30

```
ctgctacatt tcccggttct cggttctcac cgcgctgcca ttaaaatccc ccttccttgc      60

taccacggca accttgagca agcgcacact tcatgttgcc gcctcgccgc cgtagcagct     120

tacatggata cgctgtttag gtcggttagc cttcaagcct ccgagcagca gcagcagcag     180

cagtcggcgt cctacaactc gagaagcacc acgtcgagcg gctccaggtc gtcgtcgcac     240

cagaccgacg catcctacaa ctactactac cacagcaaca gcggcgtcgg cggcgtcggg     300

cagtactact acggtcagca gaaccagcag tactaccagg agccatacca gcaagaagaa     360
```

```
tgcggcaacg cccaccgcct ttacatggat gaagacttct cctcctcgtc ttcgtcgagg    420
cagcacttcc actcgcacgg cgcggcggtg cagccggcga cgtcgtccgc ggtcacagca    480
acggcgccga cgcccccgct gtccacgtcg tccacggccg caggagcggc acacgcactg    540
ttcgaggcgg ccgacctgtc gttccccccct gacctcaacc tcgacttctc gtccccggcg    600
tcttcgtccg gcgggtgcgt ggcctcctcg gcggcggtcg ggggaagatg ggcgagccag    660
ctgctgctgg agtgcgcgcg cgcggtggcg gcccgcgaca gccagcgcgt gcagcagctg    720
atgtggatgc tcaacgagct ggcctcgccg tatggggacg tcgagcagaa gctggcgtcc    780
tacttcctcc aggggctctt cgcgcgcctc acggcgtccg gcccgcagac cctgcgcacg    840
ctcgcggcgg cgtccgaccg gaacacgtcc ttcgactcca cgcggcgcac ggcgctgcgg    900
ttccaggagc tcagcccgtg gtcgtcgttc gggcacgtgg ccgccaacgg cgccatcctg    960
gagtcgttcc tggaggccgc cgcggcgtcg tcggagccgc agaggttcca catcctcgac   1020
ctgagcaaca cgttctgcac gcagtggccc acgctgctcg aggcgctggc cacgcggtcc   1080
accgacgaca cgccgcactt atcgatcacc acggtggtct cggccgcgcc gtccgcgccg   1140
acggtcgccg tgcagcgccg ccagcgcgtg atgcgggaga tcggacagcg gatagaaaag   1200
ttcgcgcggc tgatgggtgt gcccttcagc ttccgcgccg tgcaccacgc cggagacctc   1260
gcggagctcg acctcgacgc gcttgacctg cgcgatggcg gcgccaccac cgcgctcgcc   1320
atcaactgcc tcaactcgct tcgcggtgtg gtgccgggcg gtgtccgaag aagggacgcg   1380
ttcggcgcgt cgctccggcg tctcgatcca agggtagtta ctgtcgtcga ggaggaggct   1440
gatctcgtgg cttttgaccc tgacgcatcc gaggaaagcg gcgacacgga ggcagcgttc   1500
ttgaaggtgt tcggcgaggg cttgcggttc ttctcggctt acatggactc gttggaagag   1560
agctttccca agactagcaa cgagaggctg gcactggaga ggggagccgg acgtgccatt   1620
gtggacttgg tctcgtgccc gccgtcgaag tccatggaac ggcgggagac ggcggtttca   1680
tgggcacgcc gcatgcggtc tgccggcttc tctccggtgg cgttcagcga ggacgttgcc   1740
gacgatgtgc ggtcgttgct ccgtcggtat cgggaaggct ggtcgatgcg ggacaccggt   1800
ttagacgact cggcagccgg agcaggcatc ttcctggcgt ggaaggaaca gcctctcgtg   1860
tgggcaagcg cgtggaggcc atgatagaga tccatgagct cgtcgacgcg caaatgcaag   1920
ctcggtgagt gcactacatg gaccgcaggc ccgcagccca taggagaagc cggcgtggat   1980
gcgtcgatcc gtgcattgga tcgcgcgcac gtgcatgtat gtatggcgag ttctctcctc   2040
ctctgctcgt cttgaaagct gaatggctca cgcgtgtagg gttttggagc agc          2093
```

```
<210> SEQ ID NO 31
<211> LENGTH: 630
<212> TYPE: PRT
<213> ORGANISM: Zea mays

<400> SEQUENCE: 31

Met Asp Thr Leu Phe Arg Leu Val Ser Leu His Gln His His Gln Gln
1               5                   10                  15

His His Gln Gln Ala Ala Ala Ala Ala Ala Ser Ser Ser Pro Asp Gln
            20                  25                  30

His His His His Gln Ser Pro Tyr Ser Ser Arg Ser Thr Ser Arg Ser
        35                  40                  45

Asn Asp Thr Ser Thr Gly Ser Arg Ser Ser Pro Ser Ser Tyr His Thr
    50                  55                  60
```

-continued

```
His Asn His His Tyr His Ser Ser His Pro His Ser His Tyr Ser Ser
65                  70                  75                  80

Ala Ser Tyr Tyr Tyr Asp Pro Ala Gly Ser Gly Ser Gly Ser Ala Gly
                85                  90                  95

Tyr Tyr Tyr Tyr Asp His His Gln Pro Pro Pro Pro Pro Pro Tyr Gln
            100                 105                 110

Glu Glu Cys Gly Asn Asp His Gly Phe Tyr Met Asp Glu Asp Phe Ser
        115                 120                 125

Ser Ser Ser Ser Ser Arg Ser Arg His Phe Gln Ser Ser Ser Arg Ala
    130                 135                 140

Pro Pro Ser Ser Ser Pro Thr Pro Pro His Ala Gln Pro Gln Pro Pro
145                 150                 155                 160

Pro Ala Ser Thr Ser Ser Gly Ala Gly Ala Gly Ala Leu Phe Glu Ala
                165                 170                 175

Ala Asp Phe Ser Phe Pro Gln Val Asp Ile Asp Leu Asp Phe Ser Ser
            180                 185                 190

Pro Ala Ser Ser Ser Gly Ala Ala Ala Ser Ser Ser Gly Gly Gly Gly
        195                 200                 205

Ala Gly Arg Trp Ala Ala Gln Leu Leu Leu Glu Cys Ala Arg Ala Val
    210                 215                 220

Ala Ala Arg Asp Ser Gln Arg Val Gln Gln Leu Met Trp Met Leu Asn
225                 230                 235                 240

Glu Leu Ala Ser Pro Tyr Gly Asp Val Asp Gln Lys Leu Ala Ser Tyr
                245                 250                 255

Phe Leu Gln Gly Leu Phe Ala Arg Leu Thr Thr Ser Gly Pro Arg Thr
            260                 265                 270

Leu Arg Thr Leu Ala Ala Ala Ser Asp Arg Asn Thr Ser Phe Asp Ser
        275                 280                 285

Thr Arg Arg Thr Ala Leu Arg Phe Gln Glu Leu Ser Pro Trp Ala Ser
    290                 295                 300

Phe Gly His Val Ala Ala Asn Gly Ala Ile Leu Glu Ser Phe Leu Asp
305                 310                 315                 320

Ala Ala Ala Ala Ala Ala Ala Ser Ser Ser Ser Ser Ser Gln His Pro
                325                 330                 335

Pro Arg Leu His Ile Leu Asp Leu Ser Asn Thr Phe Cys Thr Gln Trp
            340                 345                 350

Pro Thr Leu Leu Glu Ala Leu Ala Thr Arg Ser Ser Asp Asp Thr Pro
        355                 360                 365

His Leu Ser Ile Thr Thr Val Val Pro Thr Ala Gly Val Pro Ser Ser
    370                 375                 380

Ala Ala Ala Gln Arg Val Met Arg Glu Ile Ala Gln Arg Leu Glu Lys
385                 390                 395                 400

Phe Ala Arg Leu Met Gly Val Pro Phe Ser Phe Arg Ala Val His His
                405                 410                 415

Ala Gly Asp Leu Ala Gly Leu Asp Leu Asp Gly Leu Gly Leu Gly Leu
            420                 425                 430

Arg Glu Gly Gly Ala Ala Thr Ala Leu Ala Ile Asn Cys Val Asn Ala
        435                 440                 445

Leu Arg Gly Val Ala Pro Gly Gly Ala Arg Arg Arg Asp Ala Phe Val
    450                 455                 460

Ala Ser Leu Arg Arg Leu Glu Pro Arg Val Val Thr Val Val Glu Glu
465                 470                 475                 480

Asp Ala Asp Leu Val Ala Ala Ser Glu Pro Ser Ser Ser Ser Ala Gly
```

```
                485                 490                 495

Glu Ala Asp Ala Glu Ala Ala Phe Met Lys Val Phe Thr Glu Gly Leu
            500                 505                 510

Arg Phe Phe Ser Ala Tyr Met Asp Ser Leu Glu Glu Ser Phe Pro Lys
        515                 520                 525

Ala Ser Asn Glu Arg Leu Ala Leu Glu Arg Ala Ala Gly Arg Ala Ile
    530                 535                 540

Val Asp Leu Val Ala Cys Pro Ala Ser Glu Ser Val Glu Arg Arg Glu
545                 550                 555                 560

Thr Gly Ala Ser Trp Ala Arg Arg Met Arg Ser Ala Gly Phe Ser Pro
                565                 570                 575

Val Ala Phe Ser Asp Asp Val Ala Asp Asp Met Arg Ser Leu Leu Arg
            580                 585                 590

Arg Tyr Arg Glu Gly Trp Thr Leu Arg Glu Pro Gly Ala Asp Asp Gly
        595                 600                 605

Ala Ala Ala Gly Val Phe Leu Ala Trp Lys Glu Gln Pro Val Val Trp
    610                 615                 620

Thr Ser Ala Trp Arg Pro
625                 630
```

<210> SEQ ID NO 32
<211> LENGTH: 2221
<212> TYPE: DNA
<213> ORGANISM: Zea mays

<400> SEQUENCE: 32

```
gcacaagccc atttgcaccg tatgcatgtt gttgttgttg ctggctccgg tgggttagat      60

ggacacactg tttagattgg ttagcctcca ccaacatcac caacaacatc accaacaggc     120

agcagcagca gcagcgtcct cctcgccgga ccagcaccac caccaccagt ccccctacag     180

ctcccgctcc acgtcccgca gcaacgacac ctccaccggc tcacgctcct ctccctcctc     240

ctaccacacc cacaaccacc actaccactc ttcccacccc cactcccact acagcagcgc     300

cagctactac tacgaccccg caggcagcgg cagcggcagc gccggctact actactacga     360

ccaccaccag ccgccgccgc cgccgccgta ccaagaagaa tgcggcaacg accacggctt     420

ttacatggat gaagacttct cctcctcgtc ctcgtcccgg tcccgccact tccagtcgtc     480

ctcgcgcgcc ccgccctcgt cgtctcccac gccaccgcac gcccagcccc agcccccgcc     540

cgcgtccacg tcgtccggcg ccggcgccgg cgccctgttc gaggcggccg acttctcgtt     600

cccgcaggtg gacatcgacc tcgacttcag ctcccccgcc tcgtcctccg gcgccgccgc     660

ctcgtcctcg ggcggcggcg gcgccgggag gtgggccgcg cagctgctgc tggagtgcgc     720

gcgcgccgtg gccgcccgcg acagccagcg cgtgcagcag ctcatgtgga tgctcaacga     780

gctggcgtcg ccgtacgggg acgtggacca gaagctggcg tcctacttcc tccagggcct     840

cttcgcgcgc ctcaccacct ccggcccgcg cacgctgcgc acgctcgccg ccgcgtcgga     900

ccggaacacg tccttcgact ccacgcgccg caccgcgctc aggttccagg agctcagccc     960

ctgggcgtcc ttcggccacg tggccgccaa cggggccata ctcgagtcgt tcctggacgc    1020

ggcggcggcg gcggccgcct cctcgtcctc ctcctcgcag cacccgccgc ggctgcacat    1080

cctggacctc agcaacacct tctgcacgca gtggccgacg ctgctggagg cgctggccac    1140

gaggtcgtcg gacgacacgc cccacctgtc catcaccacc gtggtgccca ccgccggcgt    1200

gccgtcgtcc gcggccgcgc agcgcgtgat gcgggagatc gcgcagcgcc tcgagaagtt    1260
```

```
cgcgcgcctc atgggcgtgc ccttcagctt ccgcgccgtg caccacgcgg gggacctcgc   1320

ggggctcgac ctcgacggcc tcggcctcgg cctccgcgag ggcggcgccg ccacggcgct   1380

cgcgatcaac tgcgtcaacg cgctgcgcgg ggtcgcgccg gggggcgcgc ggcggcgcga   1440

cgcgttcgtc gcctcgctcc gccgcctcga gccgcgcgtg gtcaccgtcg tggaggagga   1500

cgccgacctc gtggcggcgt ccgagccgtc gtcgtcgtcg gccggggaag ccgacgcgga   1560

ggcggcgttc atgaaggtgt tcaccgaggg cctccgcttc ttctcggcgt acatggactc   1620

cctcgaggag agcttcccca aggcgagcaa cgagaggctc gccctggaga gggcggcggg   1680

gcgtgccatt gtggacctcg tggcctgccc ggcgtccgaa tccgtcgaga ggcgggagac   1740

gggggcgtcg tgggcgcgcc gcatgcggtc tgccggcttc tctcccgtgg cattcagcga   1800

cgacgtggcc gacgacatgc ggtcgctgct gcgccggtac cgggagggat ggaccttgcg   1860

cgagccaggc gcggacgacg gcgcggcggc cggggtgttc ctcgcgtgga aggagcagcc   1920

cgtggtgtgg acgagcgcgt ggaggccatg atcatgaacc agatcgtgag ctccatcgta   1980

tcggcagcag aacaagatga tgcgtgctcc atgcatgcat gtgtatgctc tagctagcat   2040

gcagcgtagg gcatgcattg cttcgctgga tcgtgtgagt ggcggcaacg acgcgcacgg   2100

ggatcaggta gcgtgctttt tttccaatta taaatcggat gatggatctt agcactgttt   2160

accacattac ttaggttttt tcgagaggcg taagtatgta gggatcggag aagctgaaga   2220

t                                                                   2221
```

<210> SEQ ID NO 33
<211> LENGTH: 452
<212> TYPE: PRT
<213> ORGANISM: Zea mays

<400> SEQUENCE: 33

```
Met Leu Gln Gly Val Leu Ser Arg Ala Pro Ala Thr Asp Ala Ala Ala
1               5                   10                  15

Ala Met Lys Ala Lys Arg Ala Gly Ala Ser Pro Gly Glu Glu Glu Glu
            20                  25                  30

Gly Asp Gly Arg Ser Ala Arg Gly Lys Arg Gln Gln Leu Leu Gly Leu
        35                  40                  45

Gly Pro Ala Thr Ala Leu Ala Ser Ala Ala Ala Ala Glu Glu Gly Pro
    50                  55                  60

Glu Thr Arg Gly Leu Arg Leu Leu Ser Leu Leu Leu Arg Cys Ala Glu
65                  70                  75                  80

Ala Val Ala Met Asp Gln Leu Thr Glu Ala Arg Glu Leu Leu Pro Glu
                85                  90                  95

Ile Ala Glu Leu Ala Ser Pro Phe Gly Ser Ser Pro Glu Arg Val Ala
            100                 105                 110

Ala Tyr Phe Gly Asp Ala Leu Cys Ala Arg Val Leu Ser Ser Tyr Leu
        115                 120                 125

Gly Ala Tyr Ser Pro Leu Ala Leu Arg Pro Leu Ala Ala Ala Gln Ser
    130                 135                 140

Arg Arg Val Ala Val Ala Phe Gln Ala Tyr Asn Ala Leu Ser Pro Leu
145                 150                 155                 160

Val Lys Phe Ser His Phe Thr Ala Asn Gln Ala Ile Leu Gln Ala Leu
                165                 170                 175

Asp Gly Glu Asp Cys Leu His Val Ile Asp Leu Asp Ile Met Gln Gly
            180                 185                 190

Leu Gln Trp Pro Gly Leu Phe His Ile Leu Ala Ser Arg Pro Arg Lys
```

```
        195                 200                 205

Pro Arg Ser Leu Arg Ile Thr Gly Leu Gly Ala Ser Leu Asp Val Leu
    210                 215                 220

Glu Ala Thr Gly Arg Arg Leu Ala Asp Phe Ala Ala Ser Leu Gly Leu
225                 230                 235                 240

Pro Phe Glu Phe Arg Pro Ile Glu Gly Lys Ile Gly His Val Ala Asp
                245                 250                 255

Ala Ala Ala Leu Leu Gly Ser Arg Gln Arg Arg Arg Asp Asp Glu Ala
            260                 265                 270

Thr Val Val His Trp Met His His Cys Leu Tyr Asp Val Thr Gly Ser
        275                 280                 285

Asp Val Gly Thr Val Arg Leu Leu Arg Ser Leu Arg Pro Lys Leu Ile
    290                 295                 300

Thr Ile Val Glu Gln Asp Leu Gly His Ser Gly Asp Phe Leu Gly Arg
305                 310                 315                 320

Phe Val Glu Ala Leu His Tyr Tyr Ser Ala Leu Phe Asp Ala Leu Gly
                325                 330                 335

Asp Gly Ala Gly Ala Ala Glu Glu Glu Ser Ala Glu Arg Tyr Ala Val
            340                 345                 350

Glu Arg Gln Leu Leu Gly Ala Glu Ile Arg Asn Ile Val Ala Val Gly
        355                 360                 365

Gly Pro Lys Arg Thr Gly Glu Val Arg Val Glu Arg Trp Ser His Glu
    370                 375                 380

Leu Arg His Ala Gly Phe Arg Pro Val Ser Leu Ala Gly Ser Pro Ala
385                 390                 395                 400

Ala Gln Ala Arg Leu Leu Leu Gly Met Tyr Pro Trp Lys Gly Tyr Thr
                405                 410                 415

Leu Val Glu Glu Asp Ala Cys Leu Lys Leu Gly Trp Lys Asp Leu Ser
            420                 425                 430

Leu Leu Thr Ala Ser Ala Trp Glu Pro Ala Asp Asp Ala Ala Ala Ser
        435                 440                 445

Ala Pro Thr Gly
    450


<210> SEQ ID NO 34
<211> LENGTH: 1772
<212> TYPE: DNA
<213> ORGANISM: Zea mays

<400> SEQUENCE: 34

aacggcgaga ccccgtgcta ggctctccag tcaccagcgt tatcagctga gccgtcccct      60

ctcgcttcgc ttggcttacc acgcatcagt gatcaccgag tcactgacgc cttgcccgaa     120

accaaattat tgaccgacaa cgcgatgctc caaggggtgc tgtcccgcgc gcccgccacc     180

gacgctgcgg cagcaatgaa ggccaagcgg gcgggcgcgt cccccggcga agaggaggaa     240

ggggacggcc gttctgcgcg gggga agcga cagcagctgc tcgggcttgg ccccgccacc     300

gctttggcgt cggcggcggc ggcggaggaa gggccggaga cgcgaggcct gcggctgctc     360

agcctgctgc tgcggtgcgc ggaggcggtg gccatggacc agctgacgga ggcgcgggag     420

ctgctccccg agatcgcgga gctggcgtcg ccgttcgggt cgtccccgga gcgcgtggcg     480

gcctacttcg gtgacgcgct gtgcgcgcgc gtgctcagct cgtacctggg cgcctactcg     540

ccgctcgcgc tccgcccgct ggcggccgcg cagagccgcc gcgtggcggt ggcgttccag     600

gcgtacaacg cgctgtcgcc gctcgtcaag ttctcgcact tcacggccaa ccaggccatc     660
```

```
ctgcaggcgc tcgacggcga ggactgcctc cacgtgatcg acctggacat catgcagggc    720
ctgcagtggc cggggctctt ccacatcctc gcgtcccgcc cgcgcaagcc gcggtcgctc    780
cggatcaccg ggctcggcgc gtcgctcgac gtcctcgagg ccactggccg ccgcctcgcc    840
gacttcgcgg cctcgctcgg cctcccgttc gagttccgac ccatcgaggg gaagatcggg    900
cacgtcgccg acgccgcggc gctcctcggc tcgcgccagc ggcggcggga tgacgaggcc    960
accgtggtgc actggatgca ccactgcctc tatgacgtga cggggtcgga cgtgggcacg   1020
gtgcggctgc tccggagcct gcgcccgaag ctgatcacca tcgtggaaca ggacctgggc   1080
cacagcggcg atttcctggg ccggttcgtg gaggcgctgc actactactc ggcgctgttc   1140
gacgcgctgg gagacggcgc cggcgcggcc gaggaggagt ccgccgagcg gtacgcggtt   1200
gagcgacagc tcctgggcgc ggagatacgc aacatcgtgg ccgtaggggg gcccaagcgg   1260
acaggggagg tgcgcgtgga gcggtggagc cacgagctgc ggcacgccgg gttccggcca   1320
gtgtccctgg ccgggagccc tgccgcgcag gccaggctgc tcctcggcat gtatccgtgg   1380
aaggggtaca cgctggtgga ggaggacgcg tgccttaagc tgggctggaa ggacctctcc   1440
ctgctcaccg cgtcggcgtg ggagccggcg gacgacgctg ccgcttctgc gcccaccggt   1500
taacgagtac aagacaagat ttttgcagca ggtagattat gattttggaa ttcaatttca   1560
tgcctgctgc cagcctcgca gccatccttg gtggactggt cgtcttctct tcttgctgcc   1620
gccctgctcg tgtaggcgtc ttgtgagttt gtttttgtga tataatcgta taggcttcgg   1680
cattcctttc gttctcctac ctccagtatc aattaccaaa tcaactttgg attttgaata   1740
tttagtatac tgcagctttg agtcagaaaa aa                                 1772
```

```
<210> SEQ ID NO 35
<211> LENGTH: 262
<212> TYPE: PRT
<213> ORGANISM: Brachypodium distachyon

<400> SEQUENCE: 35

Cys Arg Gly Cys Asn Gly Arg Gly Cys Ser Thr Ser Ser Leu Leu Ala
1               5                   10                  15

Pro Ala Gly Arg Pro Gly Ser Gly Ser Pro Gly Ser Glu Leu Pro Trp
            20                  25                  30

Thr Arg Ser Arg Pro Pro Gly Arg Gly Cys Arg Ile Ser Arg Thr Arg
        35                  40                  45

Leu Gly Cys Arg Ser Ser Ser Val Leu Ser Leu Ile Arg Pro Gly Thr
    50                  55                  60

Leu Thr Arg Arg Ser Cys Leu Met Ala Ala Ala Ala Ala Glu Glu Gly
65                  70                  75                  80

Trp Glu Gly Gly Ala Arg Leu Leu Pro Cys Ile Gly Ser Thr Thr Arg
                85                  90                  95

Ser Thr Thr Ser Pro Gly Thr Thr Pro Thr Arg Trp Gly Ser Ser Arg
            100                 105                 110

Gly Trp Arg Arg Arg Trp Gln Trp Trp Ser Arg Thr Ala Thr Arg Ala
        115                 120                 125

Pro Ser Trp Arg Gly Ser Trp Lys Pro Ser Thr Thr Thr Arg Arg Ser
    130                 135                 140

Ser Thr Arg Trp Thr Pro Ala Thr Ala Arg Thr Val Pro Ser Gly Thr
145                 150                 155                 160

Ser Trp Ser Ser Ser Cys Tyr Arg Gly Arg Ser Ala Thr Cys Ser Pro
                165                 170                 175
```

```
Ser Ala Gly Arg Pro Ala Pro Ala Thr Pro Ser Ser Ser Ala Ala Gly
            180                 185                 190

Ala Thr Ser Trp Pro Ala Pro Gly Ser Ala Arg Arg Arg Ser Pro Ala
        195                 200                 205

Ala Pro Arg Arg Arg Arg Arg Cys Cys Ser Ala Cys Ser Pro Pro Thr
    210                 215                 220

Ala Thr Arg Ser Ser Arg Arg Thr Ala Arg Ser Ser Ser Asp Gly Arg
225                 230                 235                 240

Thr Ser Ala Cys Gln Pro Leu Pro Gly Ala Pro Trp Ser Arg Pro Arg
                245                 250                 255

Leu Pro Leu Leu Arg Ala
            260


<210> SEQ ID NO 36
<211> LENGTH: 798
<212> TYPE: DNA
<213> ORGANISM: Brachypodium distachyon

<400> SEQUENCE: 36

atgcaggggc tgcaatggcc ggggctgttc cacatcctcg cttctcgccc cggcgggccg      60

cccagggtcc ggctcaccgg gctcggagct tccatggacg cgctcgaggc caccgggaag     120

aggctgtcgg atttcgcgga cacgcttggg ctgccgttcg agttctgtgc tgtcgctgat     180

aaggccggga accttgaccc ggagaagctg cttaatggcg gcggcggcgg cggaggaggg     240

gtgggaaggc ggcgcgaggc tgttgccgtg cattggctcc accactcgct ctacgacgtc     300

accgggaacg acgccaacac gctggggctc atccagaggt tggcgccgaa ggtggtgaca     360

atggtggagc aggacctgag ccactcgggc tccttcctgg cgcggttcgt ggaagccatc     420

cactactact cggcgctctt cgactcgctg gacgccagct acggcgagga cagtcccgag     480

cggcacgtcg tggagcagca gctgctatcg cgggagatcc gcaacgtgct cgccgtcggc     540

gggccggccc gcaccggcga cgccaagttc gtcggcagct ggcgcgacaa gctggcccgc     600

tccgggttcg gcccggcgtc gctcgccggc agcgccgcgg cgcaggcggc gctgctgctc     660

ggcatgttcc cctccgacgg ctacacgctc gtcgaggaga acggcgcgct caagctcgga     720

tggaaggacc tctgcttgct gacagcctct gcctggcgcc ccatggtcca gaccacgcct     780

tcctcttctg cgcgctaa                                                   798


<210> SEQ ID NO 37
<211> LENGTH: 593
<212> TYPE: PRT
<213> ORGANISM: Brachypodium distachyon

<400> SEQUENCE: 37

Met Asp Thr Leu Phe Arg Leu Val Ser Leu Gln Ala Thr Thr Glu Gln
1               5                   10                  15

Gln Gln Gln Gln Gln Gln Gln Ser Ala Ser Tyr Asn Ser Arg Ser Thr
            20                  25                  30

Thr Ser Ser Gly Ser Arg Ser Ser Ser His His Thr Thr Ala Ser Tyr
        35                  40                  45

Ser Tyr Tyr Asn Ser Gly Ser Gly Ser Gly Gly Gln Pro Gln Gln Gln
    50                  55                  60

Tyr Tyr Tyr Ser Gln Pro Gln Gln Ser Tyr Tyr Leu Glu Pro Tyr His
65                  70                  75                  80

Glu Glu Cys Gly Gly Gly Asn Gln Leu Tyr Met Asp Glu Asp Phe Ser
```

```
                85                  90                  95

Ser Ser Ser Ser Ser Arg His Phe Gly Gly His His Gly Ser His Gly
            100                 105                 110

Gly Gln Gln Gln Gln Pro Ser Ser Thr Pro Pro Leu Ser Thr Thr Ser
        115                 120                 125

Ser Thr Ala Ala Gly His Ala Leu Phe Glu Pro Ala Glu Leu Ser Phe
    130                 135                 140

Pro Pro Asp Leu Asn Leu Asp Phe Ser Ser Pro Ala Ser Ser Ser Gly
145                 150                 155                 160

Gly Gly Ile Ala Ala Ala Ser Ala Ser Ser Pro Ala Val Ile Gly Gly
                165                 170                 175

Ala Gly Gly Gly Arg Trp Ala Ser Gln Leu Leu Met Glu Cys Ala Arg
            180                 185                 190

Ala Val Ala Ser Arg Asp Ser Thr Arg Val Gln Gln Leu Met Trp Met
        195                 200                 205

Leu Asn Glu Leu Ala Ser Pro Tyr Gly Asp Val Glu Gln Lys Leu Ala
    210                 215                 220

Ser Tyr Phe Leu Gln Ala Leu Phe Ala Arg Leu Thr Ala Ser Gly Pro
225                 230                 235                 240

Arg Thr Leu Arg Thr Leu Ala Ala Ala Thr Asp Arg Asn Thr Ser Phe
                245                 250                 255

Asp Ser Thr Arg Arg Val Ala Leu Lys Phe Gln Glu Leu Ser Pro Trp
            260                 265                 270

Ser Ser Phe Gly His Val Ala Ala Asn Gly Ala Ile Leu Glu Ser Phe
        275                 280                 285

Leu Glu Ala Ala Ala Ala Ala Pro Ser Ser Glu Pro Gln Arg Phe His
    290                 295                 300

Ile Leu Asp Leu Ser Asn Thr Phe Cys Thr Gln Trp Pro Thr Leu Leu
305                 310                 315                 320

Glu Ala Leu Ala Thr Arg Ser Pro Asp Asp Thr Pro His Leu Ser Ile
                325                 330                 335

Thr Thr Val His Val Ser Ser Ser Ser Ala Ala Ser Ser Pro Ala Val
            340                 345                 350

Gln Arg Val Met Arg Glu Ile Gly Gln Arg Met Glu Lys Phe Ala Arg
        355                 360                 365

Leu Met Gly Val Pro Phe Arg Phe Arg Ala Val His His Ser Gly Asp
    370                 375                 380

Leu Ala Glu Leu Asp Leu Asp Ala Leu Asp Val Arg Glu Gly Gly Ala
385                 390                 395                 400

Thr Thr Gly Ile Ala Val Asn Cys Val Asn Ser Leu Arg Gly Val Gly
                405                 410                 415

Ala Arg Arg Arg Gly Glu Phe Ala Ala Leu Leu Arg Arg Leu Gly Pro
            420                 425                 430

Arg Val Val Thr Val Val Glu Glu Glu Ala Asp Phe Val Ala Asp Ser
        435                 440                 445

Asp His His Arg Ser Ala Asp Gln Asp Ala Glu Thr Asp Gln Ala Ala
    450                 455                 460

Phe Leu Lys Val Phe Gly Glu Gly Leu Arg Phe Phe Ser Ala Tyr Met
465                 470                 475                 480

Asp Ser Leu Glu Glu Ser Phe Pro Lys Thr Ser Asn Glu Arg Leu Ala
                485                 490                 495

Leu Glu Arg Gly Ala Gly Arg Ala Ile Val Asp Leu Val Ser Cys Pro
            500                 505                 510
```

```
Ala Ser Glu Ser Met Glu Arg Arg Glu Thr Ala Ala Ala Trp Ala Arg
        515                 520                 525

Arg Leu Arg Cys Ala Gly Phe Ser Pro Val Ala Phe Ser Asp Asp Val
    530                 535                 540

Ala Asp Asp Val Arg Ser Leu Leu Arg Arg Tyr Arg Glu Gly Trp Ser
545                 550                 555                 560

Met Arg Asp Ala Gly Ala Glu Asp Ser Ala Ala Ala Gly Ala Gly Val
                565                 570                 575

Phe Leu Gln Trp Lys Glu Gln Pro Leu Val Trp Ala Ser Ala Trp Arg
            580                 585                 590

Pro


<210> SEQ ID NO 38
<211> LENGTH: 1782
<212> TYPE: DNA
<213> ORGANISM: Brachypodium distachyon

<400> SEQUENCE: 38

atggatacgc tgtttaggtt ggttagcctc caagccacca ccgagcagca gcagcagcag     60

cagcagcagt cggcgtcgta caactccagg agcaccacct cgagcggctc tcggtcgtcc    120

tcgcaccaca ccaccgcctc ctacagctac tacaacagcg gctccggctc cggcgggcag    180

ccgcagcagc agtactacta tagccagccg cagcagtcgt actacctgga gccgtaccac    240

gaagaatgcg gcggcggcaa ccagctctac atggatgagg acttctcgtc gtcgtcttcc    300

tcgagacact ttgggggcca ccatggttcc cacgggggc agcagcagca gccgtcgtcc    360

acgcccccgc tgtccacgac gtcttccacg gccgccgggc acgcgctgtt cgagccagcc    420

gagctctcgt tcccgccgga cctcaacctc gacttctcgt ccccggcttc gtcctccgga    480

gggggcatcg cggcggcgtc cgcttcgtct ccggcggtta ttggtggcgc aggaggcggg    540

cggtgggcga gccagctgct gatggagtgc gcgcgggccg tggcgtcccg ggacagcacg    600

cgcgtgcagc agctcatgtg gatgctcaac gagctggcgt cgccgtacgg ggacgtggag    660

cagaagctgg cctcctactt cctgcaggcg ctcttcgccc ggctcacggc gtccgggccg    720

cgcacgctgc ggacgctggc cgcggcaacg gaccggaaca cctccttcga ctccacccgc    780

cgcgtcgcgc tcaagttcca ggagctcagc ccgtggtcct ccttcggcca cgtggccgcc    840

aacggggcca tcctcgagtc cttcctcgag gccgccgccg cggcgccatc gtcggagcca    900

cagcggttcc acatcctcga cctcagcaac accttctgca cgcagtggcc gacgctcctc    960

gaggcgctcg ccacacgctc cccgacgac acgccgcacc tctccatcac caccgtccac   1020

gtgtcctcct cctccgccgc gtcgtccccc gccgtgcagc gcgtgatgcg ggagatcggc   1080

cagcggatgg agaagttcgc ccgcctcatg ggcgtcccct tccgcttccg cgccgtgcac   1140

cactcgggcg acctggccga gctcgacctc gacgcgctcg acgtccgcga gggcggcgcc   1200

acgaccggca tcgccgtcaa ctgcgtcaac tcgctccgcg gcgtcggcgc acgccggcgc   1260

ggcgagttcg cggcgctgct ccgccgcctc ggcccccggg tcgtcaccgt ggtcgaggaa   1320

gaagccgact tcgtggccga ctccgatcat cacaggtctg ctgaccaaga cgcggagaca   1380

gatcaggcgg cgttcctgaa ggtgttcggc gaagggctgc gcttcttctc ggcctacatg   1440

gactcgctgg aggagagctt ccccaagacg agcaacgaga ggctggcgct ggagaggggc   1500

gccgggcgcg ccattgtcga cctggtctcg tgcccggcgt ccgagtccat ggagcggcgg   1560

gagacggccg cggcatgggc gcggcggctg cggtgcgccg ggttctcgcc cgtggcgttc   1620
```

```
agcgatgacg tcgcggacga cgtgcgctcg ctcctgcgcc ggtaccggga gggatggtcg   1680

atgcgggacg ccggcgcgga ggattcggcg gcggccgggg ccggcgtgtt cctgcagtgg   1740

aaggagcagc ctctcgtgtg ggcgagcgcc tggaggccat ga                      1782


<210> SEQ ID NO 39
<211> LENGTH: 262
<212> TYPE: PRT
<213> ORGANISM: Brachypodium distachyon

<400> SEQUENCE: 39

Cys Arg Gly Cys Asn Gly Arg Gly Cys Ser Thr Ser Ser Leu Leu Ala
1               5                   10                  15

Pro Ala Gly Arg Pro Gly Ser Gly Ser Pro Gly Ser Glu Leu Pro Trp
            20                  25                  30

Thr Arg Ser Arg Pro Pro Gly Arg Gly Cys Arg Ile Ser Arg Thr Arg
        35                  40                  45

Leu Gly Cys Arg Ser Ser Ser Val Leu Ser Leu Ile Arg Pro Gly Thr
    50                  55                  60

Leu Thr Arg Arg Ser Cys Leu Met Ala Ala Ala Ala Ala Glu Glu Gly
65                  70                  75                  80

Trp Glu Gly Gly Ala Arg Leu Leu Pro Cys Ile Gly Ser Thr Thr Arg
                85                  90                  95

Ser Thr Thr Ser Pro Gly Thr Thr Pro Thr Arg Trp Gly Ser Ser Arg
            100                 105                 110

Gly Trp Arg Arg Arg Trp Gln Trp Trp Ser Arg Thr Ala Thr Arg Ala
        115                 120                 125

Pro Ser Trp Arg Gly Ser Trp Lys Pro Ser Thr Thr Thr Arg Arg Ser
    130                 135                 140

Ser Thr Arg Trp Thr Pro Ala Thr Ala Arg Thr Val Pro Ser Gly Thr
145                 150                 155                 160

Ser Trp Ser Ser Ser Cys Tyr Arg Gly Arg Ser Ala Thr Cys Ser Pro
                165                 170                 175

Ser Ala Gly Arg Pro Ala Pro Ala Thr Pro Ser Ser Ser Ala Ala Gly
            180                 185                 190

Ala Thr Ser Trp Pro Ala Pro Gly Ser Ala Arg Arg Arg Ser Pro Ala
        195                 200                 205

Ala Pro Arg Arg Arg Arg Arg Cys Cys Ser Ala Cys Ser Pro Pro Thr
    210                 215                 220

Ala Thr Arg Ser Ser Arg Arg Thr Ala Arg Ser Ser Ser Asp Gly Arg
225                 230                 235                 240

Thr Ser Ala Cys Gln Pro Leu Pro Gly Ala Pro Trp Ser Arg Pro Arg
                245                 250                 255

Leu Pro Leu Leu Arg Ala
            260


<210> SEQ ID NO 40
<211> LENGTH: 798
<212> TYPE: DNA
<213> ORGANISM: Brachypodium distachyon

<400> SEQUENCE: 40

atgcaggggc tgcaatggcc ggggctgttc cacatcctcg cttctcgccc cggcgggccg     60

cccagggtcc ggctcaccgg gctcggagct tccatggacg cgctcgaggc caccgggaag    120

aggctgtcgg atttcgcgga cacgcttggg ctgccgttcg agttctgtgc tgtcgctgat    180
```

```
aaggccggga accttgaccc ggagaagctg cttaatggcg gcggcggcgg cggaggaggg    240

gtgggaaggc ggcgcgaggc tgttgccgtg cattggctcc accactcgct ctacgacgtc    300

accgggaacg acgccaacac gctggggctc atccagaggt tggcgccgaa ggtggtgaca    360

atggtggagc aggacctgag ccactcgggc tccttcctgg cgcggttcgt ggaagccatc    420

cactactact cggcgctctt cgactcgctg gacgccagct acggcgagga cagtcccgag    480

cggcacgtcg tggagcagca gctgctatcg cgggagatcc gcaacgtgct cgccgtcggc    540

gggccggccc gcaccggcga cgccaagttc gtcggcagct ggcgcgacaa gctggcccgc    600

tccgggttcg gcccggcgtc gctcgccggc agcgccgcgg cgcaggcggc gctgctgctc    660

ggcatgttcc cctccgacgg ctacacgctc gtcgaggaga acggcgcgct caagctcgga    720

tggaaggacc tctgcttgct gacagcctct gcctggcgcc ccatggtcca gaccacgcct    780

tcctcttctg cgcgctaa                                                  798
```

<210> SEQ ID NO 41
<211> LENGTH: 653
<212> TYPE: PRT
<213> ORGANISM: Arabidopsis thaliana

<400> SEQUENCE: 41

```
Met Ala Glu Ser Gly Asp Phe Asn Gly Gly Gln Pro Pro Pro His Ser
1               5                   10                  15

Pro Leu Arg Thr Thr Ser Ser Gly Ser Ser Ser Ser Asn Asn Arg Gly
            20                  25                  30

Pro Pro Pro Pro Pro Pro Pro Pro Leu Val Met Val Arg Lys Arg Leu
        35                  40                  45

Ala Ser Glu Met Ser Ser Asn Pro Asp Tyr Asn Asn Ser Ser Arg Pro
    50                  55                  60

Pro Arg Arg Val Ser His Leu Leu Asp Ser Asn Tyr Asn Thr Val Thr
65                  70                  75                  80

Pro Gln Gln Pro Pro Ser Leu Thr Ala Ala Ala Thr Val Ser Ser Gln
                85                  90                  95

Pro Asn Pro Pro Leu Ser Val Cys Gly Phe Ser Gly Leu Pro Val Phe
            100                 105                 110

Pro Ser Asp Arg Gly Gly Arg Asn Val Met Met Ser Val Gln Pro Met
        115                 120                 125

Asp Gln Asp Ser Ser Ser Ser Ser Ala Ser Pro Thr Val Trp Val Asp
    130                 135                 140

Ala Ile Ile Arg Asp Leu Ile His Ser Ser Thr Ser Val Ser Ile Pro
145                 150                 155                 160

Gln Leu Ile Gln Asn Val Arg Asp Ile Ile Phe Pro Cys Asn Pro Asn
                165                 170                 175

Leu Gly Ala Leu Leu Glu Tyr Arg Leu Arg Ser Leu Met Leu Leu Asp
            180                 185                 190

Pro Ser Ser Ser Ser Asp Pro Ser Pro Gln Thr Phe Glu Pro Leu Tyr
        195                 200                 205

Gln Ile Ser Asn Asn Pro Ser Pro Pro Gln Gln Gln Gln Gln His Gln
    210                 215                 220

Gln Gln Gln Gln Gln His Lys Pro Pro Pro Pro Pro Ile Gln Gln Gln
225                 230                 235                 240

Glu Arg Glu Asn Ser Ser Thr Asp Ala Pro Pro Gln Pro Glu Thr Val
                245                 250                 255
```

```
Thr Ala Thr Val Pro Ala Val Gln Thr Asn Thr Ala Glu Ala Leu Arg
            260                 265                 270

Glu Arg Lys Glu Glu Ile Lys Arg Gln Lys Gln Asp Glu Glu Gly Leu
        275                 280                 285

His Leu Leu Thr Leu Leu Leu Gln Cys Ala Glu Ala Val Ser Ala Asp
    290                 295                 300

Asn Leu Glu Glu Ala Asn Lys Leu Leu Leu Glu Ile Ser Gln Leu Ser
305                 310                 315                 320

Thr Pro Tyr Gly Thr Ser Ala Gln Arg Val Ala Ala Tyr Phe Ser Glu
                325                 330                 335

Ala Met Ser Ala Arg Leu Leu Asn Ser Cys Leu Gly Ile Tyr Ala Ala
            340                 345                 350

Leu Pro Ser Arg Trp Met Pro Gln Thr His Ser Leu Lys Met Val Ser
        355                 360                 365

Ala Phe Gln Val Phe Asn Gly Ile Ser Pro Leu Val Lys Phe Ser His
    370                 375                 380

Phe Thr Ala Asn Gln Ala Ile Gln Glu Ala Phe Glu Lys Glu Asp Ser
385                 390                 395                 400

Val His Ile Ile Asp Leu Asp Ile Met Gln Gly Leu Gln Trp Pro Gly
                405                 410                 415

Leu Phe His Ile Leu Ala Ser Arg Pro Gly Gly Pro Pro His Val Arg
            420                 425                 430

Leu Thr Gly Leu Gly Thr Ser Met Glu Ala Leu Gln Ala Thr Gly Lys
        435                 440                 445

Arg Leu Ser Asp Phe Ala Asp Lys Leu Gly Leu Pro Phe Glu Phe Cys
    450                 455                 460

Pro Leu Ala Glu Lys Val Gly Asn Leu Asp Thr Glu Arg Leu Asn Val
465                 470                 475                 480

Arg Lys Arg Glu Ala Val Ala Val His Trp Leu Gln His Ser Leu Tyr
                485                 490                 495

Asp Val Thr Gly Ser Asp Ala His Thr Leu Trp Leu Leu Gln Arg Leu
            500                 505                 510

Ala Pro Lys Val Val Thr Val Val Glu Gln Asp Leu Ser His Ala Gly
        515                 520                 525

Ser Phe Leu Gly Arg Phe Val Glu Ala Ile His Tyr Tyr Ser Ala Leu
    530                 535                 540

Phe Asp Ser Leu Gly Ala Ser Tyr Gly Glu Glu Ser Glu Glu Arg His
545                 550                 555                 560

Val Val Glu Gln Gln Leu Leu Ser Lys Glu Ile Arg Asn Val Leu Ala
                565                 570                 575

Val Gly Gly Pro Ser Arg Ser Gly Glu Val Lys Phe Glu Ser Trp Arg
            580                 585                 590

Glu Lys Met Gln Gln Cys Gly Phe Lys Gly Ile Ser Leu Ala Gly Asn
        595                 600                 605

Ala Ala Thr Gln Ala Thr Leu Leu Leu Gly Met Phe Pro Ser Asp Gly
    610                 615                 620

Tyr Thr Leu Val Asp Asp Asn Gly Thr Leu Lys Leu Gly Trp Lys Asp
625                 630                 635                 640

Leu Ser Leu Leu Thr Ala Ser Ala Trp Thr Pro Arg Ser
                645                 650
```

<210> SEQ ID NO 42
<211> LENGTH: 2163
<212> TYPE: DNA

<213> ORGANISM: Arabidopsis thaliana

<400> SEQUENCE: 42

```
ccttatttat aaccatgcaa tctcacgacc aacaaccctt caatctccat ggcggaatcc      60
ggcgatttca acggtggtca acctcctcct catagtcctc tgagaacaac ttcttccggt     120
agtagcagca gcaacaaccg tggtcctcct cctcctcctc ctcctccttt agtgatggtg     180
agaaaaagat tagcttccga gatgtcttct aaccctgact acaacaactc ctctcgtcct     240
cctcgccgtg tctctcacct tcttgactcc aactacaata ctgtcacacc acaacaacca     300
ccgtctctta cggcggcggc tactgtatct tctcaaccaa acccaccact ctctgtttgt     360
ggcttctctg gtcttcccgt ttttccttca gaccgtggtg gtcggaatgt tatgatgtcc     420
gtacaaccaa tggatcaaga ctcttcatct tcttctgctt cacctactgt atgggttgac     480
gccattatca gagaccttat ccattcctca acttcagtct ctattcctca acttatccaa     540
aacgttagag acattatctt cccttgtaac ccaaatctcg gtgctcttct tgaatacagg     600
ctccgatctc tcatgctcct tgatccttcc tcttcctctg acccttctcc tcaaactttc     660
gaacctctct atcagatctc caacaatcct tctcctccac aacagcaaca gcagcaccaa     720
caacaacaac aacagcataa gcctcctcct cctccgattc agcagcaaga aagagaaaat     780
tcttctaccg atgcaccacc gcaaccagag acagtgacgg ccactgttcc cgccgtccaa     840
acaaatacgg cggaggcttt aagagagagg aaggaagaga ttaagaggca gaagcaagac     900
gaagaaggat tacaccttct cacattgctg ctacagtgtg ctgaagctgt ctctgctgat     960
aatctcgaag aagcaaacaa gcttcttctt gagatctctc agttatcaac tccttacggg    1020
acctcagcgc agagagtagc tgcttacttc tcggaagcta tgtcagcgag attactcaac    1080
tcgtgtctcg gaatttacgc ggctttgcct tcacggtgga tgcctcaaac gcatagcttg    1140
aaaatggtct ctgcgtttca ggtctttaat gggataagcc ctttagtgaa attctcacac    1200
tttacagcga atcaggcgat tcaagaagca tttgagaaag aagacagtgt acacatcatt    1260
gacttggaca tcatgcaggg acttcaatgg cctggtttat tccacattct tgcttctaga    1320
cctggaggac ctccacacgt gcgactcacg ggacttggta cttccatgga agctcttcag    1380
gctacaggga aacgtctttc ggatttcaca gataagcttg gcctgccttt tgagttctgc    1440
cctttagctg agaaagttgg aaacttggac actgagagac tcaatgtgag gaaaagggaa    1500
gctgtggctg ttcactggct tcaacattct ctttatgatg tcactggctc tgatgcacac    1560
actctctggt tactccaaag gtaaaataaa cattaccttt taatcactct ttatctataa    1620
attattttaa gattatatag gaaagatatg ttctaaaaag ctggcttttt tggttaatga    1680
ttggggaatg aacagattag ctcctaaagt tgtgacagta gtggagcaag atttgagcca    1740
cgctggttct ttcttaggaa gatttgtaga ggcaatacat tactactctg cactctttga    1800
ctcactggga gcaagctacg gcgaagagag tgaagagaga catgtcgtgg aacagcagct    1860
attatcgaaa gagatacgga atgtattagc ggttggagga ccatcgagaa gcggtgaagt    1920
gaagtttgag agctggaggg agaaaatgca acaatgtggg tttaaaggta tatctttagc    1980
tggaaatgca gctacacaag cgactctact gttgggaatg tttccttcgg atggttacac    2040
tttggttgat gataatggta cacttaagct tggatggaaa gatctttcgt tactcactgc    2100
ttcagcttgg acgcctcgtt cttagttttc ttctcctttt tcacaaacaa tgtgcccata    2160
aat                                                                  2163
```

```
<210> SEQ ID NO 43
<211> LENGTH: 531
<212> TYPE: PRT
<213> ORGANISM: Arabidopsis thaliana

<400> SEQUENCE: 43

Met Asp Thr Leu Phe Arg Leu Val Ser Leu Gln Gln Gln Gln Gln Ser
1               5                   10                  15

Asp Ser Ile Ile Thr Asn Gln Ser Ser Leu Ser Arg Thr Ser Thr Thr
            20                  25                  30

Thr Thr Gly Ser Pro Gln Thr Ala Tyr His Tyr Asn Phe Pro Gln Asn
        35                  40                  45

Asp Val Val Glu Glu Cys Phe Asn Phe Phe Met Asp Glu Glu Asp Leu
    50                  55                  60

Ser Ser Ser Ser Ser His His Asn His His Asn His Asn Asn Pro Asn
65                  70                  75                  80

Thr Tyr Tyr Ser Pro Phe Thr Thr Pro Thr Gln Tyr His Pro Ala Thr
                85                  90                  95

Ser Ser Thr Pro Ser Ser Thr Ala Ala Ala Ala Ala Leu Ala Ser Pro
            100                 105                 110

Tyr Ser Ser Ser Gly His His Asn Asp Pro Ser Ala Phe Ser Ile Pro
        115                 120                 125

Gln Thr Pro Pro Ser Phe Asp Phe Ser Ala Asn Ala Lys Trp Ala Asp
    130                 135                 140

Ser Val Leu Leu Glu Ala Ala Arg Ala Phe Ser Asp Lys Asp Thr Ala
145                 150                 155                 160

Arg Ala Gln Gln Ile Leu Trp Thr Leu Asn Glu Leu Ser Ser Pro Tyr
                165                 170                 175

Gly Asp Thr Glu Gln Lys Leu Ala Ser Tyr Phe Leu Gln Ala Leu Phe
            180                 185                 190

Asn Arg Met Thr Gly Ser Gly Glu Arg Cys Tyr Arg Thr Met Val Thr
        195                 200                 205

Ala Ala Ala Thr Glu Lys Thr Cys Ser Phe Glu Ser Thr Arg Lys Thr
    210                 215                 220

Val Leu Lys Phe Gln Glu Val Ser Pro Trp Ala Thr Phe Gly His Val
225                 230                 235                 240

Ala Ala Asn Gly Ala Ile Leu Glu Ala Val Asp Gly Glu Ala Lys Ile
                245                 250                 255

His Ile Val Asp Ile Ser Ser Thr Phe Cys Thr Gln Trp Pro Thr Leu
            260                 265                 270

Leu Glu Ala Leu Ala Thr Arg Ser Asp Asp Thr Pro His Leu Arg Leu
        275                 280                 285

Thr Thr Val Val Val Ala Asn Lys Phe Val Asn Asp Gln Thr Ala Ser
    290                 295                 300

His Arg Met Met Lys Glu Ile Gly Asn Arg Met Glu Lys Phe Ala Arg
305                 310                 315                 320

Leu Met Gly Val Pro Phe Lys Phe Asn Ile Ile His His Val Gly Asp
                325                 330                 335

Leu Ser Glu Phe Asp Leu Asn Glu Leu Asp Val Lys Pro Asp Glu Val
            340                 345                 350

Leu Ala Ile Asn Cys Val Gly Ala Met His Gly Ile Ala Ser Arg Gly
        355                 360                 365

Ser Pro Arg Asp Ala Val Ile Ser Ser Phe Arg Arg Leu Arg Pro Arg
    370                 375                 380
```

```
Ile Val Thr Val Val Glu Glu Glu Ala Asp Leu Val Gly Glu Glu Glu
385                 390                 395                 400

Gly Gly Phe Asp Asp Glu Phe Leu Arg Gly Phe Gly Glu Cys Leu Arg
                405                 410                 415

Trp Phe Arg Val Cys Phe Glu Ser Trp Glu Glu Ser Phe Pro Arg Thr
            420                 425                 430

Ser Asn Glu Arg Leu Met Leu Glu Arg Ala Ala Gly Arg Ala Ile Val
        435                 440                 445

Asp Leu Val Ala Cys Glu Pro Ser Asp Ser Thr Glu Arg Arg Glu Thr
    450                 455                 460

Ala Arg Lys Trp Ser Arg Arg Met Arg Asn Ser Gly Phe Gly Ala Val
465                 470                 475                 480

Gly Tyr Ser Asp Glu Val Ala Asp Asp Val Arg Ala Leu Leu Arg Arg
                485                 490                 495

Tyr Lys Glu Gly Val Trp Ser Met Val Gln Cys Pro Asp Ala Ala Gly
            500                 505                 510

Ile Phe Leu Cys Trp Arg Asp Gln Pro Val Val Trp Ala Ser Ala Trp
        515                 520                 525

Arg Pro Thr
    530


<210> SEQ ID NO 44
<211> LENGTH: 1975
<212> TYPE: DNA
<213> ORGANISM: Arabidopsis thaliana

<400> SEQUENCE: 44

gcaatataca caacaaagta ttaaatctta gatattgtgg gtctcccttt cttctattca      60

ttttcttatt cattaaaaaa aaaaaatgga tactctcttt agactagtca gtctccaaca     120

acaacaacaa tccgatagta tcattacaaa tcaatcttcg ttaagcagaa cttccaccac     180

cactactggc tctccacaaa ctgcttatca ctacaacttt ccacaaaacg acgtcgtcga     240

agaatgcttc aactttttca tggatgaaga agacctttcc tcttcttctt ctcaccacaa     300

ccatcacaac cacaacaatc ctaatactta ctactctcct ttcactactc ccacccaata     360

ccatcccgcc acatcatcaa ccccttcctc caccgccgca gccgcagctt tagcctcgcc     420

ttactcctcc tccggccacc ataatgaccc ttccgcgttc tccatacctc aaactcctcc     480

gtccttcgac ttctcagcca atgccaagtg ggcagactcg gtccttcttg aagcggcacg     540

tgccttctcc gacaaagaca ctgcacgtgc gcaacaaatc ctatggacgc tcaacgagct     600

ctcttctccg tacggagaca ccgagcaaaa actggcttct tacttcctcc aagctctctt     660

caaccgcatg accggttcag gcgaacgatg ctaccgaacc atggtaacag ctgcagccac     720

agagaagact tgctccttcg agtcaacgcg aaaaactgta ctaaagttcc aagaagttag     780

cccctgggcc acgtttggac acgtggcggc aaacggagca atcttggaag cagtagacgg     840

agaggcaaag atccacatcg ttgacataag ctccacgttt tgcactcaat ggccgactct     900

tctagaagct ttagccacaa gatcagacga cacgcctcac ctaaggctaa ccacagttgt     960

cgtggccaac aagtttgtca acgatcaaac ggcgtcgcat cggatgatga aagagatcgg    1020

aaaccgaatg gagaaattcg ctaggcttat gggagttcct ttcaaattta acattattca    1080

tcacgttgga gatttatctg agtttgatct caacgaactc gacgttaaac cagacgaagt    1140

cttggccatt aactgcgtag gcgcgatgca tgggatcgct tcacgtggaa gccctagaga    1200

cgctgtgata tcgagtttcc gacggttaag accgaggatt gtgacggtcg tagaagaaga    1260
```

```
agctgatctt gtcggagaag aagaaggtgg ctttgatgat gagttcttga gagggtttgg   1320

agaatgttta cgatggttta gggtttgctt cgagtcatgg gaagagagtt ttccaaggac   1380

gagcaacgag aggttgatgc tagagcgtgc agcgggacgt gcgatcgttg atcttgtggc   1440

ttgtgagccg tcggattcca cggagaggcg agagacagcg aggaagtggt cgaggaggat   1500

gaggaatagt gggtttggag cggtggggta tagtgatgag gtggcggatg atgtcagagc   1560

tttgttgagg agatataaag aaggtgtttg gtcgatggta cagtgtcctg atgccgccgg   1620

aatattcctt tgttggagag atcagccggt ggtttgggct agtgcgtggc ggccaacgta   1680

aagggttgtt tttatttttt cataaggaat tcgcaagttc gatttttact tgagatggtt   1740

tcacacgtgt ggtgatggtt gatgatgggc tttgagattg agagagttac gattatgatg   1800

ataatgcagt tcataatatg aatttggatt ttggaatagg actaattaag taattctgat   1860

cattgaggtg ggtatcaagg ttcatacaat tcgtgatttt ttgttttgtc tttggtattt   1920

attaatttta aaaatccatt ttggaatgaa atttgtgatt acttttgttt atccg        1975
```

<210> SEQ ID NO 45
<211> LENGTH: 405
<212> TYPE: PRT
<213> ORGANISM: Arabidopsis thaliana

<400> SEQUENCE: 45

```
Met Thr Thr Lys Arg Ile Asp Arg Asp Leu Pro Ser Ser Asp Asp Pro
1               5                   10                  15

Ser Ser Ala Lys Arg Arg Ile Glu Phe Pro Glu Glu Thr Leu Glu Asn
            20                  25                  30

Asp Gly Ala Ala Ala Ile Lys Leu Leu Ser Leu Leu Leu Gln Cys Ala
        35                  40                  45

Glu Tyr Val Ala Thr Asp His Leu Arg Glu Ala Ser Thr Leu Leu Ser
    50                  55                  60

Glu Ile Ser Glu Ile Cys Ser Pro Phe Gly Ser Ser Pro Glu Arg Val
65                  70                  75                  80

Val Ala Tyr Phe Ala Gln Ala Leu Gln Thr Arg Val Ile Ser Ser Tyr
                85                  90                  95

Leu Ser Gly Ala Cys Ser Pro Leu Ser Glu Lys Pro Leu Thr Val Val
            100                 105                 110

Gln Ser Gln Lys Ile Phe Ser Ala Leu Gln Thr Tyr Asn Ser Val Ser
        115                 120                 125

Pro Leu Ile Lys Phe Ser His Phe Thr Ala Asn Gln Ala Ile Phe Gln
    130                 135                 140

Ala Leu Asp Gly Glu Asp Ser Val His Ile Ile Asp Leu Asp Val Met
145                 150                 155                 160

Gln Gly Leu Gln Trp Pro Ala Leu Phe His Ile Leu Ala Ser Arg Pro
                165                 170                 175

Arg Lys Leu Arg Ser Ile Arg Ile Thr Gly Phe Gly Ser Ser Ser Asp
            180                 185                 190

Leu Leu Ala Ser Thr Gly Arg Arg Leu Ala Asp Phe Ala Ser Ser Leu
        195                 200                 205

Asn Leu Pro Phe Glu Phe His Pro Ile Glu Gly Ile Ile Gly Asn Leu
    210                 215                 220

Ile Asp Pro Ser Gln Leu Ala Thr Arg Gln Gly Glu Ala Val Val Val
225                 230                 235                 240

His Trp Met Gln His Arg Leu Tyr Asp Val Thr Gly Asn Asn Leu Glu
```

```
                245                 250                 255

Thr Leu Glu Ile Leu Arg Arg Leu Lys Pro Asn Leu Ile Thr Val Val
            260                 265                 270

Glu Gln Glu Leu Ser Tyr Asp Asp Gly Gly Ser Phe Leu Gly Arg Phe
        275                 280                 285

Val Glu Ala Leu His Tyr Tyr Ser Ala Leu Phe Asp Ala Leu Gly Asp
    290                 295                 300

Gly Leu Gly Glu Glu Ser Gly Glu Arg Phe Thr Val Glu Gln Ile Val
305                 310                 315                 320

Leu Gly Thr Glu Ile Arg Asn Ile Val Ala His Gly Gly Gly Arg Arg
                325                 330                 335

Lys Arg Met Lys Trp Lys Glu Glu Leu Ser Arg Val Gly Phe Arg Pro
            340                 345                 350

Val Ser Leu Arg Gly Asn Pro Ala Thr Gln Ala Gly Leu Leu Leu Gly
        355                 360                 365

Met Leu Pro Trp Asn Gly Tyr Thr Leu Val Glu Glu Asn Gly Thr Leu
    370                 375                 380

Arg Leu Gly Trp Lys Asp Leu Ser Leu Leu Thr Ala Ser Ala Trp Lys
385                 390                 395                 400

Ser Gln Pro Phe Asp
                405
```

<210> SEQ ID NO 46
<211> LENGTH: 1497
<212> TYPE: DNA
<213> ORGANISM: Arabidopsis thaliana

<400> SEQUENCE: 46

```
cgaaggagct gtaatcttca caaagagcac ttgattataa cattgaatct tttgcaaaaa     60

agataaaaat cttttcaaga aactgatcca tccaaaatac tatcttgtct tcactcttca    120

aaattcctgt cattactctc tcgaaccctt tctcttttcg aatctccact ttttttcta    180

tcttctgctt cttcttcttc tctcttcaat gattccactc tcacaaaatc tccatgacta    240

caaaacgcat agacagagat ctcccatctt ccgacgatcc ttcctccgct aaacgccgta    300

tcgaattccc cgaagaaaca ctcgaaaacg acggtgctgc cgcaatcaaa ctccttagct    360

tactcctcca atgcgccgaa tacgtagcta ctgatcatct ccgtgaagct tcaacacttt    420

tatccgaaat ctccgagata tgttctccgt tcggttcctc gccggagcga gtcgtcgctt    480

acttcgctca agcgctacaa acgcgcgtga tcagctctta cctctccggc gcgtgttctc    540

ccctctccga gaaaccactc actgttgttc agtctcagaa aatcttctcc gccttgcaga    600

cttataactc cgttagtcct ctgatcaaat tctcacattt cacggcgaat caagccattt    660

ttcaggcgct tgacggagaa gattccgttc atatcatcga tctcgatgtt atgcaaggtc    720

ttcaatggcc ggctctattt cacatcctcg cttcacgtcc tcgaaaactc cgatcaattc    780

gaatcaccgg atttggttcc tcctccgatc tactcgcttc aactggccgg agactcgccg    840

atttcgcatc atcgttaaac ctccctttcg aatttcatcc aattgaaggc ataatcggaa    900

acctaatcga tccgagccaa ctcgcaacga gacaaggaga agctgtggtg gttcattgga    960

tgcagcaccg gttatatgat gttacaggga acaatctcga gacgttggag attctacgga   1020

ggctgaaacc gaatctgatc acggtggtgg agcaagaatt gagctacgac gatggaggaa   1080

gctttttagg aagattcgtg gaggctttgc attattatag cgcgttgttt gacgcgctag   1140

gagatggatt gggtgaagag agtggtgaga gattcacggt ggagcagatt gttttgggga   1200
```

```
cggagataag aaacattgtg gcgcacggag gaggaagaag gaagagaatg aagtggaaag   1260

aagaactgag ccgggtcggg tttagacctg tttcgcttcg ggtaacccg gcgacacaag    1320

cgggtttatt gttgggtatg ttaccgtgga atggatatac tttggttgaa gagaatggaa   1380

ccctccgtct tggctggaag gatctctcgc ttttgactgc ctctgcctgg aaatctcagc   1440

cgttcgattg attttatttt tattttataa tgcaaactgc aaagtgatca ttaagat      1497
```

<210> SEQ ID NO 47
<211> LENGTH: 2001
<212> TYPE: DNA
<213> ORGANISM: Arabidopsis thaliana

<400> SEQUENCE: 47

```
ccaaacagat atttgcattt gggctatgta atgttagaat tattttataa tgtatgctat     60

tgctagatat tgtttaagtg catttgtgat ttacaaacat ttcattttta ttttggtttt    120

aatgagcatt tctattatag agactttgat gttaataaat ggtgttctaa gatatattaa    180

aatattttat atactttctt aaaattggat aaattttggg aaaatcctta atatcagtta    240

aattgaagat aaagagtatt aaaaaaaact atgtagtaaa atacatttca catttttttgt   300

gtataatagt acatggtatt cgttaagatc actcaaaaat taacaaatta agtctaaaag    360

ggcagaaaag actattcaaa tatggacttg gagaaagaca ttcagctttt tacgctgaga    420

aactttcata ttgagccgtg tgtttgtgtt gtgaagagaa gtaataaaaa ataatttgaa    480

gtgaaaaagg agaagaaaaa ataagatcgt agaaagcgtg gatggtttct tcttgggttc    540

actgccatgc gattattaaa ttggccatgg ggctagtgtt tgacgtacaa aagtctaaaa    600

attgtcagtc aaacaggtcc aaaactttgt aagaaaaata atataataat agcaaatttt    660

ctaaaaattg ttaaaaaaag aacaaaaggg aaaagatgag gatgcagatg aaagcaaaat    720

gtcaaacact agtttcagat tttatcggga actggggttt gacagttggt gtatgtatgt    780

aatggcctct catcaaaaca tgtgcatctt tttccttttt tgttatttac tgttttagct    840

ctacgtcttg tccaattcct ctcaagtaaa atgcctttaa tatgatacta atatacaagg    900

ggactaatgc tttttccctt ttcttatcct tgttttgtct aaatctttac ttggattcct    960

ttatttttct cctctcttta gattagtacg gtttaaggaa taccatcttt ctaattttag   1020

cacaaaattg caagttggtg ccccatctta gtaagcacat cgtaccacac tttgattgtg   1080

tgagagactt cttcatccca tctctcatac caaacctaaa tcaaatgact agtggtgcaa   1140

cctgctgact ccatatgacc ataactaata aatcggttta tgaatccaac tcatgtagct   1200

ctatagaata gaaacccatt catttcacat aatgaactga atctgacatt ttatttacat   1260

catttactac tcaattttgt aattagcaag atcatctttt tcattattca acaattttga   1320

tattccataa tttattaact ttgtcataca tcataatatt ctgaaatttt gttatatatt   1380

gtaccggttc cacgaaatag agctctatta ttatagacca aacaaacaaa atattatctt   1440

cttgtggtta gttcgagaga gaggtcaaga agaaacgaaa tggatcggca aacggaagac   1500

gtcaaacaca caacgacgaa cattttccga tcacccacct aatctcttcc catttttatt   1560

atttttcaaa actcaaatta attaagaaga aaaaaacaga aacagagaga gaaagagtta   1620

agatgaatag agatagaaag agtcattaaa tgtacgaagc gacattcaca ataattcgaa   1680

aggtggaaga cgacttagat acggccaggc ttcactgtcc tcctcgtcct cctcaattac   1740

ccctaacccc tttttccggg attcatctcc aacccacatc cttccaaatt ctcacccct    1800
```

```
cactgagttt ttgctttttc tcctcatcgg agatcgtgaa gacgatcaag taatttaaga   1860

atcccaccat tgataaaaga gtctagcttt tctactacca aacctttttc tgtttggaaa   1920

ttttcgattt tggatttaac ccttttctta ccttatttat aaccatgcaa tctcacgacc   1980

aacaaccctt caatctccat g                                            2001
```

<210> SEQ ID NO 48
<211> LENGTH: 1309
<212> TYPE: DNA
<213> ORGANISM: Arabidopsis thaliana

<400> SEQUENCE: 48

```
atttcaccaa ttccggcgat tgtgttctgt gtttgatcca tcaccgaata actagaaacg     60

cgattaaaac acacacaaat tagggttttg aatcacggaa acatagaggt tgagggaaac    120

aatttatgta gagatcaatt ccaattgaca caactggatg aaatttctgg gaacgatgaa    180

accctaggac caccgacgaa gaagaagaag aagaagaaga agttcagaga gcgtacatgg    240

atggatttga gaagaagatc acaggcgcaa agtcaaagtg gtcaaaagaa aattaacaat    300

cgagttttga atttgttgta gtcattaatg ggcctttggg cttttatatg gttttcaatg    360

gagttaagtc atgtccattt acggttactt aaactaatgg gtctattgtt ttgaactttt    420

gattttaaaa ggtggagatg gttctgaatc tctctggtta agtatcaatc catgagacct    480

tttttttttt tttttgaatg aatgtgtgaa attatattca actaaaacaa ctgttttaca    540

aatcaaattc aactaaaaca actgacaaat taaatctctc tggttaagtg gtacattttt    600

aatgtctcta gtctctacac ataaacgatt aacatgagag ttcaccaaat cttttccaat    660

tgggtttgtt cacttggttt cgttggtttt aatcttcaca aataaaaaaa tggttttaag    720

taaatagaaa gaaaaaagaa aagaaaaaaa gagtaatcga aggagctgta atcttcacaa    780

agagcacttg attataacat tgaatctttt gcaaaaaaga taaaaatctt ttcaagaaac    840

tgatccatcc aaaatactat cttgtcttca ctcttcaaaa ttcctgtcat tactctctcg    900

aaccctttct cttttcgaat ctccactttt ttttctatct tctgcttctt cttcttctct    960

cttcaatgat tccactctca caaaatctcc atgactacaa aacgcataga cagagatctc   1020

ccatcttccg acgatccttc ctccgctaaa cgccgtatcg aattccccga agaaacactc   1080

gaaaacgacg gtgctgccgc aatcaaactc cttagcttac tcctccaatg cgccgaatac   1140

gtagctactg atcatctccg tgaagcttca acacttttat ccgaaatctc cgagatatgt   1200

tctccgttcg gttcctcgcc ggagcgagtc gtcgcttact tcgctcaagc gctacaaacg   1260

cgcgtgatca gctcttacct ctccggcgcg tgttctcccc tctccgaga              1309
```

<210> SEQ ID NO 49
<211> LENGTH: 3000
<212> TYPE: DNA
<213> ORGANISM: Arabidopsis thaliana

<400> SEQUENCE: 49

```
tttgctctac attgttccga tttagatttt acaaaatggt acgaaattgg tcacctaaaa     60

gtctgttttt ttacctttgt gtgattgatg ggagacctac aggttttttt tgtctatggc    120

ttaattgaag gatagtagaa tatttttgta aaaatatttg atcatttcat tactaatcga    180

aaaagataag ttaacggttc atttctgggg ctaaacaatc ctaaccatgg ggaagatgtt    240

ttctccaagt atataaatct taattagcat acaggcatgc ataacaacca aattagcgaa    300

tgaatatggg tttatatgcg agaaacaaat tagggtctac tgtatacata aacaatgtaa    360
```

```
ttatgcattt atgctatggc tgtttggtgt tgtgtataaa acatagtggc acatataacc    420
gaaattatta tcgactatat atatatatat atatatatat atatatatat atatatattc    480
ttcaaaagat taagatggga cttttcctag aatgcaagaa cagatttcga gaaattacat    540
aagaaactga attgcaacac tcgataggtt tcgaagaaag ggacaaagaa gcagagcgtg    600
gggtttcttc taataattgt agaagaaact gatcatgaga acatttgatc taccagagat    660
ggtgatgact cataagatgt aaatatctac tgcattatgt ctagcctagg ctataatgta    720
gatttgatca ctttcttcat taattagttt ggaattttag catgatatag catatatcta    780
aatatgtccg aaactttcct acatactaga aaatatggag agttatgtaa tgtaggtttg    840
cttgttaata tacaaaataa catcatcatt tagtttttag atttttttatt ttattttta    900
taatggtgct acgtacgtgg cgatcaaatt attccaattt tgagacttcg ggattttaaa    960
cgaaattaaa caatgggcat gagctcgggg ggatagacaa gattaatgct ttgtatcgag   1020
acaaacgaga aaatcatgat gagcctatgc attaagtgcc gttggttaat tagaggttcg   1080
catatacata aaccagtaga catatggata aatatgaaca cacacaccaa aaaagtggga   1140
aatctaaata agtgtagaga ataataagtc ctcaggtggg agattcaaag agaggacaat   1200
gaagggtata tagactctaa acaaaaatgg catgacttag tggagagggt tttaaattga   1260
aacaagtagg attgaagaac aagaaaacaa agaagcatgc cctagatttc tgagataata   1320
attacacatt gctgtttata taaggtaaga gaatatgaca cattggttgg tttcttacgg   1380
gtaaatgtga agaaaaaaaa atagtaatat ttgagaaaat ctaaaatagt aaagaggtat   1440
atatggagaa gaagagagaa aagggaaaaa tagtggcaga gaatggagag aggttaggag   1500
gcaaaggcaa atgtggagct ttgatgatgt tgatgcacgc cgtcagcttt tcttcacgcc   1560
tgctcccact cactcacacc tatgaacatt ctctctctat tttataatta tattcacatg   1620
tctctatgtt actatgtaaa tggtgaccac ttaagtattt atatatcatg tatatatctt   1680
ataggtatca tacaaaatgg tcatgaaact tttgcaattt caatctactt gttcattgta   1740
gatgctagct tttcacatgt tttgaaaatt agtctggatc tgaaattctt taattagcat   1800
tgttttgttg gtcaacgttt aatttcttga ttattgatgt caaaaattca gagcgttcag   1860
aactcttaca ctaatttctt aaaaataatc gattaagaga aaatagagtt ttcatgcacc   1920
agtgttgata gtaacgtagt cgcggaatgt ctaaaacgat tatgagtttg gtgttttgat   1980
tggttagaat tggtattagt aggacattct aactttttttg ttagtctgtt gatttaggat   2040
gcgtaaagag tctttttatt ttacaccagt tgagacttgg gatcgatagt acttgaaaca   2100
cttggttggt ttcatgtatt tggcctatat ataaacaaac atcgtaatta tatacggatt   2160
tttttcggaa ttttacgcca tatctgtaag tatatataac atgcatgtcg ttttcaaatt   2220
catatgatga acgatccacg taagtgctac tactcctaca atattgcatg agagagatat   2280
gtatttataa attttatttt gaagaagaaa taagagggaa ggttacttgg gtggatcgat   2340
gtgaaaacaa aagaagaaaa agcgaaaccc actaagccat tacatgatat cgaccttctt   2400
atctttttcc tctttatttt atttttctca ggactttttt ctacttaatg aaacctccaa   2460
actatctaac taatacactc ccatgtagaa taaagaaaat tatataagat attgttgata   2520
ttttgtaact agaaaatata tttgctctgt aatttttcgt aagttaaatc aacatttttc   2580
agtagaaaca aatattactg caaaaagtag gatcattatt tttgtccaaa atctcagtta   2640
gctatagggt tgtagtaaaa acaaaacaca ttcttgattt gccccaaaaa ataaagagag   2700
```

agaagaatat tgttcaaaag tggtctcttc tctctctaat tatgttttca ctaaacccaa 2760
ttagattcaa acagtctaca aagtccaaaa gataaacatg ggacaacaat tcgatgcaaa 2820
aaatcctctt ttcatgctct ttttttattc tctagtcttt taaattacta ataaaaactc 2880
acaaatccac caaacccatt ctctacaact caccttcatc tagatttacc cactcccacc 2940
gagaaacaca agaaaaaaaa tatacatata taaatataca agacaacaca tgatgctgat 3000

<210> SEQ ID NO 50
<211> LENGTH: 22
<212> TYPE: DNA
<213> ORGANISM: Artificial sequence
<220> FEATURE:
<223> OTHER INFORMATION: SCL23_FW primer

<400> SEQUENCE: 50
tcattggatg cagcaccggt ta 22

<210> SEQ ID NO 51
<211> LENGTH: 22
<212> TYPE: DNA
<213> ORGANISM: Artificial sequence
<220> FEATURE:
<223> OTHER INFORMATION: SCL23_RV primer

<400> SEQUENCE: 51
tccgtgcgcc acaatgtttc tt 22

<210> SEQ ID NO 52
<211> LENGTH: 50
<212> TYPE: DNA
<213> ORGANISM: Artificial sequence
<220> FEATURE:
<223> OTHER INFORMATION: B4_pSCR_F primer

<400> SEQUENCE: 52
ggggacaact ttgtatagaa aagttgccaa acagatattt gcatttgggc 50

<210> SEQ ID NO 53
<211> LENGTH: 48
<212> TYPE: DNA
<213> ORGANISM: Artificial sequence
<220> FEATURE:
<223> OTHER INFORMATION: B1_pSCR_R primer

<400> SEQUENCE: 53
ggggactgct tttttgtaca aacttggaga ttgaagggtt gttggtcg 48

<210> SEQ ID NO 54
<211> LENGTH: 43
<212> TYPE: DNA
<213> ORGANISM: Artificial sequence
<220> FEATURE:
<223> OTHER INFORMATION: attB4_pSCL23_FW primer

<400> SEQUENCE: 54
ggggacaact ttgtatagaa aagttgattt caccaattcc ggc 43

<210> SEQ ID NO 55
<211> LENGTH: 47
<212> TYPE: DNA
<213> ORGANISM: Artificial sequence
<220> FEATURE:
<223> OTHER INFORMATION: attB1_pSCL23_RV primer

<400> SEQUENCE: 55
ggggactgct tttttgtaca aacttgtcga tacggcgttt agcggag 47

<210> SEQ ID NO 56
<211> LENGTH: 47
<212> TYPE: DNA
<213> ORGANISM: Artificial sequence
<220> FEATURE:
<223> OTHER INFORMATION: attB1_SCL23_FW primer

<400> SEQUENCE: 56
ggggacaagt ttgtacaaaa aagcaggctc catgactaca aaacgca 47

<210> SEQ ID NO 57
<211> LENGTH: 48
<212> TYPE: DNA
<213> ORGANISM: Artificial sequence
<220> FEATURE:
<223> OTHER INFORMATION: attB2_SCL23_RV primer

<400> SEQUENCE: 57
ggggaccact ttgtacaaga aagctgggta cggctgagat ttccaggc 48

<210> SEQ ID NO 58
<211> LENGTH: 21
<212> TYPE: DNA
<213> ORGANISM: Artificial sequence
<220> FEATURE:
<223> OTHER INFORMATION: SCL23_LP1 primer

<400> SEQUENCE: 58
taataatgca aagcctccac g 21

<210> SEQ ID NO 59
<211> LENGTH: 22
<212> TYPE: DNA
<213> ORGANISM: Artificial sequence
<220> FEATURE:
<223> OTHER INFORMATION: SCL23_RP1 primer

<400> SEQUENCE: 59
ttttcaagaa actgatccat cc 22

<210> SEQ ID NO 60
<211> LENGTH: 22
<212> TYPE: DNA
<213> ORGANISM: Artificial sequence
<220> FEATURE:
<223> OTHER INFORMATION: LBb1 primer

<400> SEQUENCE: 60
gcgtggaccg cttgctgcaa ct 22

<210> SEQ ID NO 61
<211> LENGTH: 22
<212> TYPE: DNA
<213> ORGANISM: Artificial sequence
<220> FEATURE:
<223> OTHER INFORMATION: SCL23_LP2 primer

<400> SEQUENCE: 61
ggtggagatg gttctgaatc tc 22

<210> SEQ ID NO 62
<211> LENGTH: 21
<212> TYPE: DNA

<213> ORGANISM: Artificial sequence
<220> FEATURE:
<223> OTHER INFORMATION: SCL23_RP2 primer

<400> SEQUENCE: 62
cagttgaagc gagtagatcg g 21

<210> SEQ ID NO 63
<211> LENGTH: 21
<212> TYPE: DNA
<213> ORGANISM: Artificial sequence
<220> FEATURE:
<223> OTHER INFORMATION: Ds3-1 primer

<400> SEQUENCE: 63
acccgaccgg atcgtatcgg t 21

<210> SEQ ID NO 64
<211> LENGTH: 21
<212> TYPE: DNA
<213> ORGANISM: Artificial sequence
<220> FEATURE:
<223> OTHER INFORMATION: SCR_F2 primer

<400> SEQUENCE: 64
ctctacgtct tgtccaattc c 21

<210> SEQ ID NO 65
<211> LENGTH: 21
<212> TYPE: DNA
<213> ORGANISM: Artificial sequence
<220> FEATURE:
<223> OTHER INFORMATION: SCR_R2 primer

<400> SEQUENCE: 65
caaagtgtgg tacgatgtgc t 21

<210> SEQ ID NO 66
<211> LENGTH: 24
<212> TYPE: DNA
<213> ORGANISM: Artificial sequence
<220> FEATURE:
<223> OTHER INFORMATION: SCR_F1 primer

<400> SEQUENCE: 66
agaaacgaaa tggatcggca aacg 24

<210> SEQ ID NO 67
<211> LENGTH: 24
<212> TYPE: DNA
<213> ORGANISM: Artificial sequence
<220> FEATURE:
<223> OTHER INFORMATION: SCR_R1 primer

<400> SEQUENCE: 67
atttggaagg atgtgggttg gaga 24

<210> SEQ ID NO 68
<211> LENGTH: 22
<212> TYPE: DNA
<213> ORGANISM: Artificial sequence
<220> FEATURE:
<223> OTHER INFORMATION: SCR_FW primer

<400> SEQUENCE: 68
acttcttccg gtagtagcag ca 22

<210> SEQ ID NO 69
<211> LENGTH: 21
<212> TYPE: DNA
<213> ORGANISM: Artificial sequence
<220> FEATURE:
<223> OTHER INFORMATION: SCR_RV primer

<400> SEQUENCE: 69
agagacggtg gttgttgtgg t 21

<210> SEQ ID NO 70
<211> LENGTH: 21
<212> TYPE: DNA
<213> ORGANISM: Artificial sequence
<220> FEATURE:
<223> OTHER INFORMATION: SCL23_F2 primer

<400> SEQUENCE: 70
tccggcgatt gtgttctgtg t 21

<210> SEQ ID NO 71
<211> LENGTH: 22
<212> TYPE: DNA
<213> ORGANISM: Artificial sequence
<220> FEATURE:
<223> OTHER INFORMATION: SCL23_R2 primer

<400> SEQUENCE: 71
cttcttcttc gtcggtggtc ct 22

<210> SEQ ID NO 72
<211> LENGTH: 22
<212> TYPE: DNA
<213> ORGANISM: Artificial sequence
<220> FEATURE:
<223> OTHER INFORMATION: SCL23_F1 primer

<400> SEQUENCE: 72
ctggttaagt atcaatccat ga 22

<210> SEQ ID NO 73
<211> LENGTH: 21
<212> TYPE: DNA
<213> ORGANISM: Artificial sequence
<220> FEATURE:
<223> OTHER INFORMATION: SCL23_R1 primer

<400> SEQUENCE: 73
accaacgaaa ccaagtgaac a 21

<210> SEQ ID NO 74
<211> LENGTH: 21
<212> TYPE: DNA
<213> ORGANISM: Artificial sequence
<220> FEATURE:
<223> OTHER INFORMATION: SCL23_FW primer

<400> SEQUENCE: 74
tgctgccgca atcaaactcc t 21

<210> SEQ ID NO 75
<211> LENGTH: 21
<212> TYPE: DNA
<213> ORGANISM: Artificial sequence
<220> FEATURE:

```
<223> OTHER INFORMATION: SCL23_RV primer

<400> SEQUENCE: 75

agctgatcac gcgcgtttgt a                                          21


<210> SEQ ID NO 76
<211> LENGTH: 20
<212> TYPE: DNA
<213> ORGANISM: Artificial sequence
<220> FEATURE:
<223> OTHER INFORMATION: 18S-5 primer

<400> SEQUENCE: 76

taccgtccta gtctcaacca                                            20


<210> SEQ ID NO 77
<211> LENGTH: 20
<212> TYPE: DNA
<213> ORGANISM: Artificial sequence
<220> FEATURE:
<223> OTHER INFORMATION: 18S-3 primer

<400> SEQUENCE: 77

aacatctaag ggcatcacag                                            20
```